(12) United States Patent
Skwierczynski et al.

(10) Patent No.: US 11,576,890 B2
(45) Date of Patent: *Feb. 14, 2023

(54) PURIFIED FORMS OF ROFECOXIB, METHODS OF MANUFACTURE AND USE

(71) Applicant: Tremeau Pharmaceuticals, Inc., Concord, MA (US)

(72) Inventors: Raymond D. Skwierczynski, Andover, MA (US); Bradford C. Sippy, Acton, MA (US); Jean-Marie Schneider, Magnaville (FR); Simon H. Drouin, Saint-Hyacinthe (CA); Charles Guerin, Mantes la Ville (FR)

(73) Assignee: Tremeau Pharmaceuticals, Inc., Concord, MA (US)

( * ) Notice: Subject to any disclaimer, the term of this patent is extended or adjusted under 35 U.S.C. 154(b) by 195 days.

This patent is subject to a terminal disclaimer.

(21) Appl. No.: 17/186,697

(22) Filed: Feb. 26, 2021

(65) Prior Publication Data

US 2021/0236455 A1 Aug. 5, 2021

Related U.S. Application Data

(63) Continuation of application No. 16/716,242, filed on Dec. 16, 2019, now Pat. No. 10,987,337, which is a continuation of application No. PCT/US2019/061178, filed on Nov. 13, 2019.

(60) Provisional application No. 62/770,563, filed on Nov. 21, 2018.

(51) Int. Cl.
*A61K 31/341* (2006.01)

(52) U.S. Cl.
CPC ................................. *A61K 31/341* (2013.01)

(58) Field of Classification Search
CPC .................................................... A61K 31/341
See application file for complete search history.

(56) References Cited

U.S. PATENT DOCUMENTS

| | | |
|---|---|---|
| 3,854,480 A | 12/1974 | Zaffaroni |
| 4,452,775 A | 6/1984 | Kent |
| 4,675,189 A | 6/1987 | Kent et al. |
| 5,075,109 A | 12/1991 | Tice et al. |
| 5,133,974 A | 7/1992 | Paradissis et al. |
| 5,407,686 A | 4/1995 | Patel et al. |
| 5,474,995 A | 12/1995 | Ducharme et al. |
| 5,631,287 A | 5/1997 | Schneider |
| 5,736,152 A | 4/1998 | Dunn |
| 5,840,924 A | 11/1998 | Desmond et al. |
| 5,849,943 A | 12/1998 | Atkinson et al. |
| 6,063,811 A | 5/2000 | Hancock et al. |
| 6,407,686 B1 | 6/2002 | Otani et al. |
| 8,329,216 B2 | 12/2012 | Kao et al. |
| 8,461,187 B2 | 6/2013 | Taneja et al. |
| 8,747,897 B2 | 6/2014 | Kidane et al. |
| 8,889,186 B2 | 11/2014 | Holm et al. |
| 8,916,195 B2 | 12/2014 | McKinney et al. |
| 9,492,408 B2 | 11/2016 | Leikauf |
| 9,511,037 B2 | 12/2016 | Desai |
| 10,076,522 B2 | 9/2018 | Huang et al. |
| 10,188,652 B2 | 1/2019 | Moline et al. |
| 10,376,463 B2 | 8/2019 | Jaffe et al. |
| 10,564,169 B2 | 2/2020 | Frantz |
| 10,945,992 B1 | 3/2021 | Sippy et al. |
| 10,987,337 B2* | 4/2021 | Skwierczynski ....... A61P 25/06 |
| 2002/0049233 A1 | 4/2002 | Kararli et al. |
| 2004/0186155 A1 | 9/2004 | Dayno et al. |
| 2005/0049291 A1 | 3/2005 | Kumar et al. |
| 2020/0206182 A1 | 7/2020 | Sippy et al. |
| 2021/0137878 A1 | 5/2021 | Sippy et al. |
| 2021/0169845 A1 | 6/2021 | Sippy et al. |
| 2022/0047542 A1 | 2/2022 | Sippy et al. |

FOREIGN PATENT DOCUMENTS

| | | |
|---|---|---|
| CN | 1224422 A | 7/1999 |
| CN | 1771240 A | 5/2006 |
| EP | 754687 A1 | 1/1997 |
| EP | 822190 A1 | 2/1998 |
| EP | 705254 B1 | 5/1998 |
| EP | 980866 A2 | 2/2000 |
| JP | 2000-38375 A | 2/2000 |
| WO | WO 1995/000501 A2 | 1/1995 |
| WO | WO 1995/018799 A1 | 7/1995 |
| WO | WO 1996/008482 A1 | 3/1996 |
| WO | WO 1996/013483 A1 | 5/1996 |
| WO | WO 1997/044028 A1 | 11/1997 |
| WO | WO 1998/000416 A1 | 1/1998 |

(Continued)

OTHER PUBLICATIONS

U.S. Appl. No. 17/856,549 filed Jul. 2022, Skwierczynski; Raymond D.*

Erk et al., Comparison of derivative spectrophotometric and liquid chromatographic methods for determination of rofecoxib, Pharmazie 59: 453-456 (2004).*

Camilleri et al., beta-Cyclodextrin interacts with the Alzheimer amyloid beta-A4 peptide. FEBS Lett. Mar. 21, 1994;341(2-3):256-8. doi: 10.1016/0014-5793(94)80467-2.

Coisne et al., Cyclodextrins as Emerging Therapeutic Tools in the Treatment of Cholesterol-Associated Vascular and Neurodegenerative Diseases. Molecules. Dec. 20, 2016;21(12):1748. doi: 10.3390/molecules21121748.

(Continued)

*Primary Examiner* — Svetlana M Ivanova
(74) *Attorney, Agent, or Firm* — Wolf, Greenfield & Sacks, P.C.

(57) ABSTRACT

The subject matter disclosed herein relates to rofecoxib, also known as TRM-201 or RXB-201, its method of manufacture, and use. In certain aspects, the highly pure or substantially pure rofecoxib as provided herein has a favorable purity profile and is the active ingredient in a pharmaceutical composition that is administered to treat or prevent a number of conditions, including pain associated with a condition caused by a bleeding disorder.

32 Claims, 37 Drawing Sheets

(56) References Cited

FOREIGN PATENT DOCUMENTS

| WO | WO 2004/072057 A1 | 8/2004 |
| WO | WO 2005/004806 A2 | 1/2005 |
| WO | WO 2005/016906 A1 | 2/2005 |
| WO | WO 2005/025564 A1 | 3/2005 |
| WO | WO 2010/033179 A1 | 3/2010 |
| WO | WO 2019/193417 A1 | 10/2019 |
| WO | WO 2020/106522 A1 | 5/2020 |

OTHER PUBLICATIONS

Coisne et al., β-Cyclodextrins Decrease Cholesterol Release and ABC-Associated Transporter Expression in Smooth Muscle Cells and Aortic Endothelial Cells. Front Physiol. May 25, 2016;7:185. doi: 10.3389/fphys.2016.00185. eCollection 2016.

Danielsson et al., Two-site binding of beta-cyclodextrin to the Alzheimer Abeta(1-40) peptide measured with combined PFG-NMR diffusion and induced chemical shifts. Biochemistry. May 25, 2004;43(20):6261-9. doi: 10.1021/bi036254p.

Danielsson et al., Two-site binding of beta-cyclodextrin to the Alzheimer Abeta(1-40) peptide measured with combined PFG-NMR diffusion and induced chemical shifts. Biochemistry. 2004. Supporting Information. 5 pages.

Del Toro et al., Altered cholesterol homeostasis contributes to enhanced excitotoxicity in Huntington's disease. J Neurochem. Oct. 2010;115(1):153-67. doi: 10.1111/j.1471-4159.2010.06912.x. Epub Aug. 12, 2010.

Loftsson et al., Cyclodextrins and their pharmaceutical applications. Int J Pharm. Feb. 1, 2007;329(1-2):1-11. doi: 10.1016/j.ijpharm.2006.10.044. Epub Nov. 9, 2006.

Monnaert et al., Behavior of alpha-, beta-, and gamma-cyclodextrins and their derivatives on an in vitro model of blood-brain barrier. J Pharmacol Exp Ther. Aug. 2004;310(2):745-51. doi: 10.1124/jpet.104.067512. Epub Apr. 13, 2004.

Takechi-Haraya et al., Molecular complex composed of β-cyclodextrin-grafted Chitosan and pH-sensitive amphipathic peptide for enhancing cellular cholesterol efflux under acidic pH. Bioconjug Chem. Mar. 18, 2015;26(3):572-81. doi: 10.1021/acs.bioconjchem.5b00037. Epub Mar. 2, 2015.

Takechi-Haraya et al., Molecular complex composed of β-cyclodextrin-grafted Chitosan and pH-sensitive amphipathic peptide for enhancing cellular cholesterol efflux under acidic pH. Bioconjug Chem. 2015. Supporting Information. 11 pages.

Wahlström et al., Specific binding of a β-cyclodextrin dimer to the amyloid β peptide modulates the peptide aggregation process. Biochemistry. May 29, 2012;51(21):4280-9. doi: 10.1021/bi300341j. Epub May 17, 2012.

Wahlström et al., Specific binding of a β-cyclodextrin dimer to the amyloid β peptide modulates the peptide aggregation process. Biochemistry. 2012. Supporting Information. 10 pages.

Walker, β-Cyclodextrin. School of Biological Sciences, University of Surrey. WHO Food Additives Series 32. 1993. Accessed: https://inchem.org/documents/jecfa/jecmono/v32je13.htm.

[No Author Listed], U.S. Department of Health and Human Services FDA Guidance for Industry—Q3A Impurities in New Drug Substances. Revision 2. Jun. 2008. 17 pages.

[No Author Listed], U.S. Department of Health and Human Services FDA Guidance for Industry—Q3C Tables and List Guidance for Industry. Revision 3. Jun. 2017. 10 pages.

[No Author Listed], Etoricoxib. USP Medicines Compendium. Version 1.1. Last modified Feb. 28, 2014. https://mc.usp.org/monographs/etoricoxib-1-1. 4 pages.

Chavanpatil et al., Enhancement of Oral Bioavailability of Rofecoxib Using β-Cyclodextrin. Journal of Inclusion Phenomena and Macrocyclic Chemistry. 2002; 44:145-149.

International Preliminary Report on Patentability, dated May 27, 2022, in connection with Application No. PCT/US2020/060152.

Extended European Search Report for Application No. 19888061.9, dated Jul. 5, 2022.

International Preliminary Report on Patentability, dated Jun. 3, 2021, in connection with Application No. PCT/US2019/061178.

[No Author Listed], Australian Product Information—ARCOXIA® (etoricoxib). MK0663-AUS-2017-015150. 2017. 27 pages.

[No Author Listed], Chapter 90: Solid Oral Dosage Form. From Remington's Pharmaceutical Salts. 17th ed. Gennaro Ed. Mack Publishing Co., Easton PA. 1985:1603-1632. 34 pages.

[No Author Listed], FDA Approval Letter for NDA 21-647, dated Mar. 26, 2004, available at www.accessdata.fda.gov/drugsatfda_docs/appletter/2004/216471ltr.pdf (last visited Dec. 22, 2021).

[No Author Listed], Food & Drug Administration. Adalat CC (nifedipine) Extended Release Tables For Oral Use, https://www.accessdata.fda.gov/drugsatfda_docs/label/2010/020198s022lbl.pdf (published Mar. 3, 2010, last accessed Apr. 8, 2022).

[No Author Listed], Food & Drug Administration. Prescribing Information Wellbutrin XL® (bupropion hydrochloride extended-release tablets). https://www.accessdata.fda.gov/drugsatfda_docs/label/2009/021515s023s024lbl.pdf (published Jul. 1, 2019, last accessed Apr. 7, 2022).

[No Author Listed], Food & Drug Administration. Ritalin® hydrochloride methylphenidate hydrochloride tables USP; Ritalin-SR® methylphenidate hydrochloride USP sustained-release tables; Rx only Prescribing Information. https://www.accessdata.fda.gov/drugsatfda_docs/label/2010/010187s073lbl.pdf (published Dec. 9, 2010, last accessed Apr. 8, 2022).

[No Author Listed], Guidance for Industry—Bioequivalence Guidance. US Department of Health and Human Service, Food and Drug Administration, Center for Veterinary Medicine (CVM). Accessible at www.fda.gov/media/70115/download. Nov. 8, 2006. 28 pages.

[No Author Listed], Guidance for Industry—Statistical Approaches to Establishing Bioequivalence. US Department of Health and Human Services, Food and Drug Administration, Center for Drug Evaluation and Research (CDER). Accessible at www.fda.gov/media/70958/download. Jan. 2001. 48 pages.

[No Author Listed], Novelty and Non-Obviousness of Tremeau's Rofecoxib Formulation and Methods of Use Thereof. Tremeau Pharmaceuticals. Nov. 12, 2020. 18 pages.

[No Author Listed], Office of the Assistant Secretary for Planning and Evaluation, HHS; Number of US FDA ANDA Approvals Per Fiscal Year, 2010-2019. https://aspe.hhs.gov/number-us-fda-anda-approvals-fiscal-year (last accessed Apr. 7, 2022).

[No Author Listed], Representative Formulation Claims from Issued Patents. Tremeau Pharmaceuticals. Date Unknown. 2 pages.

[No Author Listed], Statista; Proportion of Branded Versus Generic Drug Prescriptions Dispensed in the United States from 2005 to 2020, https://www.statista.com/statistics/205042/proportion-of-brand-to-generic-prescriptions-dispensed/ (last accessed Apr. 7, 2022).

[No Author Listed], U.S. Court of Appeals for the Federal Court—*Nalpropion Pharmaceuticals, Inc.* v. *Actavis Laboratories Fl, Inc.* Decided Aug. 15, 2019. 29 pages.

[No Author Listed], U.S. Food & Drug Administration, Generic Drugs: Questions & Answers via Wayback Machine. https://web.archive.org/web/20190612182451/https://www.fda.gov/drugs/questions-answers/generic-drugs-questions-answers (published Jun. 12, 2019, last accessed Apr. 7, 2022).

[No Author Listed], U.S. Food & Drug Administration, NINLARO® (ixazomib) capsules, for oral use, Prescribing Information. https://www.accessdata.fda.gov/drugsatfda_docs/label/2015/208462lbl.pdf (published Nov. 20, 2015, last accessed Apr. 8, 2022).

[No Author Listed], U.S. Food & Drug Administration. Procardia XL® (nifedipine) Extended Release Tables For Oral Use, https://www.accessdata.fda.gov/drugsatfda_docs/label/2011/019684s024lbl.pdf (published Sep. 27, 2011, last accessed Apr. 8, 2022).

[No Author Listed], U.S. Food & Drug Administration. Procardia® (nifedipine) Capsules For Oral Use, https://www.accessdata.fda.gov/drugsatfda_docs/label/2011/018482s049lbl.pdf (published Sep. 27, 2011, last accessed Apr. 8, 2022).

[No Author Listed], U.S. Food & Drug Administration. Ritalin LA® (methylphenidate hydrochloride) extended-release capsules; Rx only Prescribing Information, https://www.accessdata.fda.gov/drugsatfda_docs/label/2010/021284s017lbl.pdf (published Nov. 15, 2010, last accessed Apr. 8, 2022).A128.

(56) References Cited

OTHER PUBLICATIONS

[No Author Listed], VIOXX® Label. Retrieved from www.accessdata.fda.gov/drugsatfda_docs/label/2004/21647_vioxx_lbl.pdf on May 19, 2021. Mar. 26, 2004. 28 pages.
Advisory Action for U.S. Appl. No. 16/867,514, dated Nov. 25, 2020. 116 pages.
Bick et al., Hematological Complications in Obstetrics, Pregnancy, and Gynecology. Cambridge University Press; 1st edition (May 15, 2006), Chapter 3, pp. 75-102).
Breithaupt-Groegler et al., Who is a 'healthy subject'?—consensus results on pivotal eligibility criteria for clinical trials. Eur J Clin Pharmacol. Apr. 2017;73(4):409-416. doi: 10.1007/s00228-016-2189-8. Epub Jan. 7, 2017.
Chu et al., Effect of particle size on the dissolution behaviors of poorly water-soluble drugs. Arch Pharm Res. Jul. 2012;35(7):1187-95. doi: 10.1007/s12272-012-0709-3. Epub Aug. 3, 2012.
Dembo et al., Central nervous system concentrations of cyclooxygenase-2 inhibitors in humans. Anesthesiology. Feb. 2005;102(2):409-15. doi: 10.1097/00000542-200502000-00026.
Dhoot et al., Design of Experiments in Pharmaceutical Development. Pharmaceutical Chemistry Journal. Nov. 2019; 53(8):730-735.
Dressman et al., Oral Drug Absorption: Prediction and Assessment. Chapters 12-15. 2nd Edition. Informa Healthcare, Eds. 2010.
Dressman et al., Pharmaceutical Dissolution Testing. 1st Edition. Taylor & Francis, Eds. 2005.pp. v-vi.
Genaro, Remington's Pharmaceutical Sciences. Mack Publishing Co., Eds. 1985: 1605-1607.
Ghandi et al., Evaluation of two forms of sustained release nifedipine using 24 h ambulatory blood pressure monitoring. Am J Hypertens. Sep. 1997;10(9 Pt 1):992-6. doi: 10.1016/s0895-7061(97)00128-3.
Hassan et al., Headaches in vonwillebrand disease. J Haematol Blood Diseases Disorders. Feb. 2014;2(2):023-025. Accessible at www.internationalscholarsjournals.org.
Heijdra et al., Current and Emerging Options for the Management of Inherited von Willebrand Disease. Drugs. Sep. 2017;77(14):1531-1547. doi: 10.1007/s40265-017-0793-2.
Heimann, NDA 21-647 Chemistry Review. Center for Drug Evaluation and Research. Feb. 2004. 9 pages.
Leebeek et al., Von Willebrand's Disease. N Engl J Med. Nov. 24, 2016;375(21):2067-2080. doi: 10.1056/NEJMra1601561.
Loder et al., Measuring pain intensity in headache trials: which scale to use? Cephalagia. Feb. 2012;32(3):179-82. doi: 10.1177/0333102411434812. Epub Jan. 27, 2012. PMID: 22287565.
Lu et al., In vitro-in vivo correlation: perspectives on model development. Int J Pharm. Oct. 10, 2011;418(1):142-8. doi: 10.1016/j.ijpharm.2011.01.010. Epub Jan. 13, 2011. Author Manuscript. 16 pages.
Mezher, Regulatory Affairs Professionals Society; FDA Approves Fewer Generics in FY2020, Ending Record Streak. https://www.raps.org/news-and-articles/news-articles/2020/10/fda-approves-fewer-generics-in-fy2020-ending-recor (last accessed Apr. 7, 2022).
Paper, Can you recognize and respond to von Willebrand disease? Nursing. Jul. 2003;33(7):54-6. doi: 10.1097/00152193-200307000-00042.
Politis et al., Design of experiments (DoE) in pharmaceutical development. Drug Dev Ind Pharm. Jun. 2017;43(6):889-901. doi: 10.1080/03639045.2017.1291672. Epub Feb. 23, 2017.
Ramana et al., A new approach: Enhancement of solubility of rofecoxib. Asian Journal of Pharmaceutics. Apr. 2008:96-101.
Rattray et al., Rofecoxib as adjunctive therapy for haemophilic arthropathy. Haemophilia. May 2005;11(3):240-4. doi: 10.1111/j.1365-2516.2005.01087.x.
Rodriguez-Merchan et al., Treatment of Chronic Articular Pain in Adult People with Hemophilia. Cardiovasc Hematol Disord Drug Targets. 2018;18(3):182-186. doi: 10.2174/1871529X18666180503123412.
Shargel et al., Biopharmaceutic Aspects of Drug Products. Chapter 6 in: Applied Biopharmaceutics and Pharmacokinetics. 2nd Ed. Appleton-Century-Crofts, Eds. 1985. pp. 65-104.
Silberstein et al., Randomized, placebo-controlled trial of rofecoxib in the acute treatment of migraine. Neurology. May 11, 2004;62(9):1552-7. doi: 10.1212/01.wnl.0000123260.61631.c4.
Stanton, Patentability of Reach-Through Claims. USPTO Technology Center 1600. Publication date unknown. 17 pages. Wayback Machine index date: Sep. 6, 2015.
US Food and Drug Administration, Patient-Focused Drug Development Meeting on Chronic Pain. Slideshow presentation dated Jul. 9, 2018. Retrieved from https://www.fda.gov/media/114758/download on May 19, 2021. 48 pages.
International Search Report and Written Opinion, dated Feb. 10, 2021, in connection with Application No. PCT/US2020/060152.
International Search Report and Written Opinion, dated Apr. 14, 2020, in connection with Application No. PCT/US2019/061178.
[No Author Listed] Vioxx Final. N-21,042. Merck & Co. No date. 15 pages.
[No Author Listed], An Overview of USP Monographs. Retrieved from usp.org/publicstandards. 2 pages. No Date.
[No Author Listed], Analysis and Recommendations for Agency Action Regarding Nonsteroidal Anti-Inflammatory Drugs and Cardiovasuclar Risk. J Pain Palliat Car Pharmacother. 2005;19(4):83-97.
[No Author Listed], CSD Entry: CAXMUJ. Retrieved from www.ccdc.cam.acuk/structures/Search?Compound=Rofecoxib&DatabaseToSearch=Published. Accessed May 27, 2020.
[No Author Listed], Etoricoxib—Final Authorized Version 2.0. USPC Medicins Compendium. 6 pages. Retrieved from mc.usp.org/monographs/etoricoxiv-2-0 on Jul. 4, 2020. 6 pages.
[No Author Listed], First Supplement to USP 35-NF 30. Official Monographs / Celecoxib. The United States Pharmacopeial Convention. Aug. 1, 2012:5447-5448.
[No Author Listed], Guidance for Industry—ANDAs: Impurities in Drug Subtances. US Department of Health and Human Servies. Food and Drug Administration, Center for Drug Evaluation and Research (CDER). Nov. 1999. 19 pages.
[No Author Listed], Guideline on the Limits of Genotoxic Impuritites. EMEA/CHMP/QWP/251344/2006. Jun. 28, 2006. 8 pages.
[No Author Listed], M7 Assessment and Control of DNA reactive (Mutagenic) Impurities in Pharmaceuticals to Limit Potential Carcinogenic Risk: Guidance for Industry. US Department of Health and Human Services, Food and Drug Administration, Center for Drug Evaluation and Research (CDER), Center for Biologics Evaluation and Research (CBER). May 2015. 35 pages.
[No Author Listed], M7 Assessment and Control of DNA reactive (Mutagenic) Impurities in Pharmaceuticals to Limit Potential Carcinogenic Risk: Guidance for Industry. US Department of Health and Human Services, Food and Drug Administration, Center for Drug Evaluation and Research (CDER), Center for Biologics Evaluation and Research (CBER). Mar. 2018. 131 pages.
[No Author Listed], Rofecoxib (Vioxx) voluntarily withdrawn from market. CMAJ. Oct. 26, 2004;171(9). 2 pages.
[No Author Listed], Safety Data Sheet for 1,8-Diazabicyclo[5.4.0]undec-7-ene. Cat Nos. ac160610000; ac160610025; ac160610050; ac160610250; ac160611000; ac160615000. ThermoFisher Scientific. Jan. 18, 2018. 7 pages.
[No Author Listed], Safety Data Sheet for 3-Chloroperoxybenzoic acid. Cat Nos. AC255790000; AC255790010' AC255790250; AC255791000; AC255795000. ThermoFisher Scientific. Jan. 23, 2009. 8 pages.
[No Author Listed], Safety Data Sheet for Acetyl chloride. Cat Nos. A27-250. ThermoFisher Scientific. Apr. 25, 2019. 8 pages.
[No Author Listed], Safety Data Sheet for Aluminium chloride. Cat Nos. AC217460000; AC217460025; AC217460050; AC217461000; AC217465000. ThermoFisher Scientific. May 27, 2019. 7 pages.
[No Author Listed], Vioxx (rofecoxib tablets and oral suspension). Prescribing Information. Reference ID 3928121. Retrieved from https://www.accessdata.fda.gov/drugsatfda_docs/label/2016/021042s033,021052s024lbl.pdf on Dec. 18, 2020. 31 pages.
[No Author Listed], Vioxx (Rofecoxib)—Food and Drug Adminstration Office of Clinical Pharmacology and Biopharmaceutics Review. NDAs 21-042/(SE5-026) & 21-052/(SE5-019). Merck & Co., Inc., Sponsor. Retrieved from www.fda.gov/media/91448/download. 2004. 5 pages (redacted).

(56) References Cited

OTHER PUBLICATIONS

[No Author Listed], Vioxx (Rofecoxib)—US Prescribing Information. US Food and Drug Administration, Reference ID: 3928121. Retrieved from www.accessdata.fda.gov/drugsatfda_docs/label/2016/021042s033,021052s024lbl.pdf. 2002. 31 pages.
Abou-Taleb et al., Formulation and Evaluation of Rofecoxib Tablets in Comparison with Marketed Product. Saudi Pharmaceutical Journal. Jul.-Oct. 2006;14(3-4):187-195.
Ahuja et al., Rofecoxib: an update on physicochemical, pharmaceutical, pharmacodynamic and pharmacokinetic aspects. J Pharm Pharmacol. Jul. 2003;55(7):859-94. doi: 10.1211/0022357021387.
Andrews et al., A comparison of the Mutagenic Properties of Vinyl Chloride and Methyl Chloride. Mutation Resarch. 1976;40:273-275.
Azuma et al., Mutagenicity of 12 HPLC Labeling Reagents for Analysing Carboxyl Compounds. J Environ Chem. 199;7(2):249-255. Abstract Only.
Berge et al., Pharmaceutical Salts. J Pharma Sci. Jan. 1977;66(1):1-19.
Bresalier et al., Cardiovascular Events Associated with Rofecoxib in a Colorectal Adenoma Chemoprevention Trial. N Engl J Med. 2005;352:1092-1102.
Caturla et al., Racemic and chiral sulfoxides as potential prodrugs of teh COX-2 inhibitors Vioxx® and Arcoxia®. Bioorg Med Chem Lett. Apr. 17, 2006;16:3209-3212.
Chan et al., Rofecoxib [Vioxx, MK-0966; 4-(4'-Methylsulfonylphenyl)-3—phenyl-2-(5H)-furanone]: a Potent and Orally Active Cyclooxygenase-2 Inhibitor. Pharamcological and Biochemical Profiles. J Pharmacol and Exp Ther. 1999;290(2):551-560.
Davies et al., Pharamcokinetics of Rofecoxib: A Specific Cyclo-Oxygenase-2 Inhibitor. Clin Pharmacokinet. 2003;42(6):545-556.
Dean, Structural Examination of 6-Methylsulphonylphenanthro-[9,10-C]-furan-1(3H)-one—A Rofecoxib Degradation Product. Pharamceuticals. Feb. 1, 2010;3(3):369-378.
Depré et al., Pharmacokinetics, COX-2 specificity, and tolerability of supratherapeutic doses of rofecoxib in humans. Eur J Clin Pharmacol. 2000;56:167-174.
Dobo et al., In silico methods combined with expert knowledge rule out mutagenic potential of pharmaceutical impurities: an industry survey. Regulatory Toxicology and Pharmacolgy. Jan. 31, 2012;62(3):449-455.
Dong et al., Manganese-Catalyzed Selective Oxidation of Aliphatic C-H groups and Secondary Alcohols to Ketones with Hydrogen Peroxide. ChemSusCHem. 2013;6(9):1774-1778.
El-Say et al., Formulation and Evaluation of Rofecoxib Liquisolid Tablets. Int J Pharma Sci Rev Res. Jul.-Aug 2010;3(Article 028, Issue 1):135-142.
El-Say et al., Optimization of Rofecoxib Liquisolid Tablets usingBox-Behnken Design and Desirability Function. J Pharma Res. Oct. 10, 2010;3(10):2388-2392.
Erk et al., Comparison of derivative spectrophotometric and liquid chromatographic methods for the determination of rofecoxib. Pharmazie. Jun. 2004;59(6):453-6.
European Medicines Agency, Note for Guidance on Impurities Testing: Impurities in New Drug Substances. EMEA. Retreived from www.emea.europa.eu. Oct. 2006. 15 pages.
Forgione et al., Magnesium mediated carbometallation of propargyl alcohols: direct routes to furans and furanones. Tetra Lett. 2000;41:17-20.
Garde, 'I just white-knuckler it': Hemophilia patients pin their hopes on the revival of Vioxx to fill a void in pain relief. STAT. Dec. 9, 2020. 6 pages.
Groom et al., The Cambridge Structural Database. Acta Cryst. 2016;B72:171-179.
Hansen et al., Benchmark Data Set for in Silico Prediction of Ames Mutagenicity. J Chem Info Model. 2009;49:2077-2081.
Jenkins et al., Analysis and recommendation for Agency action regarding non-steroidal anti-inflammatory drugs and cardiovascular risk. Memorandum to NDA files 20-998, 21-156, 21-341, 21-042. Apr. 6, 2005. 9 pages.
Koytchev et al., Bioequivalence Study of Rofecoxib Tablets. Arzneim-Forsch/Drug Res. 2004;54(9a):624-628.
Krauskopf, Merck agrees to pay $4.85 billion in Vioxx settlement. Reuters, Business News. Nov. 9, 2007. 6 pages.
Kubota et al., An Unexpected Incident with m-CPBA. Organic Process Research & Development. 2004;8:1076-7078.
Langer, New Methods of Drug Delivery. Science. Sep. 28, 1990;249:1527-1533.
Leber et al., p-Chlorophenyl Methyl Sulfide, p-Chlorophenyl Methyl Sulfoxide, and p-Chlorophenyl Methyls Sulfone. I. Acute Toxicity and Bacterial Mutagenacity Studies. J Am Coll Toxicol. 1993;12(4):369-376.
Lenzer, FDA is incapable of protecting us 'against another Vioxx'. BMJ. Nov. 27, 2004;329:1253.
Mao et al., Mao B, Abrahim A, Ge Z, Ellison DK, Hartman R, Prabhu SV, Reamer RA, Wyvratt J. Examination of rofecoxib solution decomposition under alkaline and photolytic stress conditions. J Pharm Biomed Anal. Jun. 15, 2002;28(6):1101-13. doi: 10.1016/s0731-7085(01)00716-6.
Martin, Uster's Guide for T.E.S.T. (version 4.2) (Toxicity Estimation Software Tool): A program to estimate toxicity from molecular structure. EPA/600/R-16/058. Version 4.2.1. 2016. 63 pages.
Matthews et al., Combined Use of MC4PC, MDL-QSAR, BioEpisteme, Leadscope PDM, and Derek for WIndows Softward to Achieve High-Performance, High-Confidence, Mode of Action-Based Predictions of Chemical Carcinogenesis in Rodents. Toicol Mech Meth. Oct. 9, 2008;18:189-206.
Matthews et al., Improved procedure for the determination of rofecoxib in human plasma involving 96-well solid-phase extraction and fluorescence detection. J Chromatog A. 2002;949:83-89.
Midgley et al., Phase III randomized trial assessing rofecoxib in the adjuvant setting of colorectal cancer: final results of the Victor trial. J Clin Oncol. Oct. 20, 2010;28(30):4575-80. doi: 10.1200/JCO.2010.29.6244. Epub Sep. 13, 2010.
Morrison et al., The Optimal Analgesic Dose of Rofecoxib: Overview of Six Randomized Controlled Trials. Clin Pharmacol. JADA Dec. 2000;131:1729-1737.
Muller et al., A rationale for determing, testing, and controlling specific impurities in pharmaceuticals that possess potential for genotoxicity. Regul Toxicol Pharmcol. 2006;44:198-211.
Nicoll-Griffith et al., Synthesis, Characterization, and Activity of Metabolites Derived from the Cyclooxygenase-2 Inhibitor Rofecoxib (MK-0966, Vioxx™). Bioorg Med Chem Lett. 2000;10:2683-2686.
Porras et al., Abstract PII-89: Single and Multiple Dose Pharmacokinetics (PK): of Rofecoxib (R) in Healthy Subjects. Am Soc Clin Pharm Ther. Abstracts of Papers. 2000 Annual Meeting, Clincial Pharamacology & Therapeutics. 2000;67(2):137. 2 pages.
Rabbaa et al., Bioequivalence Study and Pharamcokinetic Evaluation of Two Brands of Rofecoxib 25mg Tablets in a Lebanese Population. J App Res. 2004;4(4):630-634.
Radhakrishna et al., LC determination of rofecoxib in bulk and pharmaceutical formulations. J Pharm Biomed Anal. Nov. 2001;26(4):617-28. doi: 10.1016/s0731-7085(01)00493-9.
Rajendrakumar et al., Comparative Study on Co-Ground Products of Rofecoxib with β-Cyclodextrin and its Sulfobutyl Ether-7 Derivative in Solution and in the Solid State. J Incl Phenom Macro Chem. 2004;49:259-266.
Rattray et al., The Use of Rofecoxib (Vioxx) in the Treatment of Hemophilia. Blood. 2004;104:3097. 6 pages.
Reddy et al., Facile air oxidation of the conjugate base of rofecoxib (Vioxx™), a possible contributor to chronic human toxicity. Tetra Lett. Dec. 25, 2004;46:927-929.
Reddy et al., Isolation and Characterisation of process-related impurities in rofecoxib. J Pharma Biomed Anal. 2002;29:355-360.
Reddy et al., Novel approaches for colon cancer prevention by cyclooxygenase-2 inhibitors. J Environ Pathol Toxicol Oncol. 2002;21(2):155-64.
Sammour et al., Formulation and optimaziation of mouth dissolve tablets containing Rofecoxib solid dispersion. AAPS PharmaSciTech. 2006;Article 55, 7(2):E1-E9. 9 pages.
Sathesh Babu et al., Solubility Enhancement of Cox-II Inhibitors by Cosolvency Approach. Dhaka Univ. J Pharm Sci. Dec. 2008;7(2):119-126.

(56) References Cited

OTHER PUBLICATIONS

Schwartz et al., Abstract 369: Rofecoxib steady-state pharmacokinetics [PK] in moderate hepatic insufficiency patients (HI). Am J Gastroenterol. Sep. 2000:2519. 2 pages.

Schwartz et al., Pharamcokinetic Evaluation of Rofecoxib: Comparison of Tablet and Suspension Formulations. Clin Drug Invest. 2003;23(8):503-509.

Seedher et al., Solubility enhancement of Cox-2 inhibitors using various solvent systems. AAPS PharmSciTech. 2003;4:(3):Article 3. 9 pages.

Sibbald, Rofecoxib (Vioxx) voluntarily withdrawn from market. Synopsis, CMJA. Oct. 26, 2004;171:1027-1028.

Sobera et al., Rofecoxib. Drugs of the Future. 1998;23(12):1287-1296.

Steinbeck et al., The Chemistry Development Kit (CDK): An open-source Java library for chemo- and bioinformatics. J Chem Info and COmp Sci. 2003;43:493-500.

Sutter et al., Use of in silico systems and expert knowledge for structure-based assessment of potentially mutagenic impurities. Regul Toxicol Pharamcol. Article in Press. 2013;67:39-52. doi: 10.1016/j.yrtph.2013.05.001.

Therien et al., Synthesis of Rofecoxib, (MK 0966, Vioxx®, 4(4'-Methylsulfonylphenyl)-3-Phenyl-2(5H)-Furanone), a selective and orally active inhibitor of cyclooxygenase-2. Synthesis (Stuttgart). 2001;12:1778.

Tsoukas et al., Evaluation of the efficacy and safety of etoricoxib in the treatment of hemophilic arthropathy. Blood. Mar. 2006;107(5):1785-1790. Epub Nov. 15, 2005.

US Food and Drug Administration, Vioxx (rofecoxib) Questions and Answers. Retrieved from https://www.fda.gov/drugs/postmarket-drug-safety-information-patients-and-providers/vioxx-rofecoxib-questions-and-answers. Sep. 30, 2004. 3 pages.

Werner et al., Selective and rapid liquid chromatography—mass spectrometry method for the quantification of rofecoxib in pharmacokinetic studies with humans. J Chromatograph B. 2001;760:83-90.

Zeiger et al., Salmonella Mutagenicity Tests: V. Results from teh TEsting of 311 Chemicals. Environ Mol Mutagenesis. 1992;19(Supplement 21):2-141.

* cited by examiner

| Batch F851 | Analytical reference | Tests | Results | Specifications |
|---|---|---|---|---|
| Re-recrystalized RXB-201, Stage 4 Before micronization | CQ18-0560 | Appearance | Conform | *White to off white powder* |
| | | Identification (UPLC) | Conform | *Conform to reference* |
| | | UPLC profile (290nm, %area): | - | - |
| | | Purity | 99.9% | *≥ 99.5%* |
| | | Total impurities | 0.1% | *≤ 0.5%* |
| | | RXB-Furanone, Stage 3 (rrt=4.40) | 0.08% | *≤ 0.15%* |
| | | RXB Sulfoxide (rrt=0.49) | < 0.05% | *Report result* |
| | | Residual solvents (ppm): | - | - |
| | | Acetonitrile | ND | *≤ 410 ppm* |
| | | Methylene chloride | ND | *≤ 600 ppm* |
| | | Isopropanol | 117 ppm | *≤ 5000 ppm* |
| | | Methanol | ND | *≤ 3000 ppm* |
| | | DMSO | 439 ppm | *≤ 5000 ppm* |
| | | Water content (KF, %) | 0.1% | *Report result* |
| | | Sulfated ashes (%) | 0.0% | *≤ 0.1%* |
| | | Polymorphism (XRPD) | Conform | *Conform to reference* |
| | | UPLC assay (%) | 99.1% | *95.0 – 105.0%* |
| | | Particle size distribution (PSD): | - | - |
| | | D10 (μm) | 78.8 μm | *Report result* |
| | | D50 (μm) | 153 μm | *Report result* |
| | | D90 (μm) | 256 μm | *Report result* |

FIG. 2

*Summary of In Silico Mutagenicity Findings*

| Structures | Rule Based | Statistical Based | | | Overall Prediction | Control Class[1] |
|---|---|---|---|---|---|---|
| | DEREK | Model Applier | E.P.A. TEST | Case Ultra | | |
| A-RSM1-00 | N | N | n/a | n/a | N | 5 |
| A-RSM1-01 | N | IND | n/a | N | N | 5 |
| A-RSM1-02 | N | IND | N | INC | N | 5 |
| A-RSM2-00 | N | N | n/a | n/a | N | 5 |
| A-RSM2-01 | N | N | n/a | n/a | N | 5 |
| A-RSM2-02 | N | N | n/a | n/a | N | 5 |
| A-CRM1-00 | N | N | n/a | n/a | N | 5 |
| A-STG1-00 | N | P | N | n/a | N | 4 |
| A-STG1-01 | P | P | n/a | n/a | P | 3 |
| A-STG2-00 | N | N | n/a | n/a | N | 5 |
| A-STG2-01 | P | P | n/a | n/a | P | 3 |
| A-STG3-00 | N | IND | n/a | N | N | 5 |
| A-STG3-01 | N | IND | n/a | INC | N | 5 |
| A-STG4-01 | N | N | n/a | n/a | N | 5 |
| A-STG4-02 | N | N | n/a | n/a | N | 5 |
| A-STG4-03 | N | N | n/a | n/a | N | 5 |

N = negative; P = positive; NID = not in domain; INC = inconclusive; n/a = not applicable; ; * = contains misclassified or unclassified features; [1] Impurities Classification with Respect to Mutagenic and Carcinogenic Potential and Resulting Control Actions (ICH M7(R1), 2018).

FIG. 23

PURIFIED FORMS OF ROFECOXIB, METHODS OF MANUFACTURE AND USE

CROSS-REFERENCE TO RELATED APPLICATIONS

This application is a continuation of U.S. application Ser. No. 16/716,242, filed Dec. 16, 2019, titled PURIFIED FORMS OF ROFECOXIB, METHODS OF MANUFACTURE AND USE, which is a continuation of International PCT Application Number PCT/US19/61178, filed Nov. 13, 2019, titled PURIFIED FORMS OF ROFECOXIB, METHODS OF MANUFACTURE AND USE, which claims priority to U.S. Provisional Application No. 62/770,563, filed Nov. 21, 2018, titled HIGHLY PURE ROFECOXIB, METHODS OF MANUFACTURE AND USE, the contents of which are incorporated herewith in their entirety.

All patents, patent applications and publications cited herein are hereby incorporated by reference in their entirety. The disclosures of these publications in their entireties are hereby incorporated by reference into this application.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Rofecoxib is a selective COX-2 inhibitor, nonsteroidal anti-inflammatory drug (NSAID), that was marketed under the brand name "VIOXX" until it was withdrawn from the market in 2004 over safety concerns. Before being withdrawn from the market, "VIOXX" was approved in the United States for the following indications: signs and symptoms of osteoarthritis (OA); signs and symptoms of rheumatoid arthritis (RA) in adults; signs and symptoms of pauciarticular or polyarticular course Juvenile Rheumatoid Arthritis; management of acute pain in adults; treatment of primary dysmenorrhea; and treatment of migraine attacks with or without aura in adults.

There is a long felt but unmet need in the art for new medications for the treatment of pain, fever, and inflammation. This is especially true with respect to subjects suffering from pain that is co-morbid or associated with diseases or conditions arising from bleeding disorders, including hemophilic arthropathy and von Willebrand's disease. Hemophilia is a bleeding disorder caused by inherited or spontaneous mutations in genes that code for clotting factor. The most common forms of hemophilia are the result of deficiencies in the coagulation factors VIII (hemophilia A) or IX (hemophilia B). The prevalence of subjects with hemophilia (PWH) in the United States is estimated at 20,000 subjects.

Blood-induced joint disease may follow acute joint injury and is associated with hemophilia, with intra-articular bleeding (hemarthrosis) accounting for more than 90% of all serious bleeding events in subjects with severe hemophilia (baseline factor (F)VII or FIX activity <1%). Over time, recurrent bleeding into the same articular joints results in progressive damage and the development of hemophilic arthropathy. Despite advances in treatment and the delivery of comprehensive care at dedicated centers, joint bleeding and arthropathy remain the single largest cause of morbidity in PWH.

Although the pathogenesis of the blood-induced joint injury of hemophilic arthropathy has not been fully elucidated, it appears to have similarities with the degenerative joint damage that occurs in mechanically-induced joint injury such as OA and the inflammatory processes associated with RA.

Arthritis as a result of hemophilia is the most common comorbidity in adult PWH, with 44-55% of subjects reporting suffering from hemophilic arthropathy. Pain/discomfort is the most frequently reported limitation for PWH, with 75% of PWH reporting this limitation. Eighty-nine percent of PWH reported that pain had interfered with their daily life in the past 4 weeks, and 50% reported suffering from constant pain.

In additional to its impact on quality of life, hemophilic arthropathy has a significant impact on the cost associated with the treatment of hemophilia. As acute pain associated with hemarthrosis and chronic pain associated with arthritis are largely indistinguishable for PWH, significant over-utilization of factor replacement to address pain symptoms have been reported and 58% of PWH report using factor replacement to treat chronic pain. In addition to being medically ineffective, this misutilization has significant economic implications, as factor replacement is one of the costliest known drug interventions.

Currently, management of the pain and inflammation associated with hemophilic arthropathy is difficult, due to a lack of approved treatments and limitations to existing off-label options. Acetaminophen is generally recommended as first-line therapy, however, it is of limited utility owing to its lack of anti-inflammatory effect and increased risk of hepatic adverse events in a subject population with a significant rate of comorbid chronic hepatitis C.

Opioids can be used to alleviate pain associated with hemophilic arthropathy, but also have little anti-inflammatory effect and long-term use of this mode of analgesic therapy may lead to tachyphylaxis, dependence, and the potential for abuse. Additionally, a 2010 observational study by Solomon et al. demonstrated that long-term chronic use of opioids to treat arthritis in the general population resulted in increased risk of (cardiovascular) CV events, fractures, hospitalization, and all-cause mortality relative to non-selective NSAIDs or a combined group of therapeutic and supra-therapeutic doses of COX-2 selective NSAIDs.

Due to their effect on platelet function, NSAIDs, particularly acetylsalicylic acid (ASA), are not recommended in PWH. In addition, even otherwise trivial NSAID-induced ulcerations might be expected to result in more severe or prolonged bleeding in the setting of an underlying coagulopathy, and it has been demonstrated that NSAIDs are associated with an increased risk of upper gastrointestinal (UGI) complications, including ulcers, bleeding and perforations, in PWH. Thus, there is a long felt but unmet need in the art for medications to treat pain in PWH.

Von Willebrand Disease (vWD) is a genetic disorder caused by defective von Willebrand factor, a clotting protein vWD is the most common form of bleeding disorder, affecting ~1% of US population, though mild cases are often undiagnosed. Generally mild and characterized by heavy mucosal bleeding, more severe forms can manifest into significant broad-ranging internal bleeding. Evidence suggests that vWD subjects are more susceptible to migraine headaches. Due to risk of exacerbating hemorrhaging, NSAIDs are not recommended for pain management in subjects with vWD.

Juvenile idiopathic arthritis, including systemic juvenile idiopathic arthritis (SJIA) is one of several rheumatic diseases that affect children. SJIA affects the entire body, including the joints. SJIA typically occurs in flares with some subjects having healthy periods between flares. Diagnosis may be delayed by these ups and downs over the course of the disease. SJIA is generally easier to diagnose during a flare. The most common symptoms of SJIA are recurrent bouts of fever with high daily temperature spikes, skin rash, and painful, stiff joints.

SUMMARY OF THE INVENTION

In certain aspects, the subject matter disclosed herein provides a pharmaceutical composition comprising highly pure rofecoxib or a pharmaceutically acceptable salt thereof and a pharmaceutically acceptable carrier.

In some embodiments, the highly pure rofecoxib comprises less than about 0.10%, about 0.075%, about 0.05%, about 0.025%, about 0.02%, about 0.01%, or about 0.001% total impurities. In some embodiments, the highly pure rofecoxib is essentially free of, or free of, 4-[4-(methylsulfonyl)phenyl]-3-phenyl-2,5-furandione. In some embodiments, the highly pure rofecoxib comprises less than about 0.10%, about 0.05%, about 0.02%, or about 0.01% of 4-[4-(methylthio)phenyl]-3-phenyl-2(5H)-furanone. In some embodiments, the highly pure rofecoxib comprises less than about 0.10%, about 0.05%, about 0.02%, or about 0.01% of 4-[4-(methylsulfinyl)phenyl]-3-phenyl-2(5H)-furanone.

In certain aspects, the subject matter disclosed herein provides a pharmaceutical composition comprising substantially pure rofecoxib or an acceptable salt thereof and a pharmaceutically acceptable carrier.

In some embodiments, the substantially pure rofecoxib comprises less than about 0.40%, about 0.30%, about 0.25%, about 0.20%, or about 0.15% total impurities. In some embodiments, the substantially pure rofecoxib is substantially free of 4-[4-(methylsulfonyl)phenyl]-3-phenyl-2,5-furandione. In some embodiments, the substantially pure rofecoxib comprises less than about 0.25%, about 0.20%, or about 0.15% of 4-[4-(methylthio)phenyl]-3-phenyl-2(5H)-furanone. In some embodiments, the substantially pure rofecoxib comprises less than about 0.25%, about 0.20%, or about 0.15% of 4-[4-(methylsulfinyl)phenyl]-3-phenyl-2(5H)-furanone.

In some embodiments, the highly pure rofecoxib comprises less than about 0.10%, about 0.05%, about 0.02%, about 0.01%, or is free of 4-[4-(methylsulfonyl)phenyl]-3-phenyl-5-hydroxyfuran-2-one. In some embodiments, the highly pure rofecoxib comprises less than about 0.10%, about 0.05%, about 0.02%, about 0.01%, or is free of 4-[4-(methylsulfonyl)phenyl]-3-phenyl-2,5-furandione.

In certain aspects, the subject matter disclosed herein provides a method of treating pain, fever, or inflammation in a subject in need thereof, the method comprising administering to the subject a pharmaceutical composition comprising an effective amount of highly pure rofecoxib and a pharmaceutically acceptable carrier.

In some embodiments, the pain, fever, or inflammation is caused by one or more conditions selected from the group comprising of hemophilic arthropathy, osteoarthritis, rheumatoid arthritis, pauciarticular or polyarticular course Juvenile Rheumatoid Arthritis (JRA), juvenile idiopathic arthritis, acute pain, primary dysmenorrhea, migraine attacks, or migraine associated with von Willebrand disease. In other embodiments, the pain or inflammation is caused by psoriatic arthritis or fibromyalgia.

In certain aspects, the subject matter disclosed herein provides a method of treating pain, fever, or inflammation in a subject in need thereof, the method comprising administering to the subject a pharmaceutical composition comprising an effective amount of substantially pure rofecoxib and a pharmaceutically acceptable carrier.

In some embodiments, the pain, fever, or inflammation is caused by one or more conditions selected from the group comprising of hemophilic arthropathy, osteoarthritis, rheumatoid arthritis, pauciarticular or polyarticular course Juvenile Rheumatoid Arthritis (JRA), juvenile idiopathic arthritis, acute pain, primary dysmenorrhea, migraine attacks, or migraine associated with von Willebrand disease. In other embodiments, the pain or inflammation is caused by psoriatic arthritis or fibromyalgia.

In certain aspects, the subject matter disclosed herein provides a method of treating pain or migraine associated with a condition caused by a bleeding disorder in a subject in need thereof, the method comprising administering to the subject a pharmaceutical composition comprising an effective amount of highly pure rofecoxib and a pharmaceutically acceptable carrier.

In certain aspects, the subject matter disclosed herein provides a method of treating pain or migraine associated with a condition caused by a bleeding disorder in a subject in need thereof, the method comprising administering to the subject a pharmaceutical composition comprising an effective amount of substantially pure rofecoxib and a pharmaceutically acceptable carrier.

In some embodiments, the subject is age 2 or older. In some embodiments, the subject is 12 years old to 75 years old. In some embodiments, the subject does not have a history or current symptoms of cardiovascular disease. In some embodiments, the subject does not have a history or current symptoms of gastrointestinal bleeding, ulceration, or perforation. In some embodiments, the pharmaceutical composition is administered once daily. In some embodiments, the pharmaceutical composition is administered two times or more daily. In some embodiments, the condition is caused by a bleeding disorder. In some embodiments, the bleeding disorder is hemophilia A or B, C von Willebrand Disease, or a drug-induced bleeding disorder. In some embodiments, the condition is hemophilic arthropathy, juvenile idiopathic arthritis, or migraine associated with von Willebrand disease.

In some embodiments, the treatment is effective at treating pain without co-administration of an analgesic. In some embodiments, the treatment results in a subject decreasing or discontinuing use of analgesics or rescue medications during the treatment as compared to before initiation of the treatment. In some embodiments, the treatment results in a subject decreasing or discontinuing use of opioid medications during the treatment.

In some embodiments, the method further includes administering a gastro-protective agent. In some embodiments, the gastro-protective agent is co-administered with the pharmaceutical composition. In some embodiments, the treatment does not include administering gastro-protective agent.

In some embodiments, the treatment achieves a reduction of at least 1 from baseline in a Pain Intensity Numerical Rating Scale. In some embodiments, the treatment achieves a reduction of at least 2 from baseline in a Pain Intensity Numerical Rating Scale. In some embodiments, the treatment achieves a reduction of at least 3 from baseline in a Pain Intensity Numerical Rating Scale. In some embodiments, the treatment achieves a reduction of at least 4 from baseline in a Pain Intensity Numerical Rating Scale. In some embodiments, the treatment achieves a reduction of at least 5 from baseline in a Pain Intensity Numerical Rating Scale.

In some embodiments, the reduction in the Pain Intensity Numerical Rating Scale is achieved within 1, 2, 3, 4, 5, 6 days, 1 week, or 2 weeks of administering the pharmaceutical composition.

In some embodiments, the effective amount of the rofecoxib administered to a subject is 12.5 mg. In some embodiments, the effective amount of the rofecoxib administered to a subject is 17.5 mg. In some embodiments, the effective amount of the rofecoxib administered to a subject is 20 mg. In some embodiments, the effective amount of the rofecoxib administered to a subject is 25 mg.

In some embodiments, the effective amount of the rofecoxib administered to a subject is selected from the group comprising of 1 mg, 2 mg, 3 mg, 5 mg, 6.25 mg, 7.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22.5 mg, 25 mg, 30 mg, 35 mg, 40 mg, 45 mg, 50 mg, 55 mg, 60 mg, 65 mg, and 70 mg. In some embodiments, the effective amount of the rofecoxib administered to a subject is selected from the group comprising of 0.10 mg/kg, 0.15 mg/kg, 0.20 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, or 0.70 mg/kg.

In certain aspects, the subject matter disclosed herein provides a method of treating pain associated with a condition caused by a bleeding disorder in a subject in need thereof, the method comprising administering once daily to the subject a pharmaceutical composition comprising 12.5 mg of substantially pure rofecoxib or 12.5 mg of highly pure rofecoxib as a sole active ingredient, wherein the treatment achieves a reduction of at least 1 from baseline in a Pain Intensity Numerical Rating Scale.

In certain aspects, the subject matter disclosed herein provides a method of treating pain associated with a condition caused by a bleeding disorder in a subject in need thereof, the method comprising administering once daily to the subject a pharmaceutical composition comprising 17.5 mg of substantially pure rofecoxib or 17.5 mg of highly pure rofecoxib as a sole active ingredient, wherein the treatment achieves a reduction of at least 1 from baseline in a Pain Intensity Numerical Rating Scale.

In certain aspects, the subject matter disclosed herein provides a method of treating pain associated with a condition caused by a bleeding disorder in a subject in need thereof, the method comprising administering once daily to the subject a pharmaceutical composition comprising 20 mg of substantially pure rofecoxib or 20 mg of highly pure rofecoxib as a sole active ingredient, wherein the treatment achieves a reduction of at least 1 from baseline in a Pain Intensity Numerical Rating Scale.

In some embodiments, the pharmaceutical composition achieves a reduction in a Pain Intensity Numerical Rating Scale that is equal to or greater than the once daily administration of a pharmaceutical composition comprising 25 mg of rofecoxib that is not highly pure. In some embodiments, the condition is hemophilic arthropathy.

In certain aspects, the subject matter disclosed herein provides a method of treating pain associated with hemophilic arthropathy in a subject in need thereof, wherein the subject is 12 years old or older, the method comprising administering once daily a pharmaceutical composition comprising 12.5 mg of substantially pure rofecoxib or 12.5 mg of highly pure rofecoxib, wherein the treatment achieves a reduction of at least 1 from baseline in a Pain Intensity Numerical Rating Scale.

In certain aspects, the subject matter disclosed herein provides a method of treating pain associated with hemophilic arthropathy in a subject in need thereof, wherein the subject is 12 years old or older, the method comprising administering once daily a pharmaceutical composition comprising 17.5 mg of substantially pure rofecoxib or 17.5 mg of highly pure rofecoxib, wherein the treatment achieves a reduction of at least 1 from baseline in a Pain Intensity Numerical Rating Scale.

In certain aspects, the subject matter disclosed herein provides a method of treating pain associated with hemophilic arthropathy in a subject in need thereof, wherein the subject is 12 years old or older, the method comprising administering once daily a pharmaceutical composition comprising 20 mg of substantially pure rofecoxib or 20 mg of highly pure rofecoxib, wherein the treatment achieves a reduction of at least 1 from baseline in a Pain Intensity Numerical Rating Scale.

In certain aspects, the subject matter disclosed herein provides a method of treating pain associated with a condition caused by a bleeding disorder in a subject in need thereof, the method comprising: determining whether the subject has a history or current symptoms of cardiovascular disease; administering once daily to the subject a pharmaceutical composition comprising at least 12.5 mg substantially pure rofecoxib if it is determined that the subject does not have a history or current symptoms of cardiovascular disease, wherein the treatment achieves a reduction of at least 1 from baseline in a Pain Intensity Numerical Rating Scale within 1 week of first administering the pharmaceutical composition to the subject.

In some embodiments, the pharmaceutical composition comprises 1 mg, 2 mg, 3 mg, 5 mg, 6.25 mg, 7.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 20 mg, 20.5 mg, 21 mg, 21.5 mg, 22.5 mg, 25 mg, 30 mg, 35 mg, 40 mg, 45 mg, 50 mg, 55 mg, 60 mg, 65 mg, or 70 mg of substantially pure rofecoxib.

In certain aspects, the subject matter disclosed herein provides a method of treating pain in a subject in need thereof, the method comprising administering to the subject a pharmaceutical composition comprising an effective amount of highly pure rofecoxib, wherein the treatment achieves a greater reduction in Pain Intensity Numerical Rating Scale compared to the administering of the same amount of a pharmaceutical composition comprising rofecoxib that is not highly pure.

In some embodiments, the pain is caused by one or more conditions selected from the group comprising of hemophilic arthropathy, osteoarthritis, rheumatoid arthritis, pauciarticular or polyarticular course Juvenile Rheumatoid Arthritis (JRA), juvenile idiopathic arthritis, including systemic juvenile idiopathic arthritis, acute pain, primary dysmenorrhea, migraine attacks, or migraine associated with von Willebrand disease. In other embodiments, the pain is caused by psoriatic arthritis or fibromyalgia.

In certain aspects, the subject matter disclosed herein provides a method of treating pain, fever, or inflammation in a subject in need thereof, the method comprising administering to the subject a pharmaceutical composition comprising an effective amount of highly pure rofecoxib, wherein the treatment results in fewer side effects compared to administering the same amount of a pharmaceutical composition comprising of rofecoxib that is not highly pure. In some embodiments, the pain, fever, or inflammation is caused by one or more conditions selected from the group comprising of hemophilic arthropathy, osteoarthritis, rheumatoid arthritis, pauciarticular or polyarticular course Juvenile Rheumatoid Arthritis (JRA), juvenile idiopathic arthritis, acute pain, primary dysmenorrhea, migraine attacks, or migraine associated with von Willebrand disease. In other embodiments, the pain or inflammation is caused by psoriatic arthritis or fibromyalgia.

In certain aspects, the subject matter disclosed herein provides a method of treating pain, fever or inflammation caused by one or more conditions, the method comprising administering to a subject in need thereof a pharmaceutical composition comprising an effective amount of substantially pure rofecoxib and a pharmaceutically acceptable carrier or highly pure rofecoxib and a pharmaceutically acceptable carrier wherein the treatment results in a reduction in pain, fever, or inflammation, further wherein the treatment results in reduction of effects associated with administration of rofecoxib that is not highly pure.

In some embodiments, the one or more conditions is selected from the group comprising of hemophilic arthropathy, osteoarthritis, rheumatoid arthritis, pauciarticular or polyarticular course Juvenile Rheumatoid Arthritis (JRA), acute pain, primary dysmenorrhea, migraine attacks, or migraine associated with von Willebrand disease. In other embodiments, the one or more conditions is psoriatic arthritis or fibromyalgia.

In certain aspects, the subject matter disclosed herein provides a method of manufacturing substantially pure rofecoxib or highly pure rofecoxib as set forth in FIG. 1, the method comprising the steps of: bromination of 4'-(methylthio)acetophenone (RSM1) in the presence of TBABr$_3$ to obtain an intermediate RXB-Bromocetone product at stage 1; involving the intermediate product with Phenylacetic acid (RSM2) in a nucleophilic substitution reaction in the presence of sodium hydroxide to obtain a RXB-Phenylacetate product at stage 2; crystallizing the product of stage 2 in isopropanol and achieving filterable crystals; intramolecularly cyclizing of the product of stage 2 at 70° C. in DMSO in presence of diisopropylamine; converting 4-[4-(methylthio)phenyl]-3-phenyl-2(5H)-furanone to highly pure rofecoxib or substantially pure rofecoxib by use of hydrogen peroxide with a catalytic amount of dihydrate sodium tungsten in acetonitrile; and recrystallizing the rofecoxib in a mixture of DMSO and water.

In certain aspects, the subject matter disclosed herein provides a pharmaceutical composition comprising rofecoxib comprising less than 0.05% of 4-[4-(methylsulfonyl) phenyl]-3-phenyl-2,5-furandione and a pharmaceutically acceptable carrier.

In certain aspects, the subject matter disclosed herein provides a pharmaceutical composition comprising highly pure, or substantially pure, rofecoxib having at least one impurity that is a prodrug of rofecoxib and a pharmaceutically acceptable carrier.

In some embodiments, the rofecoxib is essentially free of, or free of, 4-[4-(methylsulfonyl)phenyl]-3-phenyl-5-hydroxyfuran-2-one and/or 4-[4-(methylsulfonyl)phenyl]-3-phenyl-2,5-furandione. In some embodiments, the rofecoxib comprises less than 0.02% 4-[4-(methylsulfonyl)phenyl]-3-phenyl-5-hydroxyfuran-2-one and/or 4-[4-(methylsulfonyl) phenyl]-3-phenyl-2,5-furandione.

In certain aspects, the subject matter disclosed herein provides a method for treating pain, fever, or inflammation in a subject, the method comprising administering to the subject a pharmaceutical composition comprising an effective amount of rofecoxib comprising less than 0.05% 4-[4-(methylsulfonyl)phenyl]-3-phenyl-2,5-furandione and a pharmaceutically acceptable carrier, wherein the subject is within a subject population having a reduced risk of a serious cardiovascular thrombotic event.

In some embodiments, the effective amount of rofecoxib is 12.5 mg. In some embodiments, the effective amount of rofecoxib is 17.5 mg. In some embodiments, the effective amount of rofecoxib is 20 mg. In some embodiments, the rofecoxib comprises less than 0.02% 4-[4-(methylsulfonyl) phenyl]-3-phenyl-2,5-furandione.

In certain aspects, the subject matter disclosed herein provides a method for treating pain, fever, or inflammation in a subject, while reducing one or more side effects associated with the administration of 4-[4-(methylsulfonyl) phenyl]-3-phenyl-2,5-furandione, comprising administering to the subject a pharmaceutical composition comprising an effective amount of rofecoxib comprising less than 0.05% of 4-[4-(methylsulfonyl)phenyl]-3-phenyl-2,5-furandione and a pharmaceutically acceptable carrier.

In some embodiments, the effective amount of rofecoxib is 12.5 mg. In some embodiments, the effective amount of rofecoxib is 17.5 mg. In some embodiments, the effective amount of rofecoxib is 20 mg. In some embodiments, the rofecoxib comprises less than 0.05% 4-[4-(methylsulfonyl) phenyl]-3-phenyl-2,5-furandione.

In certain aspects, the subject matter disclosed herein provides a pharmaceutical composition comprising 12.5 mg highly pure rofecoxib or an acceptable salt thereof and a pharmaceutically acceptable carrier.

In certain aspects, the subject matter disclosed herein provides a pharmaceutical composition comprising 17.5 mg highly pure rofecoxib or an acceptable salt thereof and a pharmaceutically acceptable carrier.

In certain aspects, the subject matter disclosed herein provides a pharmaceutical composition comprising 20 mg highly pure rofecoxib or an acceptable salt thereof and a pharmaceutically acceptable carrier.

In certain aspects, the subject matter disclosed herein provides a pharmaceutical composition comprising 12.5 mg substantially pure rofecoxib or an acceptable salt thereof and a pharmaceutically acceptable carrier.

In certain aspects, the subject matter disclosed herein provides a pharmaceutical composition comprising 17.5 mg substantially pure rofecoxib or an acceptable salt thereof and a pharmaceutically acceptable carrier.

In certain aspects, the subject matter disclosed herein provides a pharmaceutical composition comprising 20 mg substantially pure rofecoxib or an acceptable salt thereof and a pharmaceutically acceptable carrier.

In certain aspects, the subject matter disclosed herein provides a method of treating pain, fever, or inflammation in a subject in need thereof, the method comprising administering an effective amount of highly pure rofecoxib.

In some embodiments, the effective amount of highly pure rofecoxib is 12.5 mg. In some embodiments, the effective amount of highly pure rofecoxib is 17.5 mg. In some embodiments, the effective amount of highly pure rofecoxib is 20 mg.

In certain aspects, the subject matter disclosed herein provides a method of treating pain, fever, or inflammation in a subject in need thereof, the method comprising administering an effective amount of substantially pure rofecoxib.

In some embodiments, the effective amount of substantially pure rofecoxib is 12.5 mg. In some embodiments, the effective amount of substantially pure rofecoxib is 17.5 mg. In some embodiments, the effective amount of substantially pure rofecoxib is 20 mg.

In certain aspects, the subject matter disclosed herein provides a pharmaceutical composition comprising an effective amount of rofecoxib having less than 0.10%, 0.05%, 0.02%, or 0.01% 4-[4-(methylsulfonyl)phenyl]-3-phenyl-2, 5-furandione, and a pharmaceutically acceptable carrier.

In some embodiments, the effective amount of rofecoxib is 17.5 mg. In some embodiments, the effective amount of rofecoxib is 20 mg.

In certain aspects, the subject matter disclosed herein provides a pharmaceutical composition comprising an effective amount of rofecoxib having less than 0.10%, 0.05%, 0.02%, or 0.01% 4-[4-(methylsulfonyl)phenyl]-3-phenyl-5-hydroxyfuran-2-one, and a pharmaceutically acceptable carrier.

In some embodiments, the effective amount is 10 mg. In some embodiments, the effective amount is 12.5 mg. In some embodiments, the effective amount of rofecoxib is 17.5 mg. In some embodiments, the effective amount of rofecoxib is 20 mg. In some embodiments, the effective amount of rofecoxib is 25 mg.

BRIEF DESCRIPTION OF FIGURES

FIG. 2 shows that after a recrystallization step rofecoxib is about 99.9% pure, with about 0.1% or less total impurities. Rofecoxib prepared according to the subject matter described herein is also known by the compound identifier TRM-201 or RXB-201.

FIG. 5A shows the 600 MHz $^1$H-NMR spectrum of rofecoxib in DMSO-$d_6$.

FIG. 5B shows the expanded 600 MHz $^1$H-NMR spectrum of rofecoxib in DMSO-$d_6$. FIG. 5C shows the 125 MHz $^{13}$C-NMR spectrum of rofecoxib in DMSO-$d_6$. FIG. 5D shows the expanded 125 MHz $^{13}$C-NMR spectrum of rofecoxib in DMSO-$d_6$.

FIG. 6A shows the H-H COSY NMR spectrum of rofecoxib in DMSO-$d_6$. FIG. 6B shows the HSQC multiplicity edited NMR Spectrum of rofecoxib in DMSO-$d_6$. FIG. 6C shows the HMBC NMR spectrum of rofecoxib in DMSO-$d_6$.

FIG. 10A shows differential scanning calorimetry (DSC) analysis of rofecoxib. FIG. 10B shows a thermogravimetric analysis (TGA) of rofecoxib.

FIG. 15A shows 4-[4-(methylthio)phenyl]-3-phenyl-2(5H)-furanone oxidation follow-up for CHG P059-074. FIG. 15B shows 4-[4-(methylthio)phenyl]-3-phenyl-2(5H)-furanone oxidation follow-up for CHG P059-078.

FIG. 23 shows a summary of in silico mutagenicity findings.

DETAILED DESCRIPTION

Definitions

Figure 1:
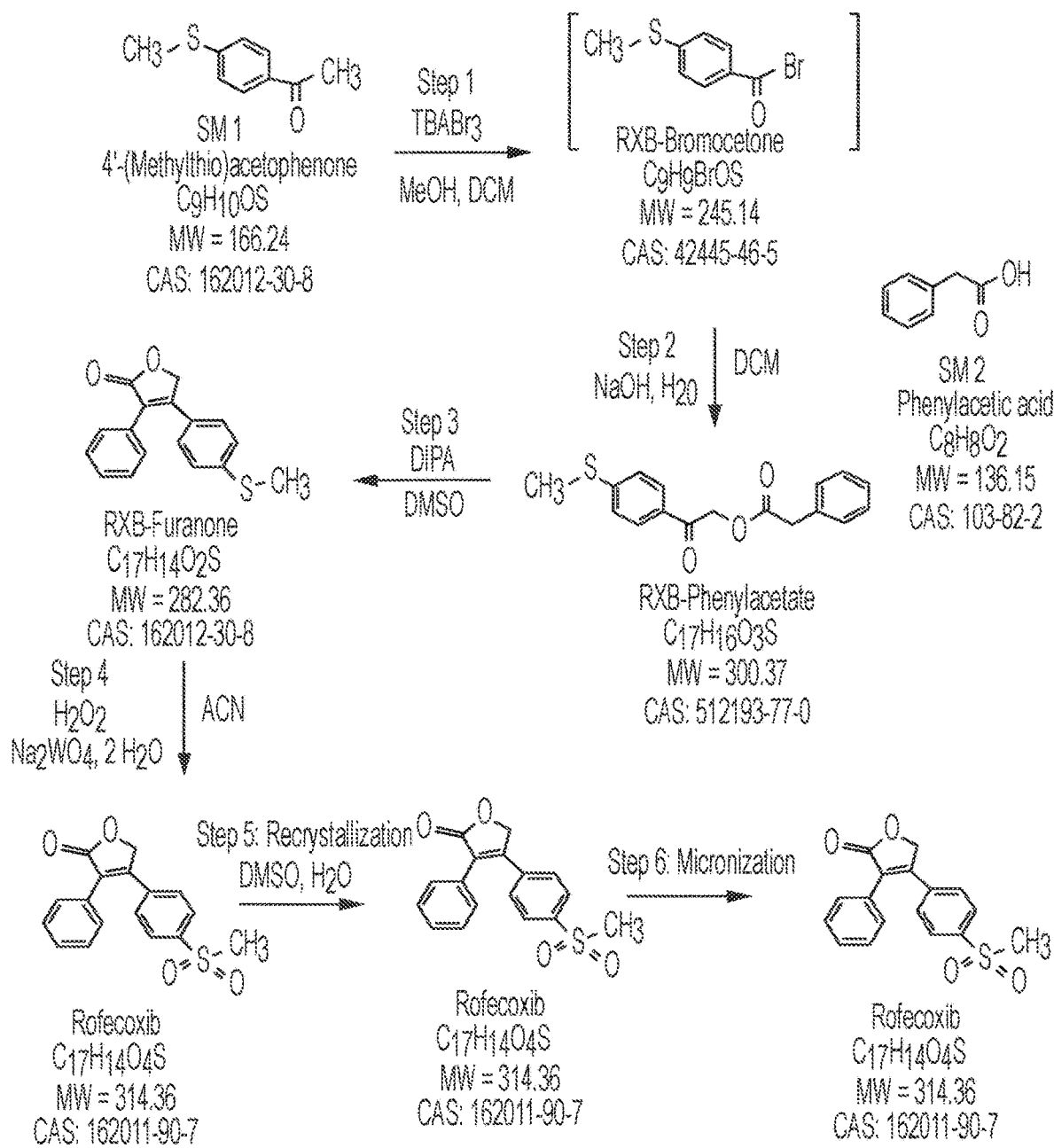
FIG. 1 shows a flow diagram for rofecoxib manufacturing process $A_1$, which avoids production of one or more of the impurities found in previously available rofecoxib bulk drug product: 4-[4-(methylsulfonyl)phenyl]-3-phenyl-5-hydroxyfuran-2-one; and 4-[4-(methylsulfonyl)phenyl]-3-phenyl-2,5-furandione.

The following are definitions of terms used in the present specification. The initial definition provided for a group or term herein applies to that group or term throughout the present specification individually or as part of another group, unless otherwise indicated. Unless otherwise defined, all technical and scientific terms used herein have the same meaning as commonly understood by one of ordinary skill in the art.

As used herein, "rofecoxib" refers to the active ingredient 4-[4-(methylsulfonyl)phenyl]-3-phenyl-2(5H)-furanone or a pharmaceutically acceptable salt or solvate thereof. Rofecoxib, and a method of manufacturing rofecoxib, are described in U.S. Pat. No. 5,474,995, which is incorporated herein by reference in its entirety. The rofecoxib as provided herein is produced consistent with and according to GMP requirements and is suitable for use in humans. The rofecoxib as described herein may be in amorphous or crystalline form.

The purity of rofecoxib resulting from the manufacturing process as described herein is determined as a percent (%)

area basis, typically as quantified by analytical chromatography, such as using HPLC, UHPLC or UPLC.

In some embodiments, the highly pure rofecoxib, resulting from the manufacturing process as described herein, comprises less than or equal to about 0.10%, 0.075%, 0.050%, 0.025%, 0.020%, or 0.001% area basis total impurities. In some embodiments, the highly pure rofecoxib is essentially free of, or free of, 4-[4-(methylsulfonyl)phenyl]-3-phenyl-2,5-furandione. In some embodiments, the highly pure rofecoxib is essentially free of, or free of, 4-[4-(methylsulfonyl)phenyl]-3-phenyl-5-hydroxyfuran-2-one. In some embodiments, the highly pure rofecoxib comprises less than or equal to about 0.10%, 0.05%, 0.02%, or 0.01% area basis of 4-[4-(methylthio)phenyl]-3-phenyl-2(5H)-furanone. In some embodiments, the highly pure rofecoxib comprises less than or equal to about 0.10%, 0.05%, 0.02%, or 0.01% area basis of 4-[4-(methylsulfinyl)phenyl]-3-phenyl-2(5H)-furanone.

As used herein, "co-administration" means the administration of two agents (e.g. concomitantly or sequentially) in any manner in which the pharmacological effects of both are manifest in the subject at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

As used herein, "essentially free" means, with respect to an impurity, having less than about 0.10% area basis of the impurity.

As used herein, "free of" means, with respect to an impurity having an amount of the impurity that is below the limitation of detection i.e. less than 0.02% area basis of the impurity.

As used herein, "highly pure" means, with respect to an active ingredient, having less than or equal to about 0.10% area basis total impurities.

As used herein, "substantially free" means, with respect to an impurity, having less than or equal to about 0.50% area basis of the impurity.

As used herein, "substantially pure" means, with respect to an active ingredient, having less than or equal to about 0.50% area basis total impurities.

As used herein, "limit of detection" means, with respect to an impurity, having at least 0.02% area basis of the impurity.

Prodrugs and solvates of the compounds of the present subject matter are also contemplated herein. The term "prodrug" as employed herein denotes a compound that, upon administration to a subject, undergoes chemical conversion by metabolic or chemical processes to yield a compound of the present subject matter, or a salt and/or solvate thereof. Solvates of the compounds of the present subject matter include, for example, hydrates.

As used herein, "effective amount" refers to any amount that is necessary or sufficient for achieving or promoting a desired outcome. In some instances, an effective amount is a therapeutically effective amount. A therapeutically effective amount is any amount that is necessary or sufficient for promoting or achieving a desired biological response in a subject. The effective amount for any particular application can vary depending on such factors as the disease or condition being treated, the particular agent being administered, the size of the subject, or the severity of the disease or condition. One of ordinary skill in the art can empirically determine the effective amount of a particular agent without necessitating undue experimentation.

As used herein, the term "subject" refers to a vertebrate animal. In one embodiment, the subject is a mammal or a mammalian species. In one embodiment, the subject is a human. In other embodiments, the subject is a non-human vertebrate animal, including, without limitation, non-human primates, laboratory animals, livestock, racehorses, domesticated animals, and non-domesticated animals.

As used herein, the term "patient" refers to a human or animal.

The term "mammal" includes, but is not limited to, a human, mouse, rat, guinea pig, dog, cat, horse, cow, pig, or non-human primate, such as a monkey, chimpanzee, baboon or rhesus. In one embodiment, the mammal is a human.

As used herein, "gastro-protective agent" includes, but is not limited to, an antacid therapy, a proton pump inhibitor, a H2 receptor antagonist, or misoprostol.

As used herein, "bleeding disorder" includes, but is not limited to, hemophilia A (factor VIII deficiency), hemophilia B (factor IX deficiency), von Willebrand disease, rare factor deficiencies including I, II, V, VII, X, XI, XII and XIII, and drug-induced bleeding disorders.

Compositions of the Present Subject Matter

Rofecoxib (also known as 4-[4-(methylsulfonyl)phenyl]-3-phenyl-2(5H)-furanone) is a nonsteroidal anti-inflammatory drug that exhibits anti-inflammatory, analgesic, and antipyretic activities. Without being bound by theory, the mechanism of action of rofecoxib is believed to be due to inhibition of prostaglandin synthesis, via inhibition of cyclooxygenase-2 (COX-2). Additionally, at therapeutic concentrations in humans, rofecoxib does not inhibit the cyclooxygenase-1 (COX-1) isoenzyme. The chemical structure of rofecoxib is shown below. Rofecoxib bears no chiral centers and has a molecular weight of 314.355 g $\text{mol}^{-1}$.

Chemical Structure of Rofecoxib

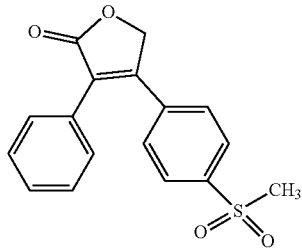

Despite being withdrawn from the market many years ago, and considered unsafe for human use, a surprising discovery shows that rofecoxib is safe to treat a number of conditions and diseases. For example, there is a long felt but unmet need for new, non-opioid based pain medications for subjects suffering from pain that is co-morbid or associated with diseases or conditions arising from bleeding disorders, including but not limited to hemophilic arthropathy and von Willebrand's disease.

In addition to discovering that rofecoxib may be used to safely treat a number of diseases, it has been surprisingly discovered that the safety and efficacy profile of rofecoxib may be enhanced by administering a pharmaceutical composition comprising rofecoxib as described herein that is substantially pure or highly pure, or essentially free or free of one or more impurities found in previously available rofecoxib drug product.

Prior methods of manufacturing rofecoxib produced rofecoxib drug substance containing certain impurities, some of which have been linked to the safety concerns that prompted the withdrawal of the previously available "VIOXX" product from the market in 2004. Without being bound by theory, oxidation of the conjugate base of rofecoxib is one process thought to introduce impurities, which upon entry into a subject's system may survive long enough to react with nucleophilic groups of biomolecules, tissues and amino groups. Therefore, it is thought that these impurities may lead to a low-level chronic toxicity that is cumulative and dangerous over periods of many months. It is thought that for this reason the cardiotoxicity of VIOXX was not readily observed during short-term (one year or less) studies. The impurities thought to result from oxidation of rofecoxib include 4-[4-(methylsulfonyl)phenyl]-3-phenyl-5-hydroxyfuran-2-one and 4-[4-(methylsulfonyl)phenyl]-3-phenyl-2,5-furandione. See Reddy et al., Facile air oxidation of the conjugate base of rofecoxib (Vioxx), a possible contributor to chronic human toxicity, Tetrahedron Lett 46: 927-929 (2005).

The novel manufacturing process described herein surprisingly produces high yields of substantially pure or highly pure rofecoxib, or rofecoxib essentially free or free of those undesirable impurities. As further described herein, it was also surprisingly discovered that this novel manufacturing process produces one or more prodrugs of rofecoxib having beneficial therapeutic properties.

In certain aspects, the subject matter disclosed herein provides a pharmaceutical composition comprising highly pure rofecoxib or a pharmaceutically acceptable salt thereof and a pharmaceutically acceptable carrier.

In some embodiments, the highly pure rofecoxib comprises less than about 0.10%, about 0.075%, about 0.05%, about 0.025%, about 0.02%, about 0.01, or about 0.001% total impurities. In some embodiments, the highly pure rofecoxib is essentially free of, or free of, 4-[4-(methylsulfonyl)phenyl]-3-phenyl-2,5-furandione. In some embodiments, the highly pure rofecoxib comprises less than about 0.10%, about 0.05%, about 0.02%, or about 0.01% of 4-[4-(methylthio)phenyl]-3-phenyl-2(5H)-furanone. In some embodiments, the highly pure rofecoxib comprises less than about 0.10%, about 0.05%, about 0.02%, or about 0.01% of 4-[4-(methylsulfinyl)phenyl]-3-phenyl-2(5H)-furanone.

In certain aspects, the subject matter disclosed herein provides a pharmaceutical composition comprising substantially pure rofecoxib or an acceptable salt thereof and a pharmaceutically acceptable carrier.

In some embodiments, the substantially pure rofecoxib comprises less than about 0.40%, about 0.30%, about 0.25%, about 0.20%, or about 0.15% total impurities. In some embodiments, the substantially pure rofecoxib is substantially free of 4-[4-(methylsulfonyl)phenyl]-3-phenyl-2,5-furandione. In some embodiments, the substantially pure rofecoxib comprises less than about 0.25%, about 0.20%, or about 0.15% of 4-[4-(methylthio)phenyl]-3-phenyl-2(5H)-furanone. In some embodiments, the substantially pure rofecoxib comprises less than about 0.25%, about 0.20%, or about 0.15% of 4-[4-(methylsulfinyl)phenyl]-3-phenyl-2(5H)-furanone.

In some embodiments, the highly pure rofecoxib comprises less than about 0.10%, about 0.05%, about 0.02%, about 0.01%, or is free of 4-[4-(methylsulfonyl)phenyl]-3-phenyl-5-hydroxyfuran-2-one. In some embodiments, the highly pure rofecoxib comprises less than about 0.10%, about 0.05%, about 0.02%, about 0.01%, or is free of 4-[4-(methylsulfonyl)phenyl]-3-phenyl-2,5-furandione.

In certain aspects, the subject matter disclosed herein provides a method of treating pain, fever, or inflammation in a subject in need thereof, the method comprising administering to the subject a pharmaceutical composition comprising an effective amount of highly pure rofecoxib and a pharmaceutically acceptable carrier.

In some embodiments, the pain, fever, or inflammation is caused by one or more conditions selected from the group comprising of hemophilic arthropathy, osteoarthritis, rheumatoid arthritis, pauciarticular or polyarticular course Juvenile Rheumatoid Arthritis (JRA), juvenile idiopathic arthritis, acute pain, primary dysmenorrhea, migraine attacks, or migraine associated with von Willebrand disease. In other embodiments, the pain or inflammation is caused by psoriatic arthritis or fibromyalgia.

In certain aspects, the subject matter disclosed herein provides a method of treating pain, fever, or inflammation in a subject in need thereof, the method comprising administering to the subject a pharmaceutical composition comprising an effective amount of substantially pure rofecoxib and a pharmaceutically acceptable carrier.

In some embodiments, the pain, fever, or inflammation is caused by one or more conditions selected from the group comprising of hemophilic arthropathy, osteoarthritis, rheumatoid arthritis, pauciarticular or polyarticular course Juvenile Rheumatoid Arthritis (JRA), juvenile idiopathic arthritis, acute pain, primary dysmenorrhea, migraine attacks, or migraine associated with von Willebrand disease. In other embodiments, the one or more conditions is psoriatic arthritis or fibromyalgia.

In certain aspects, the subject matter disclosed herein provides a method of treating pain or migraine associated with a condition caused by a bleeding disorder in a subject in need thereof, the method comprising administering to the subject a pharmaceutical composition comprising an effective amount of highly pure rofecoxib and a pharmaceutically acceptable carrier.

In certain aspects, the subject matter disclosed herein provides a method of treating pain or migraine associated with a condition caused by a bleeding disorder in a subject in need thereof, the method comprising administering to the subject a pharmaceutical composition comprising an effective amount of substantially pure rofecoxib and a pharmaceutically acceptable carrier.

In some embodiments, the subject is 2 years of age or older. In some embodiments, the subject is 12 years old or older. In some embodiments, the subject is 12 years old to 75 years old. In some embodiments, the subject does not have a history or current symptoms of cardiovascular disease. In some embodiments, the subject does not have a history or current symptoms of gastrointestinal bleeding, ulceration, or perforation. In some embodiments, the pharmaceutical composition is administered once daily. In some embodiments, the pharmaceutical composition is administered two times or more daily. In some embodiments, the condition is caused by a bleeding disorder. In some embodiments, the bleeding disorder is hemophilia A or B, C von Willebrand Disease, or a drug-induced bleeding disorder. In some embodiments, the condition is hemophilic arthropathy, juvenile idiopathic arthritis, or migraine associated with von Willebrand disease.

In some embodiments, the treatment is effective at treating pain without co-administration of an analgesic. In some embodiments, the treatment results in a subject decreasing or discontinuing use of analgesics or rescue medications during the treatment as compared to before initiation of the treatment. In some embodiments, the treatment results in a subject decreasing or discontinuing use of opioid medications during the treatment.

In some embodiments, the method further includes administering a gastro-protective agent. In some embodiments, the gastro-protective agent is co-administered with the pharmaceutical composition. In some embodiments, the treatment does not include administering gastro-protective agent.

In some embodiments, the treatment achieves a reduction of at least 1 from baseline in a Pain Intensity Numerical Rating Scale. In some embodiments, the treatment achieves a reduction of at least 2 from baseline in a Pain Intensity Numerical Rating Scale. In some embodiments, the treatment achieves a reduction of at least 3 from baseline in a Pain Intensity Numerical Rating Scale. In some embodiments, the treatment achieves a reduction of at least 4 from baseline in a Pain Intensity Numerical Rating Scale. In some embodiments, the treatment achieves a reduction of at least 5 from baseline in a Pain Intensity Numerical Rating Scale. In some embodiments, the reduction in the Pain Intensity Numerical Rating Scale is achieved within 1, 2, 3, 4, 5, 6 days, 1 week, or 2 weeks of administering the pharmaceutical composition.

In some embodiments, the effective amount of the rofecoxib administered to a subject is 12.5 mg. In some embodiments, the effective amount of the rofecoxib administered to a subject is 17.5 mg. In some embodiments, the effective amount of the rofecoxib administered to a subject is 20 mg. In some embodiments, the effective amount of the rofecoxib administered to a subject is 25 mg.

In some embodiments, the effective amount of the rofecoxib administered to a subject is selected from the group comprising of 1 mg, 2 mg, 3 mg, 5 mg, 6.25 mg, 7.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 20 mg, 20.5 mg, 21 mg, 21.5 mg, 22.5 mg, 25 mg, 30 mg, 35 mg, 40 mg, 45 mg, 50 mg, 55 mg, 60 mg, 65 mg, and 70 mg. In some embodiments, the effective amount of the rofecoxib administered to a subject is selected from the group comprising of 0.10 mg/kg, 0.15 mg/kg, 0.20 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, or 0.70 mg/kg.

In certain aspects, the subject matter disclosed herein provides a method of treating pain associated with a condition caused by a bleeding disorder in a subject in need thereof, the method comprising administering once daily to the subject a pharmaceutical composition comprising 12.5 mg of substantially pure rofecoxib or 12.5 mg of highly pure rofecoxib as a sole active ingredient, wherein the treatment achieves a reduction of at least 1 from baseline in a Pain Intensity Numerical Rating Scale.

In certain aspects, the subject matter disclosed herein provides a method of treating pain associated with a condition caused by a bleeding disorder in a subject in need thereof, the method comprising administering once daily to the subject a pharmaceutical composition comprising 17.5 mg of substantially pure rofecoxib or 17.5 mg of highly pure rofecoxib as a sole active ingredient, wherein the treatment achieves a reduction of at least 1 from baseline in a Pain Intensity Numerical Rating Scale.

In certain aspects, the subject matter disclosed herein provides a method of treating pain associated with a condition caused by a bleeding disorder in a subject in need thereof, the method comprising administering once daily to the subject a pharmaceutical composition comprising 20 mg of substantially pure rofecoxib or 20 mg of highly pure rofecoxib as a sole active ingredient, wherein the treatment achieves a reduction of at least 1 from baseline in a Pain Intensity Numerical Rating Scale.

In some embodiments, the pharmaceutical composition achieves a reduction in a Pain Intensity Numerical Rating Scale that is equal to or greater than the once daily administration of a pharmaceutical composition comprising 25 mg of rofecoxib that is not highly pure. In some embodiments, the condition is hemophilic arthropathy.

In certain aspects, the subject matter disclosed herein provides a method of treating pain associated with hemophilic arthropathy in a subject in need thereof, wherein the subject is 12 years old or older, the method comprising administering once daily a pharmaceutical composition comprising 12.5 mg of substantially pure rofecoxib or 12.5 mg of highly pure rofecoxib, wherein the treatment achieves a reduction of at least 1 from baseline in a Pain Intensity Numerical Rating Scale.

In certain aspects, the subject matter disclosed herein provides a method of treating pain associated with hemophilic arthropathy in a subject in need thereof, wherein the subject is 12 years old or older, the method comprising administering once daily a pharmaceutical composition comprising 17.5 mg of substantially pure rofecoxib or 17.5 mg of highly pure rofecoxib, wherein the treatment achieves a reduction of at least 1 from baseline in a Pain Intensity Numerical Rating Scale.

In certain aspects, the subject matter disclosed herein provides a method of treating pain associated with hemophilic arthropathy in a subject in need thereof, wherein the subject is 12 years old or older, the method comprising administering once daily a pharmaceutical composition comprising 20 mg of substantially pure rofecoxib or 20 mg of highly pure rofecoxib, wherein the treatment achieves a reduction of at least 1 from baseline in a Pain Intensity Numerical Rating Scale.

In certain aspects, the subject matter disclosed herein provides a method of treating pain associated with a condition caused by a bleeding disorder in a subject in need thereof, the method comprising: determining whether the subject has a history or current symptoms of cardiovascular disease; administering once daily to the subject a pharmaceutical composition comprising at least 12.5 mg substantially pure rofecoxib if it is determined that the subject does not have a history or current symptoms of cardiovascular disease, wherein the treatment achieves a reduction of at least 1 from baseline in a Pain Intensity Numerical Rating Scale within 1 week of first administering the pharmaceutical composition to the subject.

In some embodiments, the pharmaceutical composition comprises 1 mg, 2 mg, 3 mg, 5 mg, 6.25 mg, 7.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 20 mg, 20.5 mg, 21 mg, 21.5 mg, 22.5 mg, 25 mg, 30 mg, 35 mg, 40 mg, 45 mg, 50 mg, 55 mg, 60 mg, 65 mg, or 70 mg of substantially pure rofecoxib.

In certain aspects, the subject matter disclosed herein provides a method of treating pain in a subject in need thereof, the method comprising administering to the subject a pharmaceutical composition comprising an effective amount of highly pure rofecoxib, wherein the treatment achieves a greater reduction in Pain Intensity Numerical Rating Scale compared to the administering of the same amount of a pharmaceutical composition comprising rofecoxib that is not highly pure.

In some embodiments, the pain is caused by one or more conditions selected from the group comprising of hemophilic arthropathy, osteoarthritis, rheumatoid arthritis, pauciarticular or polyarticular course Juvenile Rheumatoid Arthritis (JRA), juvenile idiopathic arthritis, including systemic juvenile idiopathic arthritis, acute pain, primary dysmenorrhea, migraine attacks, or migraine associated with von Willebrand disease. In other embodiments, the pain is caused by psoriatic arthritis or fibromyalgia.

In certain aspects, the subject matter disclosed herein provides a method of treating pain, fever, or inflammation in a subject in need thereof, the method comprising administering to the subject a pharmaceutical composition comprising an effective amount of highly pure rofecoxib, wherein the treatment results in fewer side effects compared to administering the same amount of a pharmaceutical composition comprising of rofecoxib that is not highly pure. In some embodiments, the pain, fever, or inflammation is caused by one or more conditions selected from the group comprising of hemophilic arthropathy, osteoarthritis, rheumatoid arthritis, pauciarticular or polyarticular course Juvenile Rheumatoid Arthritis (JRA), juvenile idiopathic arthritis, acute pain, primary dysmenorrhea, migraine attacks, or migraine associated with von Willebrand disease. In other embodiments, the pain or inflammation is caused by psoriatic arthritis or fibromyalgia.

In certain aspects, the subject matter disclosed herein provides a method of treating pain, fever or inflammation caused by one or more conditions, the method comprising administering to a subject in need thereof a pharmaceutical composition comprising an effective amount of substantially pure rofecoxib and a pharmaceutically acceptable carrier or highly pure rofecoxib and a pharmaceutically acceptable carrier wherein the treatment results in a reduction in pain, further wherein the treatment results in reduction of effects associated with administration of rofecoxib that is not highly pure.

In some embodiments, the one or more conditions is selected from the group comprising of hemophilic arthropathy, osteoarthritis, rheumatoid arthritis, pauciarticular or polyarticular course Juvenile Rheumatoid Arthritis (JRA), acute pain, primary dysmenorrhea, migraine attacks, or migraine associated with von Willebrand disease. In other embodiments, the one or more conditions is psoriatic arthritis or fibromyalgia.

In certain aspects, the subject matter disclosed herein provides a method of manufacturing substantially pure rofecoxib or highly pure rofecoxib as set forth in FIG. 1, the method comprising the steps of: bromination of 4'-(methylthio)acetophenone (RSM1) in the presence of TBABr$_3$ to obtain an intermediate RXB-Bromocetone product at stage 1; involving the intermediate product with Phenylacetic acid (RSM2) in a nucleophilic substitution reaction in the presence of sodium hydroxide to obtain a RXB-Phenylacetate product at stage 2; crystallizing the product of stage 2 in isopropanol and achieving filterable crystals; intramolecularly cyclizing of the product of stage 2 at 70° C. in DMSO in presence of diisopropylamine; converting 4-[4-(methylthio)phenyl]-3-phenyl-2(5H)-furanone to highly pure rofecoxib or substantially pure rofecoxib by use of hydrogen peroxide with a catalytic amount of dihydrate sodium tungsten in acetonitrile; and recrystallizing the rofecoxib in a mixture of DMSO and water.

In certain aspects, the subject matter disclosed herein provides a pharmaceutical composition comprising rofecoxib comprising less than 0.05% of 4-[4-(methylsulfonyl) phenyl]-3-phenyl-2,5-furandione and a pharmaceutically acceptable carrier.

In certain aspects, the subject matter disclosed herein provides a pharmaceutical composition comprising highly pure, or substantially pure, rofecoxib having at least one impurity that is a prodrug of rofecoxib and a pharmaceutically acceptable carrier.

In some embodiments, the rofecoxib is essentially free of, or free of, 4-[4-(methylsulfonyl)phenyl]-3-phenyl-5-hydroxyfuran-2-one and/or 4-[4-(methylsulfonyl)phenyl]-3-phenyl-2,5-furandione. In some embodiments, the rofecoxib comprises less than 0.02% 4-[4-(methylsulfonyl)phenyl]-3-phenyl-5-hydroxyfuran-2-one and/or 4-[4-(methylsulfonyl) phenyl]-3-phenyl-2,5-furandione.

In certain aspects, the subject matter disclosed herein provides a method for treating pain, fever, or inflammation in a subject, the method comprising administering to the subject a pharmaceutical composition comprising an effective amount of rofecoxib comprising less than 0.05% 4-[4-(methylsulfonyl)phenyl]-3-phenyl-2,5-furandione and a pharmaceutically acceptable carrier, wherein the subject is within a subject population having a reduced risk of a serious cardiovascular thrombotic event.

In some embodiments, the effective amount of rofecoxib is 12.5 mg. In some embodiments, the effective amount of rofecoxib is 17.5 mg. In some embodiments, the effective amount of rofecoxib is 20 mg. In some embodiments, the rofecoxib comprises less than 0.02% 4-[4-(methylsulfonyl) phenyl]-3-phenyl-2,5-furandione.

In certain aspects, the subject matter disclosed herein provides a method for treating pain, fever, or inflammation in a subject, while reducing one or more side effects associated with the administration of 4-[4-(methylsulfonyl) phenyl]-3-phenyl-2,5-furandione, comprising administering to the subject a pharmaceutical composition comprising an effective amount of rofecoxib comprising less than 0.05% of 4-[4-(methylsulfonyl)phenyl]-3-phenyl-2,5-furandione and a pharmaceutically acceptable carrier.

In some embodiments, the effective amount of rofecoxib is 12.5 mg. In some embodiments, the effective amount of rofecoxib is 17.5 mg. In some embodiments, the effective amount of rofecoxib is 20 mg. In some embodiments, the rofecoxib comprises less than 0.05% 4-[4-(methylsulfonyl) phenyl]-3-phenyl-2,5-furandione.

In certain aspects, the subject matter disclosed herein provides a pharmaceutical composition comprising 12.5 mg highly pure rofecoxib or an acceptable salt thereof and a pharmaceutically acceptable carrier.

In certain aspects, the subject matter disclosed herein provides a pharmaceutical composition comprising 17.5 mg highly pure rofecoxib or an acceptable salt thereof and a pharmaceutically acceptable carrier.

In certain aspects, the subject matter disclosed herein provides a pharmaceutical composition comprising 20 mg highly pure rofecoxib or an acceptable salt thereof and a pharmaceutically acceptable carrier.

In certain aspects, the subject matter disclosed herein provides a pharmaceutical composition comprising 12.5 mg substantially pure rofecoxib or an acceptable salt thereof and a pharmaceutically acceptable carrier.

In certain aspects, the subject matter disclosed herein provides a pharmaceutical composition comprising 17.5 mg substantially pure rofecoxib or an acceptable salt thereof and a pharmaceutically acceptable carrier.

In certain aspects, the subject matter disclosed herein provides a pharmaceutical composition comprising 20 mg substantially pure rofecoxib or an acceptable salt thereof and a pharmaceutically acceptable carrier.

In certain aspects, the subject matter disclosed herein provides a method of treating pain, fever, or inflammation in a subject in need thereof, the method comprising administering an effective amount of highly pure rofecoxib.

In some embodiments, the effective amount of highly pure rofecoxib is 12.5 mg. In some embodiments, the effective amount of highly pure rofecoxib is 17.5 mg. In some embodiments, the effective amount of highly pure rofecoxib is 20 mg.

In certain aspects, the subject matter disclosed herein provides a method of treating pain, fever, or inflammation in a subject in need thereof, the method comprising administering an effective amount of substantially pure rofecoxib.

In some embodiments, the effective amount of substantially pure rofecoxib is 12.5 mg. In some embodiments, the effective amount of substantially pure rofecoxib is 17.5 mg. In some embodiments, the effective amount of substantially pure rofecoxib is 20 mg.

In certain aspects, the subject matter disclosed herein provides a pharmaceutical composition comprising an effective amount of rofecoxib having less than 0.10%, 0.05%, 0.02%, or 0.01% 4-[4-(methylsulfonyl)phenyl]-3-phenyl-2,5-furandione, and a pharmaceutically acceptable carrier.

In some embodiments, the effective amount of rofecoxib is 17.5 mg. In some embodiments, the effective amount of rofecoxib is 20 mg.

In certain aspects, the subject matter disclosed herein provides a pharmaceutical composition comprising an effective amount of rofecoxib having less than 0.10%, 0.05%, 0.02%, or 0.01% 4-[4-(methylsulfonyl)phenyl]-3-phenyl-5-hydroxyfuran-2-one, and a pharmaceutically acceptable carrier.

In some embodiments, the effective amount is 10 mg. In some embodiments, the effective amount is 12.5 mg. In some embodiments, the effective amount of rofecoxib is 17.5 mg. In some embodiments, the effective amount of rofecoxib is 20 mg. In some embodiments, the effective amount of rofecoxib is 25 mg.

In certain aspects, the subject matter disclosed herein provides a pharmaceutical composition comprising rofecoxib or an acceptable salt thereof that is substantially free of one or more of the impurities selected from the group consisting of: 4-[4-(methylsulfonyl)phenyl]-3-phenyl-2,5-furandione, 4-[4-(methylsulfonyl)phenyl]-3-phenyl-5-hydroxyfuran-2-one, 4-[4-(methylthio)phenyl]-3-phenyl-2(5H)-furanone, and 4-[4-(methylsulfinyl)phenyl]-3-phenyl-2(5H)-furanone, and a pharmaceutically acceptable carrier.

In certain aspects, the subject matter disclosed herein provides a pharmaceutical composition comprising rofecoxib or an acceptable salt thereof that is essentially free of one or more impurities selected from the group consisting of: 4-[4-(methylsulfonyl)phenyl]-3-phenyl-2,5-furandione, 4-[4-(methylsulfonyl)phenyl]-3-phenyl-5-hydroxyfuran-2-one, 4-[4-(methylthio)phenyl]-3-phenyl-2(5H)-furanone, and 4-[4-(methylsulfinyl)phenyl]-3-phenyl-2(5H)-furanone, and a pharmaceutically acceptable carrier.

In some aspects, the subject matter disclosed herein provides a method of treating pain, fever, or inflammation caused by one or more conditions in a subject in need thereof, the method comprising administering to the subject a pharmaceutical composition comprising rofecoxib or an acceptable salt thereof that is essentially free of one or more impurities selected from the group consisting of: 4-[4-(methylsulfonyl)phenyl]-3-phenyl-2,5-furandione, 4-[4-(methylsulfonyl)phenyl]-3-phenyl-5-hydroxyfuran-2-one, 4-[4-(methylthio)phenyl]-3-phenyl-2(5H)-furanone, and 4-[4-(methylsulfinyl)phenyl]-3-phenyl-2(5H)-furanone, and a pharmaceutically acceptable carrier.

In certain aspects, the subject matter disclosed herein provides a method of treating pain associated with a condition caused by a bleeding disorder in a subject in need thereof, the method comprising administering to the subject a pharmaceutical composition comprising an effective amount of rofecoxib or an acceptable salt thereof that is essentially free of one or more impurities selected from the group consisting of: 4-[4-(methylsulfonyl)phenyl]-3-phenyl-2,5-furandione, 4-[4-(methylsulfonyl)phenyl]-3-phenyl-5-hydroxyfuran-2-one, 4-[4-(methylthio)phenyl]-3-phenyl-2(5H)-furanone, and 4-[4-(methylsulfinyl)phenyl]-3-phenyl-2(5H)-furanone, and a pharmaceutically acceptable carrier.

The subject matter disclosed herein relates to substantially pure or highly pure rofecoxib, also known as TRM-201 or RXB-201, or a pharmaceutically acceptable salt or solvate thereof, having a favorable impurity profile, rofecoxib method of manufacture, and the use of pharmaceutical compositions containing rofecoxib to treat or prevent various conditions and diseases.

In one embodiment, the rofecoxib as provided herein is, with respect to all impurities, substantially pure or highly pure. In another embodiment, the rofecoxib as provided herein is substantially free of, essentially free of, or free of, 4-[4-(methylthio)phenyl]-3-phenyl-2(5H)-furanone. In one aspect, the rofecoxib as provided herein is substantially free of, essentially free of, or free of, 4-[4-(methylsulfinyl)phenyl]-3-phenyl-2(5H)-furanone.

As described herein, it has been found that rofecoxib, although previously considered to be unsafe for human use, may be manufactured in a substantially pure or highly pure form, substantially free, essentially free, or free of impurities including those found in previously available rofecoxib bulk drug product, and may be safely administered to humans as the active ingredient in a pharmaceutical composition for a number of diseases or conditions including, but not limited to, diseases or conditions arising from or comorbid with bleeding disorders, such as hemophilic arthropathy. In one aspect, the subject matter described herein addresses the long felt, but unmet need, for new treatments for hemophilic arthropathy through the safe administration of rofecoxib or a pharmaceutically acceptable salt or solvate thereof.

In another aspect, the subject matter described herein relates to treatments for juvenile idiopathic arthritis, including systemic juvenile idiopathic arthritis (SJIA) through the safe administration of rofecoxib or a pharmaceutically acceptable salt or solvate thereof. In yet another aspect, the subject matter described herein relates to treatments for migraine associated with von Willebrand disease through the safe administration of rofecoxib or a pharmaceutically acceptable salt or solvate thereof, wherein the subjects who are treated express von Willebrand factor at a level about 50% below normal.

The subject matter disclosed herein includes, but is not limited to, the treatment of various diseases or conditions through the administration of a pharmaceutical composition comprising rofecoxib or a pharmaceutically acceptable salt or solvate thereof, which is essentially free of, or free of, 4-[4-(methylsulfonyl)phenyl]-3-phenyl-5-hydroxyfuran-2-one and/or 4-[4-(methylsulfonyl)phenyl]-3-phenyl-2,5-furandione, wherein the treatment results in greater efficacy and/or reduced side effects, including those reported as adverse events or serious adverse events, compared to previously available rofecoxib bulk drug product, thus facilitating safe, long term use of the pharmaceutical composition.

Purity of the rofecoxib resulting from the manufacturing process described herein is determined as a percent (%) area basis, typically as quantified by analytical chromatography, such as using HPLC, UHPLC, UPLC or other analytical means in the art.

Manufacture of Rofecoxib

In certain aspects, the rofecoxib as provided herein is manufactured in a manner that produces rofecoxib that is essentially free of, or free of, 4-[4-(methylsulfonyl)phenyl]-3-phenyl-5-hydroxyfuran-2-one and/or 4-[4-(methylsulfonyl)phenyl]-3-phenyl-2,5-furandione, both of which are impurities found in previously available rofecoxib bulk drug product.

In one aspect, rofecoxib as provided herein may be manufactured according to a process as shown in FIG. 1. In one aspect, the process relies on two starting materials. In one aspect, rofecoxib is manufactured via a four-step sequential process followed by a crystallization step and a micronization step. The first step may include the bromination of 4'-(Methylthio)acetophenone (SM1) in the presence of $TBABr_3$, leading to the formation of intermediate step 1, RXB-Bromoacetone. In one embodiment, 4'-(Methylthio) acetophenone is dissolved in a methanol and dichloromethane mixture to which tetrabutylammonium tribromide ($TBAB_3$) dissolved in dichloromethane is added to form RXB-Bromocetone. Upon completion, water can be added to quench the reaction. The layers can then be separated, and the water layer decanted. In one embodiment, the RXB-Bromocetone is not isolated.

In one embodiment, the bromination reaction of step one is followed by an esterification reaction in step two of the rofecoxib manufacturing process. In step two, phenylacetic acid and sodium hydroxide can be dissolved in water. The solution of phenylacetate can then be added to the RXB-Bromocetone solution from step one to form the step 2 product, RXB-Phenylacetate. At step two, there may be distillation and crystallization in isopropanol. The solvent volume can be reduced by distillation at about 55° C. under atmospheric pressure and isopropanol can be added to the mixture, which is then cooled to about 0° C. to yield solid RXB-Phenylacetate. Seed crystals may be added during the cooling process. In one embodiment, the RXB-Phenylacetate is isolated from the resulting slurry by centrifugation at about 0° C., and the collected solids are then washed with isopropanol. The resulting filter cake can be dried under vacuum at about 60° C.

In one embodiment, step three of the rofecoxib manufacturing process as shown in FIG. 1 involves preparation of 4-[4-(methylthio)phenyl]-3-phenyl-2(5H)-furanone (referred to in FIG. 1 as "RXB-furanone"). In one embodiment, RXB-Phenylacetate is in dimethylsulfoxide (DMSO) and heated to about 70° C. To this solution, diisopropylamine (DTPA) and additional DMSO can be added and the resulting solution can be maintained at temperature until the reaction is complete. Isopropanol can be added to the mixture, which can then cooled to about 0° C. to yield solid 4-[4-(methylthio)phenyl]-3-phenyl-2(5H)-furanone (referred to in FIG. 1 as "RXB-furanone"). Seed crystals may be added during the cooling process. The 4-[4-(methylthio)phenyl]-3-phenyl-2(5H)-furanone (referred to in FIG. 1 as "RXB-furanone") can be isolated from the resulting slurry by centrifugation at about 0° C., and the collected solids can then be washed with isopropanol. In one embodiment, the isolated 4-[4-(methylthio)phenyl]-3-phenyl-2(5H)-furanone (referred to in FIG. 1 as "RXB-furanone") is not dried.

In one embodiment, step four of the process involves preparation of rofecoxib. In one embodiment, step four involves sulfoxide formation. In step four of the process, 4-[4-(methylthio)phenyl]-3-phenyl-2(5H)-furanone (referred to in FIG. 1 as "RXB-furanone") and a catalytic amount of sodium tungstate dihydrate can be suspended in acetonitrile and heated to about 65° C. To this suspension, aqueous hydrogen peroxide can be added. In one embodiment, the resulting slurry is maintained at temperature until the reaction is complete, then it is allowed to cool to ambient temperature. Aqueous sodium sulfite solution can be added to the slurry and mixed. In one embodiment, the crude rofecoxib is isolated from the slurry by centrifugation at about 0° C., and the collected solids are then washed with water and isopropanol. In one embodiment, the isolated rofecoxib is not dried.

In one embodiment, step five involves crystallization of rofecoxib. Crude rofecoxib can be dissolved in DMSO and filtered at about 40° C. The filtrate can then be heated to about 50° C., and purified water can be added to induce crystallization. The suspension can then be cooled slowly to about 20° C. The resulting slurry can be filtered, and the collected solids can be washed with a DMSO-water mixture, water, and isopropanol. In one embodiment, the resulting filter cake is dried at about 60° C. under vacuum. In one embodiment, step six of the process includes micronization of crystalized rofecoxib using a jet mill. In some embodiments, the d90 particle size of the rofecoxib following micronization is less than about 15 µm, 14 µm, 13 µm, 12 µm, 11 µm, 10 µm, 9 µm, 8 µm, 7 µm, 6 µm, 5 µm, or 4 µm. In some embodiments, the d50 particle size of the rofecoxib following micronization is less than about 8 µm, 7 µm, 6 µm, 5 µm, 4 µm, 3 µm, 2 µm, or 1 µm. In some embodiments, the d10 particle size of the rofecoxib following micronization is less than about 4 µm, 3 µm, 2 µm, 1 µm, 0.9 µm, 0.8 µm, 0.7 µm, 0.6 µm, or 0.5 µm. In some embodiments, the particle size distribution of the rofecoxib following micronization is as follows: a) the d90 particle size is about 10-12 µm; b) the d50 particle size is about 3-4 µm; and c) the d10 particle size is about 0.5-1.0 µm.

In accordance with the process shown in FIG. 1, the final intermediate, 4-[4-(methylthio)phenyl]-3-phenyl-2(5H)-furanone (CAS Number 162012-30-8) (referred to in FIG. 2 as "RXB-furanone"), can be converted to rofecoxib through an oxidation step, for example, by use of an oxidizing agent. In one aspect, the oxidizing agent is hydrogen peroxide with a catalytic amount of dihydrate sodium tungsten in acetonitrile. In another aspect, the oxidizing agent is not potassium peroxymonosulfate (oxone). The oxidation reaction can transform the sulfide function of step 3 into the corresponding sulfone using hydrogen peroxide with a catalytic amount of dihydrate sodium tungsten in acetonitrile. It was surprisingly discovered that increasing the reaction temperature to at least 50° C., preferably to at least 60° C., and more preferably to 65° C., as well as increasing the amount of solvent (acetonitrile), can decrease the amount of impurities that resulted in substantially pure rofecoxib prior to any recrystallization step. In one aspect, the oxidation step may produce rofecoxib that is at least 99.7% pure, i.e. contains less than 0.30% impurities, prior to any recrystallization step. In another aspect, the oxidation step produces rofecoxib that contains less than 0.15% or 0.10% 4-[4-(methylthio)phenyl]-3-phenyl-2(5H)-furanone prior to any recrystallization step. In one aspect, the oxidation step produces rofecoxib that contains less than 0.15%, 0.10%, 0.075%, or 0.05% 4-[4-(methylsulfinyl)phenyl]-3-phenyl-2 (5H)-furanone (referred to in FIG. 2 as "RXB-Sulfoxide") prior to any recrystallization step. In another aspect, the oxidation step in acetonitrile may produce rofecoxib that does not require any drying prior to recrystallization.

In one aspect, the oxidation product is recrystallized in a mixture of DMSO and water, which can remove a pale-yellow coloration and residual impurities, and can afford the desired active pharmaceutical ingredient, rofecoxib as described herein. It was surprisingly discovered that DMSO may be used as a solvent in the recrystallization step, producing yields similar to those where dimethyl formamide (DMF) is used as the recrystallization solvent, while avoiding the safety concerns associated with use of DMF in the final recrystallization step. In one aspect, the rofecoxib as described herein contains no detectable DMF.

It was also surprisingly discovered that the process of recrystallization described herein produced rofecoxib essentially free, or free of, 6-methylsulfonylphenanthro-[9,10-C]furan-1(3H)-one, which has been described as a photo-cyclization degradation product of rofecoxib that may be present "without appropriate control of the recrystallisation procedures". See Dean P M. Structural Examination of 6-Methylsulfonylphenanthro-[9,10-C]-furan-1(3H)-one—A Rofecoxib Degradation Product. Pharmaceuticals (Basel). 2010; 3(2):369-378. Published 2010 Feb. 1. doi:10.3390/ph3020369.

In one aspect, the process shown in FIG. 1 produces rofecoxib as described herein that is substantially pure or highly pure. In another aspect, the rofecoxib produced from the final intermediate is recrystallized, for example in DMSO and water, to produce substantially pure or highly pure rofecoxib as described herein.

It was surprisingly found that the oxidation step (Stage 3 to Stage 4) results in the formation of rofecoxib as provided herein that contains only two impurities at or above the limit of detection, 4-[4-(methylthio)phenyl]-3-phenyl-2(5H)-furanone and 4-[4-(methylsulfinyl)phenyl]-3-phenyl-2(5H)-furanone. In one aspect, the oxidation step results in the formation of rofecoxib that contains less than 0.25%, 0.20%, 0.15%, or 0.10% 4-[4-(methylthio)phenyl]-3-phenyl-2(5H)-furanone and/or 4-[4-(methylsulfinyl)phenyl]-3-phenyl-2(5H)-furanone. In one aspect, the oxidation step results in the formation of rofecoxib as provided herein that is essentially free of, or free of, 4-[4-(methylsulfonyl)phenyl]-3-phenyl-5-hydroxyfuran-2-one and/or 4-[4-(methylsulfonyl)phenyl]-3-phenyl-2,5-furandione, or contains either or both of those impurities in an amount that is otherwise below the limit of detection. As a result, the manufacturing process described herein avoids the production of a compound, 4-[4-(methylsulfonyl)phenyl]-3-phenyl-2,5-furandione, which has been identified in the literature as "a possible contributor to chronic human toxicity". See Reddy et al., Facile air oxidation of the conjugate base of rofecoxib (Vioxx), a possible contributor to chronic human toxicity, Tetrahedron Lett 46: 927-929 (2005).

It was also surprisingly discovered that the manufacturing process described herein produced at least one impurity that has beneficial properties, specifically 4-[4-(methylsulfinyl) phenyl]-3-phenyl-2(5H)-furanone, which is a prodrug of rofecoxib and has been described as having "a slightly improved pharmacokinetic profile and a better pharmacological activity in an arthritis model . . . when compared with rofecoxib". See Caturla, Francisco et al., "Racemic and chiral sulfoxides as potential prodrugs of the COX-2 inhibitors Vioxx® and Arcoxia®," Bioorganic & Medicinal Chemistry Letters, 16:3209-3212 (2006).

In one embodiment, evaluation of the potential toxicity of starting materials and intermediates is conducted in silica. Rule-based DEREK software using all 51 endpoints, which covers all the major organ systems as well as mutagenicity and skin sensitization, can be used to evaluate each compound. Additionally, for prediction of potential mutagenicity, the structures can be evaluated using the statistical-based Leadscope Model Applier. Per ICH M7, use of two complementary in silica methods is adequate for the overall determination of mutagenicity. The in silica evaluations have demonstrated that both starting materials and all intermediates in the manufacturing process of rofecoxib are predicted negative for mutagenicity in two complementary methods. Therefore, special controls for mutagenic compounds does not have to be necessarily employed in the manufacture of rofecoxib.

In one embodiment, acetic acid is an excellent solvent for 4-[4-(methylsulfinyl)phenyl]-3-phenyl-2(5H)-furanone (>1000 g/L). In one embodiment, a the starting material may include a spiking of 4-[4-(methylsulfinyl)phenyl]-3-phenyl-2(5H)-furanone.

The purity of the resulting rofecoxib described as herein is determined as a percent (%) area basis, typically as quantified by analytical chromatography, such as using HPLC, UHPLC, UPLC or other analytical means in the art.

Impurity Profile

It was found that the process shown in FIG. 1 can avoid production of one or more of the impurities found in previously available rofecoxib bulk drug product: 4-[4-(methylsulfonyl)phenyl]-3-phenyl-5-hydroxyfuran-2-one; and 4-[4-(methylsulfonyl)phenyl]-3-phenyl-2,5-furandione. See Ahuja et al., Rofecoxib: an update on physicochemical, pharmaceutical, pharmacodynamic and pharmacokinetic aspects, Journal of Pharmacy and Pharmacology, 2003, 55: 859-894.

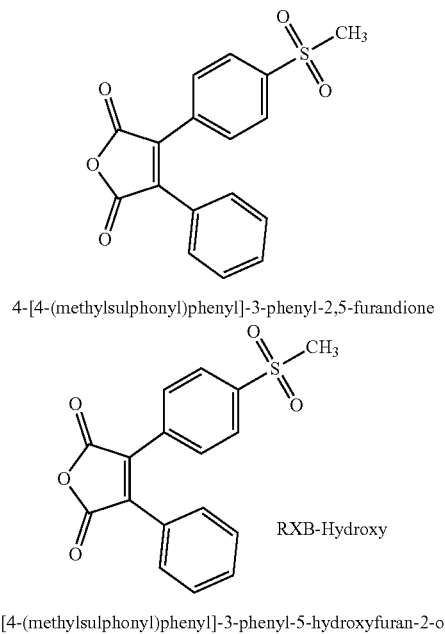

4-[4-(methylsulphonyl)phenyl]-3-phenyl-2,5-furandione

RXB-Hydroxy

4-[4-(methylsulphonyl)phenyl]-3-phenyl-5-hydroxyfuran-2-one

Additionally, there are two potential impurities that can arise during the last bond-forming step (Step 4) of the rofecoxib manufacturing process: 4-[4-(methylthio)phenyl]-3-phenyl-2(5H)-furanone and 4-[4-(methylsulfinyl)phenyl]-

3-phenyl-2(5H)-furanone. 4-[4-(methylthio)phenyl]-3-phenyl-2(5H)-furanone is the Step 3 product, and 4-[4-(methylsulfinyl)phenyl]-3-phenyl-2(5H)-furanone is a partially-oxidized intermediate.

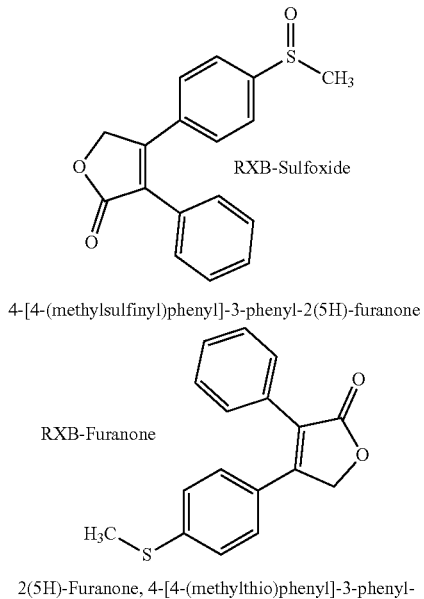

4-[4-(methylsulfinyl)phenyl]-3-phenyl-2(5H)-furanone

2(5H)-Furanone, 4-[4-(methylthio)phenyl]-3-phenyl-

Figure 3:
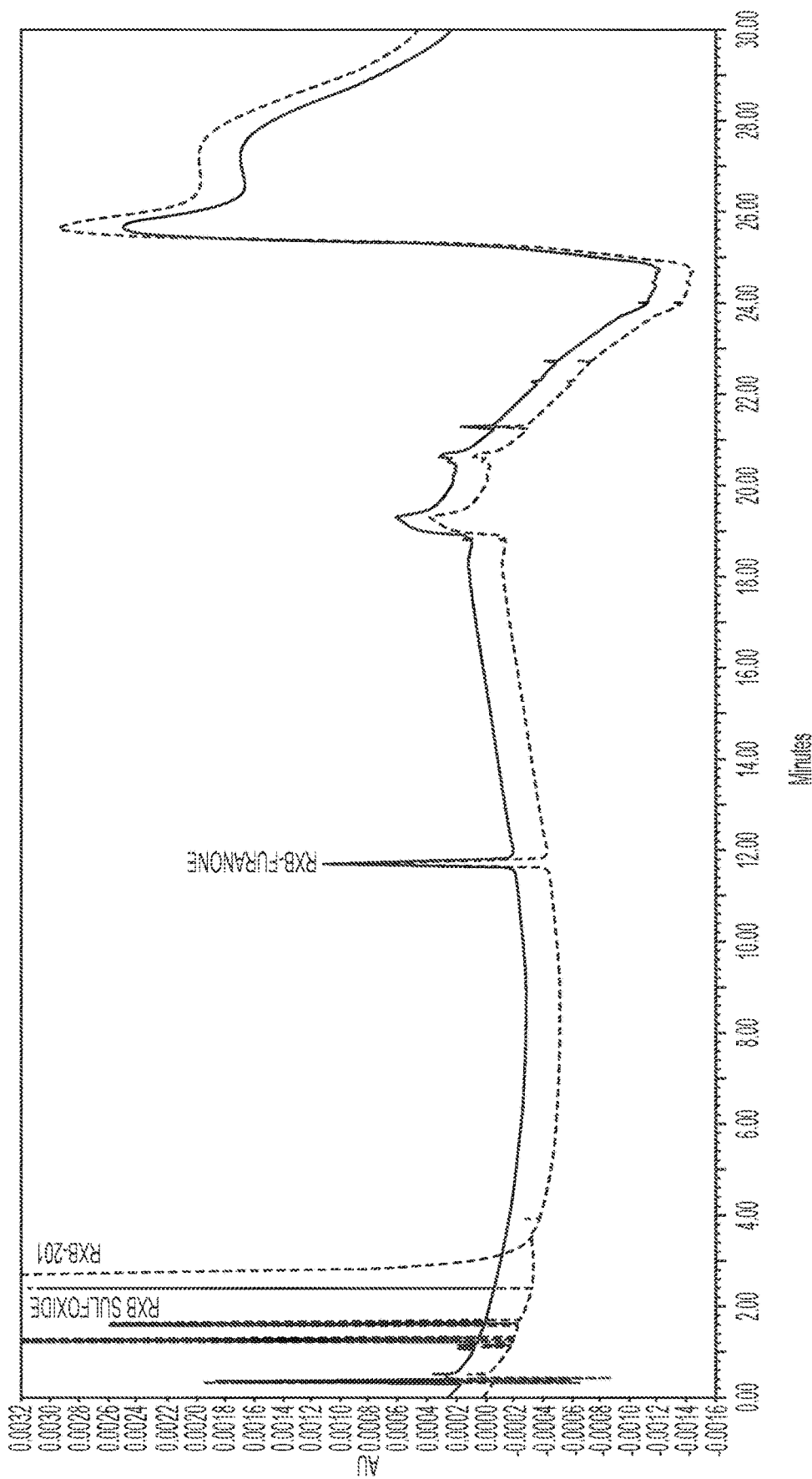
FIG. 3 shows representative chromatograms of a mixture that contains 1 mg/mL rofecoxib, 1.5 µg/mL 4-[4-(methylsulfinyl)phenyl]-3-phenyl-2(5H)-furanone, and 1.5 µg/mL 4-[4-(methylthio)phenyl]-3-phenyl-2(5H)-furanone and the blank solution.

FIG. 3 shows representative chromatograms of a mixture that contains 1 mg/mL rofecoxib, 1.5 µg/mL 4-[4-(methylsulfinyl)phenyl]-3-phenyl-2(5H)-furanone, and 1.5 µg/mL 4-[4-(methylthio)phenyl]-3-phenyl-2(5H)-furanone and the blank solution. Table 1 shows that the components of the mixture are well-resolved. The limit of quantitation is <0.05% area basis, which is the reporting threshold. Other potential impurities that may arise during manufacture are residual solvents (acetonitrile, dichloromethane, dimethylsulfoxide, isopropanol, and methanol) and inorganic material.

TABLE 1

Specificity Results for the UHPLC Purity Method

| Component | RT, (min) | RRT | $R_s$ |
|---|---|---|---|
| Unknown impurity 1 | 1.13 | 0.45 | — |
| RXB-sulfoxide | 1.27 | 0.50 | 2.0 |
| Unknown impurity 2 | 1.62 | 0.64 | 5.7 |
| Rofecoxib | 2.52 | 1.00 | 11.4 |
| RXB-furanone | 11.69 | 4.64 | 67.4 |

RT = retention time; RRT = relative retention time; $R_s$ = resolution

As a result, in one aspect of the subject matter disclosed herein, the rofecoxib incorporated into a pharmaceutical composition may be essentially free of, or free of, 4-[4-(methylsulfonyl)phenyl]-3-phenyl-5-hydroxyfuran-2-one and/or 4-[4-(methylsulfonyl)phenyl]-3-phenyl-2,5-furandione.

In addition to reducing or eliminating known impurities in prior formulations of rofecoxib, it was found that the process shown in FIG. 1 can produce substantially pure, or highly pure, rofecoxib. Specifically, after the recrystallization step described above, the rofecoxib as described herein can be about 99.9% pure, with about 0.1% or less total impurities as detailed in FIG. 2. It was also found that the process shown in FIG. 1 can produce substantially pure, or highly pure, rofecoxib that contains at least one impurity having beneficial therapeutic effects that is in an amount above the limit of detection. In one embodiment, the impurity having beneficial therapeutic effects is a prodrug of rofecoxib, such as 4-[4-(methylsulfinyl)phenyl]-3-phenyl-2(5H)-furanone.

In one aspect of the subject matter disclosed herein, the substantially pure rofecoxib contains less than about 0.40%, 0.30%, 0.25%, 0.20%, or 0.15% total impurities.

In another aspect, highly pure rofecoxib as provided herein contains less than about 0.075%, 0.050%, 0.025%, 0.020%, or 0.001% total impurities.

In one aspect, the rofecoxib as provided herein contains less than about 0.25%, 0.20%, 0.15%, 0.10%, 0.05%, 0.02% or 0.01% of 4-[4-(methylthio)phenyl]-3-phenyl-2(5H)-furanone and/or 4-[4-(methylsulfinyl)phenyl]-3-phenyl-2(5H)-furanone as an impurity. In other aspects, the rofecoxib as provided herein contains greater than or equal to about 0.001%, 0.005%, 0.01%, 0.02%, 0.05%, or 0.10%, but in all cases less than or equal to about 0.15%, of 4-[4-(methylthio)phenyl]-3-phenyl-2(5H)-furanone and/or 4-[4-(methylsulfinyl)phenyl]-3-phenyl-2(5H)-furanone as an impurity.

In other aspects, the rofecoxib as provided herein contains less than about 0.10%, 0.05%, 0.02%, 0.01%, or is free of 4-[4-(methylsulfonyl)phenyl]-3-phenyl-5-hydroxyfuran-2-one. In another aspect, the rofecoxib as provided herein contains less than about 0.10%, 0.05%, 0.02%, 0.01%, or is free of 4-[4-(methylsulfonyl)phenyl]-3-phenyl-2,5-furandione.

In one embodiment, representative sampling by taking and analyzing a suspension in a stirred suspension shows that a full conversion of 4-[4-(methylsulfinyl)phenyl]-3-phenyl-2(5H)-furanone can be reached, wherein 4-[4-(methylsulfinyl)phenyl]-3-phenyl-2(5H)-furanone is not detected. In one embodiment, sampling 1 mL reaction medium by cooling to room temperature, filtration and analyzing cake and mother liquors shows the presence of 4-[4-(methylsulfinyl)phenyl]-3-phenyl-2(5H)-furanone at 0.02% area basis in the cake. In one embodiment, sampling 1 mL reaction medium by cooling to room temperature and addition of 2V water, filtration and analysis of cake and mother liquors shows 4-[4-(methylsulfinyl)phenyl]-3-phenyl-2(5H)-furanone at 0.02% area basis in the cake. In one embodiment, analysis of the whole product of the experiment, obtained after cooling the reaction medium to room temperature, addition of 2V water, cooling to 0° C., filtration and standard cake washings, shows 4-[4-(methylsulfinyl)phenyl]-3-phenyl-2(5H)-furanone content at 0.02% area basis in the cake.

Without being bound by theory, in one embodiment, the presence of a basic salt in the crude or final product, such as sodium sulfite, sodium sulfide, sodium acetate, sodium bicarbonate, calcium carbonate, or potassium cyanide is thought to contribute to the production of the 4-[4-(methylsulfonyl)phenyl]-3-phenyl-5-hydroxyfuran-2-one impurity. In one embodiment, control of the rate of production of basic salts in the manufacture of crude rofecoxib, or avoidance of using or forming a basic salt in the oxidation or recrystallization step, is crucial for the UHPLC profile of the recrystallized compound. Clarifying filtration can be efficient in avoiding increased 4-[4-(methylsulfonyl)phenyl]-3-phenyl-5-hydroxyfuran-2-one levels during UHPLC analysis. In one embodiment, quench of the basic salt, e.g. sodium sulfite, sodium sulfide, sodium acetate, sodium bicarbonate, calcium carbonate, or potassium cyanide, is suppressed in the oxidation process of step 4. In another embodiment, the basic salt may be removed from the crude or final product by polishing filtration. In yet another embodiment, performing the manufacturing process in an inert atmosphere alone, or in combination with a basic salt quench, can be efficient in avoiding increased 4-[4-(methylsulfonyl)phenyl]-3-phenyl-5-hydroxyfuran-2-one levels during UHPLC analysis. In some embodiments, performing the manufacturing process in an inert atmosphere alone, or in combination with a basic salt quench, forms rofecoxib substantially free of 4-[4-(methylsulfonyl)phenyl]-3-phenyl-5-hydroxyfuran-2-one levels during UHPLC analysis. In some embodiments, crude rofecoxib is formed by sulfoxide formation. In some embodiments, crude rofecoxib is formed by suspending 4-[4-(methylthio)phenyl]-3-phenyl-2(5H)-furanone and a catalytic amount of sodium tungstate dihydrate are suspended in acetonitrile. In some embodiments, crude rofecoxib is formed by heating the 4-[4-(methylthio)phenyl]-3-phenyl-2(5H)-furanone and tungstate suspension to about 65° C. In some embodiments, crude rofecoxib is formed by maintaining the slurry at temperature until the reaction is complete, then it is allowed to cool to ambient temperature. In some embodiments, crude rofecoxib is formed by adding aqueous sodium sulfite solution to the slurry. In some embodiments, crude rofecoxib is formed by isolating it from the slurry by centrifugation at 0° C. In some embodiments, crude rofecoxib is obtained by washing the collected solids with water and isopropanol. In some embodiments, rofecoxib is formed by the steps of bromination of 4'-(methylthio)acetophenone in the presence of TBABr$_3$ to obtain an intermediate RXB-Bromocetone product, involving the intermediate product with Phenylacetic acid (RSM2) in a nucleophilic substitution reaction in the presence of sodium hydroxide to obtain a RXB-Phenylacetate product, crystallizing the product in isopropanol and achieving filterable crystals, intramolecularly cyclizing of the product of stage 2 at 70° C. in DMSO in presence of diisopropylamine, converting 4-[4-(methylthio)phenyl]-3-phenyl-2(5H)-furanone to highly pure rofecoxib or substantially pure rofecoxib by use of hydrogen peroxide with a catalytic amount of dihydrate sodium tungsten in acetonitrile, and recrystallizing the rofecoxib in a mixture of DMSO and water.

Purity of the resulting rofecoxib as described herein is determined as a percent area basis, typically as quantified by analytical chromatography, such as using HPLC, UHPLC, UPLC or other analytical means in the art.

Manufacturing Process Development

Several routes for synthesizing rofecoxib are described in the literature and in patent references. See International Patent Application Publication No. WO 98/00416, which is incorporated herein in its entirety. Some of the key results from the lab-scale development of rofecoxib manufacturing process A$_1$ are summarized below.

Some of the early laboratory trials included oxidation of 4'-(Methylthio)acetophenone in the first step of rofecoxib synthesis. This approach may be abandoned in favor of performing the oxidation of the sulfide in the last bond forming step in order to decrease the level of impurities in intermediates and rofecoxib.

Dimethylformamide (DMF) was used in prior manufacturing processes. This high boiling-point Class 2 solvent may be replaced with acetonitrile (a lower boiling-point Class 2 solvent) or DMSO (Class 3 solvent).

A safer alternative to bromine (Br$_2$) may be desired. Therefore, alternative reagents were explored and tetrabutylammonium bromide (TBAB$_3$) can be a useful alternative.

In one embodiment, the amount of TBAB$_3$ used is less than one equivalent relative to the starting material, 4'-(Methylthio)acetophenone, in order to prevent formation of a dibromacetone impurity.

In some embodiments, the step 1 product, RXB-Bromacetone, is not isolated because the intermediate may be a sensitizer and lachrymator.

The solvent system used in crystallization of RXB-Phenylacetate in step 2 is important for reducing impurity levels and for increasing yield. In one embodiment, a solvent system including isopropanol and dichloromethane provides the best results at lab scale.

The yield and purity of the cyclization reaction in step 3 is solvent dependent. In one embodiment, solvents used for the reaction (DMSO) and crystallization (DMSO and isopropanol) provide the best results for purity and yield of 4-[4-(methylthio)phenyl]-3-phenyl-2(5H)-furanone at lab scale. In addition, no drying step may be needed.

Although step 4 (oxidation) and step 5 (crystallization) result in highly pure rofecoxib, in one embodiment the reaction conditions may need to be optimized to minimize the amount of the incomplete oxidation product, 4-[4-(methylsulfinyl)phenyl]-3-phenyl-2(5H)-furanone, observed during scale up.

In one embodiment, only one crystal form was observed in crude rofecoxib of step 4 and crystallized rofecoxib of step 5 during the lab scale development.

Rofecoxib Characterization

The structure and physical properties of rofecoxib have been established by spectroscopic and solid-state characterization of the analytical reference standard, lot SHD390-187. The molecular formula $C_{17}H_{14}O_4S$ and structure are confirmed by elemental analysis, high-resolution mass spectrometry, nuclear magnetic resonance spectroscopy, IR spectroscopy, and X-ray powder diffractometry. Solid-state characterization data support the anhydrous crystalline form.

In one embodiment, the results of the elemental analysis, shown in Table 2, are consistent with the empirical formula for rofecoxib, $C_{17}H_{14}O_4S$.

TABLE 2

Elemental Analysis of Rofecoxib
Amount of Element, (%)

|  | C | H | S | O |
|---|---|---|---|---|
| Theoretical[a] | 64.95 | 4.49 | 10.20 | 20.36 |
| Experimental | 64.90 | 4.55 | 10.18 | 20.37[b] |

[a]Theoretical values were determined on the basis of the expected molecular formula of rofecoxib, $C_{17}H_{14}O_4S$.
[b]The experimental percentage of oxygen was calculated as follows: 100%-% C-% H-% S.

Figure 4:
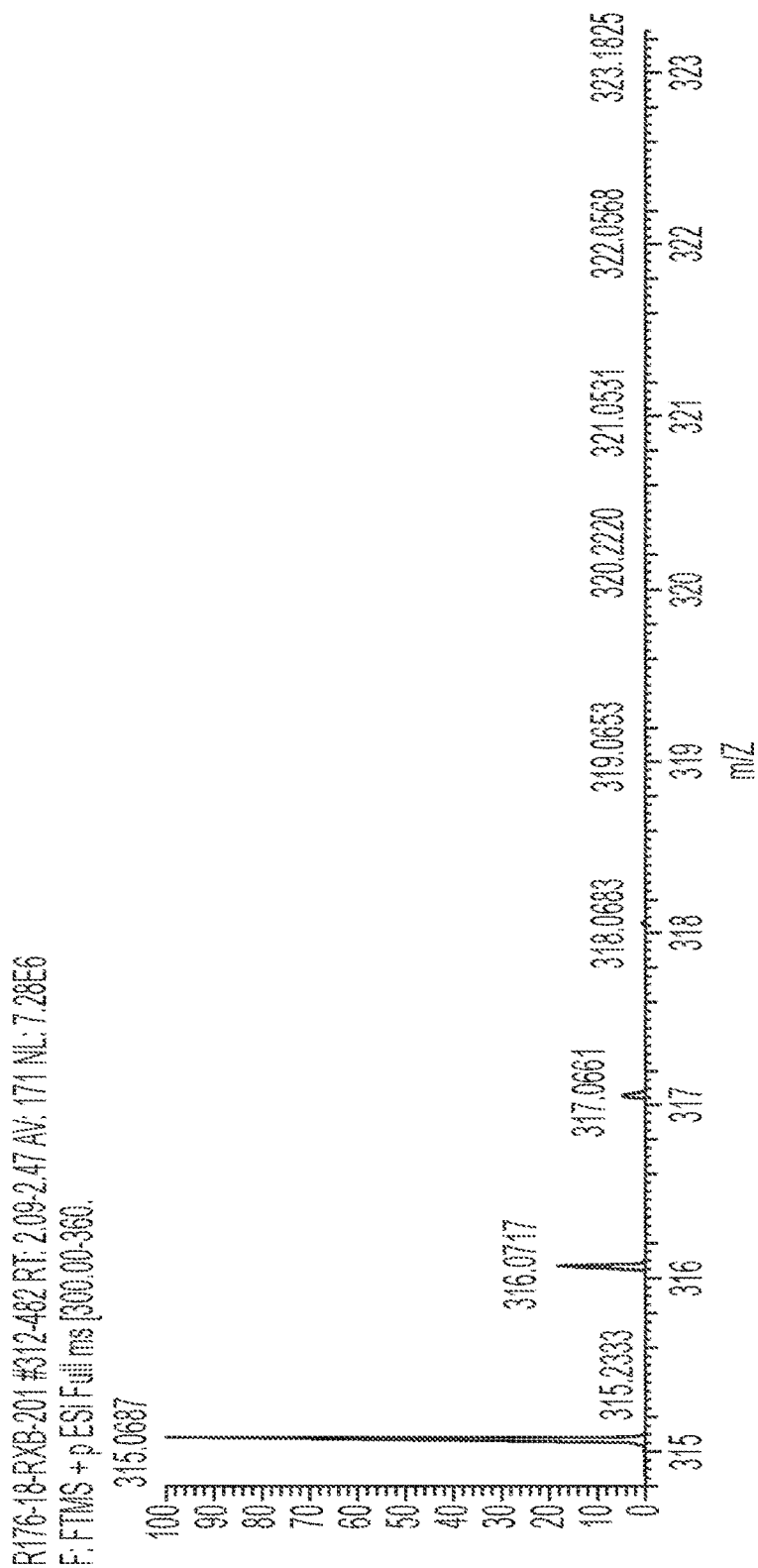
FIG. 4 shows the mass spectrum of rofecoxib in acetonitrile.

In one embodiment, high-resolution mass spectrometry data were obtained on rofecoxib in electrospray ionization positive mode (ESI-Pos) mode. The mass spectrum of rofecoxib in acetonitrile is shown in FIG. 4. The accurate mass of the [M+H]$^+$ ion is 315.0687 Daltons, which is a 0.3 ppm difference from the theoretical mass, 315.0686 Daltons.

Figure 5A:
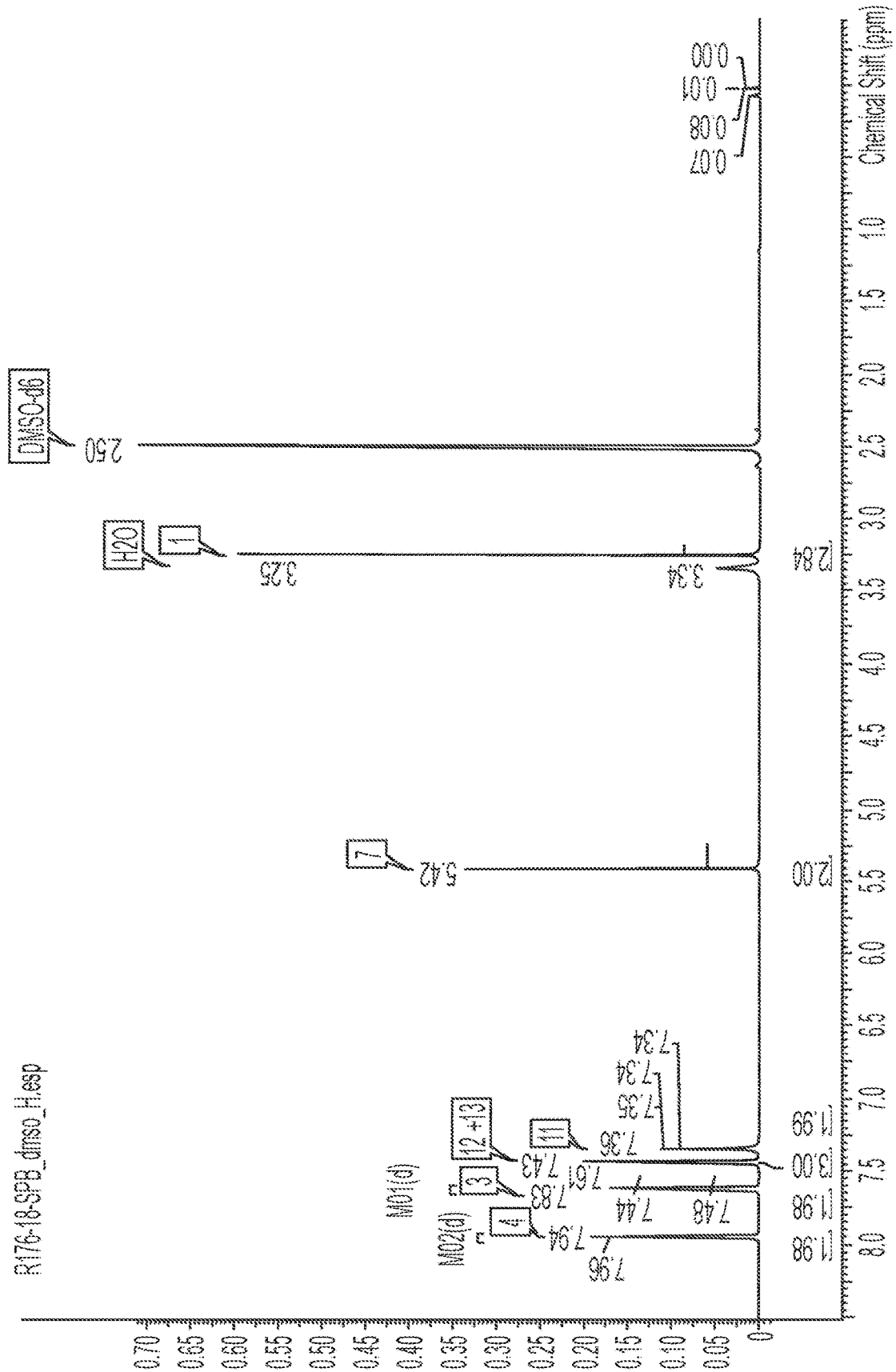
FIGS. 5A-D show the Nuclear Magnetic Resonance (NMR) spectroscopy analysis of rofecoxib.
Figure 5B:
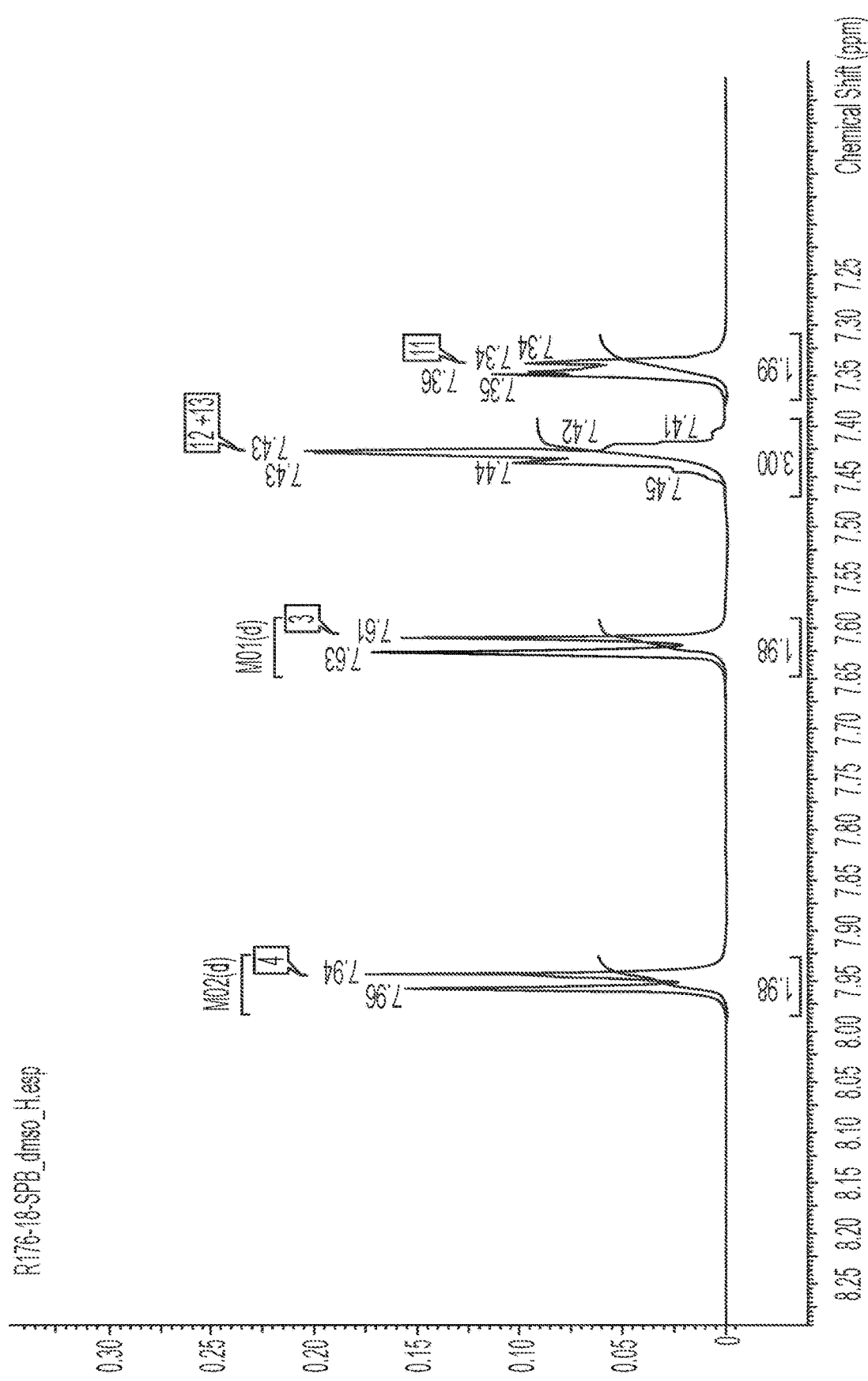
Figure 5C:
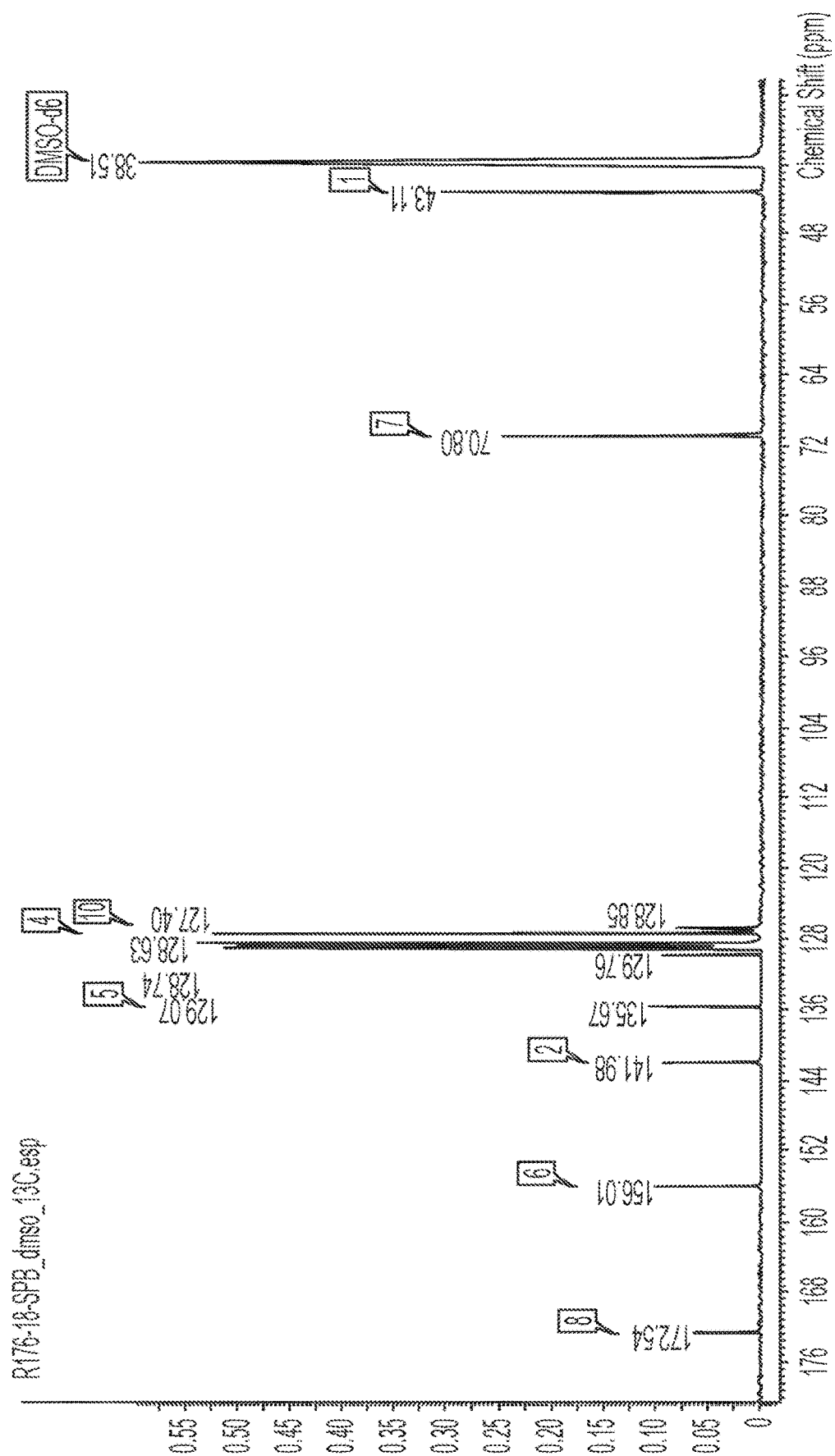
Figure 5D:
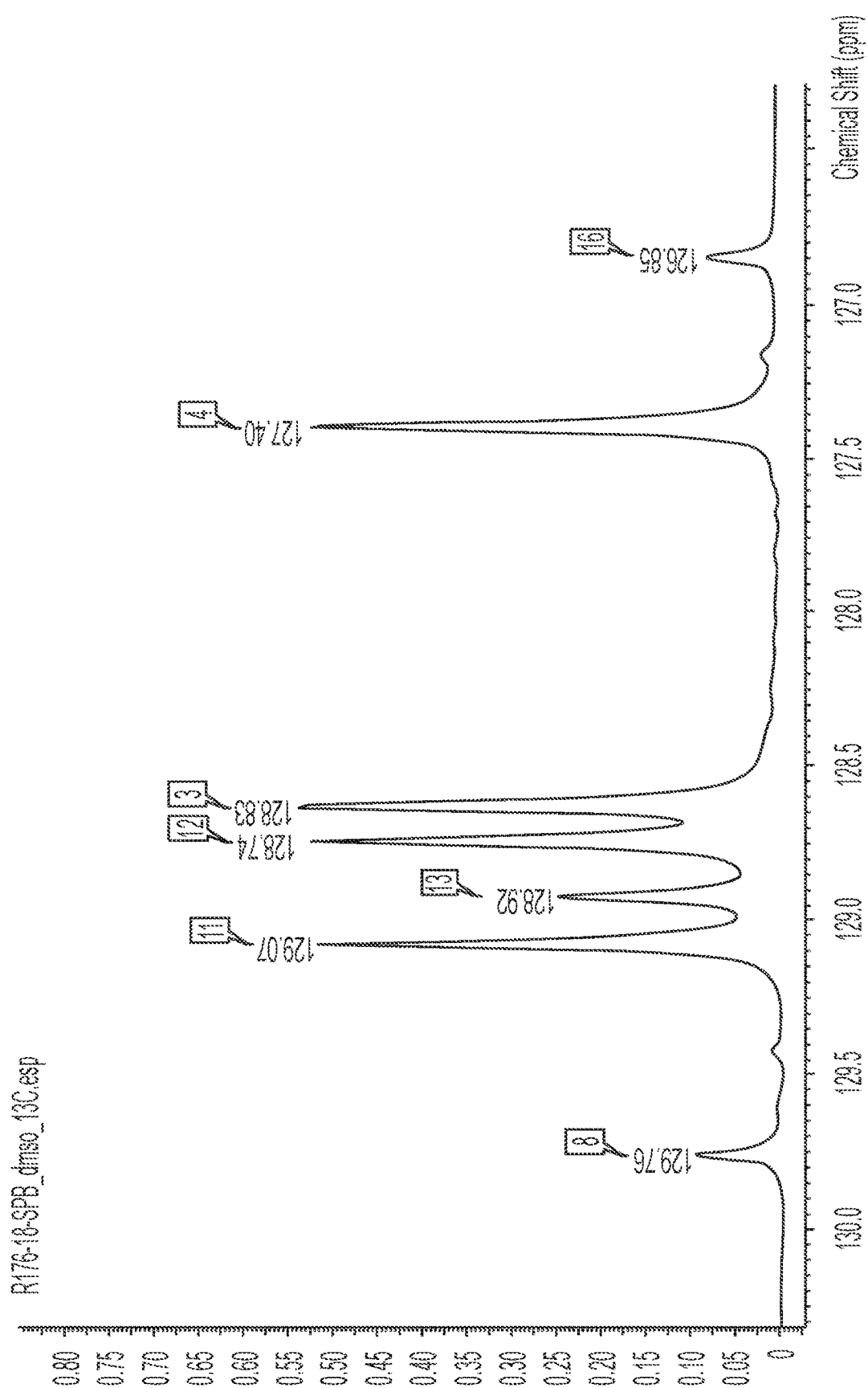

The Nuclear Magnetic Resonance (NMR) spectroscopy data also support the structure of rofecoxib as shown in analysis in FIGS. 5A-D. FIG. 5A shows the 600 MHz $^1$H-NMR spectrum of rofecoxib in DMSO-d$_6$. FIG. 5B shows the expanded 600 MHz $^1$H-NMR spectrum of rofecoxib in DMSO-d$_6$. FIG. 5C shows the 125 MHz $^{13}$C-NMR spectrum of rofecoxib in DMSO-d$_6$. FIG. 5D shows the expanded 125 MHz $^{13}$C-NMR spectrum of rofecoxib in DMSO-d$_6$.

Below is the numbering scheme for assigning NMR resonances in rofecoxib

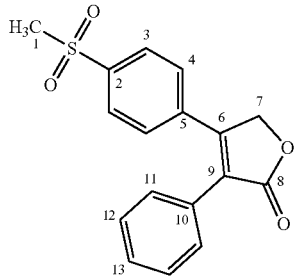 [SMILES: CS(=O)(=O)c1ccc(C2=C(c3ccccc3)C(=O)OC2)cc1]

Figure 6A:
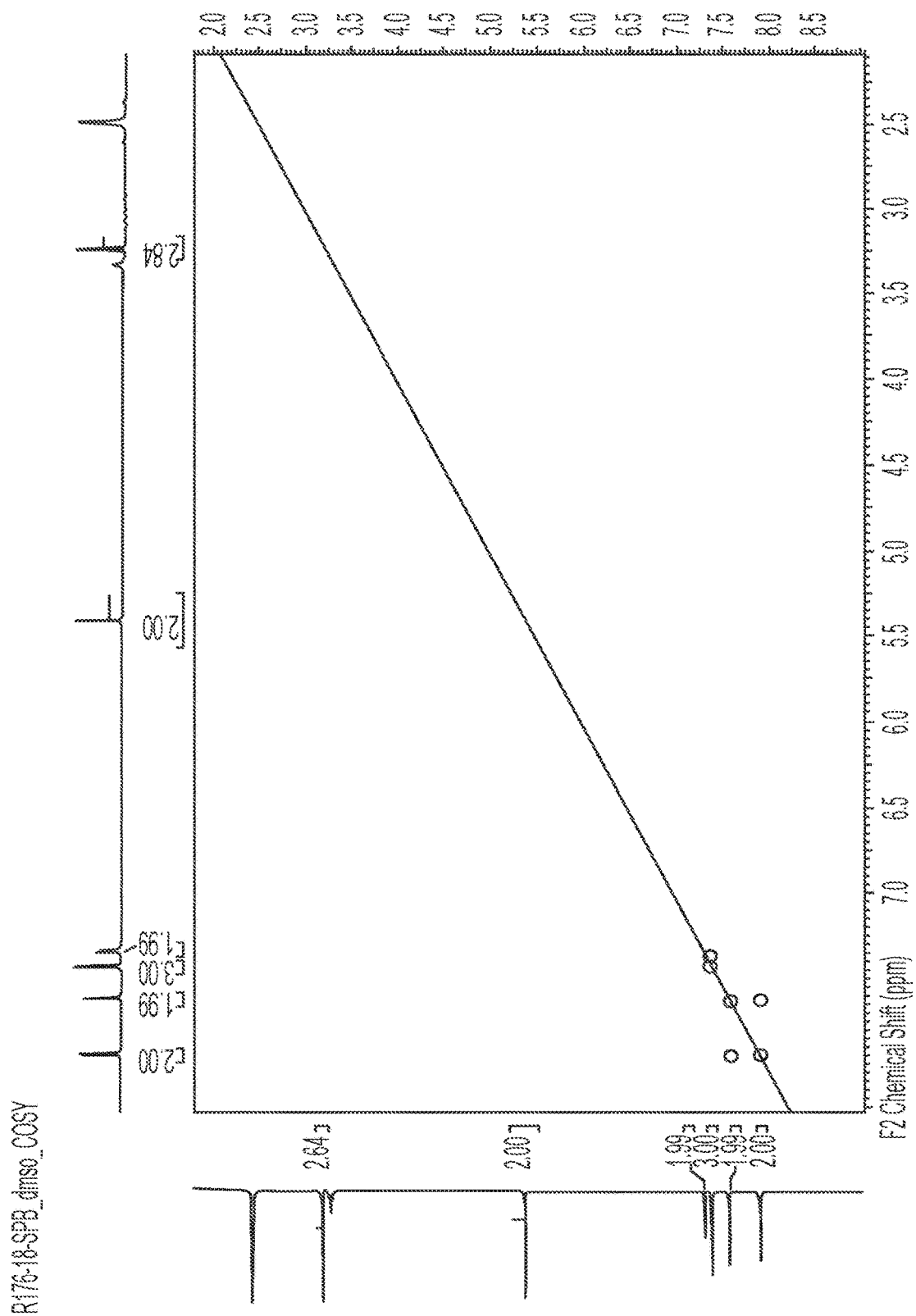
FIGS. 6A-C show the 2-dimension spectra of rofecoxib.
Figure 6B:
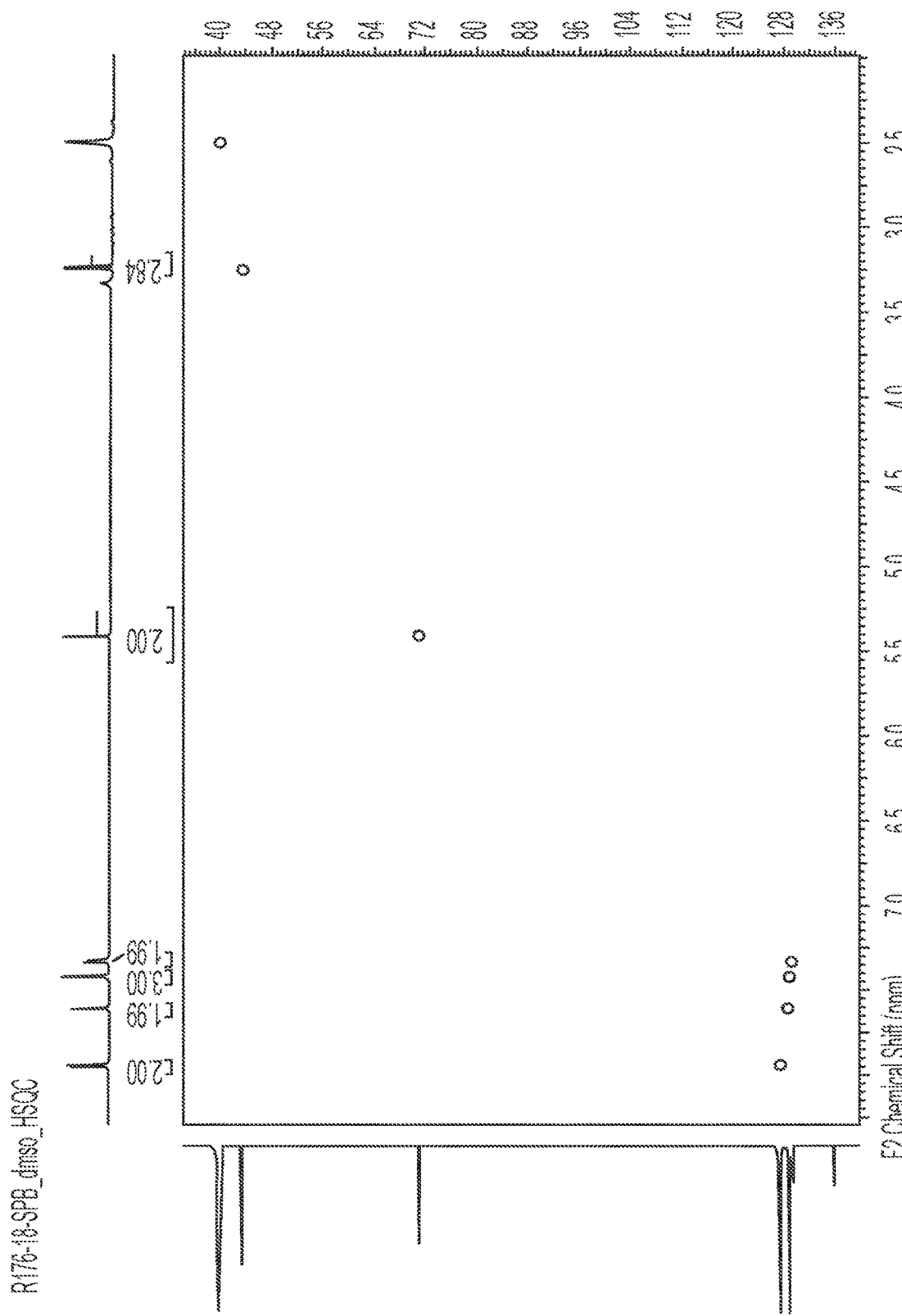
Figure 6C:
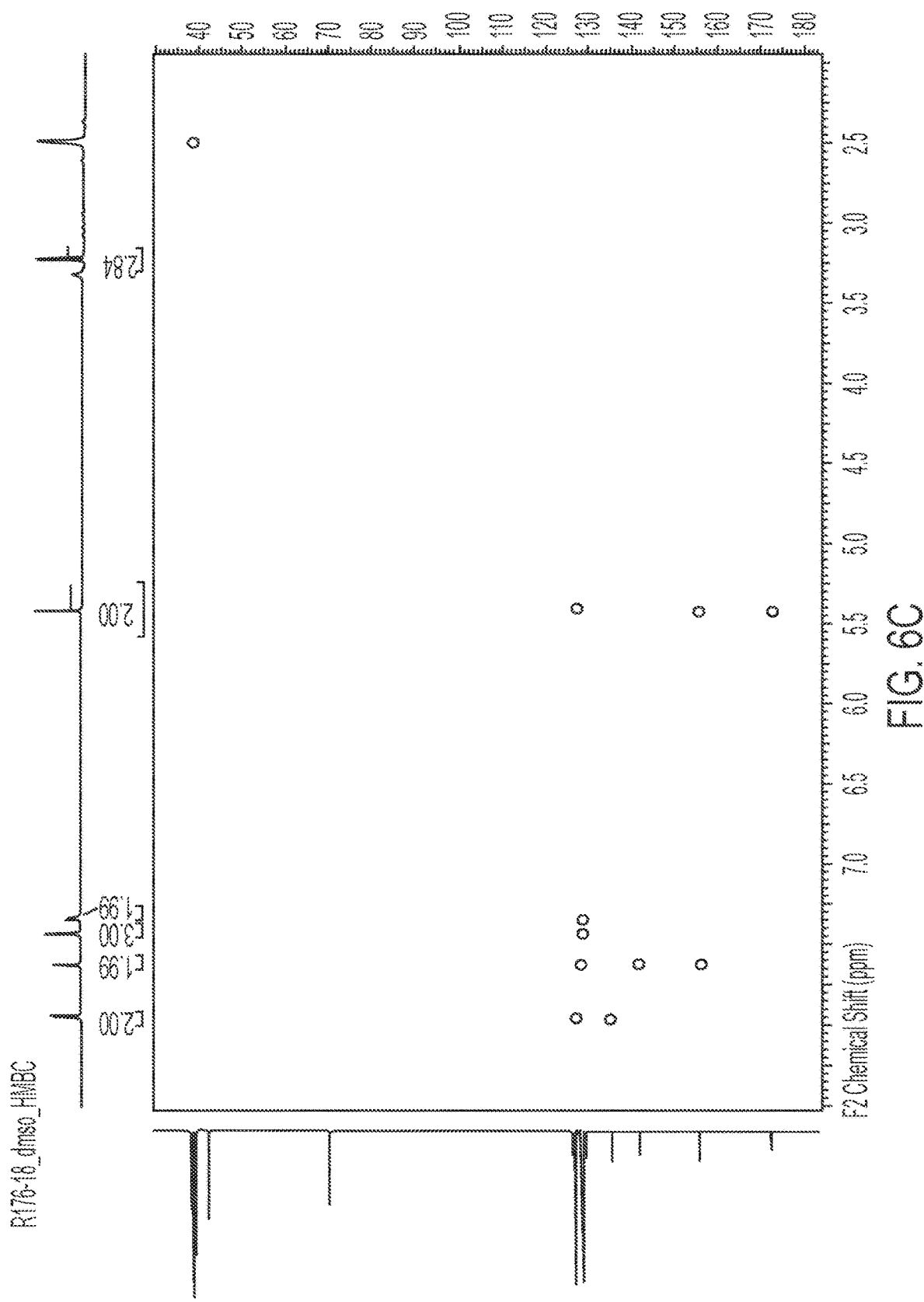

The proton and carbon resonances listed in Table 2 were assigned from 2-dimensional (2D) correlation spectroscopy (COSY), heteronuclear single quantum coherence (HSQC), and heteronuclear multiple bond correlation (HMBC) experiments. The 2-dimension spectra are shown in FIGS. 6A-C. FIG. 6A shows the H-H COSY NMR spectrum of rofecoxib in DMSO-$d_6$. FIG. 6B shows the HSQC multiplicity edited NMR Spectrum of rofecoxib in DMSO-$d_6$. FIG. 6C shows the HMBC NMR spectrum of rofecoxib in DMSO-$d_6$.

Figure 7:
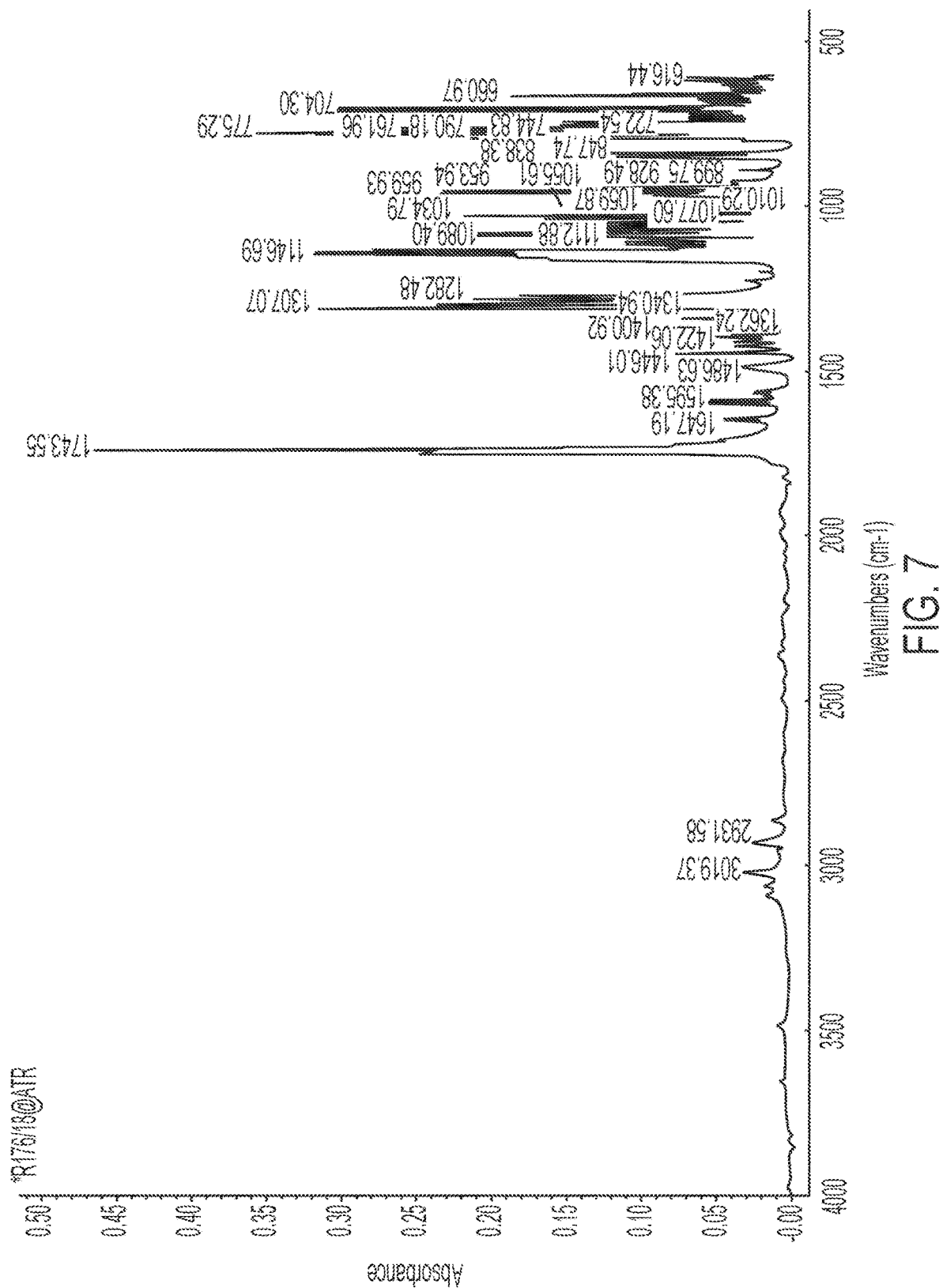
FIG. 7 shows the infrared (IR) absorbance spectrum of solid rofecoxib acquired using an Attenuated Total Reflectance (ATR) cell.

In one embodiment, the infrared (IR) absorbance spectrum of solid rofecoxib was acquired using an Attenuated Total Reflectance (ATR) cell and is shown in FIG. 7. The analysis of the absorbance is provided in Table 3. The results of IR spectroscopy support the assigned structure.

TABLE 3

Proposed IR Absorbance Analysis of Rofecoxib

| Wavenumber (cm$^{-1}$) | Tentative Assignment |
|---|---|
| 3019, 2932 | C—H stretch |
| 1744 | C=O stretch |
| 1647, 1595 | C=C stretch |
| 1446 | C—H bending |
| 1307, 1282 | C—O stretch |
| 1147 | S=O stretch |
| 1035 | In-plane C—H bending |
| 775 | Out-of-plane C—H bending |

Figure 8:
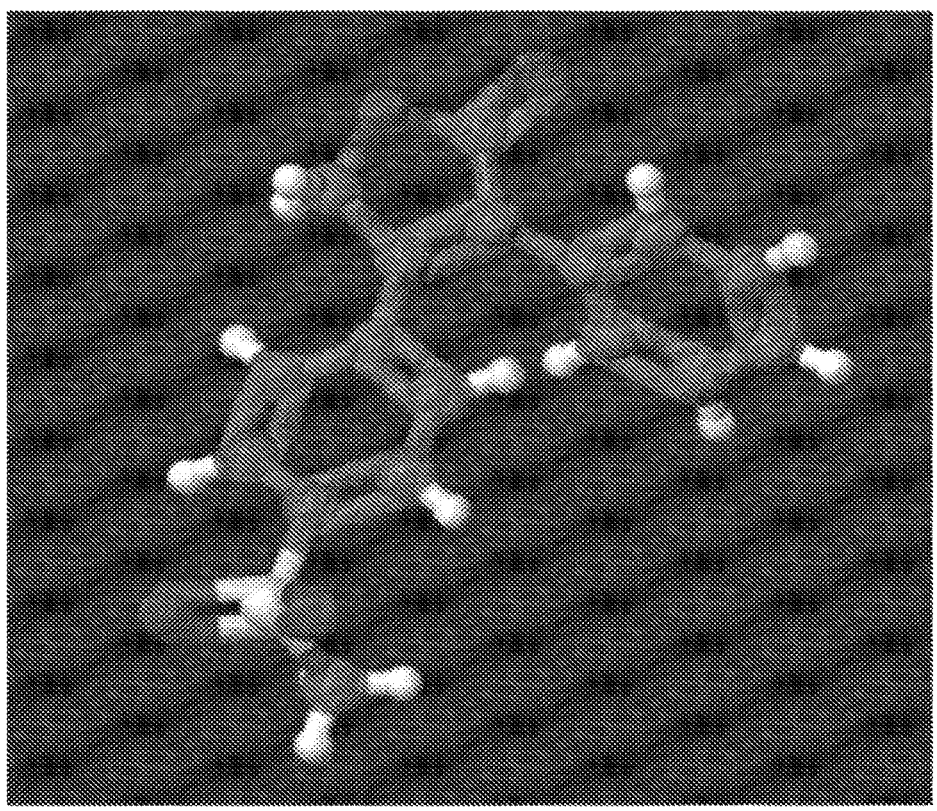
FIG. 8 shows the single crystal structure of rofecoxib in the Cambridge Structural Database.
Figure 9:
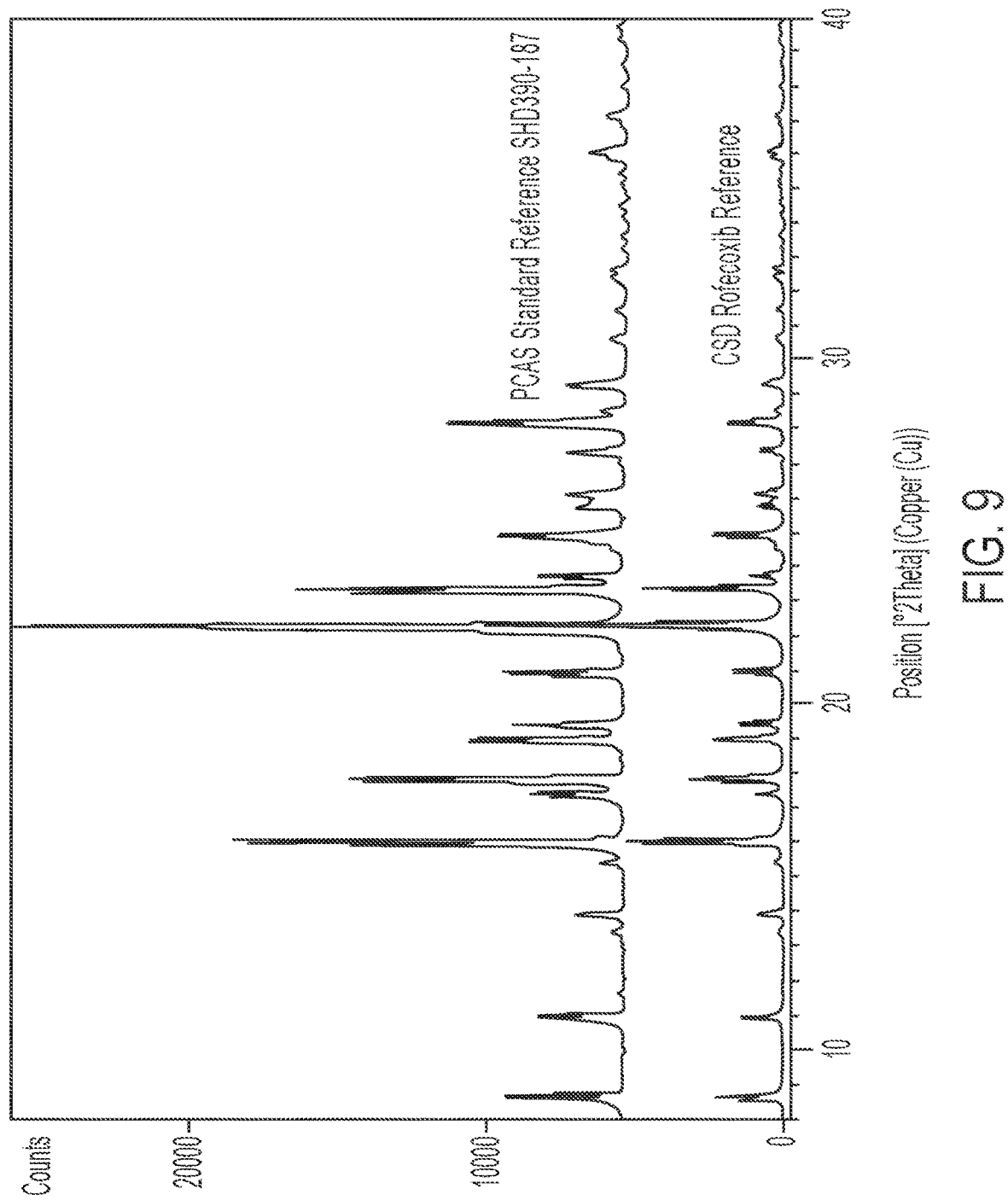
FIG. 9 shows an overlay plot showing that the X-ray powder diffraction (XRPD) patterns of the rofecoxib reference standard compares favorably to the XRPD pattern that was calculated from the crystal structure reported in the Cambridge Structural Database.

In one embodiment, rofecoxib is a single crystal form (Form A), which is the only structure reported in the Cambridge Structural Database as shown in FIG. 8. See Groom C. R., Bruno M P, Lightfoot S C, et al. The Cambridge Structural Database. Acta Cryst. 2016; B72:171-179. The overlay plot shown in FIG. 9 shows that the X-ray powder diffraction (XRPD) patterns of the manufactured rofecoxib reference standard compares favorably to the XRPD pattern that was calculated from the crystal structure reported in the Cambridge Structural Database.

In one embodiment, the analytical procedure employed herein uses reversed-phase ultra-high performance liquid chromatography with gradient elution and UV detection at 290 nm for the determination of identity, assay and impurities of rofecoxib drug substance. The separation is performed using an acid-modified, polar mobile phase on a phenyl-hexyl column. Assay is calculated using an external reference standard. Impurities are reported as area percent. Identity is confirmed by comparison of the sample retention time to that of the reference standard.

The physical properties of rofecoxib are provided in Table 4.

TABLE 4

Rofecoxib Specification

| Test Item | Analytical Procedure | Acceptance Criteria |
|---|---|---|
| Appearance | Visual inspection | White to off-white to light yellow powder |
| Identification | FTIR; USP <197> | Confirms to reference |
| Identification | UHPLC | Confirms to reference |
| Assay | UHPLC | 95.0-105.0 % w/w on the anhydrous basis |
| Impurities | UHPLC | Any Individual Impurity ≤ 0.50 % area Total Impurities ≤ 1.0 % area |
| Water Content | Coulometric titration (KF); USP <921>, Method IC | Report result |
| Residual Solvents | GC | Acetonitrile ≤ 410 ppm Dichloromethane ≤ 600 ppm Dimethylsulfoxide ≤ 5000 ppm Isopropanol ≤ 5000 ppm Methanol ≤ 3000 ppm |
| Polymorphic Form | XRPD;USP <941> | Conforms to reference (Form A) |
| Particle size | Laser diffraction, USP <429> | Report result |
| Residue on Ignition | USP <281> | ≤ 0.1 % w/w |

Figure 10A:
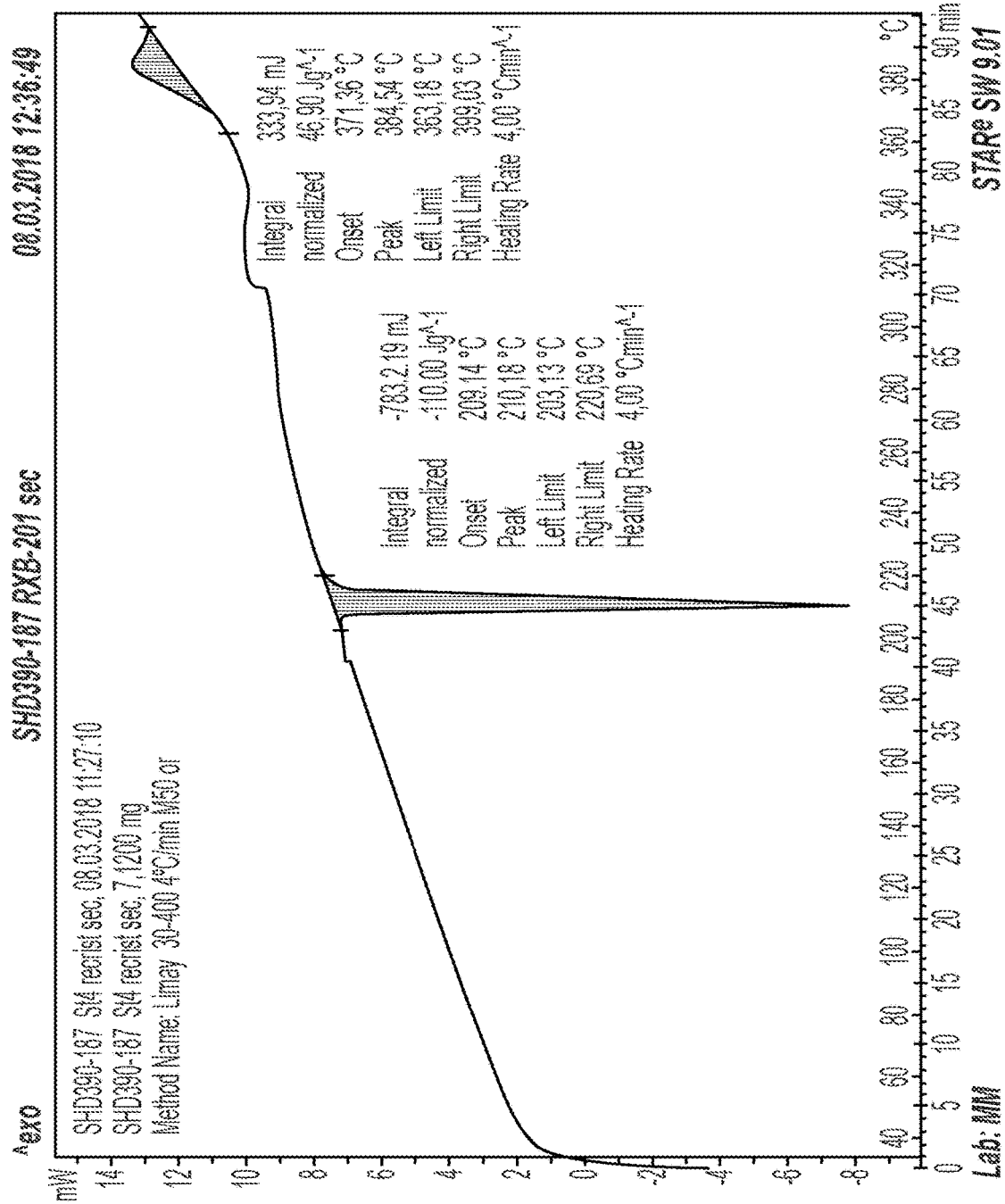
FIGS. 10A-B show rofecoxib characteristics.

The thermal properties of rofecoxib were evaluated using differential scanning calorimetry (DSC). In one embodiment, rofecoxib was heated from 30 to 400° C. at a ramp rate of 4° C. min$^{-1}$. The DSC thermogram in FIG. 10A shows an endothermic event with onset temperature of 209° C. and peak maxima at 201° C., corresponding to melting, and a broad exothermic event with onset temperature of 371° C. and peak maxima at 385° C., corresponding to decomposition. The absence of an endotherm at temperature below the melting temperature is consistent with the anhydrous crystal structure of rofecoxib.

Figure 10B:
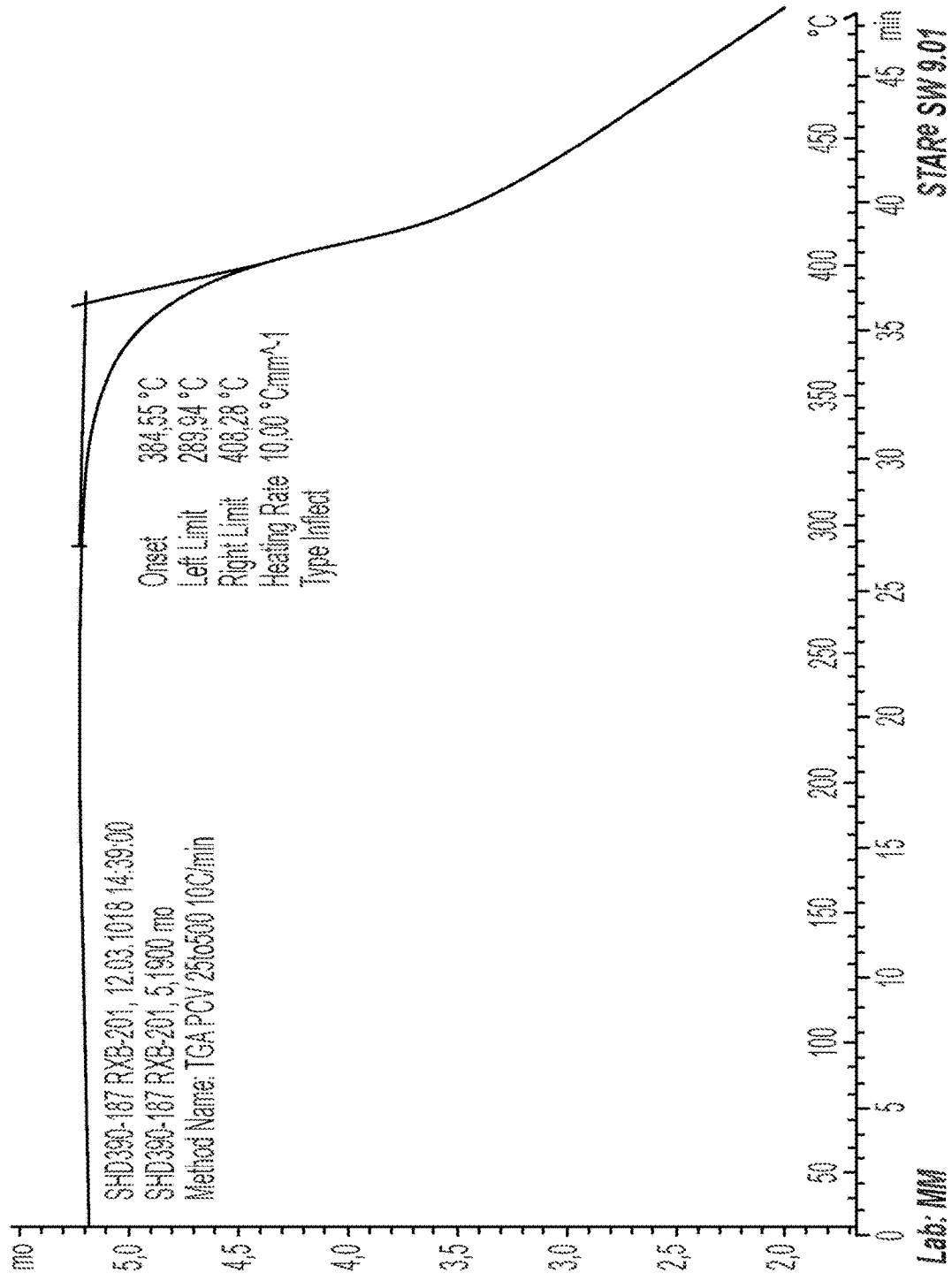

Thermogravimetric analysis (TGA) was performed by heating rofecoxib from ambient to 500° C. at a ramp rate of 10° C. min$^{-1}$. The TGA data as shown in FIG. 10B indicate no weight loss prior to or during the melt; this result is consistent with the anhydrous crystal structure of rofecoxib. The weight loss at temperatures above 370° C. corresponds to decomposition of rofecoxib.

Residual DMSO in rofecoxib drug substance is quantified against an external standard using direct-injection gas chromatography and FID detection. The separation is performed using a dimethylpolysiloxane column and helium carrier gas. Residual acetonitrile, dichloromethane, isopropanol, and methanol in rofecoxib drug substance are quantified against external standards using headspace gas chromatography and FID detection. The separation is performed using a bonded-wax column and helium carrier gas.

Formulation

In certain aspects, the substantially pure or highly pure rofecoxib as provided herein can be formulated as a pharmaceutically acceptable salt or solvate thereof to produce a pharmaceutical composition. In certain aspects, the substantially pure or highly pure rofecoxib or a pharmaceutically acceptable salt or solvate thereof as provided herein may be formulated with a pharmaceutically acceptable carrier to produce a pharmaceutical composition. Pharmaceutical compositions comprising substantially pure or highly pure rofecoxib or a pharmaceutically acceptable salt or solvate thereof as provided herein may include the excipients, and may otherwise be formulated, as described in U.S. Pat. No. 6,063,811, which is incorporated herein by reference in its entirety, including but not limited to the formulations specified in Examples 2, 2a, 2b, and 2c of U.S. Pat. No. 6,063,811. The term "pharmaceutically-acceptable salt," in this respect, refers to the relatively non-toxic, inorganic and organic acid salts of compounds of the subject matter described herein.

In some embodiments, the compounds of the subject matter described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the subject matter described herein. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like. See, for example, Berge et al., supra.

Formulations of the subject matter described herein include but are not limited to those suitable for oral, nasal, inhalation, topical (including buccal and sublingual), rectal, vaginal, and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient, which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association a compound of the subject matter described herein with the carrier and, optionally, one or more accessory ingredients. In general, the formulations are prepared by uniformly and intimately bringing into association a compound of the subject matter described herein with liquid carriers, or finely divided solid carriers, or both, and then, if necessary, shaping the product.

Formulations of the subject matter described herein suitable for oral administration may be in the form of capsules, cachets, chewable gels, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), and/or as mouthwashes and the like, each containing a predetermined amount of a compound of the subject matter described herein as an active ingredient. A compound of the subject matter described herein may also be administered as a bolus, electuary or paste.

In solid dosage forms of the subject matter described herein for oral administration (capsules, tablets, pills, dragees, powders, granules, and the like), the active ingredient is mixed with one or more pharmaceutically-acceptable carriers, such as microcrystalline cellulose, lactose, or dicalcium phosphate, and/or any of the following: fillers or extenders, such as starches, lactose, microcrystalline cellulose sucrose, glucose, mannitol, and/or silicic acid; binders, such as, for example, carboxymethylcellulose, hydroxypropylcellulose, alginates, gelatin, polyvinyl pyrrolidone, sucrose, and/or acacia; humectants, such as glycerol; disintegrating agents, such as agar-agar, calcium carbonate, croscarmellose sodium, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, sodium lauryl sulfate, and polyethylene oxide-polybutylene oxide copolymer; absorbents, such as kaolin and bentonite clay; lubricants, such as talc, calcium stearate, magnesium stearate, solid polyethylene glycols, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxybutylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the subject matter described herein, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxybutylmethyl cellulose in varying proportions, to provide the desired release profile, other polymer matrices, liposomes, and/or microspheres. They may be sterilized by, for example, filtration through a bacteria-retaining filter, or by incorporating sterilizing agents in the form of sterile solid compositions, which can be dissolved in sterile water or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration of the compounds of the subject matter disclosed herein include pharmaceutically-acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxybutyl-β-cyclodextrin, may be used to solubilize compounds.

Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar, and tragacanth, and mixtures thereof.

Dosage forms for the topical or transdermal administration of a compound of the subject matter disclosed herein include powders, sprays, ointments, pastes, creams, lotions, gels, solutions, patches, and inhalants. The active compound may be mixed under sterile conditions with a pharmaceutically-acceptable carrier, and with any preservatives, buffers, or propellants which may be required.

The ointments, pastes, creams and gels may contain, in addition to an active compound of the subject matter disclosed herein, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the subject matter disclosed herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane.

Transdermal patches have the added advantage of providing controlled delivery of a compound of the subject matter disclosed herein to the body. Such dosage forms can be made by dissolving, or dispersing the pharmaceutical agents in the proper medium. Absorption enhancers can also be used to increase the flux of the pharmaceutical agents of the subject matter disclosed herein across the skin. The rate of such flux can be controlled, by either providing a rate-controlling membrane or dispersing the compound in a polymer matrix or gel.

Ophthalmic formulations, eye ointments, powders, solutions, and the like, are also contemplated as being within the scope of the subject matter disclosed herein.

Pharmaceutical compositions of the subject matter disclosed herein suitable for parenteral administration comprise one or more compounds of the subject matter disclosed herein in combination with one or more pharmaceutically-acceptable sterile isotonic aqueous or nonaqueous solutions, dispersions, suspensions, or emulsions; or sterile powders which may be reconstituted into sterile injectable solutions or dispersions just prior to use, which may contain antioxidants, buffers, bacteriostats, or solutes which render the formulation isotonic with the blood of the intended recipient or suspending or thickening agents.

In some cases, in order to prolong the effect of a drug, it is desirable to slow the absorption of the drug from subcutaneous or intramuscular injection, which may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle. One strategy for depot injections includes the use of polyethylene oxide-polypropylene oxide copolymers wherein the vehicle is fluid at room temperature and solidifies at body temperature.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot-injectable formulations are also prepared by entrapping the drug in liposomes or microemulsions, which are compatible with body tissue.

When the compounds of the subject matter disclosed herein are administered as pharmaceuticals, to subjects, they can be given per se or as a pharmaceutical composition containing, for example, 0.1% to 99.5% (more preferably, 0.5% to 90%) of active ingredient in combination with a pharmaceutically-acceptable carrier.

The compounds and pharmaceutical compositions of the subject matter disclosed herein can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the subject matter disclosed herein may be administered concurrently with another anticancer agents).

The compounds of the subject matter disclosed herein may be administered intravenously, intramuscularly, intraperitoneally, subcutaneously, topically, orally, or by other acceptable means. The compounds may be used to treat arthritic conditions in mammals (e.g., humans, livestock, and domestic animals), racehorses, birds, lizards, and any other organism which can tolerate the compounds.

The subject matter disclosed herein also provides a pharmaceutical pack or kit comprising one or more containers filled with one or more of the ingredients of the pharmaceutical compositions of the subject matter disclosed herein. Optionally associated with such container(s) can be a notice in the form prescribed by a governmental agency regulating the manufacture, use, or sale of pharmaceuticals or biological products, which notice reflects approval by the agency of manufacture, use, or sale for human administration.

Wetting agents, emulsifiers, and lubricants, such as sodium lauryl sulfate, magnesium stearate, and polyethylene oxide-polybutylene oxide copolymer, as well as coloring agents, release agents, coating agents, sweetening, flavoring and perfuming agents, preservatives, and antioxidants can also be present in the pharmaceutical compositions described herein.

In one embodiment, the pharmaceutical compositions useful according to the methods of the subject matter described herein can be formulated in any manner suitable for pharmaceutical use.

In one embodiment, the formulations of the subject matter disclosed herein can be administered in pharmaceutically-acceptable solutions, which may routinely contain pharmaceutically-acceptable concentrations of salt, buffering agents, preservatives, compatible carriers, adjuvants, and optionally other therapeutic ingredients.

Administration

Some aspects of the subject matter disclosed herein involve administering a pharmaceutical composition comprising an effective amount of an active agent to a subject to achieve a specific outcome.

For use in therapy, an effective amount of the compound can be administered to a subject by any mode allowing the compound to be taken up by the appropriate target cells. "Administering" the pharmaceutical composition of the subject matter described herein can be accomplished by any means known to the skilled artisan. Specific routes of administration include, but are not limited to, oral, transdermal (e.g., via a patch), parenteral injection (subcutaneous, intradermal, intramuscular, intravenous, intraperitoneal, intrathecal, etc.), or mucosal (intranasal, intratracheal, inhalation, intrarectal, intravaginal, etc.). An injection can be in a bolus or a continuous infusion.

For example, the pharmaceutical compositions according to the subject matter disclosed herein can be administered by intravenous, intramuscular, or other parenteral means. They can also be administered by intranasal application, inhalation, topically, orally, or as implants; even rectal or vaginal use is possible. Suitable liquid or solid pharmaceutical preparation forms are, for example, aqueous or saline solutions for injection or inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops, or preparations with protracted release of active compounds in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, See Langer R (1990) *Science* 249:1527-33, which is incorporated herein by reference in its entirety.

The pharmaceutical compositions disclosed herein can be prepared and administered in dose units. Liquid dose units are vials or ampoules for injection or other parenteral administration. Solid dose units are tablets, capsules, powders, and suppositories. For treatment of a subject, different doses may be necessary depending on activity of the compound, manner of administration, purpose of the administration (i.e., prophylactic or therapeutic), nature and severity of the disorder, age and body weight of the subject. The administration of a given dose can be carried out both by single administration in the form of an individual dose unit or else several smaller dose units. Repeated and multiple administration of doses at specific intervals of days, weeks, or months apart are also contemplated by the subject matter described herein.

The pharmaceutical compositions described herein can be administered per se (neat) or in the form of a pharmaceutically-acceptable salt. When used in medicine the salts should be pharmaceutically acceptable, but non-pharmaceutically-acceptable salts can conveniently be used to prepare pharmaceutically-acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Compositions suitable for parenteral administration conveniently include sterile aqueous preparations, which can be isotonic with the blood of the recipient. Among the acceptable vehicles and solvents are water, Ringer's solution, phosphate buffered saline, dextrose 5% w/w, and isotonic sodium chloride solution. In addition, sterile, fixed oils are conventionally employed as a solvent or suspending medium. For this purpose, any bland fixed mineral or non-mineral oil may be employed including synthetic mono- or diglycerides. In addition, fatty acids such as oleic acid find use in the preparation of injectables. Carrier formulations suitable for subcutaneous, intramuscular, intraperitoneal, intravenous, etc. administrations can be found in *Remington's Pharmaceutical Sciences*, Mack Publishing Company, Easton, Pa.

The compounds useful in the subject matter disclosed herein can be delivered in mixtures of more than two such compounds. A mixture can further include one or more adjuvants in addition to the combination of compounds.

A variety of administration routes is available. The particular mode selected will depend, of course, upon the particular compound selected, the age and general health status of the subject, the particular condition being treated, and the dosage required for therapeutic efficacy. The methods of the subject matter described herein, generally speaking, can be practiced using any mode of administration that is medically acceptable, meaning any mode that produces effective levels of response without causing clinically unacceptable adverse effects. Preferred modes of administration are discussed above.

The compositions can conveniently be presented in unit dosage form and can be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Other delivery systems can include time-release, delayed release, or sustained-release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids, or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the subject matter described herein is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854, 480, 5,133,974 and 5,407,686. In addition, pump-based hardware delivery systems can be used, some of which are adapted for implantation.

In one aspect, the pharmaceutical composition comprising rofecoxib as provided herein can be administered in a variety of manners, including without limitation orally, by subcutaneous or other injection, intravenously or parenterally. The form in which the drug will be administered (e.g., tablet, capsule, solution, suspension, emulsion) will depend on the route by which it is administered. In one aspect, the subject matter disclosed herein includes a pharmaceutical composition comprising substantially pure or highly pure rofecoxib as provided herein and a pharmaceutically acceptable carrier, wherein the pharmaceutical composition is in the form of a tablet, and wherein the amount of the rofecoxib as provided herein is 12.5 mg or 25 mg. In another aspect, the subject matter disclosed herein includes a pharmaceutical composition comprising substantially pure or highly pure rofecoxib as provided herein and a pharmaceutically acceptable carrier, wherein the pharmaceutical composition is in the form of a tablet, and wherein the amount of the rofecoxib as provided herein is about 1 mg, 2 mg, 3 mg, 5 mg, 6.25 mg, 7.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 20 mg, 20.5 mg, 21 mg, 21.5 mg, 22.5 mg, 25 mg, 30 mg, 35 mg, 40 mg, 45 mg, 50 mg, 55 mg, 60 mg, 65 mg, or 70 mg.

In another aspect, the subject matter disclosed herein includes a pharmaceutical composition comprising substantially pure or highly pure rofecoxib as provided herein and a pharmaceutically acceptable carrier, wherein the pharmaceutical composition is in the form of a tablet, and wherein the amount of the rofecoxib as provided herein is about 0.10 mg/kg, 0.15 mg/kg, 0.20 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, or 0.70 mg/kg.

In one aspect, the pharmaceutical composition comprising rofecoxib as provided herein may be packaged with a set of instructions warning the subject of cardiovascular and/or gastrointestinal risks associated with administration of the composition.

The formulations, both for human medical use and veterinary use, of compounds according to the subject matter described herein typically include such compounds in association with a pharmaceutically acceptable carrier.

As used herein, the phrase "pharmaceutically-acceptable carrier" includes but is not limited to a pharmaceutically-acceptable material, composition or vehicle, such as a liquid or solid filler, diluent, excipient, solvent, or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: sugars, such as lactose, microcrystalline cellulose, glucose, and sucrose; starches, such as corn starch and potato starch; cellulose and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as butylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The term "carrier" denotes an organic or inorganic ingredient, natural or synthetic, with which the active ingredient is combined to facilitate the application. The components of the pharmaceutical compositions also are capable of being comingled with the compounds of the present subject matter, and with each other, in a manner such that there is no interaction which would substantially impair the desired pharmaceutical efficiency.

The carrier should be "acceptable" in the sense of being compatible with compounds of the subject matter described herein and not deleterious to the recipient. Pharmaceutically acceptable carriers, in this regard, are intended to include any and all solvents, dispersion media, coatings, absorption delaying agents, and the like, compatible with pharmaceutical administration. The use of such media and agents for pharmaceutically active substances is known in the art. Except insofar as any conventional medium or agent is incompatible with the active compound, use thereof in the compositions is contemplated. Supplementary active compounds (identified or designed according to the subject matter disclosed herein and/or known in the art) also can be incorporated into the compositions. The formulations can conveniently be presented in dosage unit form and can be prepared by any of the methods well known in the art of pharmacy. In general, some formulations are prepared by bringing the compound into association with a liquid carrier or a finely divided solid carrier or both, and then, if necessary, shaping the product into the desired formulation. A pharmaceutical composition of the subject matter disclosed herein should be formulated to be compatible with its intended route of administration. Solutions or suspensions can include the following components: a sterile diluent such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

A wide variety of formulations and administration methods, including, e.g., intravenous formulations and administration methods can be found in S. K. Niazi, ed., Handbook of Pharmaceutical Formulations, Vols. 1-6 [Vol. 1 Compressed Solid Products, Vol. 2 Uncompressed Drug Products, Vol. 3 Liquid Products, Vol. 4 Semi-Solid Products, Vol. 5 Over the Counter Products, and Vol. 6 Sterile Products], CRC Press, Apr. 27, 2004.

Useful solutions for oral administration can be prepared by any of the methods well known in the pharmaceutical art, described, for example, in Remington's Pharmaceutical Sciences, 18th ed. (Mack Publishing Company, 1990). Formulations of the subject matter described herein suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste, or a topical composition comprising, e.g., a cream or gel. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as hydroxypropylcellulose, gum tragacanth or gelatin; an excipient such as starch or lactose; a disintegrating agent such as croscarmellose sodium alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Oral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the subject matter disclosed herein are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Topical compositions can be formulated as creams, ointments, jellies, solutions or suspensions, etc.

Methods of Use

A pharmaceutical composition comprising rofecoxib as presented herein may be used in the treatment or prevention of conditions or diseases in subjects, including humans.

In one aspect, the subject matter disclosed herein includes administering a pharmaceutical composition comprising rofecoxib having a favorable impurity profile to a subject to treat or prevent a disease or condition, including but not limited to one of the following: osteoarthritis, rheumatoid arthritis, analgesia, juvenile idiopathic arthritis, including systemic juvenile idiopathic arthritis, migraine or headaches, juvenile rheumatoid arthritis, ankylosing spondylitis, acute pain, primary dysmenorrhea, psoriatic arthritis and fibromyalgia.

In other aspects, the disease or condition is pain-associated with a condition caused by a bleeding disorder, including migraine associated with von Willebrand disease. In another aspect, a subject receiving treatment for migraine associated with von Willebrand disease expresses von Willebrand factor at a level about 50% below normal.

In one aspect, the treatment described herein may be administered to a subject of any age. In another aspect, the subject is age 2 or older, or age 12 years or older. In another aspect, the subject is of age 12 to 75 years old, inclusive.

In one aspect, the subject is screened for all or certain of the study protocol inclusion or exclusion criteria described below as part of the treatment.

In another aspect, the subject is within a subject population that has a reduced risk of arterial thrombosis, cardiovascular thrombotic events, or other serious cardiovascular disease or events, for example subjects with inherited bleeding disorders or coagulopathies such as hemophilia or von Willebrand disease, or subjects with medically-induced bleeding disorders or coagulopathies.

In one aspect, the subject is screened for a history or current symptoms of cardiovascular disease. In one aspect, if the subject is determined to have a history or current symptoms of cardiovascular disease, the subject is not administered the pharmaceutical composition. In another aspect, if it is determined that the subject does not have a history or current symptoms of cardiovascular disease, the subject is administered the pharmaceutical composition as further set forth herein. In yet another aspect, the subject is screened for one or more risk factors that would increase the likelihood of the subject having a serious cardiovascular thrombotic event following administration of the pharmaceutical composition as further set forth herein. In one aspect, if it is determined that the subject may be safely administered the pharmaceutical composition as further set forth herein without increasing the likelihood of the subject having a serious cardiovascular thrombotic event, then the subject is administered the pharmaceutical composition as further set forth herein.

In another aspect, the subject is screened for a history or current symptoms of gastrointestinal bleeding, ulceration, and perforation. In one aspect, if the subject is determined to have a history or current symptoms of gastrointestinal bleeding, ulceration, and perforation, the subject is not administered the pharmaceutical composition. In another aspect, if it is determined that the subject does not have a history or current symptoms of gastrointestinal bleeding, ulceration, and perforation, the subject is administered the pharmaceutical composition as further set forth herein.

The subject may be screened for a history or current symptoms of both cardiovascular disease or gastrointestinal bleeding, ulceration, and perforation, in addition to any of the study protocol inclusion or exclusion criteria listed below.

A pharmaceutical composition comprising rofecoxib that is administered for any of the diseases or conditions described herein may be substantially pure or highly pure, or may be essentially free of, or free of, one or more of the impurities described herein.

In another aspect, a pharmaceutical composition comprising rofecoxib as provided herein is administered to a subject who has mild, moderate, or severe pain associated with a condition caused by a bleeding disorder. Pain may be measured through any clinically-validated pain assessment measure. In one aspect, pain is measured through the Pain Intensity Numerical Rating Scale. In another aspect, pain associated with a specific condition caused by a bleeding disorder, hemophilic arthropathy, is measured through the Pain Intensity Numerical Rating Scale or the Patient Assessment of Arthropathy Pain (Visual Analog Scale; VAS).

In one aspect, a pharmaceutical composition comprising rofecoxib as provided herein is administered to a subject who has pain associated SJIA. In another aspect, a pharmaceutical composition comprising rofecoxib as provided herein is administered to a subject who has migraine associated with von Willebrand disease, wherein the subject receiving treatment expresses von Willebrand factor at a level about 50% below normal.

In one aspect, the treatment of the subject matter disclosed herein includes administration of a pharmaceutical composition comprising about 12.5 mg of rofecoxib as provided herein per day. In another aspect, the treatment includes the administration of a pharmaceutical composition comprising about 25 mg of rofecoxib as provided herein per day. In another aspect, the treatment includes the administration of a pharmaceutical composition comprising about 1 mg, 2 mg, 3 mg, 5 mg, 6.25 mg, 7.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 20 mg, 20.5 mg, 21 mg, 21.5 mg, 22.5 mg, 25 mg, 30 mg, 35 mg, 40 mg, 45 mg, 50 mg, 55 mg, 60 mg, 65 mg, or 70 mg of rofecoxib as provided herein per day. Treatment may be administered once daily in the form of one or more tablets. In other aspects, the pharmaceutical composition comprising rofecoxib as provided herein is administered two times or more daily.

In one aspect, a treatment regimen is provided for the safe treatment of pain, inflammation, migraine and/or arthritis. The pain, inflammation, migraine and/or arthritis may be associated with a disease or condition caused by a bleeding disorder. In one aspect, the treatment subject is a human patient of any age. In another aspect, the patient is age 12 years or older.

The treatment regimen may comprise the administration of an initial (or first) dose of a pharmaceutical composition comprising 10 mg, 10.5 mg, 11 mg, 11.5 mg, 12 mg, or 12.5 mg of rofecoxib once daily as further described herein. The treatment regimen may further comprise evaluating the subject after administration of the initial dose to determine if the initial dose was fully, partially, or not effective at treating the pain, inflammation, migraine and/or arthritis. In another aspect, the treatment regimen may comprise determining if the subject could benefit from the administration of a higher dose of rofecoxib. The evaluation and determination steps may take place after a single administration of the initial dose, or after multiple administrations of the initial dose (e.g. two days, three days, one week, two weeks, or longer after the first administration of the initial dose), and may be performed by a physician, physician's assistant, nurse, or other health care provider. In one aspect, the evaluation and determination steps may be based on subject-reported outcomes, and may include an assessment of the benefit of a higher dose of rofecoxib compared to any potential safety risks associated with that higher dose. For example, if a subject experiences a clinically meaningful decrease in pain after administration of the initial dose, it may be determined that the subject should continue on the initial dose through the duration of the bleeding episode that caused the pain.

The treatment regimen may further comprise the administration of a subsequent (or second) dose of a pharmaceutical composition comprising 17.5 mg, 20 mg, or 25 mg of rofecoxib once daily if it was determined that the initial dose was not effective or only partially effective at treating the pain, inflammation, migraine and/or arthritis, or if it is determined that the subject could benefit from a higher daily dose of rofecoxib to treat the pain, inflammation, migraine and/or arthritis (e.g. that a higher dose could achieve a greater reduction in pain in the subject). In one aspect, the subsequent dose is administered if it is determined that the initial dose did not achieve a clinically meaningful reduction in pain, inflammation, migraine and/or arthritis in the subject. In another aspect, the subsequent dose is administered if it is determined that the subsequent dose may increase the effectiveness of the treatment without increasing the risk of adverse events or other side effects. In another aspect, a higher dose is not administered if it is determined that the initial dose was effective at treating the pain, inflammation, migraine and/or arthritis. In another aspect, a higher dose is not administered if it is determined that the higher dose would increase the risk of adverse events or other side effects in the subject. In another aspect, a higher dose is not administered if it is determined that the risk of administering the higher dose (e.g. in terms of adverse events or side effects) outweigh the benefits (e.g. in terms of effectiveness of treating the pain, inflammation, migraine and/or arthritis). In another aspect, the step of not administering a higher dose includes instructing the subject not to take a higher dose of the pharmaceutical composition (e.g. not to take 12.5 mg of the pharmaceutical composition more than once daily).

In one aspect, the treatment includes the administration of pharmaceutical composition comprising about 0.10 mg/kg, 0.15 mg/kg, 0.20 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, or 0.70 mg/kg.

In one aspect, an effective amount of rofecoxib as provided herein for treating pain associated with a disease or condition caused by a bleeding disorder is about 12.5 mg once daily, and, in another aspects, results fewer side effects or in a reduction of pain equal to or better than the use of a pharmaceutical composition comprising about 25 mg rofecoxib that is not substantially pure or highly pure, or essentially free of, or free of, one or more of the impurities described herein that was present in previously available rofecoxib bulk drug product. In one aspect, an effective amount of rofecoxib as provided herein for treating pain associated with a disease or condition caused by a bleeding disorder is about 17.5 mg once daily, and, in another aspects, results fewer side effects or in a reduction of pain equal to or better than the use of a pharmaceutical composition comprising about 25 mg rofecoxib that is not substantially pure or highly pure, or essentially free of, or free of, one or more of the impurities described herein that was present in previously available rofecoxib bulk drug product. In one aspect, an effective amount of rofecoxib as provided herein for treating pain associated with a disease or condition caused by a bleeding disorder is about 20 mg once daily, and, in another aspects, results fewer side effects or in a reduction of pain equal to or better than the use of a pharmaceutical composition comprising about 25 mg rofecoxib that is not substantially pure or highly pure, or essentially free of, or free of, one or more of the impurities described herein that was present in previously available rofecoxib bulk drug product. In one aspect, an effective amount of rofecoxib as provided herein for treating pain associated with a disease or condition caused by a bleeding disorder is about 1 mg, 2 mg, 3 mg, 5 mg, 6.25 mg, 7.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 20 mg, 20.5 mg, 21 mg, 21.5 mg, 22.5 mg, 25 mg, 30 mg, 35 mg, 40 mg, 45 mg, 50 mg, 55 mg, 60 mg, 65 mg, or 70 mg once daily. As a result, a subject may not need to be administered the higher quantity of active ingredient in order to experience a reduction in pain.

In one aspect, an effective amount rofecoxib as provided herein for treating pain associated with a disease or condition caused by a bleeding disorder, pain associated with juvenile idiopathic arthritis, including systemic juvenile idiopathic arthritis, or migraine associated with von Willebrand disease is about 0.10 mg/kg, 0.15 mg/kg, 0.20 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, or 0.70 mg/kg.

In one aspect, the treatment described herein is effective at treating mild, moderate, or severe pain in a subject without the co-administration of another pain medication or analgesic.

In another aspect, the treatment described herein results in the subject decreasing or discontinuing the use of another pain medication or analgesic, including rescue medications, during the course of the treatment when compared to before the initiation of the treatment. In yet another aspect, the treatment results in the subject decreasing or discontinuing the use of acetaminophen and/or opioid medications during the treatment during the course of the treatment when compared to before the initiation of the treatment.

In one aspect, a pharmaceutical composition comprising rofecoxib as provided herein is co-administered with factor replacement therapy to a subject having a bleeding disorder. In another aspect, the treatment described herein is administered to a subject having a bleeding disorder who is being administered or is taking factor replacement therapy prophylactically. In one aspect, the pharmaceutical composition comprising 12.5 mg, 17.5 mg, 20 mg or 25 mg rofecoxib as provided herein is administered once daily to a subject who is also being administered or is taking factor replacement therapy prophylactically.

In one aspect, a pharmaceutical composition comprising rofecoxib as provided herein is administered daily and does not increase risk of cardiovascular diseases and/or gastrointestinal bleeding, ulceration, or perforation during the course of the treatment, as determined at 2 weeks, 4 weeks, 8 weeks, 12 weeks, 24 weeks, 52 weeks, and/or two or more years. In another aspect, the rofecoxib as provided herein may be administered during the course of the treatment without the use or co-administration of a gastro-protective agent including but not limited to an antacid therapy, an H2 antagonist, a proton pump inhibitor, or misoprostol.

In another aspect, a pharmaceutical composition comprising rofecoxib as provided herein is administered only on an as-needed basis, for example when a subject experiences a pain "flare" described as an increase in pain rating of >1 or a pain rating of ≥4 to ≤9 based on the Pain Intensity Numerical Rating Scale. In yet another aspect, the pharmaceutical composition comprising rofecoxib as further set forth herein is not administered as a maintenance therapy, prophylactically, or for long term use (e.g., >1 year). In one aspect, a pharmaceutical composition comprising rofecoxib as provided herein is administered only on an as-needed basis and for short term use, for example, less than one week, two weeks, three weeks, or four weeks, or until the pain, migraine, arthritis, inflammation, or other conditions or symptoms subside or resolve, for example, until there is a clinically significant improvement in pain rating based on the based on the Pain Intensity Numerical Rating Scale.

In one aspect, the subject uses or is co-administered a gastro-protective agent during the course of treatment with a pharmaceutical composition comprising rofecoxib as provided herein, which prevents or treats gastrointestinal bleeding, ulceration, and perforation in the subject. In another aspect, the subject uses or is co-administered an antiviral therapy such as famciclovir or penciclovir during the course of treatment with a pharmaceutical composition comprising rofecoxib as provided herein to treat or prevent fibromyalgia.

In one aspect, the treatment described herein achieves a reduction in at least 1 from baseline in the Pain Intensity Numerical Rating Scale. In another aspect, the treatment described herein achieves a reduction in at least 2, 3, 4, or 5 from baseline in the Pain Intensity Numerical Rating Scale.

In one aspect, the reduction in the Pain Intensity Numerical Rating Scale is achieved within 1, 2, 3, 4, 5, or 6 days, or 1 week, or 2 weeks of first administering the pharmaceutical composition.

In one aspect, the treatment of a disease or condition by the administering of a pharmaceutical composition comprising substantially pure or highly pure rofecoxib does not result in one or more of the following adverse events: upper respiratory infection, headache, nausea, vomiting, and cough, or one or more of the following serious adverse events: hemorrhage and hypotension. In one aspect, the treatment of a disease or condition caused by a bleeding disorder by the administering of a pharmaceutical composition comprising substantially pure or highly pure rofecoxib does not result in an increased number of joint bleeding events. In another aspect, the treatment of a disease or condition caused by a bleeding disorder by the administering of a pharmaceutical composition comprising substantially pure or highly pure rofecoxib does not increase the risk of joint bleeding events. In one aspect, the treatment of a disease or condition caused by a bleeding disorder by the administering of a pharmaceutical composition comprising substantially pure or highly pure rofecoxib does not result in an increase in the amount of factor use in the subject. In another aspect, the treatment of a disease or condition by the administering of a pharmaceutical composition comprising substantially pure or highly pure rofecoxib does not result in an increased risk of side effects (including but not limited to hemorrhaging, hypotension or serious cardiovascular thrombotic events) compared to the previously marketed "VIOXX" product when used in that disease or condition. In another aspect, a pharmaceutical composition comprising substantially pure or highly pure rofecoxib as provided herein results in greater efficacy in a disease or condition compared to the previously marketed "VIOXX" product when used in that disease or condition (as measured by a clinically-validated measure, such as the Pain Intensity Numerical Rating Scale).

In another aspect, the treatment of a disease or condition by the administering of a pharmaceutical composition comprising highly pure rofecoxib that is essentially free of, or free of, 4-[4-(methylsulfonyl)phenyl]-3-phenyl-5-hydroxyfuran-2-one and/or 4-[4-(methylsulfonyl)phenyl]-3-phenyl-2,5-furandione does not result in one or more of the following adverse events: upper respiratory infection, headache, nausea, vomiting, and cough, or one or more of the following serious adverse events: hemorrhage and hypotension. In another aspect, a pharmaceutical composition comprising highly pure rofecoxib that is essentially free of, or free of, 4-[4-(methylsulfonyl)phenyl]-3-phenyl-5-hydroxyfuran-2-one and/or 4-[4-(methylsulfonyl)phenyl]-3-phenyl-2,5-furandione as provided herein results in greater efficacy in a disease or condition, or reduced side effects (e.g. hemorrhaging, hypotension or serious cardiovascular thrombotic events) compared to the previously marketed "VIOXX" product when used in that disease or condition (as measured by a clinically-validated measure, such as the Pain Intensity Numerical Rating Scale). The purity of the resulting rofecoxib described as herein is determined as a percent area basis, typically as quantified by analytical chromatography, such as using HPLC, UHPLC, UPLC or other analytical means in the art.

EXAMPLES

Example 1—Protocol for Treating Hemophilic Arthropathy (HA)

Study Objective: Evaluate the efficacy of a pharmaceutical composition comprising rofecoxib as provided herein (the study drug) versus placebo in subjects with hemophilic arthropathy.

Secondary objectives include:
To evaluate the effect on sleep interference due to pain, subject global impression, and quality of life in subjects treated with rofecoxib as provided herein versus placebo.
To evaluate the safety and tolerability of rofecoxib as provided herein in subjects with hemophilic arthropathy.
To evaluate the long-term safety and efficacy of 2 dose regimens of rofecoxib as provided herein in subjects with hemophilic arthropathy.

Study Endpoints:
Primary endpoint: Change from baseline to Week 12 in the weekly average of the daily pain score as measured using a Pain Intensity Numerical Rating Scale [PI-NRS], an 11-point numerical scale where 0=no pain and 10=pain as bad as can be imagined.

Secondary endpoints: Change from baseline to Month 15 in the weekly average of the daily pain score as measured using a Pain Intensity Numerical Rating Scale [PI-NRS]
Secondary endpoints at Week 12 and Month 15:
30% and 50% responders on the weekly average of the daily pain score
Change from baseline in the weekly average of the daily sleep interference score.
Percentage of subjects who are much or very much improved using the Patient Global Impression of Change (PGIC)
Euroqol (EQ-5D-5L)
SF-36

Safety endpoints (during the double blind and open-label phase separately):
Incidence of thrombotic events
Incidence of GI bleeding events
Incidence of any bleeding event
Adverse Events, Laboratory Safety Tests (hematology, coagulation, clinical chemistry), blood pressure, pulse rate, ECG, C-SSRS
Factor use
Percentage of subjects who discontinue due to adverse events.

Other endpoints:
Percentage of subjects who discontinue due to lack of efficacy
Average acetaminophen usage per day and percentage of subjects using rescue medication.

Study Design: Multicenter, double-blind, randomized, placebo-controlled, parallel-group study to evaluate the efficacy and safety of rofecoxib as provided herein in subjects with hemophilic arthropathy. Eligible subjects must have a diagnosis of hemophilia A, B (factor VIII or factor IX deficiency with or without inhibitor) or von Willebrand disease (Von Willebrand factor level of ≤30 IU per dL), a history of joint bleeding, chronic symptomatic pain in one or more joints on 20 of the 30 days prior to screening, and a diagnosis of hemophilic arthropathy at least 6-months prior to screening, with the primary source of pain or disability in the hip, knee, ankle or elbow.

At screening, the pain over the last week will be assessed using the 11-point PI-NRS (0-10), and pain intensity needs to be at least 3. Following Screening, subjects who meet eligibility criteria will need to discontinue ongoing NSAID and Cox-2 inhibitor medications at least 7 days prior to randomization. Subjects who are using weak or low dose opiates or other non-NSAID analgesics are allowed to continue those at stable dose during the study.

Subjects will daily record their average pain intensity over the last 24 hours in an electronic diary using the 11-point PI NRS for the duration of the study treatment period. Rescue medication can be used (paracetamol/acetaminophen) if needed up to 3 g/day. If rescue medication is used for more than 2 consecutive days, the maximum dosage is 2.5 g. Subjects who need rescue medication for more than 7 consecutive days at a dose of 2.5 g/day need to discontinue study drug. The dosage of any rescue medication must be recorded in the electronic diary.

The weekly average of the PI-NRS collected on the 7 days prior to randomization will be defined as the baseline. Subjects with a flair of pain intensity indicated by an increase in the weekly mean of the daily pain score of at least 1.5 points and having at least moderate pain intensity (weekly average baseline arthritic pain score: >4 and <9) will be eligible to enter the double-blind treatment period.

On Day 1, eligible subjects will be randomized in a 1:1:1 ratio to receive rofecoxib as provided herein at 25 mg QD, rofecoxib as provided herein 12.5 mg QD, or matching placebo. Double-blind treatment will continue for 12 weeks. Following the initial double blind treatment period, subjects will be re-randomized in a 1:1 ratio to receive rofecoxib as provided herein at 25 mg QD or 12.5 mg QD for an additional 12-months. Subjects will attend a Follow Up Visit approximately 1 week after the last dose of study treatment, and will receive a follow up phone call 4 weeks after the last dose.

Study Population:
Inclusion Criteria

To be eligible to participate in the study, and to receive the study drug, candidates must meet the following eligibility criteria:

1. Ability of the subject to understand the purpose and risks of the study and provide signed and dated informed consent and authorization to use confidential health information in accordance with national and local subject privacy regulations.
2. Aged 12 to 75 years, inclusive, at the time of informed consent.
3. All women of childbearing potential and all men must practice effective contraception during the study and for 5 weeks for women and 14 weeks for men, after their last dose of study treatment.
4. Diagnosis of hemophilia A, B (factor VIII or IX deficiency with or without inhibitor) or von Willebrand disease (Von Willebrand factor level of ≤30 IU per dL)
5. History of joint bleeding
6. Diagnosis of hemophilic arthropathy for at least 6-months prior to Screening with history of joint bleeding and the primary source of pain or disability in the hip, knee, ankle or elbow.
7. Chronic symptomatic pain in one or more joints on 20 of the 30 days prior to screening.
8. Has an intensity of ≥3 and ≤9 on the Numerical Rating Scale based on a paper-based question at Screening that asks for the average pain intensity of arthritic pain due to hemophilic arthropathy over the last week.
9. If on analgesic medication to manage pain due to hemophilic arthropathy, subject must have had stable analgesic medication for a minimum of 30 days prior to Screening.
10. Has a flair of pain intensity indicated by an increase in the weekly mean of the daily pain score of at least 1.5 points
11. Has a baseline weekly average of the daily pain score ≥4 and ≤9 on the electronic diary PI-NRS; baseline is defined as the 7 days prior to randomization (Day 1).

Exclusion Criteria

Candidates will be excluded from study entry, and receiving the study drug, if any of the following exclusion criteria exist:

Medical History
1. Is pregnant or lactating (female subjects only).
2. Known hypersensitivity to rofecoxib or any other component of the formulation
3. History of asthma, urticaria, or allergic-type reactions after taking aspirin or other NSAIDs
4. Has a history of advanced renal disease.
5. Has a history of any liver disease within the last 6-months, with the exception of known Gilbert's disease.
6. Has a history of alcohol or substance abuse.
7. Currently has uncontrolled or poorly controlled hypertension.
8. Has a history of major cardiac ischemic symptoms, events or interventions such as angina pectoris, myocardial infarction, acute coronary syndrome, decompensated congestive heart failure, coronary stent or bypass.
9. Has a history of cerebrovascular ischemic events (TIA or stroke). Subjects with a history of intra- or extracerebral hemorrhage may be eligible if their condition is stable.
10. Has a history of major vascular ischemic symptoms such as claudicatio intermittens, or vascular bypass or replacement surgery.
11. Has a history or presence of significant cardiovascular, gastrointestinal, or renal disease, or other condition known to interfere with the absorption, distribution, metabolism, or excretion of drugs.
12. Has a history or presence of any clinically significant abnormality in vital signs, ECG, or laboratory tests or has any medical or psychiatric condition that, in the opinion of the Investigator, may interfere with the study procedures or compromise subject safety.
13. History of a major upper GI event (upper GI perforation, obstruction or major upper GI bleeding) within 6-months prior to screening
14. Has had an episode of major depression within 6-months before Screening.
15. Has a history of suicide attempt within 6-months before Screening.

Vitals and Laboratory Procedures
1. Has BP ≥160 mmHg systolic and/or ≥100 mmHg diastolic at Screening after repeated measurements.
2. Has a QT interval corrected using Fridericia's formula (QTcF) ≥450 msec (males) or ≥470 msec (females) [average of 3 measurements at least 5 minutes apart and done within 15 minutes] at Screening.
3. Has a positive pregnancy test at Screening (women of childbearing potential only).
4. Estimated creatine clearance (using Cockroft-Gault equation)<30 ml/min
5. Has AST or ALT ≥2× the upper limit of normal (ULN) or has alkaline phosphatase or bilirubin ≥1.5×ULN at Screening.
6. History or positive test result at Screening for human immunodeficiency virus (HIV).
7. History or positive test result at Screening for hepatitis C virus (HCV) antibody or hepatitis B virus (defined as positive for hepatitis B surface antigen [HBsAg] or hepatitis B core antibody [HBcAb]).
8. Has a positive drug screen for drugs of abuse at Screening (amphetamine, barbiturates, benzodiazepines, cocaine, opiates, tetrahydrocannabinol) except if explained by use of allowed prescription medicines).

Other Screening Assessments

Has a positive response on Item 4 or 5 on the C-SSRS at Screening.

General
1. Is mentally or legally incapacitated.
2. Is unable to comply with the restrictions related to prohibited concomitant therapy restrictions.
3. Previous registration in this study or previous studies with rofecoxib.
4. Has participated in an interventional study and received study treatment within 3-months before Screening.

5. Has donated blood or blood products within a 30-day period prior to Screening.
6. Inability to comply with study requirements.
7. Other unspecified reasons that, in the opinion of the Investigator, make the subject unsuitable for enrollment.

Medications
1. Concomitant use rifampin
2. Failed to discontinue concomitant NSAID or Cox-2 pain medications 7 days prior to randomization
3. Has used rescue medication at a dose of 2.5 g acetaminophen/paracetamol for more than 5 days consecutively prior to randomization.

Baseline Pain Scores
1. Has missed more than 2 of 7 daily pain score entries during the last 7 days of treatment prior to randomization.
2. Has a daily pain score of ≤2 on 1 or more days during the last 7 days of treatment prior to randomization.
3. Has a difference between the lowest and highest daily pain score of ≥4 during the last 7 days of treatment prior to randomization.

Treatment Groups:
Subjects will be randomized to receive double-blind study drug in a 1:1:1 ratio:
  Rofecoxib as presented herein (25 mg QD orally)
  Rofecoxib as presented herein (12.5 mg QD orally)
  Placebo (matching tablets QD orally)

Concomitant Medications:
  Allowed Medications
  PPI therapy will be provided to all study participants for gastric protection
  Stable low opioids or other non-NSAID pain medications
  Prohibited Medications
  NSAIDs or Cox-2 inhibitors Visit Schedule: There will be 7 visits: screening visit up to 28 days prior to start of dosing; Randomization (Day 1); Double-Blind Treatment visits (Weeks 4, 8 and 12); Open-Label Treatment Visits (months 4, 6, 9, 12) and a Follow Up visit 7 to 10 days after the last dose. In addition, there will be a follow up phone call 28 days after the last dose.

Discontinuation of Treatment: A subject must permanently discontinue study treatment for any of the following reasons:
  The subject becomes pregnant.
  The subject withdraws consent to continue study treatment.
  The subject experiences a medical emergency that necessitates permanent discontinuation of study treatment.
  The subject experiences a medical emergency that necessitates unblinding of the subject's treatment assignment.
  The subject is unwilling or unable to comply with the protocol.
  The subject meets individual liver chemistry, vital signs or ECG, C-SSRS or adverse event discontinuation criteria
  At the discretion of the Investigator for medical reasons.

Efficacy Assessments:
  Eleven-point PI-NRS for average daily pain (assessed daily in the evening) [PI NRS scores will be collected in the electronic diary.]
  Eleven-point S-NRS score for daily sleep interference (DSIS, assessed daily in the morning) [S NRS scores will be collected in the electronic diary.]
  PGIC
  EQ-5D-5L
  SF-36

Safety Assessments:
  Incidence of thrombotic events
  Incidence of GI bleeding events
  Adverse Events
  Laboratory Safety Tests (hematology, coagulation clinical chemistry)
  Blood Pressure
  Pulse Rate
  ECG
  C-SSRS Example 2—Batch Analysis Batch analysis of two rofecoxib batches, batch SHD390-187 and batch 16P3140F851, is summarized in Table 5. If an individual impurity is ≥0.05% area, the result is reported to the nearest 0.01%. If an individual impurity is <0.02% (LOD), the result is reported as "not detected" (ND). If an individual impurity is <0.05% area but ≥0.02% area, the result is recorded as <0.05% area.

TABLE 5

| Batch Analysis Data for Rofecoxib Drug Substance | | | | |
| --- | --- | --- | --- | --- |
| Lot No. (manufacturing process) | Appearance | Identification by HPLC | Identification by FTIR | Assay % w/w on anhydrous basis |
| SHD390-187 (A$_1$) | White powder | NA | NA | NA |
| 16P3140F851 (A$_1$) | Off-white powder | Conforms to Reference | Conforms to Reference | 99.8 |

| Impurities by HPLC Area % | | | | | |
| --- | --- | --- | --- | --- | --- |
| Lot No. (manufacturing process) | Total Impurities | RXB-Furanone | RXB-Sulfoxide | RRT ~0.5 | RRT ~0.66 |
| SHD390-187 (A$_1$) | 0.2 | ND | 0.12 | ND | 0.11 |
| 16P3140F851 (A$_1$) | 0.1 | 0.08 | ND | <0.05 | ND |

TABLE 5-continued

Batch Analysis Data for Rofecoxib Drug Substance

Residual Solvents by GC ppm

| Lot No. (manufacturing process) | Acetonitrile | Dichloromethane | Dimethylsulfoxide | Isopropanol | Methanol |
|---|---|---|---|---|---|
| SHD390-187 ($A_1$) | ND | ND | 506 | 14 | ND |
| 16P3140F851 ($A_1$) | ND | ND | 484 | ND | ND |

| Lot No. (manufacturing process) | Water Content Karl Fischer % w/w | Polymorphic Form XRPD | Residue on Ignition % w/w | Particle Size Analysis by Laser Diffraction, μm | | |
|---|---|---|---|---|---|---|
| | | | | $d_{10}$ | $d_{50}$ | $d_{90}$ |
| SHD390-187 ($A_1$) | 0.0 | Form A | 0.0 | NT | NT | NT |
| 16P3140F851 ($A_1$) | 0.1 | Form A | 0.0 | 0.859 | 3.83 | 11.1 |

Example 3—Stability Data for Rofecoxib

Stability data for rofecoxib drug substance (Lot 16P3140F851) are provided in Tables 6A-B. If an individual impurity is ≥0.05% area, the result is reported to the nearest 0.01%. If an individual impurity is <0.02% (LOD), the result is reported as "not detected" (ND). If an individual impurity is <0.05% area but ≥0.02% area, the result is recorded as <0.05% area.

TABLE 6A

Stability of Rofecoxib Drug Substance (Lot 16P3140F851) at 40° C./75% RH

| Lot: 16P3140F851 | | Manufactured At: PCAS | | | |
|---|---|---|---|---|---|
| Batch Scale: | 17.74 kg | | | Container/Closure: | Double HDPE bags in HDPE drum |
| Condition: | 40° C./75% RH | Manufacture Date: | 3 Jul. 2018 | Stability Initiation Date: | 24 Aug. 2018 |

| Test | Initial | 1 Month | 3 Month | 6 Month |
|---|---|---|---|---|
| Appearance | Off-white powder | Off-white powder | White powder | |
| Assay by HPLC (w/w) | 99.8 | 99.6 | 100.5 | |
| Impurities by HPLC (% area) | | | | |
| RXB-furanone | 0.08 | 0.08 | 0.08 | |
| RRT ~ 0.5 | <0.05 | <0.05 | <0.05 | |
| Total Impurities | 0.11 | 0.11 | 0.12 | |
| Water Content by Karl Fischer (%) | 0.12 | 0.07 | 0.09 | |
| Polymorphic form by XRPD | Form A | NT | NT | |

TABLE 6B

Stability of Rofecoxib Drug Substance (Lot 16P3140F851) at 25° C./60% RH

| Lot: 16P3140F851 | | Manufactured At: PCAS | | | |
|---|---|---|---|---|---|
| Batch Scale: | 17.74 kg | | | Contain/Closure: | Double HDPE bags in HDPE drum |
| Condition: | 25° C./60% RH | Manufacture Date: | 3 Jul. 2018 | Stability Initiation Date: | 24 Aug. 2018 |

TABLE 6B-continued

Stability of Rofecoxib Drug Substance (Lot 16P3140F851) at 25° C./60% RH

| Test | Initial | 3 Month | 6 Month | 9 Month | 12 Month |
|---|---|---|---|---|---|
| Appearance | Off-white powder | White powder | | | |
| Assay by HPLC (% w/w) | 99.8 | 100.4 | | | |
| Impurities by HPLC (% area) | | | | | |
| RXB-furanone | 0.08 | 0.08 | | | |
| RRT ~ 0.5 | <0.05 | <0.05 | | | |
| Total Impurities | 0.11 | 0.11 | | | |
| Water Content by Karl Fischer (%) | 0.12 | 0.08 | | | |
| Polymorphic form by XRPD | Form A | NT | | | |

Example 4—Oxidation Reaction

TABLE 7

Effect of solvents on the kinetics.

| | | VLA P075-176 | VLA P075-178 | CHG P059-084 |
|---|---|---|---|---|
| Materials | RXB-Furanone | 3.00 g | 3.00 g | 3.00 g |
| | $H_2O_2$ 35% | 2.5 eq. | 2.5 eq. | 2.5 eq. |
| | $Na_2WO_4 \cdot 2H_2O$ | 1 mol % | 1 mol % | 1 mol % |
| | ACN | 6 V | 6 V | 7 V |
| | IPA | 36 % wt. | None | 36 % wt. |
| | $H_2O$ | 0.25 V | 0.25 V | 0.25 V |
| Process | $H_2O_2$ addition time | 2 h 20 | 2 h 00 | 2 h 00 |
| | RXB-201 seeding | None | 1 seed, end of $H_2O_2$ addition | 2 seeds during $H_2O_2$ addition |
| | Aspect Comments | Slightly clouded during whole process. Addition 1 V ACN after IPC2:white suspension | White suspension at the end of $H_2O_2$ addition. | White suspension after first seeding. |
| UHPLC (% area) RXB-201/ Sulfoxide | IPC 1 (End of $H_2O_2$ addition) | 97.23/2.50 | 99.20/0.53 | Not performed |
| | IPC 2 (time) | 99.72/n.d. (1 h) | 99.68/0.02 (30 min) | 99.40/n.d. (45 min) |
| | Work-up | Not isolated | Not isolated | 2 V water |
| | Isolated RXB-201 | Not isolated | Not isolated | 99.85/0.02 |

Effect of solvents (ACN, IPA, water) on oxidation reaction completion and the effect of solvents on the kinetic are studied in several trials as shown in Table 7. The use of 0.25V deionized water allowed to start the reaction from the beginning of hydrogen peroxide addition. The first trial (VLA P075-176) was conducted using the standard process (at 65° C.), with addition of 0.25V pure water. Addition of hydrogen peroxide was achieved in 2 h 20 min. A slightly clouded reaction medium was obtained, with a very low amount of solid in suspension. At the end of $H_2O_2$ addition, 4-[4-(methylthio)phenyl]-3-phenyl-2(5H)-furanone was never detected, and only 2.5% 4-[4-(methylsulfinyl)phenyl]-3-phenyl-2(5H)-furanone for this trial. After an additional hour of stirring at 65° C., 4-[4-(methylsulfinyl)phenyl]-3-phenyl-2(5H)-furanone was not detected in UHPLC.

This trial resulted in very fast conversion of species into rofecoxib. At the end of reaction, 1V ACN was added to the reaction to try to get a full solubilization of the reaction medium. In fact, the reaction medium turned immediately heterogeneous, as white suspension. This indicates an oversaturation of the reaction medium. Rofecoxib crystallized out with the perturbation generated by the addition of acetonitrile.

The effect of isopropanol content was then studied in the second trial (VLA P075-178). The reaction was performed without IPA, which should have a negative effect of rofecoxib species solubility. The reaction medium was already in suspension at the end of hydrogen peroxide addition, before seeding with rofecoxib. A co-crystallization of 4-[4-(methylsulfinyl)phenyl]-3-phenyl-2(5H)-furanone and rofecoxib could lead to a low conversion of 4-[4-(methylsulfinyl)phenyl]-3-phenyl-2(5H)-furanone, with long time to reach IPC specification.

Finally, a better conversion was observed at the end of $H_2O_2$ addition compared to VLA P075-176. Moreover, the $H_2O_2$ addition was performed faster than the first trial (2 h instead of 2 h 20 min). The absence of IPA reveals faster oxidation conditions than with 36% IPA. This could be attributed to a slightly higher concentration of reaction medium. The crystallization of the reaction medium seems to have no effect on the 4-[4-(methylsulfinyl)phenyl]-3-phenyl-2(5H)-furanone oxidation kinetics.

The trial CHG P059-084 was launched in 7V ACN with usual amount of IPA. This higher dilution revealed to have no effect on reaction medium aspect at the beginning of oxidation. Two seedings were performed during $H_2O_2$ addition to get the white suspension while addition. Reaction medium aspect was similar to VLA P075-178. 45 minutes after hydrogen peroxide addition completion, 4-[4-(methylsulfinyl)phenyl]-3-phenyl-2(5H)-furanone was not detected. After addition of 2V water as quench, cooling to 0° C., filtration and cake washings, the solid obtained contained 0.02% 4-[4-(methylsulfinyl)phenyl]-3-phenyl-2(5H)-furanone. Therefore, reaction medium could be both slightly clouded or a heterogeneous white suspension, the IPC specification was achieved after only 1 h of heating after hydrogen peroxide addition completion. The oversaturation of the reaction medium is with 6V ACN seems to not be an issue for conversion of rofecoxib species into rofecoxib.

Figure 24:
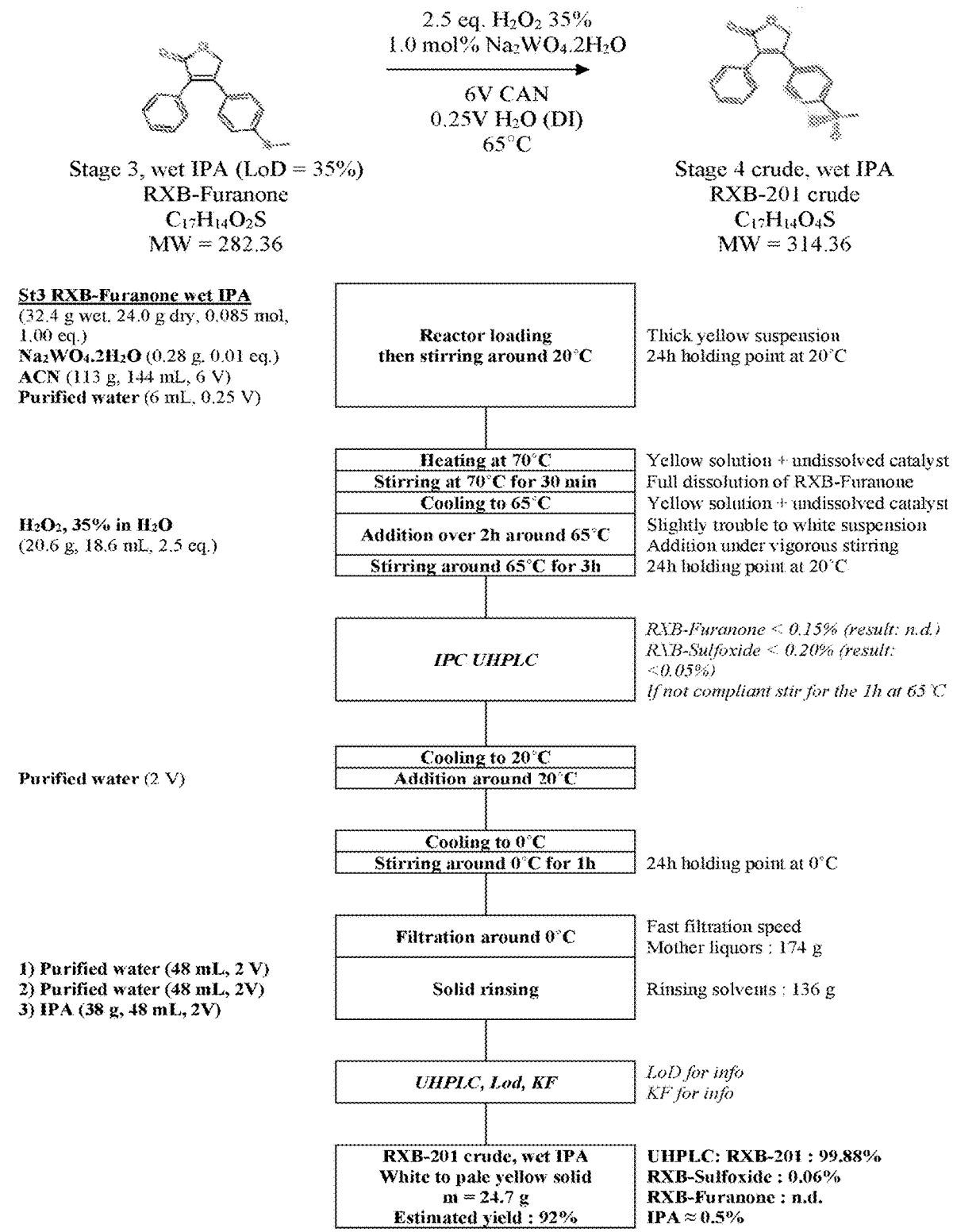
FIG. 24 shows an optimized oxidation process.

Example 5—Process Optimization—Oxidation of 4-[4-(methylthio)phenyl]-3-phenyl-2(5H)-furanone Process optimization has led to the following oxidation process. The demo batch was performed on 24 g 4-[4-(methylthio)phenyl]-3-phenyl-2(5H)-furanone in jacketed reactor equipped with mechanical stirring (CHG P059-092). The process was performed as shown in FIG. 24.

Example 6—Optimization of Rofecoxib (RXB-201) Recrystallization

Figure 11:
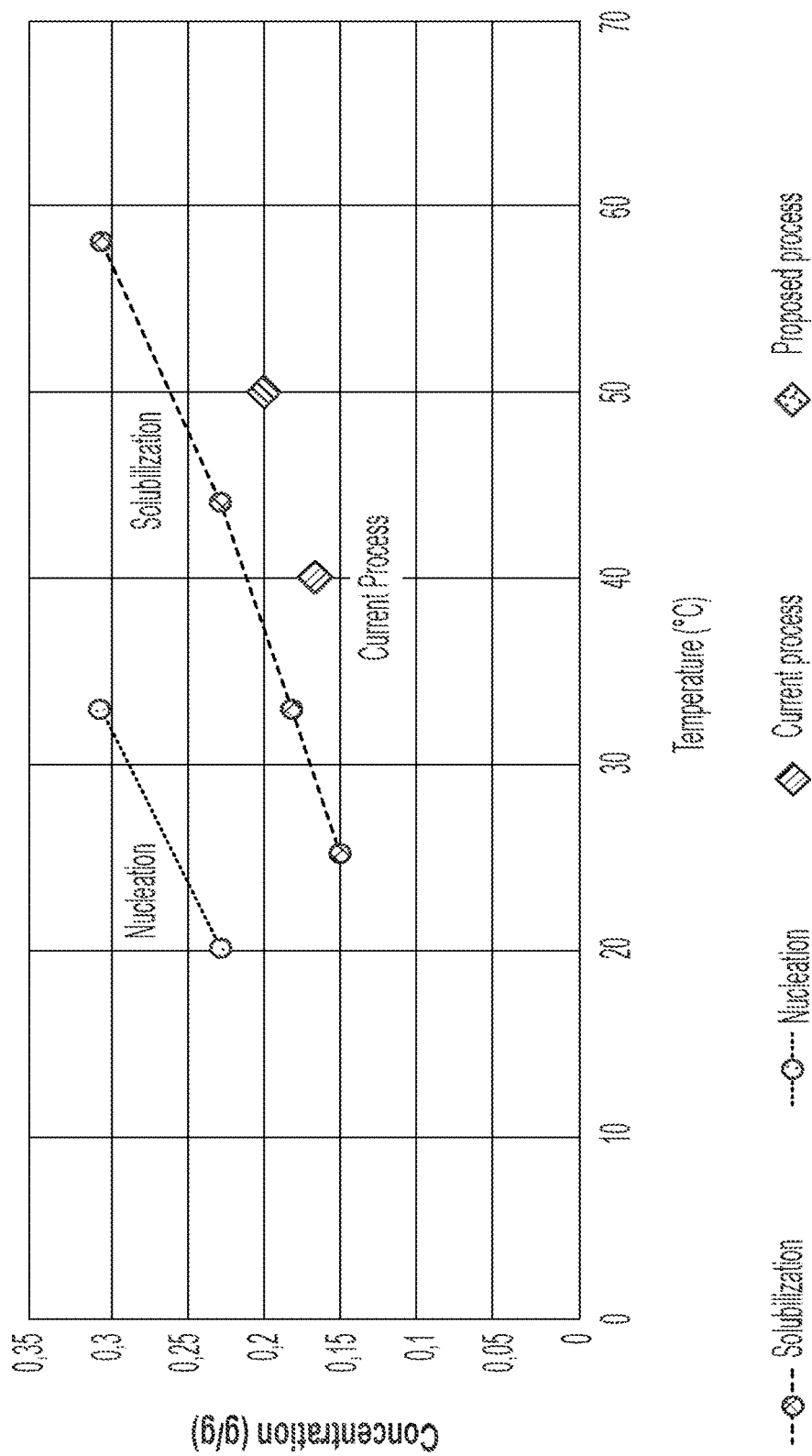
FIG. 11 shows a solubilization and nucleation curve of rofecoxib in DMSO.

Solubility and nucleation of rofecoxib was measured at four different concentrations: 3 V, 4 V, 5 V, and 6 V. As shown in FIG. 11 the solubilization curve is reported in blue, and nucleation in red. The process used for solubilization of rofecoxib at the beginning is reported as the purple spot (5.5V at 40° C.). In one embodiment, the productivity can be improved by increasing the concentration to 4.5V, with heating at 50° C. (green spot). These conditions allow a good solubilization of rofecoxib, with a large safety margin compared to the nucleation temperature (at least 30° C.). This margin is required to avoid spontaneous crystallization during clarifying filtration. An extra-amount of DMSO (+0.5 V) can be used for rinsing of the filtration system.

Trial VLA P075-180 was conducted with rofecoxib containing a high amount of ashes (1.5%). This led to high level of 4-[4-(methylsulphonyl)phenyl]-3-phenyl-5-hydroxyfuran-2-one impurity. With higher DMSO rate (6V), and lower temperature (50° C.), trial VLA P075-184 produced rofecoxib in good yield, with satisfying purge of 4-[4-(methylsulphonyl)phenyl]-3-phenyl-5-hydroxyfuran-2-one impurity. These good results were obtained even with high ashes rate as trials 180 and 184 were conducted on the same starting material. The trial CHG P059-090 was conducted using the process described in the recrystallyzation flowsheet below. The product was obtained in good yield, with the slightly lower purge of 4-[4-(methylsulfinyl)phenyl]-3-phenyl-2(5H)-furanone. Formation of 4-[4-(methylsulphonyl)phenyl]-3-phenyl-5-hydroxyfuran-2-one was avoided due to the clarifying filtration used.

The trials are presented in Tables 8A-B below:

TABLE 8A

Study trials

| Reference | Scale | Solvents DMSO | Solvents Water | Spiking Sulfoxide (% a/a) | Temperature Initial | Temperature Final |
|---|---|---|---|---|---|---|
| VLA P075-180 | 10.1 g | 5.5 V | 5 V | 0.23 | 60° C. | 20° C. |
| VLA P075-184 | 10.1 g | 6 V | 5.5 V | 0.22 | 50° C. | 0° C. |

TABLE 8A-continued

Study trials

| Reference | Scale | Solvents DMSO | Solvents Water | Spiking Sulfoxide (% a/a) | Temperature Initial | Temperature Final |
|---|---|---|---|---|---|---|
| CHG P059-090 | 10.0 g | 5 V | 5.5 V | 0.47 | 50° C. | 0° C. |
| Demo batch | | 5 V | 5.5 V | | 50° C. | 20° C. |

TABLE 8B

Study trials (cont.)

| Reference | Yield (%) | UHPLC results (% a/a) Furanone | UHPLC results (% a/a) Sulfoxide | UHPLC results (% a/a) Hydroxy | UHPLC results (% a/a) RXB-201 | Purge factor (UHPLC) Furanone | Purge factor (UHPLC) Hydroxy | Purge factor (UHPLC) Sulfoxide |
|---|---|---|---|---|---|---|---|---|
| VLA P075-180 | 89 | n.d. | 0.10 | 0.47 | 99.43 | n.a. | 5.6 | 2.3 |
| VLA P075-184 | 92 | n.d. | 0.11 | 0.08 | 99.81 | n.a. | 6 | 2.0 |
| CHG P059-090 | 92 | n.d. | 0.28 | 0.04 | 99.37 | n.a. | 10 | 1.7 |
| Demo batch | | | | To be performed | | | | |

Figure 25:
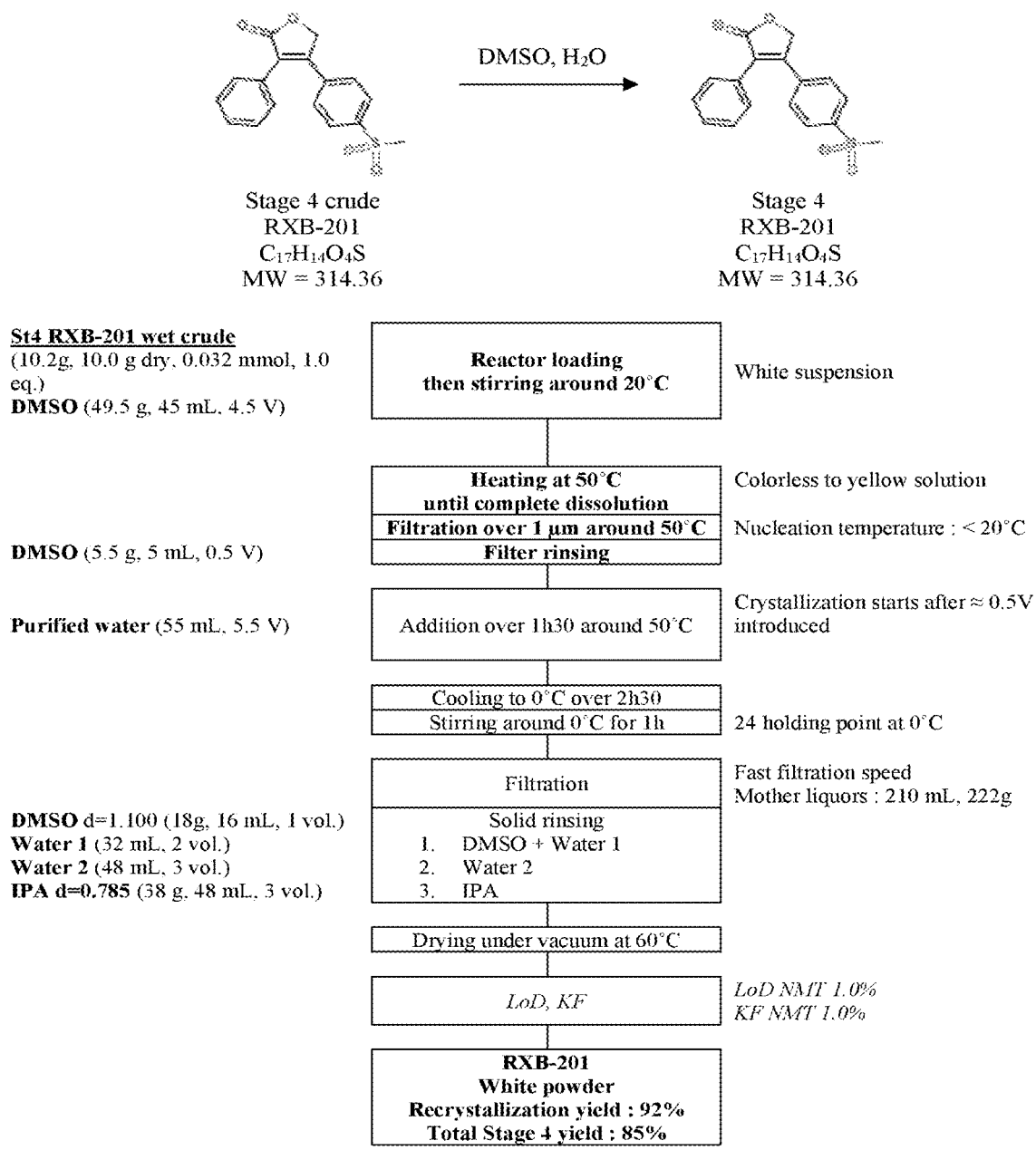
FIG. 25 shows a recrystallization flowsheet of rofecoxib (RXB-201).

The recrystallization flowsheet is shown in FIG. 25.

Figure 26:
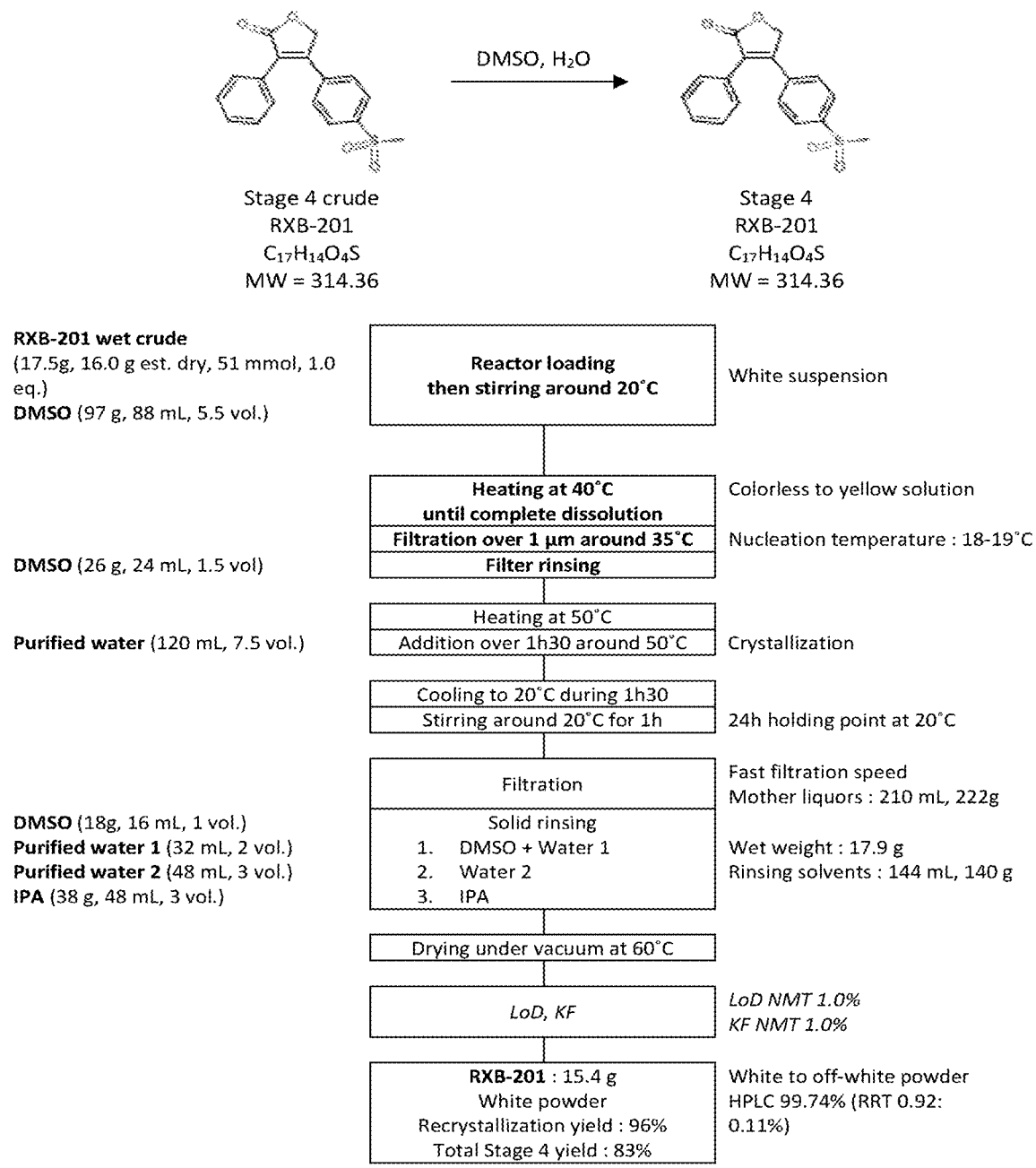
FIG. 26 shows a process flowsheet for 4-[4-(methylthio)phenyl]-3-phenyl-2(5H)-furanone oxidation.

Example 7—Further Optimization of Rofecoxib (RXB-201) Recrystallization Context of Study FIG. 26 shows a process flowsheet for 4-[4-(methylthio)phenyl]-3-phenyl-2(5H)-furanone oxidation.

Oprimization was conducted with respect to the following factors:
  The purge factor of 4-[4-(methylsulfinyl)phenyl]-3-phenyl-2(5H)-furanone is low. The recrystallization process allows to half the amount of 4-[4-(methylsulfinyl) phenyl]-3-phenyl-2(5H)-furanone (purge factor=2). This poor efficiency of impurity removal leads to the need of a low specification at oxidation IPC (4-[4-(methylsulfinyl)phenyl]-3-phenyl-2(5H)-furanone <0.20% area) to get an API in specifications.
  High volumes of solvents are used. 7 volumes of DMSO and 7.5 volumes of purified water are needed to perform the recrystallization. The 14.5 volumes in total could be an issue for productivity during upscale.

The first part of the optimization work has been focused on solvents screening to find the best solvents for solubilization and crystallization of rofecoxib (RXB-201). The purge factor of 4-[4-(methylsulfinyl)phenyl]-3-phenyl-2 (5H)-furanone was then studied with various solvents. The formation of another impurity, 4-[4-(methylsulphonyl)phenyl]-3-phenyl-5-hydroxyfuran-2-one, was also studied. Finally, the optimization work was concentrated on improvement of recrystallization productivity.

Solvents Screening Assisted by Dynochem Software

The tool called "Early phase solvent selection: solubility prediction" was used. This tool allows to predict the solubility of material in a large scope of solvents, knowing the solubility in some of them. The solubility can be also predicted in function of temperature, and for solvent combinations. The solubility prediction is based on similar structures moieties between solvents. Therefore, the measurement of solubility in 16 different solvents allowed for the estimate of solubility in up to 106 solvents. Table 9 below reports the solubility measurements of rofecoxib (RXB-201) performed in 14 solvents and predicted solubilities of anisole and isopropanol. Solubilities were obtained by UHPLC assay. Among these 106 solvents, 27 seemed interesting as solvent or antisolvent. DMF, NMP and DMSO are the solvents in which rofecoxib (RXB-201) is the most soluble (>100 g/L at 30° C.). Nevertheless, ICH Q3C, DMF and NMP were less suitable than DMSO which remains the best option. Thus, no changes were implemented regarding the solvent.

TABLE 9

Solubility of rofecoxib (RXB-201) in various solvents

| Solvent | Temperature (° C.) | Solubility (g/L) | Data |
|---|---|---|---|
| n-heptane | 30 | <0.1 | Measured |
| Anisole | 30 | 22 | Measured |
| Toluene | 30 | 1.2 | Measured |
| Methanol | 30 | 1.8 | Measured |
| Ethanol | 30 | <0.1 | Dynochem |
| n-butanol | 30 | 0.2 | Measured |
| IPA | 20 | 0.4 | Dynochem |
| Water | 30 | <0.1 | Measured |
| Acetone | 30 | 28 | Measured |
| Ethyl acetate | 30 | 4.7 | Measured |
| Acetonitrile | 30 | 41 | Measured |
| Acetic acid | 30 | 5 | Measured |
| Dichloromethane | 30 | 45 | Measured |
| Chlorobenzene | 30 | 2.3 | Measured |
| DMF | 30 | 133 | Measured |
| NMP | 30 | 140 | Measured |
| DMSO | 20 | 93 | Measured |
|  | 30 | 107 | Measured |
|  | 40 | 133 | Measured |
|  | 50 | 181 | Measured |
|  | 60 | 181 | Measured |

Regarding the antisolvent, rofecoxib (RXB-201) is very poorly soluble in water (insoluble regarding US pharmacopeia). This implies rapid crystallization occurs upon addition of water an antisolvent. It may be the origin of the bad impurity purge. Among the solvents studied for solubility measurements, and similarly to previous stages, IPA seems to be a good candidate. Indeed, rofecoxib (RXB-201) is slightly more soluble in IPA than in water, which can lead to a smoother crystallization.

Since the main purpose of the recrystallization is to decrease the rate of one single identified impurity, 4-[4-(methylsulfinyl)phenyl]-3-phenyl-2(5H)-furanone solubilities were measured in a couple of probable antisolvents identified in Table 9. A reference of 4-[4-(methylsulfinyl)phenyl]-3-phenyl-2(5H)-furanone (CHG P059-038) was synthesized at lab on 8 g for this study, with 98% purity, as per International Patent Application No. WO/2005/120584, which is incorporated herein in its entirety. Table 10 below reports the solubility of 4-[4-(methylsulfinyl)phenyl]-3-phenyl-2(5H)-furanone in various antisolvent candidates. It is noteworthy that 4-[4-(methylsulfinyl)phenyl]-3-phenyl-2(5H)-furanone is very soluble in acetic acid. As acetic acid is a potential antisolvent to crystallize rofecoxib (RXB-201) (solubility=5 g/L), and it seems to be a good candidate that should allow a good crystallization of rofecoxib (RXB-201) while keeping in solution the 4-[4-(methylsulfinyl)phenyl]-3-phenyl-2(5H)-furanone. Alcohols can alternatively be employed as antisolvent.

TABLE 10

Solubility of 4-[4-(methylsulfinyl)phenyl]-3-phenyl-2(5H)-furanone in various solvents

| Solvent | Temperature (° C.) | Solubility (g/L) | Data |
|---|---|---|---|
| Acetic acid | 30 | 1540 | Measured |
| n-Butanol | 30 | 14 | Measured |
| Ethanol | 30 | 28 | Measured |
| IPA | 30 | 0.2 | Measured |
| Water | 30 | 0.7 | Measured |

Recrystallization Trials with Various Antisolvents

Isopropanol was tested first as antisolvent, following the processed shown in Tables 11A-B below, LMC P045-157. The recrystallization yield was poor, only 64%. Purge factor of 4-[4-(methylsulfinyl)phenyl]-3-phenyl-2(5H)-furanone is almost unchanged compared to the use of water. The low yield is surprising considering the low solubility of rofecoxib (RXB-201) in IPA. A mix between IPA and water was tested as antisolvent (LMC P045-165). This trial led to a much better yield of 93%, while purge of 4-[4-(methylsulfinyl)phenyl]-3-phenyl-2(5H)-furanone stayed around 2. The very high solubility of 4-[4-(methylsulfinyl)phenyl]-3-phenyl-2(5H)-furanone in acetic acid suggests that this solvent would be a good option to improve the impurity elimination. Moreover, the low solubility of rofecoxib (RXB-201) should lead to a high yield. LMC P045-076 was launched with acetic acid instead of water. This trial gave a low yield of 68%, with a purge of 4-[4-(methylsulfinyl) phenyl]-3-phenyl-2(5H)-furanone slightly increased to 3. This purge factor is far from what was expected according to solubility data. Two final trials were performed with the same process, but with spiking of 4-[4-(methylsulfinyl) phenyl]-3-phenyl-2(5H)-furanone at the beginning to reach around 1% and 2% of impurity before recrystallization. This led to the same yield as LMC P045-076, without real effect on purge efficiency. These trials with new antisolvent did not help to significantly improve purge efficiency of 4-[4-(methylsulfinyl)phenyl]-3-phenyl-2(5H)-furanone. Therefore, water is used as antisolvent.

TABLE 11A

Rofecoxib (RXB-201) recrystallization trials with various antisolvents

| | Crude RXB-201, process | | | |
|---|---|---|---|---|
| Reference | Scale | RXB-Sulfoxide (% a/a) | Solvent | Antisolvent |
| LMC P045-157 | 8 g | | 7 V DMSO | 7.5 V IPA |
| LMC P045-165 | 8 g | | 7 V DMSO | 1.88 V IPA 5.62 V Water |
| LMC P045-176 | 8 g | | 7 V DMSO | 7.5 V AcOH |
| LMC P045-180-R1 | 8 g | 1.0 | 7 V DMSO | 7.5 V AcOH |
| LMC P045-180-R2 | 8 g | 1.9 | 7 V DMSO | 7.5 V AcOh |

TABLE 11B

Rofecoxib (RXB-201) recrystallization trials with various antisolvents (cont.)

| | Recrystallized RXB-201 | | | | | |
|---|---|---|---|---|---|---|
| | Yield (%) | UHPLC results (% a/a) | | | Purge factor (UHPLC) | |
| Reference | | Fura-none | Sulf-oxide | RXB-201 | Fura-none | Sulf-oxide |
| LMC P045-157 | 64 | 0.05 | 0.04 | 99.89 | 3.0 | 2.3 |
| LMC P045-165 | 93 | 0.11 | 0.05 | 99.83 | 1.4 | 1.8 |
| LMC P045-176 | 68 | 0.06 | 0.03 | 99.83 | 2.5 | 3.0 |
| LMC P045-180-R1 | 66 | 0.04 | 0.38 | 99.32 | 3.8 | 2.6 |
| LMC P045-180-R2 | 65 | n.d. | 0.49 | 99.28 | >15 | 3.8 |

TABLE 12A

Optimization of rofecoxib (RXB-201) recrystallization with DMSO/water

| | | Crude RXB-201, process | | | | |
|---|---|---|---|---|---|---|
| | | RXB-Sulfoxide | Solvents | | Temperature | |
| Reference | Scale | (% a/a) | DMSO | Water | Initial | Final |
| LMC P045-186-R1 | 8 g | 1.1 | 7 V | 7.5 V | 50° C. | 20° C. |
| LMC P045-186-R2 | 8 g | 1.8 | 7 V | 7.5 V | 50° C. | 20° C. |
| VLA P075-180 | 10.1 g | 0.23 | 5.5 V | 5 V | 60° C. | 20° C. |
| VLA P075-184 | 10.1 g | 0.22 | 6 V | 5.5 V | 50° C. | 0° C. |
| CHG P059-090 | 10.1 g | 0.47 | 5 V | 5.5 V | 50° C. | 0° C. |
| CHG P059-098 | 20 g | 0.08 | 5 V | 5.5 V | 50° C. | 20° C. |
| CHG P059-104 | 19 g | 0.22 | 5 V | 3 V | 50° C. | 20° C. |

TABLE 12B

Optimization of rofecoxib (RXB-201) recrystallization with DMSO/water (cont.)

| | Recrystalized RXB-201 | | | | | | | |
|---|---|---|---|---|---|---|---|---|
| | Yield (%) | UHPLC results (% a/a) | | | | Purge factor (UHPLC) | | |
| Reference | | Fura-none | Sulf-oxide | Hy-droxy | RXB-201 | Fura-none | Hy-droxy | Sulf-oxide |
| LMC P045-186-R1 | 83 | 0.12 | 0.45 | n.d. | 99.34 | 1.3 | n.a. | 2.4 |
| LMC P045-186-R2 | 92 | 0.12 | 0.79 | n.d. | 99.04 | 1.3 | n.a. | 2.3 |
| VLA P075-180 | 89 | n.d. | 0.10 | 0.47 | 99.43 | n.a. | 5.6 | 2.3 |
| VLA P075-184 | 92 | n.d. | 0.11 | 0.08 | 99.81 | n.a. | 6 | 2.0 |
| CHG P059-090 | 92 | n.d. | 0.28 | 0.04 | 99.67 | n.a. | 10 | 1.7 |
| CHG P059-098 | 97 | n.d. | 0.05 | 0.01 | 99.93 | n.a. | 2.3 | 1.6 |
| CHG P059-104 | 96 | 0.05 | 0.12 | 0.02 | 99.82 | n.a. | 2 | 1.8 |

Study of Formation of 4-[4-(methylsulphonyl)phenyl]-3-phenyl-5-hydroxyfuran-2-one (RXB-Hydroxy) Impurity There are report of the synthesis of 4-[4-(methylsulphonyl)phenyl]-3-phenyl-5-hydroxyfuran-2-one under air. This impurity was not detected in pilot batch F801, but is always observed in trials. In trial VLA P075-180, the rate of 4-[4-(methylsulphonyl)phenyl]-3-phenyl-5-hydroxyfuran-2-one rose to 2.66% at 60° C., before addition of water. The sodium sulfite is suspected to generate this impurity, as depicted in the Scheme 2 below. At pilot, the polishing filtration removes the traces of salt, while this filtration is not performed in lab trials. Moreover, the inert atmosphere is better controlled at pilot then at lab.

Scheme 2. Formation of 4-[4-(methylsulphonyl)phenyl]-3-phenyl-5-hydroxyfuran-2-one(RXB-Hydroxy) impurity

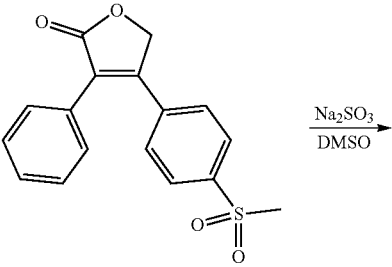

RXB-201
$C_{17}H_{14}O_4S$
MW = 314.36

$\xrightarrow{Na_2SO_3}{DMSO}$

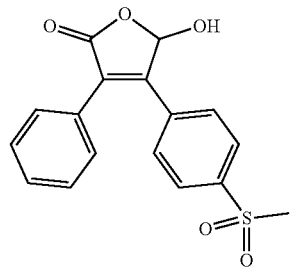

RXB-Hydroxy
$C_{17}H_{14}O_5S$
MW = 330.36

Trials were performed to check the effect of both temperature and sodium sulfite on the 4-[4-(methylsulphonyl)phenyl]-3-phenyl-5-hydroxyfuran-2-one rate. Pure rofecoxib (RXB-201) (F851) was solubilized in 5.5V DMSO, on which Na2SO3 was added. Three amounts of Na$_2$SO$_3$ were tested:

0%: rofecoxib (RXB-201) post filtration
0.5%: ashes result obtained on pilot batch (crude rofecoxib (RXB-201) F801)
1.5%: ashes result obtained on APG P052-110 batch Samples were subjected to 2 different temperatures under air atmosphere:

40° C.: current heating temperature for polishing filtration
60° C.: possible future temperature for polishing filtration if DMSO volumes are reduced for better productivity.

UHPLC results are reported in the Table 13 below.

TABLE 13

UHPLC rate of 4-[4-(methylsulphonyl)phenyl]-3-phenyl-5-hydroxyfuran-2-one (RXB-Hydroxy) in function of RoI and temperature

| Residue on ignition | IPC | RXB-Hydroxy (UPLC % a/a) | |
|---|---|---|---|
| | | 40° C. | 60° C. |
| 0% | IPC1 (3 h) | 0.08 | 0.16 |
| | IPC2 (6 h) | 0.14 | 0.17 |
| 0.5% | IPC1 (3 h) | 0.30 | 0.35 |
| | IPC2 (6 h) | 0.45 | 0.52 |
| 1.5% | IPC1 (3 h) | 0.38 | 0.67 |
| | IPC2 (6 h) | 0.60 | 0.73 |

UHPLC results clearly show that the recrystallization medium (rofecoxib (RXB-201) in 5.5V DMSO) is almost stable at 40° C. and 60° C. for 6 h with an amount of 4-[4-(methylsulphonyl)phenyl]-3-phenyl-5-hydroxyfuran-2-one up to 0.17%. However, the introduction of sodium sulfite has a negative effect of purity profile, as well as increasing temperature. The worst case gave an amount of 4-[4-(methylsulphonyl)phenyl]-3-phenyl-5-hydroxyfuran-2-one 9 times higher than at the beginning. The control of the sodium sulfite rate in the crude rofecoxib (RXB-201) is crucial for the UHPLC profile of the recrystallized compound. To solve this issue, the optimized oxidation process was designed without sodium sulfite quench. The suppression of Na$_2$SO$_3$ was use tested (Oxidation CHG P059-092 followed by recrystallization CHG P059-098) and succeeded to give an API that meets specifications, as visible in Tables 12A-B above.

Optimization of Recrystallization in DMSO/Water
A. Preliminary Trials

All recrystallization trials conducted with DMSO and water are reported in Tables 12A-B. The third column "4-[4-(methylsulfinyl)phenyl]-3-phenyl-2(5H)-furanone" refers to the amount of 4-[4-(methylsulfinyl)phenyl]-3-phenyl-2(5H)-furanone before recrystallization in crude rofecoxib (RXB-201). As most of crude rofecoxib (RXB-201) engaged in recrystallization were clean, spikings with 4-[4-(methylsulfinyl)phenyl]-3-phenyl-2(5H)-furanone (CHG P059-038) were performed to evaluate the purge efficiency. Trials LMC P045-186 were conducted to evaluate the purge factor of 4-[4-(methylsulfinyl)phenyl]-3-phenyl-2(5H)-furanone, with the current recrystallization process, with much higher rates of this impurity than usually (up to 1.8% a/a). Trials R1 and R2 gave the same purge factor (2.4 and 2.3) as usually. This recrystallization process has then the same purification efficiency, from 0.10% to 1.8% of 4-[4-(methylsulfinyl)phenyl]-3-phenyl-2(5H)-furanone. The study was then focused at reducing total amounts of solvent, to increase productivity. VLA P075-180 was conducted with lower amounts of DMSO (−1.5V) and water (−2.5V) compared to current process. After having performed the standard recrystallization process with these reduced solvent amounts, the product was obtained with 89% yield, with again 2.3 as 4-[4-(methylsulfinyl)phenyl]-3-phenyl-2(5H)-furanone purge factor. However, the purity of rofecoxib (RXB-201) was not satisfying (99.43%) due to the formation of 4-[4-(methylsulphonyl)phenyl]-3-phenyl-5-hydroxyfuran-2-one (0.47%). This trial was launched on a crude rofecoxib (RXB-201) which contained a high level of RoI (APG P052-110, 1.5% RoI). The high amount of RXB-Hydroxy was explained by the presence of Na2SO3. With higher DMSO rate (6V), and lower temperature (50° C.), the trial VLA P075-184 allowed to give rofecoxib (RXB-201) in good yield after filtration at 0° C., with an average purge of 4-[4-(methylsulphonyl)phenyl]-3-phenyl-5-hydroxyfuran-2-one and 4-[4-(methylsulfinyl)phenyl]-3-phenyl-2(5H)-furanone.

B. Rofecoxib (RXB-201) Solubility Study

Figure 12:
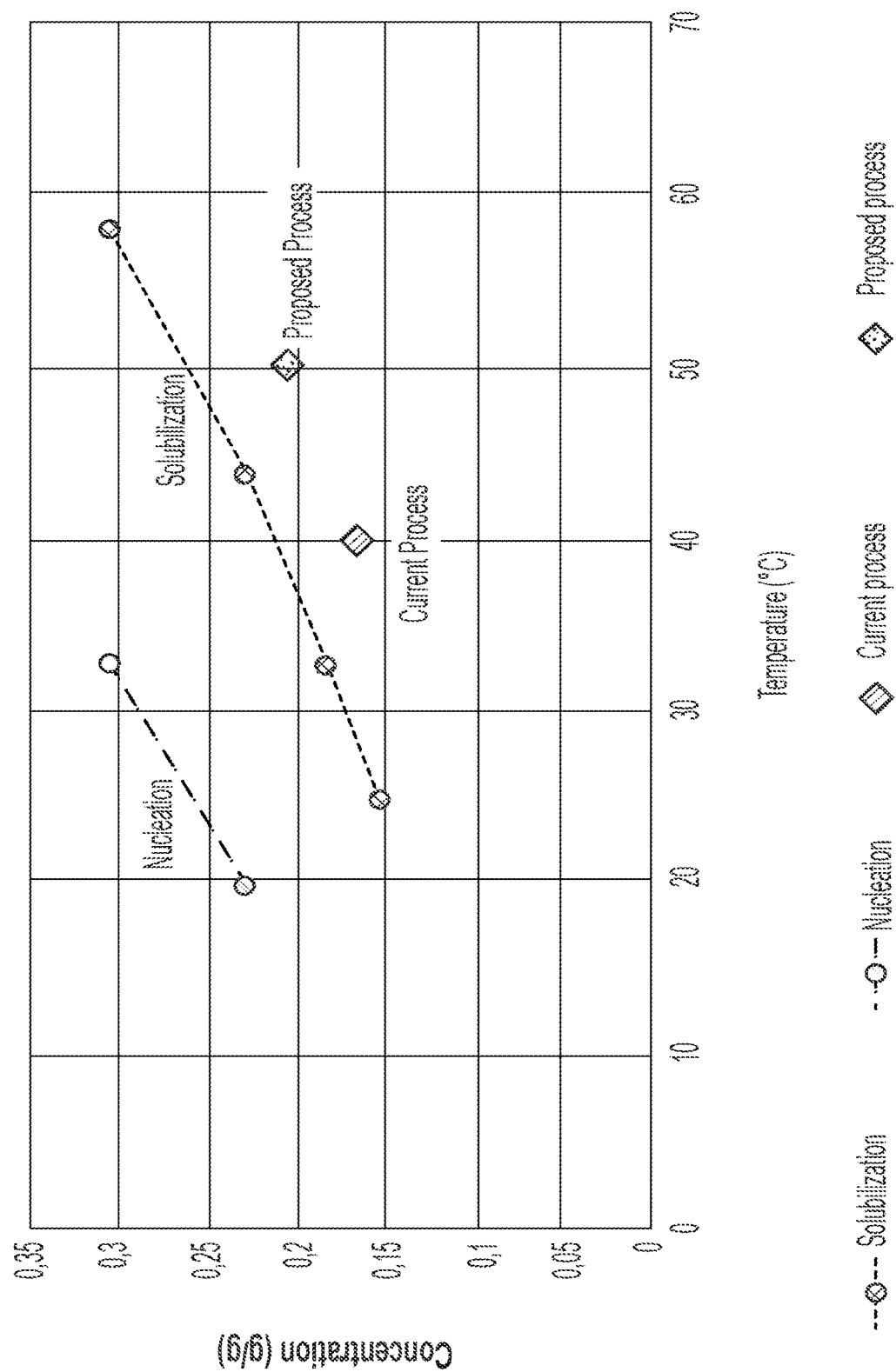
FIG. 12 shows solubilization and nucleation curves of rofecoxib in DMSO.

To have a precise view of solvents volume reduction capabilities, it was needed to know properly the solubility of rofecoxib (RXB-201) depending on DMSO volumes. Thanks to the Crystal 16 apparatus, solubility and nucleation of rofecoxib (RXB-201) was measured at four different concentrations: 3 V, 4 V, 5 V and 6 V. Results are depicted in FIG. 12. The solubilization curve is reported in blue, and nucleation in orange. The process used for solubilization of RXB-201 at the beginning or recrystallization process batch F851 is reported as the purple spot (5.5V at 40° C.). To improve the productivity, the concentration can be increased to 4.5V, with heating at 50° C. (red spot). These conditions allows a good solubilization of rofecoxib (RXB-201), with a large safety margin compared to the nucleation temperature (at least 30° C.). This margin is required to avoid spontaneous crystallization during clarifying filtration. An extra-amount of DMSO (+0.5 V) is used for rinsing of the filtration system, leading to 5V DMSO in total.

C. Optimization of Recrystallization Productivity

A recrystallization trial was launched on 20 g of crude rofecoxib (RXB-201) (CHG P059-098) with 5V DMSO in total. 5.5V water were used to ensure crystallization, and led to a very high yield (97%) with satisfying purity. Nevertheless, the crude engaged in recrystallization was already pretty clean. A low 4-[4-(methylsulfinyl)phenyl]-3-phenyl-2(5H)-furanone purge was observed in this case (purge factor=1.6). It has been demonstrated previously that the purge factor of 4-[4-(methylsulfinyl)phenyl]-3-phenyl-2 (5H)-furanone is almost constant (purge factor=2) starting on crude containing 0.1% to 2% 4-[4-(methylsulfinyl)phenyl]-3-phenyl-2(5H)-furanone. It is unknown whether the low purge factor is due to the low amount of impurity to removed (rupture of purge linearity), the recrystallization conditions (solvents amount and ratio), reproducibility issues or measures of uncertainty. A last trial (CHG P059-104) was performed with lowered amount of water (3V) to try to improve purging efficiency while keeping high yield. The yield stayed high (96%) with 1.8 as purge factor of 4-[4-(methylsulfinyl)phenyl]-3-phenyl-2(5H)-furanone, which is in the average. 4-[4-(methylthio)phenyl]-3-phenyl-2(5H)-furanone is detected in this batch, at low rate (0.05%). The crude rofecoxib (RXB-201) used in this trial had the particularity to come from the calorimetry study of 4-[4-(methylthio)phenyl]-3-phenyl-2(5H)-furanone oxidation. This crude contained traces of 4-[4-(methylthio)phenyl]-3-phenyl-2(5H)-furanone and 0.22% 4-[4-(methylsulfinyl)phenyl]-3-phenyl-2(5H)-furanone. Therefore, the presence of 4-[4-(methylthio)phenyl]-3-phenyl-2(5H)-furanone in this demo batch should not be considered as an alert. The solvent ratio (5V DMSO/3V Water) was chosen as the most optimized recrystallization process. This process is the less solvent consuming, and improves the productivity of this recrystallization step of +45% compared to current process, without affecting the purge efficiency. The slight yellow coloration of crude rofecoxib (RXB-201) is efficiently removed to afford a white recrystallized rofecoxib (RXB-201) solid.

Figure 27:
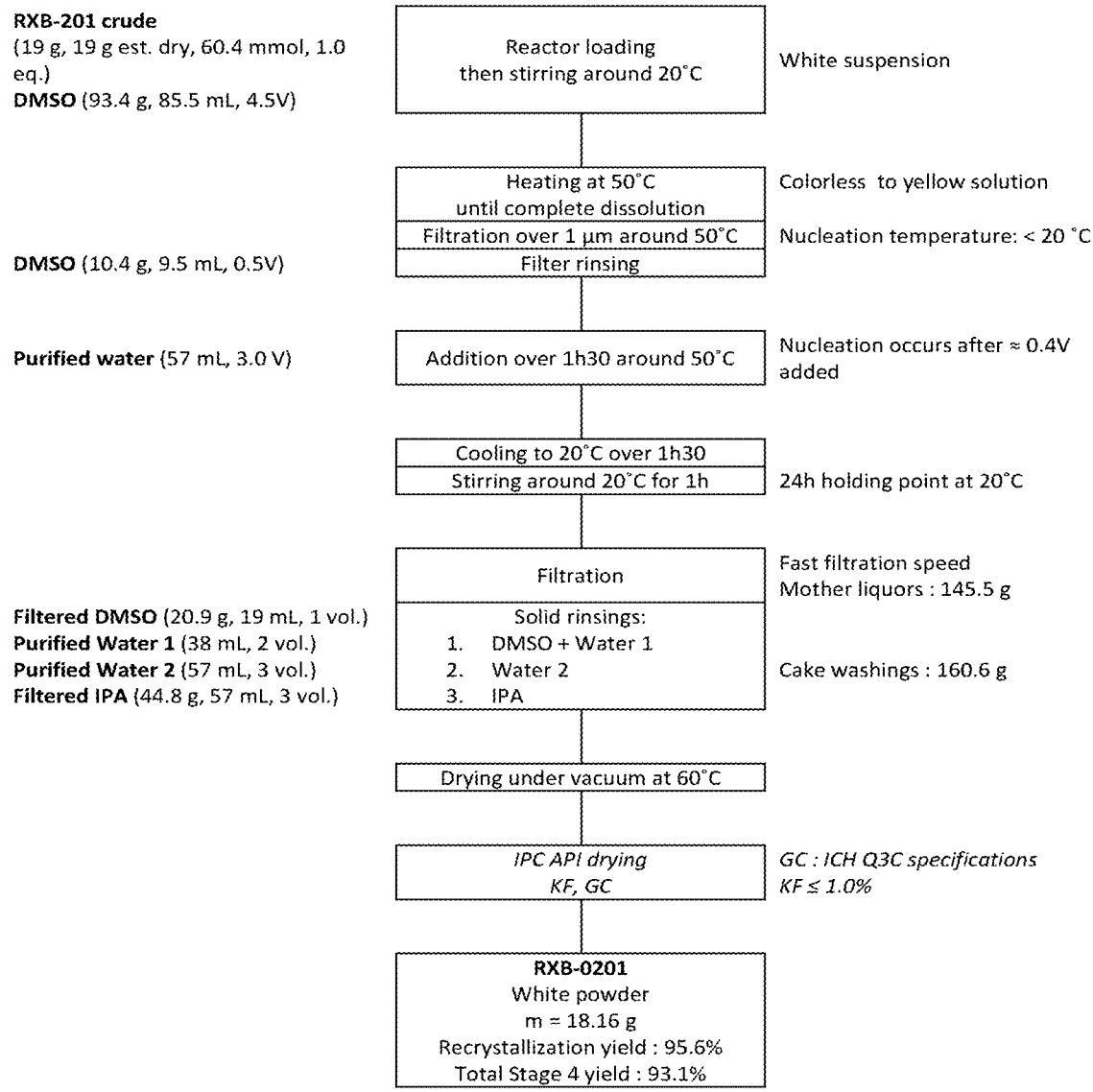
FIG. 27 shows a flowsheet of optimized recrystallization of rofecoxib (RXB-201).

Flowsheet of optimized recrystallization of rofecoxib (RXB-201) is shown in FIG. 27.

The solvent screening, assisted by Dynochem software, has highlighted only 3 candidates as good solvent, and 6 candidates as antisolvent. DMSO was kept as good solvent for recrystallization. Isopropanol and acetic acid were tried as antisolvent, without success of 4-[4-(methylsulfinyl)phenyl]-3-phenyl-2(5H)-furanone purge improvement. The combination of DMSO and water is still the best option for crude rofecoxib (RXB-201) recrystallization. Optimization has led to the reduction of 45% of the total volume, which has a signification impact on process productivity. The rate of 4-[4-(methylsulfinyl)phenyl]-3-phenyl-2(5H)-furanone is almost only halved after recrystallization.

To address this issue, IPC and crude rofecoxib (RXB-201) specifications as follows in Table 14:

TABLE 14

Oxidation IPC

| Oxidation IPC and isolated crude RXB-201 | | |
|---|---|---|
| | Current specification | New specification |
| RXB-Furanone | ≤0.5% | <0.15% |
| RXB-Sulfoxide | ≤0.2% | <0.20% |

The formation 4-[4-(methylsulphonyl)phenyl]-3-phenyl-5-hydroxyfuran-2-one is also now better understood, and should be significantly reduced due to the suppression of sodium sulfite used for oxidation quench. 4-[4-(methylsulphonyl)phenyl]-3-phenyl-5-hydroxyfuran-2-one is sufficiently eliminated during recrystallization.

Figure 28:
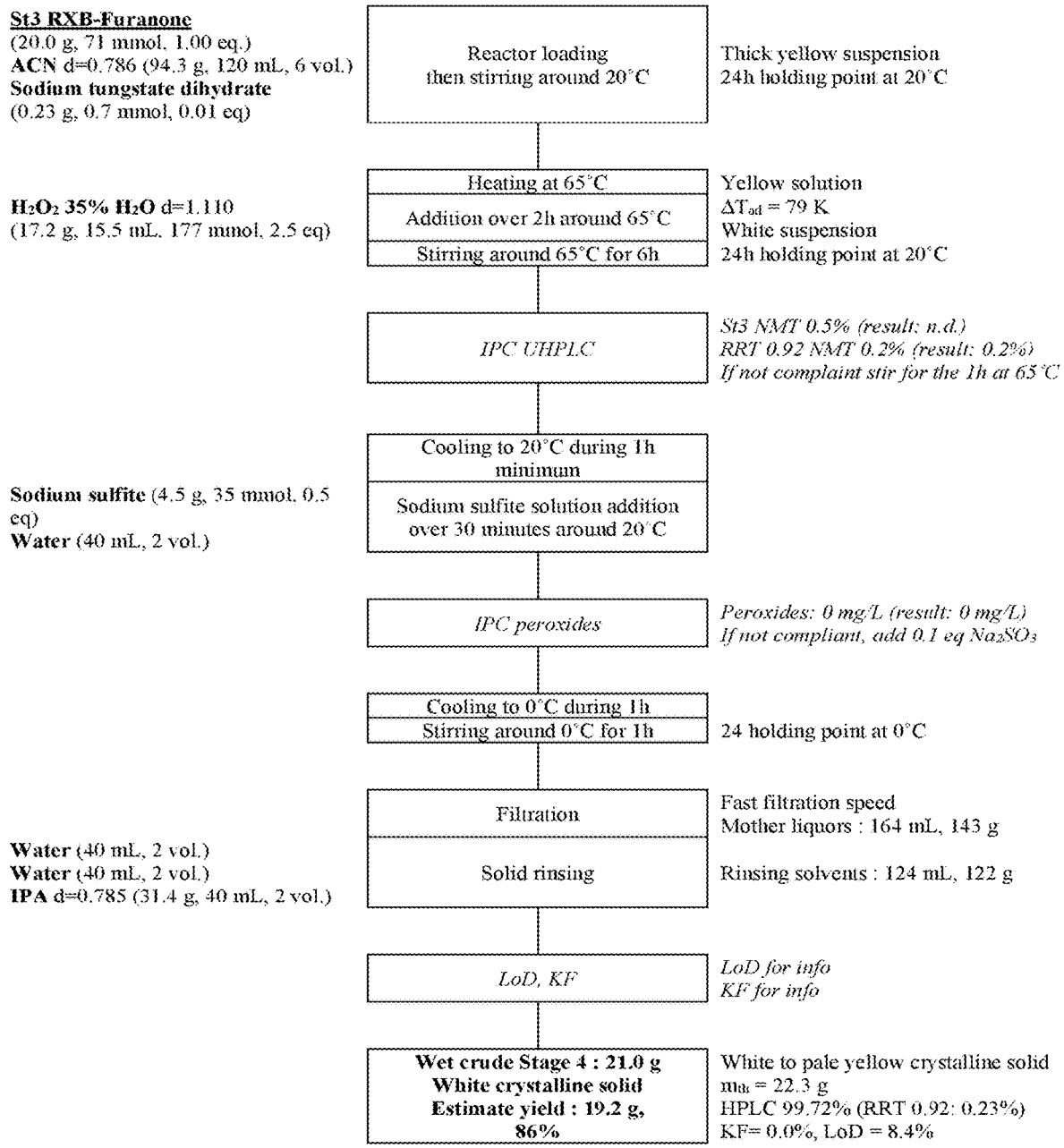
FIG. 28 shows the current flowsheet for 4-[4-(methylthio)phenyl]-3-phenyl-2(5H)-furanone (RXB-furanone) oxidation.

Example 8—Further Process Optimization of Oxidation of 4-[4-(methylthio)phenyl]-3-phenyl-2(5H)-furanone Context of the Study FIG. 28 shows the current flowsheet for 4-[4-(methylthio)phenyl]-3-phenyl-2(5H)-furanone (RXB-furanone) oxidation.

Oprimization was conducted with respect to the following factors:

The oxidation is classed 5/5 on the Stoessel scale, with high thermic accumulation phenomenon observed at the beginning of the oxidation.

The time of heating to reach IPC specification (4-[4-(methylsulfinyl)phenyl]-3-phenyl-2(5H)-furanone≤0.2% area UHPLC) was 14 h instead of 6 h. This long reaction time could be due to a slower reaction or difficulties to get representative IPC sample of the batch composition. The impurity profile was not affected, even after this long heating time.

A high amount of RoI (0.5%, analysis #CQ18-0487) was obtained in the isolated crude rofecoxib (RXB-201). This material led to filter clogging during clarification before recrystallization.

The presence of insoluble matters could be attributed to sodium sulfite, as difficulties were encountered during its dissolution prior to quench. The first part of the oprimization work is focused to the research of solvents for oxidation process. The second part is focused on the suppression of energy accumulation to improve the process safety. The conversion of 4-[4-(methylsulfinyl)phenyl]-3-phenyl-2(5H)-furanone (RXB-Sulfoxide) traces at the end of the oxidation was then studied, as well as IPC samples preparation. Finally, the need of sodium sulfite quench was evaluated.

Research of Solvents for the Oxidation Process

In the current oxidation process, depicted in Scheme 3, the solvent used is acetonitrile. In the process conditions, 6 volumes of ACN allow a full dissolution of 4-[4-(methylthio)phenyl]-3-phenyl-2(5H)-furanone at 65° C. at the beginning of the process. 6 h after hydrogen peroxide addition completion, the reaction medium is heterogeneous, with a high amount of white solid in suspension. This solid is mostly composed of rofecoxib (RXB-201) (>99%) with traces of 4-[4-(methylsulfinyl)phenyl]-3-phenyl-2(5H)-furanone (<1%). This reveals that rofecoxib (RXB-201) has a lower solubility in ACN than 4-[4-(methylthio)phenyl]-3-phenyl-2(5H)-furanone. While rofecoxib (RXB-201) crystallizes out, 4-[4-(methylsulfinyl)phenyl]-3-phenyl-2(5H)-furanone could be stacked into the crystals. Therefore, a better solubility of RXB species was researched to allow a full oxidation of the 4-[4-(methylsulfinyl)phenyl]-3-phenyl-2(5H)-furanone traces. In the aim of recrystallization improvement, the solubility of rofecoxib (RXB-201) was measured in a large panel of solvents. Before these solubilities were measured, several trials were conducted. Scheme 4 below shows oxidation of 4-[4-(methylthio)phenyl]-3-phenyl-2(5H)-furanone in DCM/H$_2$O.

Scheme 4. Oxidation of 4-[4-(methylthio)phenyl]-3-phenyl-2(5H)-furanone in DCM/H$_2$O

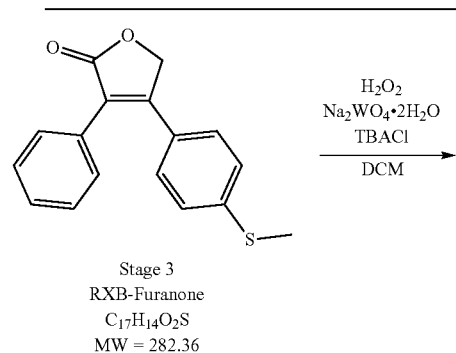

Stage 3
RXB-Furanone
C$_{17}$H$_{14}$O$_2$S
MW = 282.36

-continued

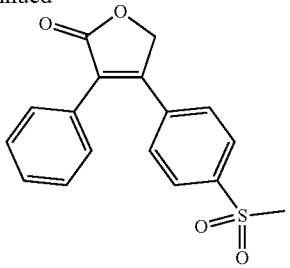

Stage 4 crude
RXB-201
C$_{17}$H$_{14}$O$_4$S
MW = 314.36

In this trial (CHG P059-058), 6V ACN were substituted by 5V DCM, which is expected to be a good solvent for polar organic molecules, such as rofecoxib derivatives. Five conditions were studied, as shown in the Table 15 below.

TABLE 15

Screening of conditions for 4-[4-(methylthio)phenyl]-3-phenyl-2(5H)-furanoneoxidation in DCM/H2O.

| Trial | RXB-Furanone | Mass (g) | H$_2$O$_2$ | Na$_2$WO$_4$·2H$_2$0 | TBACl | DCM |
|---|---|---|---|---|---|---|
| A | F801 dried | 2.00 | 1.55 mL; 2.5 eq | 23.3 mg; 1 mol % | 0 mol % | 10 mL; 5 V |
| B | VLA P075-132 (PP = 44.8%) | 3.62 | 1.55 mL; 2.5 eq | 23.3 mg; 1 mol % | 0 mol % | 10 mL; 5 V |
| C | VLA P075-132 (PP = 44.8%) | 3.62 | 1.55 mL: 2.5 eq | 23.3 mg; 1 mol % | 98 mg; 5 mol % | 10 mL: 5 V |
| D | VLA P075-132 (PP = 44.8%) | 3.62 | 1.55 mL; 2.5 eq | 23.3 mg; 1 mol % | 393 mg; 20 mol % | 10 mL: 5 V |
| E | VLA P075-132 (PP = 44.8%) | 3.62 | 1.55 mL; 2.5 eq | 23.3 mg; 1 mol % | 983 mg; 50 mol % | 10 mL: 5 V |

Figure 13:
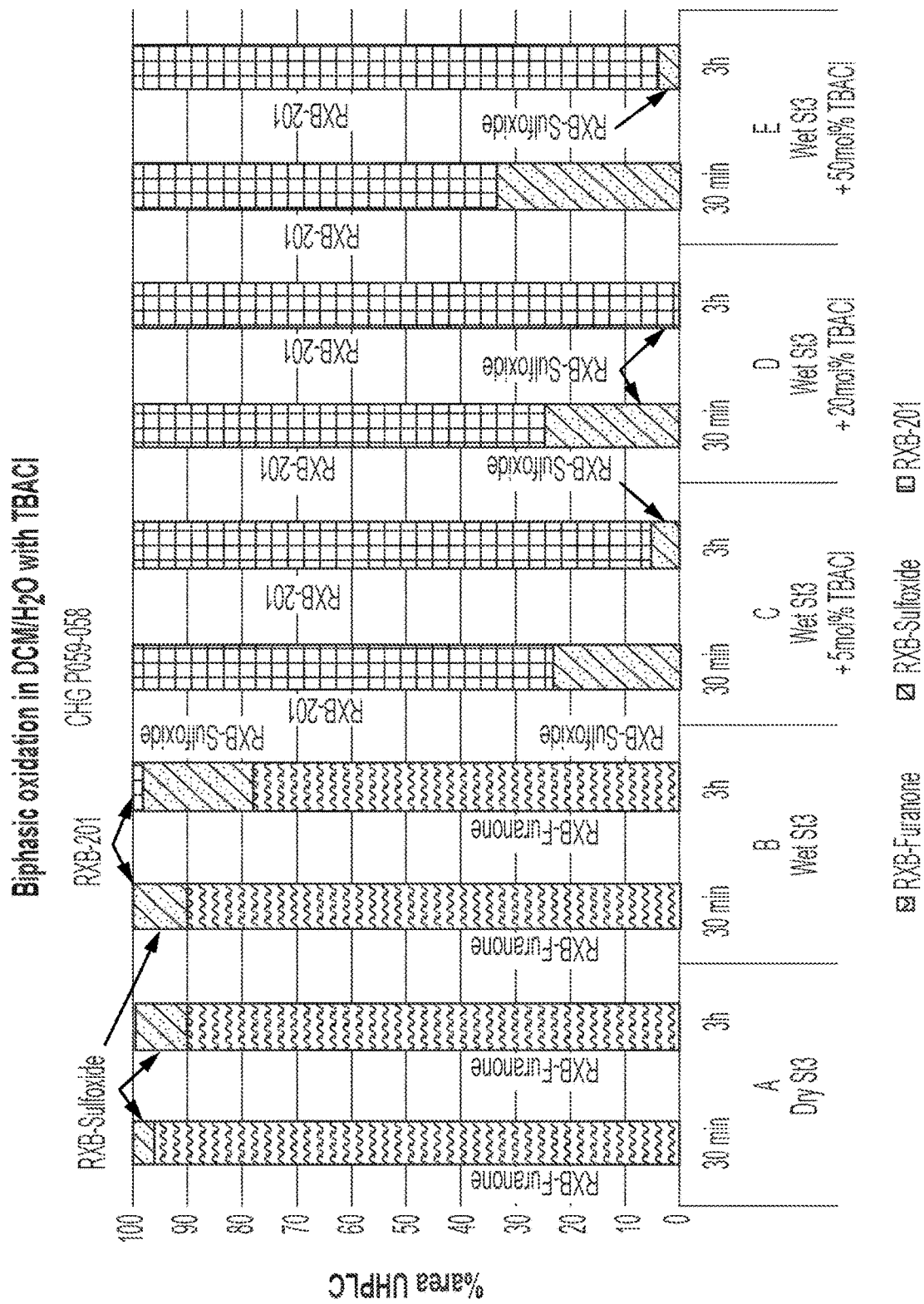
FIG. 13 shows UHPLC results of 4-[4-(methylthio)phenyl]-3-phenyl-2(5H)-furanone oxidation in biphasic conditions.

Trials A and B allowed the study of the effect of residual IPA in 4-[4-(methylthio)phenyl]-3-phenyl-2(5H)-furanone on the kinetics. Trials C, D and E employed a phase transfer catalyst, the tetrabutylammonium chloride (TBACl), to improve the mixing between organic and aqueous layers. All trials were run at room temperature. For practicality, 0.5V of a solution of catalyst (Na$_2$WO$_4$.2H$_2$O) in pure water was introduced. FIG. 13 shows the results of oxidation trials.

Trial A shows a very low conversion of 4-[4-(methylthio)phenyl]-3-phenyl-2(5H)-furanone with UHPLC. Only 10% of 4-[4-(methylsulfinyl)phenyl]-3-phenyl-2(5H)-furanone is observed after 3 h reaction at room temperature. The influence of IPA content in 4-[4-(methylthio)phenyl]-3-phenyl-2(5H)-furanone is visible, with a slightly better conversion (22% 4-[4-(methylsulfinyl)phenyl]-3-phenyl-2(5H)-furanone after 3 h at r.t.) obtained in trial B. A dramatic difference was observed with the use of the TBACl as phase transfer catalyst. Trials C, D and E show the formation of rofecoxib (RXB-201) as main product, even after 30 min reaction. The three trials do not show a real difference for kinetics. Crystallization occurred during oxidation, suggesting a poor solubility of rofecoxib (RXB-201) in DCM. Results obtained in DCM are not better than with the current process in ACN, considering the lack of conversion and solubility. Scheme 5 below shows oxidation in acetonitrile/sulfolane.

Scheme 5. Oxidation in acetonitrile/sulfolane

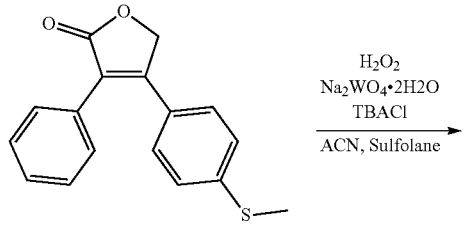

Stage 3
RXB-Furanone
C$_{17}$H$_{14}$O$_2$S
MW = 282.36

-continued

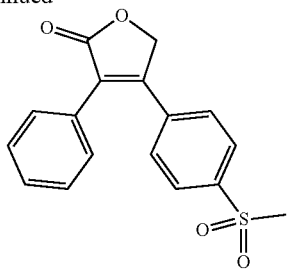

Stage 4 crude
RXB-201
C$_{17}$H$_{14}$O$_4$S
MW = 314.36

The following trials were conducted in 6V ACN as main solvent. An extra addition of sulfolane (1V or 2V) was performed to check the effect on solubility (CHG P059-062). Sulfolane was chosen due to its structure likeness compared to the rofecoxib (RXB-201). The reaction was launched on the wet 4-[4-(methylthio)phenyl]-3-phenyl-2(5H)-furanone, with catalyst previously solubilized in water as in biphasic trials as shown in Table 16 below. Results of oxidation trials are reported in FIG. 14.

TABLE 16

Screening of conditions for 4-[4-(methylthio)phenyl]-3-phenyl-2(5H)-furanoneoxidation with sulfolane.

| Trial | RXB-Furanone | Mass (g) | $H_2O_2$ | $Na_2WO_4 \cdot 2H_2O$ | Sulfolane | ACN |
|---|---|---|---|---|---|---|
| A | VLA P075-132 (PP = 44.8%) | 3.62 | 1.55 mL; 2.5 eq | 23.3 mg; 1 mol % | 0 | 12 mL; 6 V |
| B | VLA P075-132 (PP = 44.8%) | 3.62 | 1.55 mL; 2.5 eq | 23.3 mg; 1 mol % | 2 mL; 1 V | 12 mL; 6 V |
| C | VLA P075-132 (PP = 44.8%) | 3.62 | 1.55 mL; 2.5 eq | 23.3 mg; 1 mol % | 4 mL; 2 V | 12 mL; 6 V |

As for the biphasic trials, 0.5V of a solution of catalyst ($Na_2WO_4 \cdot 2H_2O$) in pure water was introduced, to bring 1 mol % catalyst in the reaction medium. Then, only 0.25 eq. of $H_2O_2$ was first introduced to observe a potential energy accumulation. Upon addition of the first drops of $H_2O_2$ in the mixture at 65° C., an exotherm was observed in the 3 reaction medium. UHPLC confirmed the formation of ≈30% area 4-[4-(methylsulfinyl)phenyl]-3-phenyl-2(5H)-furanone after 5 min in each trials (see FIG. 14).

Trial A is equivalent to the current process. Therefore, an addition of 0.5V water seems to be efficient to suppress the energy accumulation phenomenon. The rest of the hydrogen peroxide was then introduced and reaction media were let under stirring at 65° C. 30 min after $H_2O_2$ addition, an UHPLC analysis was performed and indicated a total conversion of 4-[4-(methylthio)phenyl]-3-phenyl-2(5H)-furanone. However, sulfolane has a negative effect on conversion of 4-[4-(methylsulfinyl)phenyl]-3-phenyl-2(5H)-furanone, with 1.48% remaining intermediate for trial C, 0.98% for trial B, while the standard process (trial A) shows only 0.23% of 4-[4-(methylsulfinyl)phenyl]-3-phenyl-2(5H)-furanone. The dilution effect may be responsible for such a lack of conversion: 8V in total for C, while 6V in total for A. The use of sulfolane seems to not be very effective for improving oxidation of RXB species. Moreover, sulfolane has a low PDE, the concentration limit in ICH Q3C is 160 ppm. Therefore, the risk-benefit ratio is not favorable for the use of this solvent. The 3 solvents below provide rofecoxib (RXB-201) with solubility of more than 100 g/L at 30° C.:

DMSO: 107 g/L
DMF: 133 g/L
NMP: 140 g/L

Figure 14:
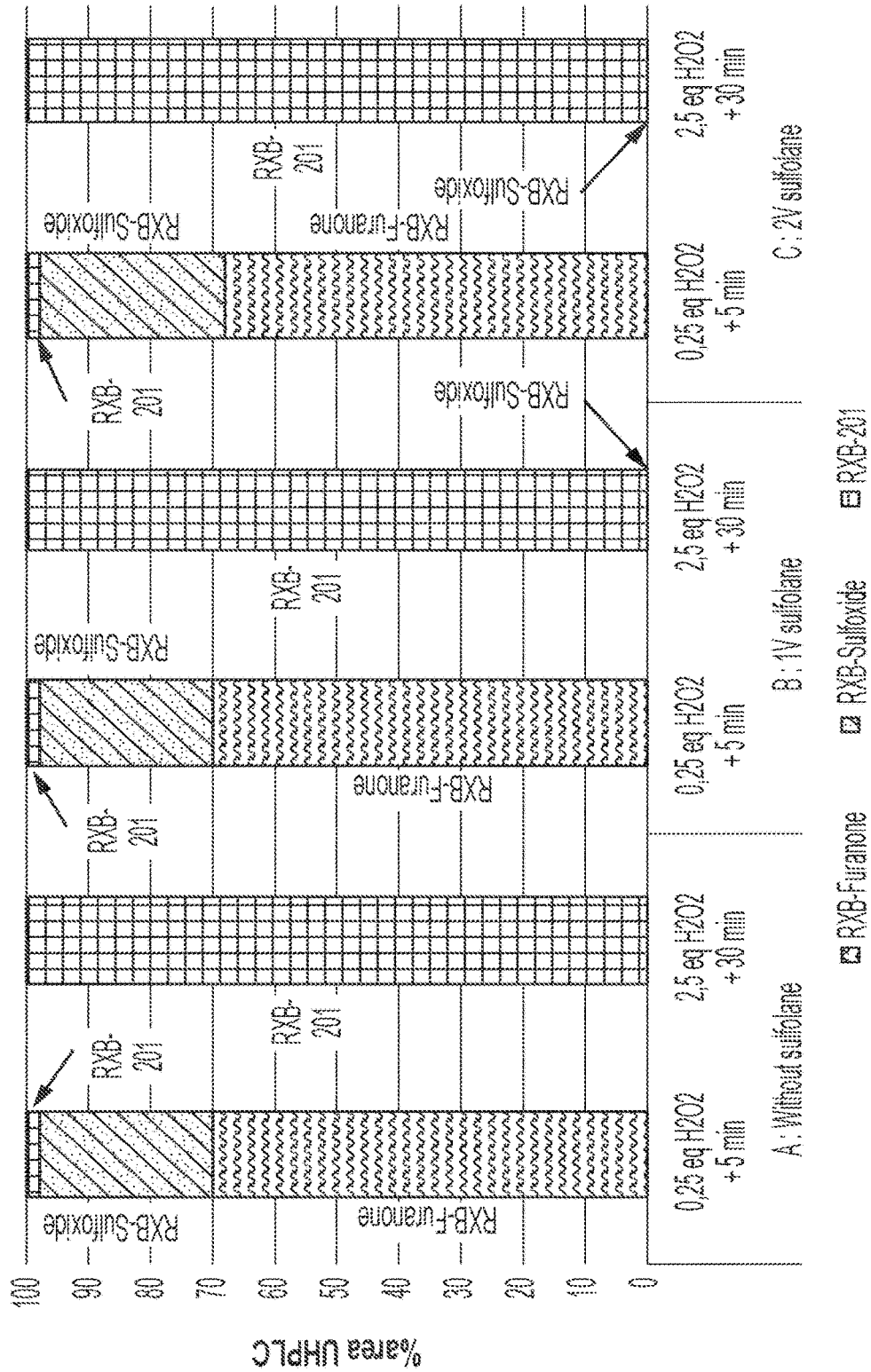
FIG. 14 shows UHPLC results of 4-[4-(methylthio)phenyl]-3-phenyl-2(5H)-furanone oxidation in acetonitrile/sulfolane mixtures.

Being reactive toward the oxidation process, DMSO cannot be used as solvent for the oxidation step. DMF was a solvent widely used previously. This solvent was substituted in all steps due to safety reasons. Therefore, DMF cannot be considered as an alternative. Finally, NMP revealed to be the best solvent, with a rofecoxib (RXB-201) solubility at 30° C. up to 140 g/L. However, the literature mentions the oxidation of NMP into N-methylsuccinimide with hydrogen peroxide under metal catalysis at 0° C. See Dong, J J., et al, ChemSusChem, 2013, 6, 1-6, which is incorporated herein in its entirety. The process conditions at 65° C. makes it risky to envisage the use of NMP without checking the potential formation of 5-hydroxy-N-methylpyrrolidone and N-methylsuccinimide. Ultimately, NMP was withdrawn from the list of candidate solvents for oxidation process. ACN was kept as the solvent for the oxidation process. Addition of water seems to have a positive effect on the reaction kinetics as Trial A in FIG. 14 shows only 0.23% 4-[4-(methylsulfinyl)phenyl]-3-phenyl-2(5H)-furanone 30 min after hydrogen peroxide addition completion. A kinetic model was built to better understand the evolution of RXB species over the time. The thermic accumulation phenomenon of the current process requires a precise appreciation of the reaction kinetic.

Kinetic Model of RXB Species Oxidation

Previous trials have shown that the use of DCM and sulfolane does not allow to obtain a better conversion. The dissolution of the catalyst prior to addition of hydrogen peroxide avoided the accumulation phenomenon. A kinetic model was built to better understand the oxidation reactions that take place in reaction media with the current process. Dynochem® software was used, with the tool "Simple fed batch reaction" to achieve this goal. Two trials were conducted, with the parameters described in Table 17, with reaction follow-up by UHPLC.

TABLE 17

Trials performed for kinetic model building.

| | RXB-Furanone | $H_2O_2$ 35% | $Na_2WO_4 \cdot 2H_2O$ | ACN | Temperature |
|---|---|---|---|---|---|
| CHG P059-074 | 9.05 g LoD = 53% | 2.9 eq. | 0.012 mol % in 0.59 V $H_2O$ | 7.1 V | 65° C. |
| CHG P059-78 | 9.05 g LoD = 53% | 2.9 eq. | 0.18 mol % in 0.59 V $H_2O$ | 28.2 V | 45° C. |

Figure 15A:
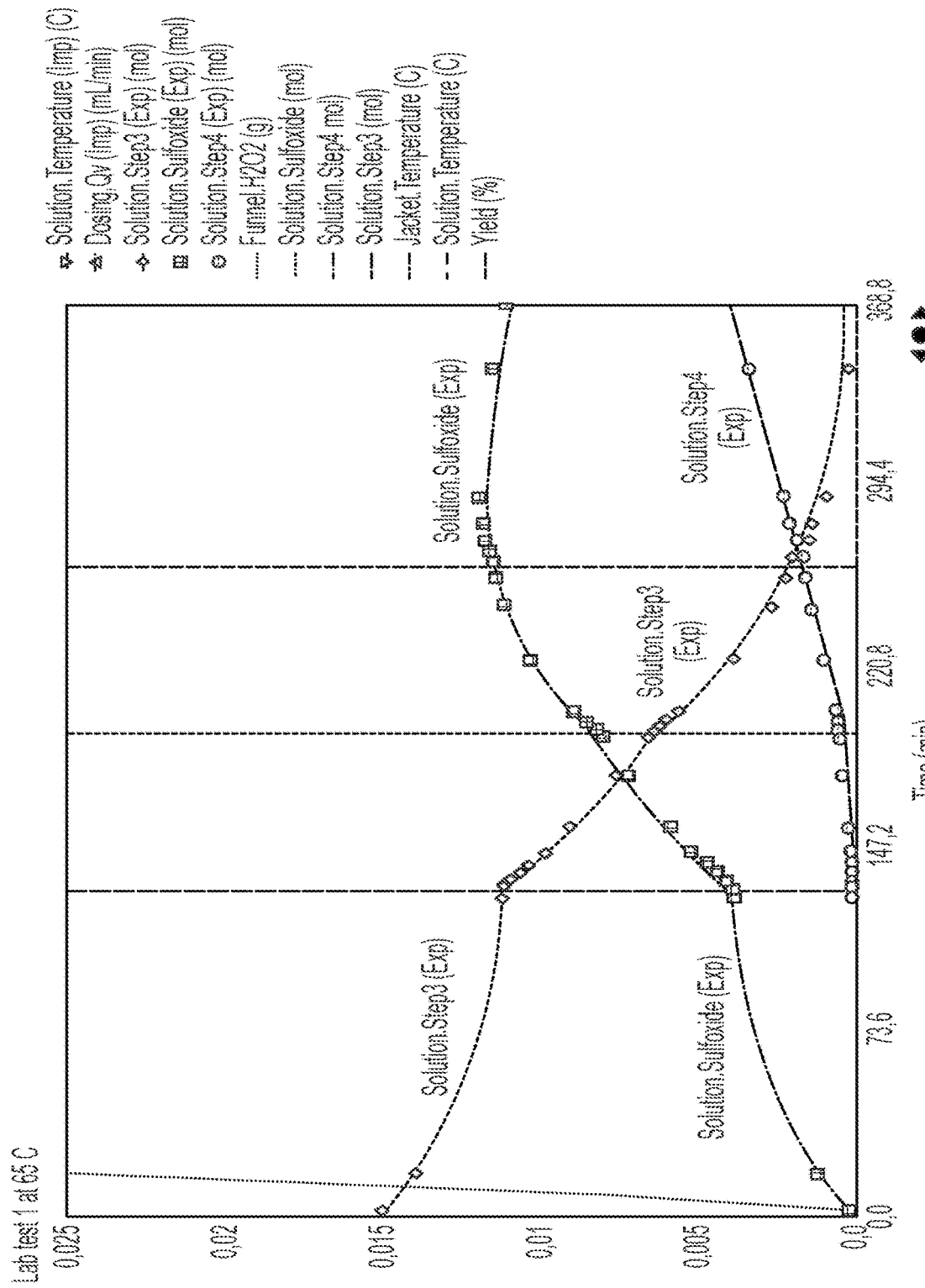
FIGS. 15A-B show 4-[4-(methylthio)phenyl]-3-phenyl-2(5H)-furanone oxidation follow-up.
Figure 15B:
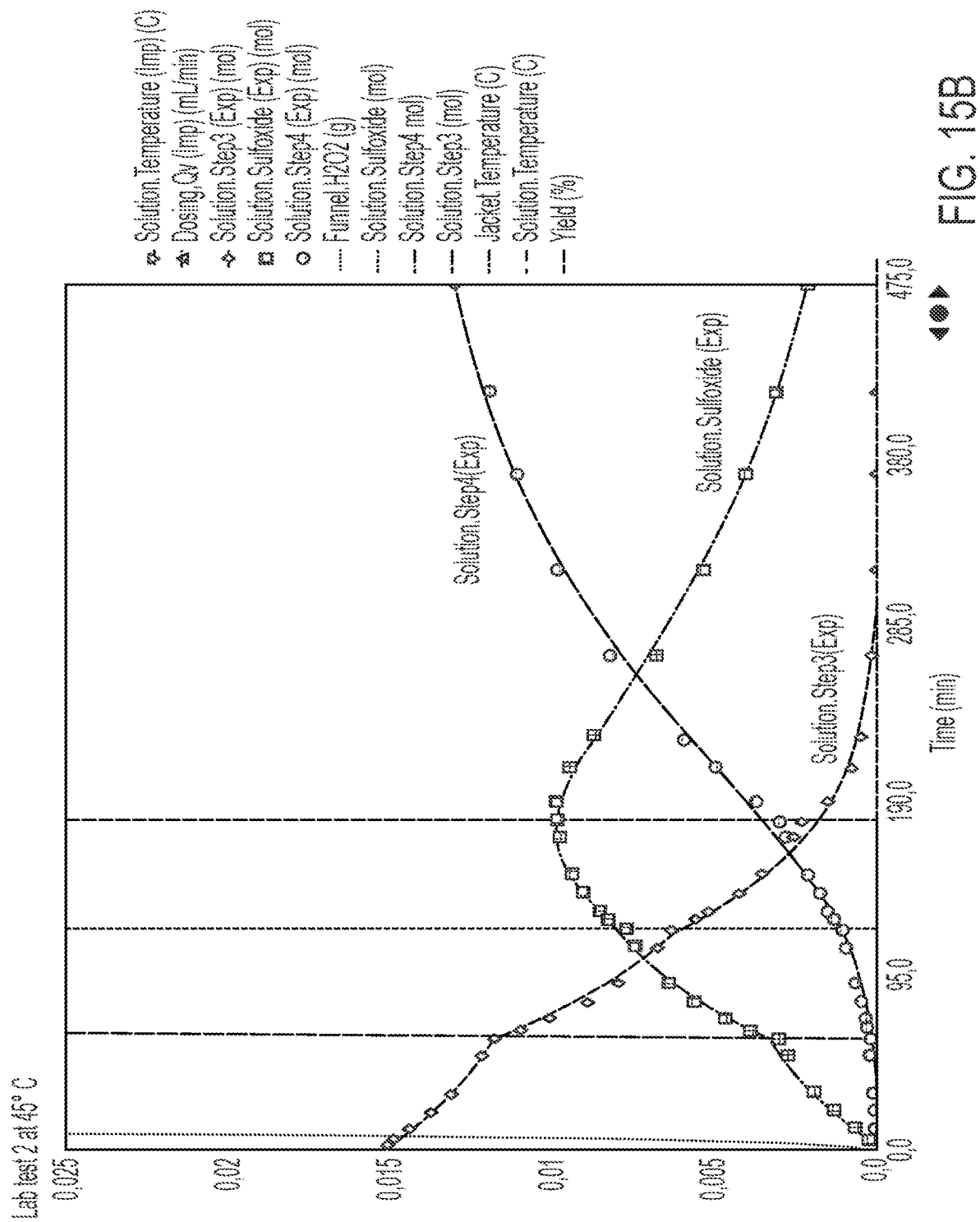

To allow for reaction follow up in a reasonable amount of time, trial CHG P059-074 was conducted with an amount of catalyst divided by 100 (0.012 mol %). To achieve all kinetic parameters of the reaction, the second trial CHG P059-078 was performed at lower temperature (45° C.). To increase the solubility of RXB species in the reaction media, the acetonitrile amount was multiplied by 4 (28.2V). The counterbalance of the lower temperature and higher dilution was brought by increasing the catalyst amount to 0.18 mol %. FIGS. 15A-B show the rate of the species in the reaction media over the time. FIG. 15A shows 4-[4-(methylthio) phenyl]-3-phenyl-2(5H)-furanone oxidation follow-up for CHG P059-074. FIG. 15B shows 4-[4-(methylthio)phenyl]-3-phenyl-2(5H)-furanone oxidation follow-up for CHG P059-078. Hydrogen peroxide was added in 4 portions (10%, 20%, 30%, and 40%). Each vertical line belongs to an instantaneous addition of $H_2O_2$. Instantaneous addition of reagent is mandatory to avoid the limitation of the reaction kinetic by the addition rate of reagent. Three reactions are considered to take place in the reaction media:

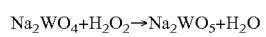

$Na_2WO_4 + H_2O_2 \rightarrow Na_2WO_5 + H_2O$

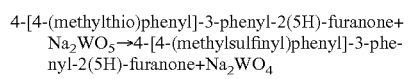

4-[4-(methylthio)phenyl]-3-phenyl-2(5H)-furanone + $Na_2WO_5 \rightarrow$ 4-[4-(methylsulfinyl)phenyl]-3-phenyl-2(5H)-furanone + $Na_2WO_4$

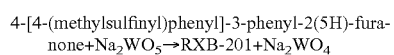

4-[4-(methylsulfinyl)phenyl]-3-phenyl-2(5H)-furanone + $Na_2WO_5 \rightarrow$ RXB-201 + $Na_2WO_4$ The fitting between the model (lines) and the experimental points (dots) were found to be satisfactory. The reaction rate coefficient and activation energy were determined for the 3 reactions.

The first oxidation (4-[4-(methylthio)phenyl]-3-phenyl-2 (5H)-furanone→4-[4-(methylsulfinyl)phenyl]-3-phenyl-2 (5H)-furanone: k≈10 L/mol·s) was revealed to be ten times faster than the second one (4-[4-(methylsulfinyl)phenyl]-3-phenyl-2(5H)-furanone→RXB-201: k≈1 L/mol·s). Regeneration of the catalyst ($Na_2WO_4$→$Na_2WO_5$) has a reaction rate constant of k≈8.5 L/mol·s. These data reflect the difficulty to fully convert the 4-[4-(methylsulfinyl)phenyl]-3-phenyl-2(5H)-furanone into rofecoxib (RXB-201) as the second oxidation is ten times slower. However, these kinetic data have to be cautiously considered in regard to reaction completion. Both oxidations were performed without going too far in the formation of rofecoxib (RXB-201). This was done on purpose to avoid the crystallization of rofecoxib (RXB-201) at the end of the process. Both processes were conducted with fully soluble RXB species all along the data acquisition, which simplified the model. This model shows again the start of oxidation immediately after the addition of $H_2O_2$, suggesting a highly decreased energy accumulation. Both trials were performed with addition of 0.5V water with the catalyst. This addition leads to a diminution of solubility of RXB species in the oxidation media, as RXB species are almost insoluble in water. Therefore, the volume of water was studied to introduce the minimum amount needed for energy accumulation suppression, with the lowest impact possible on RXB solubilities. Kinetic parameters of reactions taking place during the oxidation process are shown in Table 18 below.

TABLE 19

Screening of IPA and water content to suppress accumulation phenomenon.

| | | Pure water | |
| --- | --- | --- | --- |
| | | 0.15 V | 0.25 V |
| | 0% | VLA P075-168 Slightly clouded IPC (2 min) = 8.6% | |
| IPA | 36% | VLA P075-166 Slightly clouded IPC (2 min) = 9% | VIA P075-174 Slightly clouded IPC (2 min) = 14.3% |
| | 50% | VLAP075-170 Clear + unsoluble solid IPC (2 min) = 4.6% | VIA P075-172 Slightly clouded IPC (2 min) = 11.7% |

It is noted that the use of 0.25V of $H_2O$ allows the best conversion into 4-[4-(methylsulfinyl)phenyl]-3-phenyl-2 (5H)-furanone after only 2 minutes, up to 14% area UHPLC. When water volume was decreased to 0.15V, the reaction started anyway but the conversion is almost halved. All trials have shown a slightly clouded reaction media, except the one with the maximum amount of IPA and minimum of water (VLA P075-170). This indicates a positive effect of IPA and negative effect of water of 4-[4-(methylthio)phenyl]-3-phenyl-2(5H)-furanone solubility. Nevertheless, a high rate of IPA combined with low rate of water generates a different suspension (VLA P075-170), with high-density colorless solid, probably insoluble catalyst. It can be

TABLE 18

Kinetic parameters of reactions taking place during the oxidation process Reactions

| Phase/Flow | Reaction | Equation | Rate Exp. | kref | | | Tref | Ea | |
| --- | --- | --- | --- | --- | --- | --- | --- | --- | --- |
| Solution | rxn1 | cata-red + H2O2 --> cata + water | k [cata-red] [H2O2] | k> | 8,492 | L/mol · s | 65.0 C. | Ea> | 59,604 kJ/mol |
| Solution | rxn2 | cata + Step 3 --> cata-red + Sulfoxide | k [cata] [Step 3] | k> | 10,169 | L/mol · s | 65.0 C. | Ea> | 62,736 kJ/mol |
| Solution | rxn3 | cata + Sulfoxide --> cata-red + Step 4 | k [cata] [Sulfoxide] | k> | 1,038 | L/mol · s | 65.0 C. | Ea> | 27,446 kJ/mol |

Optimization of Solvents

A. Research of Optimum Water and IPA Contents to Suppress Accumulation Phenomenon Trials were performed to evaluate the appropriate amount of water to introduce at the beginning of the reaction to solubilize the catalyst and suppress the accumulation phenomenon.

Trials below were performed using the current process in 6V ACN, with dry 4-[4-(methylthio)phenyl]-3-phenyl-2 (5H)-furanone, catalyst, addition of IPA to represent different values of LoD and addition of water. Starting this trial, catalyst and water were successively introduced in the reaction media. The mixture was heated at 65° C., then 0.125 eq $H_2O_2$ were added instantaneously. An IPC was performed after 2 min of contact to check the reaction. IPC results reported in Table 19 below are for 4-[4-(methylsulfinyl) phenyl]-3-phenyl-2(5H)-furanone.

assumed that 0.25V of pure water allows for a partial dissolution of the catalyst, enough to avoid the accumulation effect. Therefore, this water volume was chosen. This water amount combines the suppression of the accumulation effect, with an acceptable solubility of wet 4-[4-(methylthio) phenyl]-3-phenyl-2(5H)-furanone for averages LoDs. The use of purified water is mandatory. A trial was conducted with dissolution of 12 samples of $Na_2WO_4 \cdot 2H_2O$ in pure water, and 12 samples in tap water. The 24 samples were prepared at the same concentration, around working concentration during oxidation synthesis. All samples dissolved quickly after stirring at room temperature. After few hours, the 12 samples in tap water showed white precipitate while the 12 samples in pure water stayed as a clear solution. Calcium cations (Can in tap water are thought to associate with the $WO_4^{2-}$ anion to form calcium tungstate $CaWO_4$, an almost insoluble salt in water (0.02 g/L).

B. Research into the Effects of Solvents on Oxidation Reaction Completion.

Previous trials have shown the best conditions to suppress the accumulation phenomenon. The use of 0.25V of deionized water allowed to start the reaction at the beginning of hydrogen peroxide addition. This was demonstrated with different values of IPA content in 4-[4-(methylthio)phenyl]-3-phenyl-2(5H)-furanone (LoD=36% or 50%). After having focused on reaction start, the effect of solvents was then studied on reaction completion as shown in Table 20 below.

TABLE 20

Effect of Solvents in Reaction Completion.

| | | VLA P075-176 | VLA P075-178 | CHG P059-084 |
|---|---|---|---|---|
| Materials | RXB-Furanone | 3.00 g | 3.00 g | 3.00 g |
| | $H_2O_2$ 35% | 2.5 eq. | 2.5 eq. | 2.5 eq. |
| | $Na_2WO_4 \cdot 2H_2O$ | 1 mol % | 1 mol % | 1 mol % |
| | ACN | 6 V | 6 V | 7 V |
| | IPA | 36 % wt. | none | 36 % wt. |
| | $H_2O$ | 0.25 V | 0.25 V | 0.25 V |
| Process | $H_2O_2$ addition time | 2 h 20 | 2 h 00 | 2 h 00 |
| | RXB-201 seeding | None | 1 seed, end of $H_2O_2$ addition | 2 seeds during $H_2O_2$ addition |
| | Aspect | Slightly clouded | White suspension at the end of $H_2O_2$ addition, before seeding | White suspension after first seeding. |
| | Comments | during whole process. Addition 1 V ACN after IPC2: white suspension | | |
| UHPLC (% area) RXB-201/ Sulfoxide | IPC 1 (End of $H_2O_2$ addition) | 97.23/2.50 | 99.20/0.53 | Not performed |
| | IPC 2 (time) | 99.72/n.d. (1 h) | 99.68/0.02 (30 min) | 99.40/n.d. (45 min) |
| | Work-up | Not isolated | Not isolated | 2 V water |
| | Isolated RXB-201 | Not isolated | Not isolated | 99.82/0.02 |

The first trial (VLA P075-176) was conducted using the standard process (at 65° C.), with addition of 0.25V pure water. Addition of hydrogen peroxide was achieved in 2 h. A slightly clouded reaction media was obtained, with a very low amount of solid in suspension. At the end of $H_2O_2$ addition, 4-[4-(methylthio)phenyl]-3-phenyl-2(5H)-furanone was not detected, and only 2.5% 4-[4-(methylsulfinyl)phenyl]-3-phenyl-2(5H)-furanone for this trial (IPC 1). After an additional hour of stirring at 65° C., 4-[4-(methylsulfinyl)phenyl]-3-phenyl-2(5H)-furanone was not detected in UHPLC (IPC 2). IPC were performed with sampling of a heterogeneous mixture. This trial is very satisfactory considering the very fast conversion of species into rofecoxib (RXB-201). As a reminder, the current process without water addition needed at least 6 h to reach IPC specification. At the end of the reaction, 1V ACN was added to the reaction to attempt to achieve a full solubilization of the reaction media. In fact, the reaction media turned immediately heterogeneous, as white suspension. This indicates an oversaturation of the reaction media. Rofecoxib (RXB-201) crystallized out with the perturbation generated by the addition of acetonitrile.

The effect of isopropanol content was then studied in the second trial (VLA P075-178). The reaction was performed without IPA, which should have a negative effect of RXB species solubility considering Table 19. In this trial, performed in the same conditions, the reaction media was already in suspension at the end of hydrogen peroxide addition. A better conversion was observed at the end of $H_2O_2$ addition compared to VLA P075-176. Moreover, the $H_2O_2$ addition was performed faster than the first trial (2 h instead of 2 h20). The absence of IPA reveals then a faster oxidation conditions than with 36% IPA. This could be attributed to a slightly higher concentration of reaction media because of the absence of IPA. The crystallization of the reaction media seems to have no effect on the 4-[4-(methylsulfinyl)phenyl]-3-phenyl-2(5H)-furanone oxidation kinetics.

A third trial was performed to confirm that point. The trial CHG P059-084 was launched in 7V ACN with usual amount of IPA. This higher dilution revealed to have no effect on reaction media aspect at the beginning of oxidation. Two seedings were performed during $H_2O_2$ addition to force the reaction media to be in suspension while addition. Reaction media aspect was similar to VLA P075-178. 45 minutes after hydrogen peroxide addition completion, 4-[4-(methylsulfinyl)phenyl]-3-phenyl-2(5H)-furanone was not detected. After addition of 2V water as quench, cooling to 0° C., filtration and cake washings, the solid obtained contained 0.02% 4-[4-(methylsulfinyl)phenyl]-3-phenyl-2(5H)-furanone. This trial confirms the satisfactory results obtained in VLA P075-178.

Therefore, the reaction media could be both slightly clouded or a heterogeneous white suspension, the IPC specification was achieved after only 1 h of heating after hydrogen peroxide addition completion. The oversaturation of the reaction media with 6V ACN seems to not be an issue for conversion of RXB species into rofecoxib (RXB-201). The 0.25V pure water addition has a dramatic effect on oxidation kinetic improvement. The oversaturation of RXB species in oxidation media leads to the crystallization of samples dedicated to IPCs. A study was conducted to establish the best sample preparation.

Optimization of IPC Sample Preparation

IPCs were performed by direct sampling of stirred reaction mixture. This heterogeneous sampling was difficult to perform representatively. Therefore, the stirred suspension sampling was replaced. The suspended aliquot was filtrated, and the solid analyzed. Due to the low solubility of RXB species, it was assumed that the cake analysis representativeness was satisfactory, particularly in regard to the 4-[4-(methylsulfinyl)phenyl]-3-phenyl-2(5H)-furanone rate. This assumption was verified in this work. A study of IPC preparation was performed during trial CHG P059-084 and shown in Table 21 below.

TABLE 21

Screening of conditions of IPC sample preparations.

| Time | Temp. | H₂O | Phase | RXB-Furanone | RXB-Sulfoxide | RXB-Hydroxy | RXB-201 |
|---|---|---|---|---|---|---|---|
| IPC1 | 65° C. | 0 V | Representative | n.d. | 7.90 | 0.44 | 91.66 |
| IPC2 | 65° C. | 0 V | Representative | n.d. | n.d. | 0.58 | 99.40 |
| IPC3a | 20° C. | 0 V | Unwashed cake | n.d. | 0.02 | 0.09 | 99.86 |
|  |  |  | ML | n.d. | 0.07 | 2.13 | 96.91 |
| IPC3b | 20° C. | 2 V | Unwashed cake | n.d. | 0.02 | 0.12 | 99.82 |
|  |  |  | ML | n.d. | 0.09 | 4.39 | 93.57 |
| Isolated | 0° C. | 2 V | Washed cake | n.d. | 0.02 | 0.07 | 99.85 |
|  |  |  | ML | n.d. | 0.13 | 7.85 | 88.80 |

The two first IPCs (IPC1 and IPC2) were performed with representative sampling (taking a sample in a stirred suspension). The IPC2 indicated a full conversion: 4-[4-(methylsulfinyl)phenyl]-3-phenyl-2(5H)-furanone=n.d. IPC3a was performed with sampling of ≈1 mL reaction media, cooling to room temperature and filtration. Cake and mother liquors were analyzed. 4-[4-(methylsulfinyl)phenyl]-3-phenyl-2(5H)-furanone=0.02% in the cake. IPC3b was performed with sampling of ≈1 mL reaction media, cooling to room temperature and addition of ≈2V water and filtration. Cake and mother liquors were analyzed. 4-[4-(methylsulfinyl)phenyl]-3-phenyl-2(5H)-furanone=0.02% in the cake. The whole product of the experiment was obtained after cooling the reaction media to room temperature, addition of 2V water, cooling to 0° C., filtration and standard cake washings. 4-[4-(methylsulfinyl)phenyl]-3-phenyl-2(5H)-furanone=0.02% in the cake.

Figure 16:
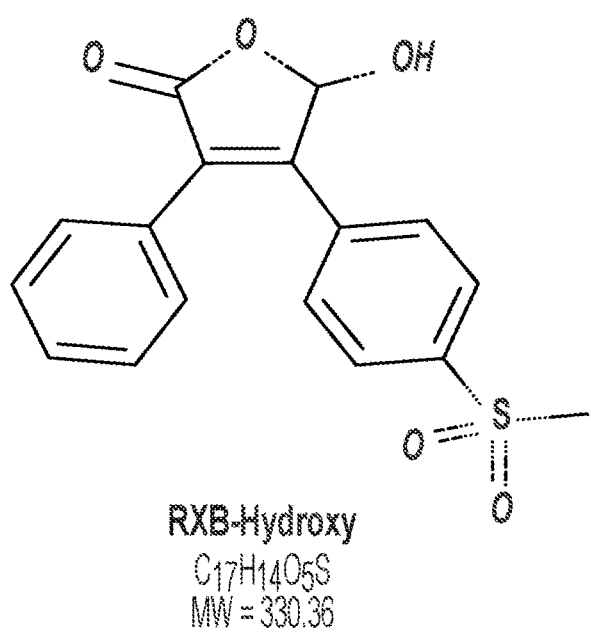
FIG. 16 shows the proposed structure of the 4-[4-(methylsulphonyl)phenyl]-3-phenyl-5-hydroxyfuran-2-one (RXB-Hydroxy) impurity.

These trials reveal that IPC 3a and IPC 3b techniques give the same results of 4-[4-(methylsulfinyl)phenyl]-3-phenyl-2(5H)-furanone rate as the isolated compound of the trial CHG P059-084. If we consider all RXB derivatives, IPC3a technique give the closest results. Another impurity was reported in the Table 21, called 4-[4-(methylsulphonyl) phenyl]-3-phenyl-5-hydroxyfuran-2-one (RXB-Hydroxy). Its proposed structure is shown in FIG. 16. This impurity is detected at RRT 0.63. LCMS analysis performed during pre-degradation tests has shown a mass equivalent to [RXB-201+16]. This hydroxylation is reported in the literature, notably with oxygen. See D. A. Nicoll-Griffith et al. Bioorg. Med. Chem. Lett. 2000, 10, 2683 and E. J. Corey et al. Tetrahedron Lett. 2005, 46, 927, which are incorporated herein in their entireties. This impurity is always observed in rofecoxib (RXB-201) samples, where nitrogen flow was not used during oxidation process. 4-[4-(methylsulphonyl)phenyl]-3-phenyl-5-hydroxyfuran-2-one rate was only 0.03% in the crude rofecoxib (RXB-201), batch F801. This lower rate could be explained by the nitrogen atmosphere used.

Suppression of Sodium Sulfite Quench

In the current synthesis process depicted in Scheme 3, sodium sulfite is used as water solution to quench the excess of hydrogen peroxide added in the reaction media. Crude rofecoxib (RXB-201) F801 was previously obtained with 0.5% residue on ignition. This material is thought to have led to filter clogging during clarification before recrystallization.

The effect of ashes during recrystallization process was also studied. The suppression of sodium sulfite quench was envisaged and use-tested. This quench was replaced by an addition of 2V pure water (CHG P059-092). This trial has shown many advantages:

A better yield was obtained without Na2SO3 use: 92% instead of 86%

No effect encountered on crude rofecoxib (RXB-201) UHPLC profile.

No particles in suspension during hot filtration when engaged in recrystallization (CHG P059-098)

Several verifications were performed to confirm the feasibility of hydrogen peroxide removal:

No corrosion of Stainless steel 316L in contact with crude rofecoxib (RXB-201) mother liquors (enriched in excess hydrogen peroxide) after 10 days at 20° C. (CHG P059-084).

Crude rofecoxib (RXB-201) does not need to be dried.

Strip peroxide test negative for both crude and recrystallized rofecoxib (RXB-201) (CHG P059-098). Crude washings seem to be efficient enough to remove peroxide traces in cake washings.

Stability of isolated crude rofecoxib (RXB-201) towards hydrogen peroxide is very satisfying. Crude unwashed rofecoxib (RXB-201) was stored at room temperature for 17 days. No evolution of UHPLC profile was observed (CHG P059-104).

Considering all these advantages, it was decided to replace the sodium sulfite quench by an addition of 2V pure water.

Flowsheet of Optimized Oxidation of 4-[4-(methylthio)phenyl]-3-phenyl-2(5H)-furanone.

Figure 29:
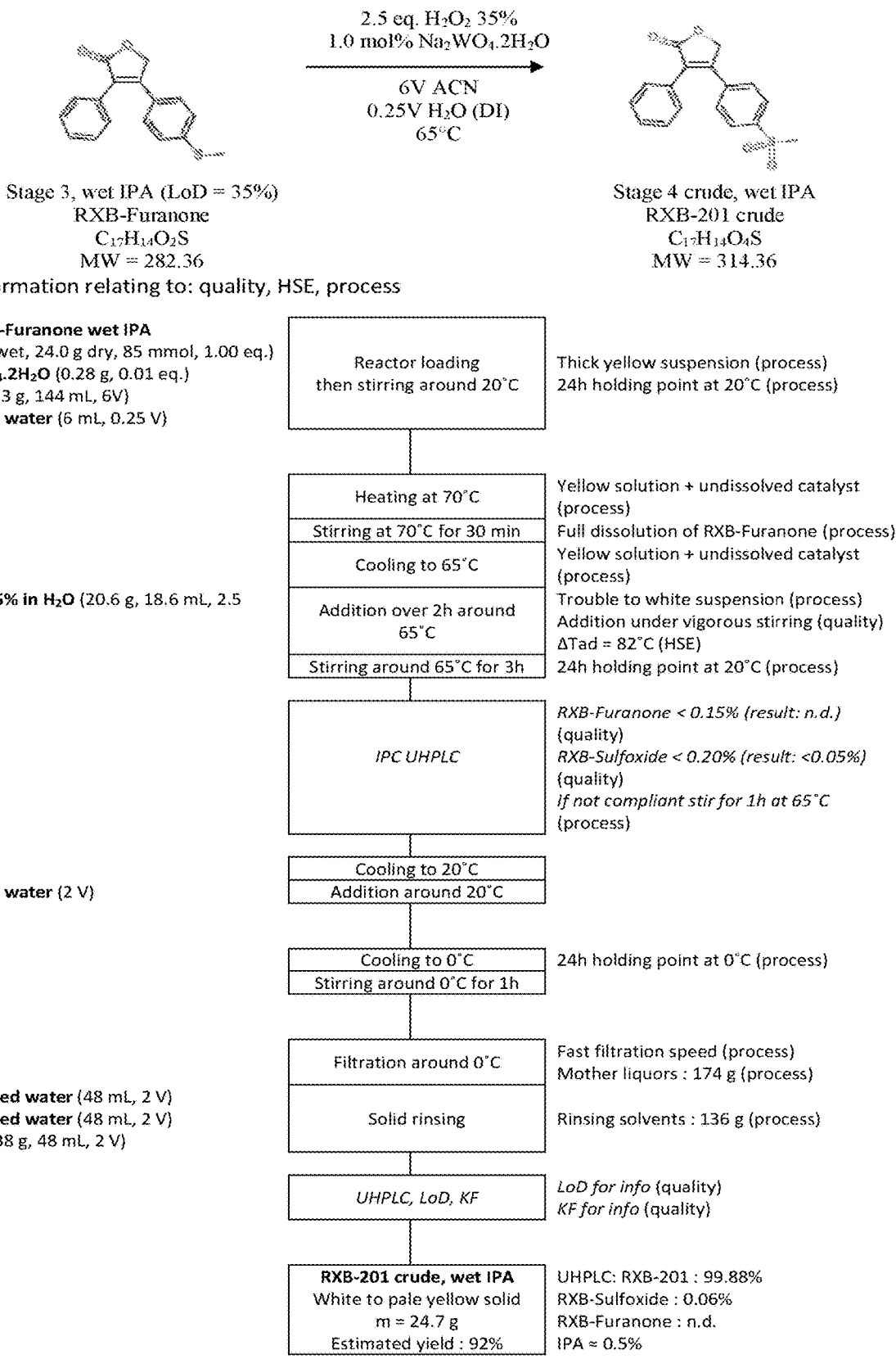
FIG. 29 shows an optimized flowsheet of 4-[4-(methylthio)phenyl]-3-phenyl-2(5H)-furanone oxidation.

FIG. 29 shows an optimized flowsheet of 4-[4-(methylthio)phenyl]-3-phenyl-2(5H)-furanone oxidation.

Calorimetry Study

This optimized process depicted in Scheme 6 was subjected to a calorimetry study. The thermal study was performed on Algochem ARLA FD reactor apparatus on 40 g 4-[4-(methylthio)phenyl]-3-phenyl-2(5H)-furanone. The results of the calorimetry, focused on 4-[4-(methylthio) phenyl]-3-phenyl-2(5H)-furanone oxidation, are summed up in the Table 22 below.

TABLE 22

Calorimetric data of 4-[4-(methylthio)phenyl]-3-phenyl-2(5H)-furanone oxidation with optimized process.

| symbols | description | unit | step 1: addition of H₂O₂ |
|---|---|---|---|
| n | mol number of step3 | mol | 0.14 |
| m | reaction weight after addition | g | 285.4 |
| m | added reactant weight | g | 32.3 |
| Tp | process temperature | ° C. | 65 |
| Dadd | addition time | min | 120 |
| Cp | average specific heat | J/g/° C. | 2.3 |
| tfin | End of thermal power after the addition | min | 60 |
| Q | released energy (if exotherm, negative result) | kJ | −53.5 |
| ΔHr | reaction enthalpy by mol of Hyox (if exotherm, negative result) | kJ/mol | −382.1 |
| Qr | reaction heat by kg of the total reaction mixture (if exotherm, negative result) | kJ/kg | −187.5 |
| Qr | reaction heat by kg of added reactant (if exotherm, negative result) | kJ/kg | −1656.3 |
| Pmax | maximum observed power | W/kg | 52 |
| Pr | average observed power | W/kg | 32 |
| Acc max | maximum accumulation of xx % of the addition | % | 6% after 20% added |

TABLE 22-continued

Calorimetric data of 4-[4-(methylthio)phenyl]-3-phenyl-2(5H)-furanone oxidation with optimized process.

| symbols | description | unit | step 1:addition of $H_2O_2$ |
|---|---|---|---|
| Acc fin | Accumulation at the end of the addition | % | 5% |
|  | gas release | Y/N | N |
| $\Delta$tad | potential adiabatic temperature rise | °C. | 81.5 |
| Tf batch | maximum final temperature with 100% accumulation | °C. | 146.5 |
| MTSR max | maximum final temperature with max observed accumulation | °C. | 70.2 |

The reaction enthalpy was measured at $\Delta Hr=-187$ kJ/kg with $Cp=2.3$ J/g/°C. This leads to a potential temperature rise under adiabatic conditions $\Delta Tad=82°$ C. The exothermal properties of the reaction was already known, but the main improvement of the new process is the maximum of accumulation, now measured at 6% after 20% hydrogen peroxide added. This accumulation is divided by 3 compared to the former process. Therefore, the exothermy is well controlled by the addition of hydrogen peroxide. After having taken in account all calorimetric parameters, the rank of reaction is class 4 over 5 according to Stoessel Scale.

This optimization work has led to the implementation of 0.25V pure water addition at the beginning of the process. Due to this water addition, the thermic accumulation phenomenon was dramatically decreased. Furthermore, this addition revealed to have a very positive effect on RXB species oxidation. The IPC specification is now reached after 1 or 2 hours after hydrogen peroxide addition completion, instead of 6 h. For a better reproducibility of IPC results, a new technique of IPC preparation was also tested. The kinetic model has allowed for the better understanding of the evolution of oxidation. The oxidation starts from the beginning of hydrogen peroxide addition, with a first oxidation ten times faster than the second one. The removal of this sodium sulfite quench is validated after having checked all advantages it brings.

Thermal Study Report

The reaction scheme is shown in Scheme 7 below:

Scheme 7. Reaction scheme

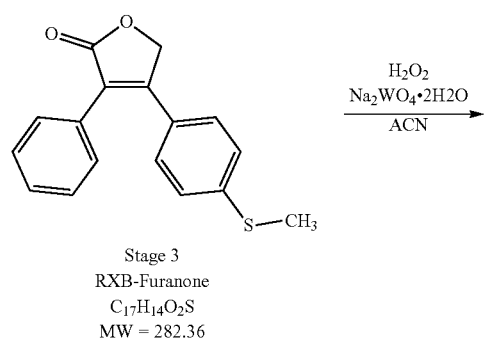

Stage 3
RXB-Furanone
$C_{17}H_{14}O_2S$
MW = 282.36

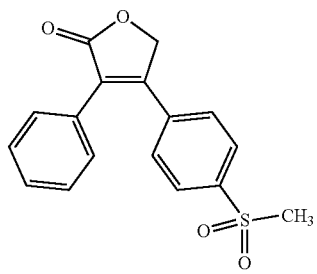

Stage 4
RXB-201 crude
$C_{17}H_{14}O_4S$
MW = 314.36

The raw materials are shown in Table 23.

TABLE 23

Raw Materials

| BATCH | MW | mol Nb | Eq Nb | Mass (g) | Density | Volume (mL) |
|---|---|---|---|---|---|---|
| RXB furanone st3 dry (VLA P072-132) | 282.36 | 1.417E−1 | 1.000 | 40.0 | 1 | 40.0 |
| isopropyl alcohol (Aldrich) | 60 | 2.333E−1 | 1.646 | 14 | 0.785 | 17.8 |
| acetonitrile (carlo erba) | 41 | 4.600E+0 | 32.46 | 188.6 | 0.786 | 239.9 |
| DI Water | 18 | 5.556E−1 | 3.921 | 10 | 1 | 10.0 |
| sodium tungstate dihydrate (alfa) | 329.9 | 1.394E−3 | 0.010 | 0.46 | 3.2 | 0.14 |
| hydrogen peroxide 37.3% | 34 | 3.541E−1 | 2.499 | 32.3 | 1.135 | 38.5 |

Figure 30:
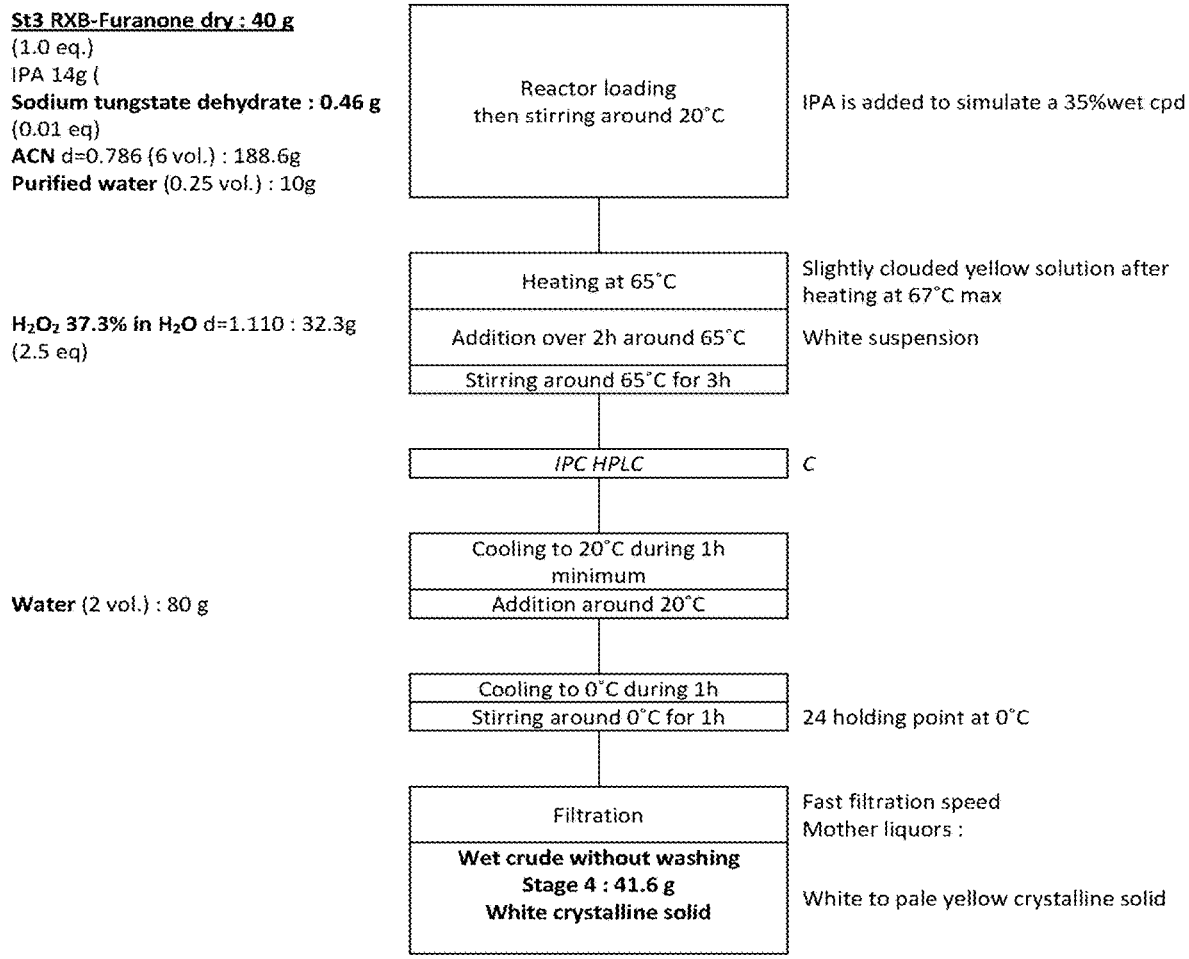
FIG. 30 shows a flowsheet for the calorimetric test.

A flowsheet for the calorimetric test is shown in FIG. 30. Calorimetric data are shown in Table 24 below.

TABLE 24

Calorimetric Data

| symbols | description | unit | step 1:addition of $H_2O_2$ |
|---|---|---|---|
| n | mol number of step3 | mol | 0.14 |
| m | reaction weight after addition | g | 285.4 |
| m | added reactant weight | g | 32.3 |
| Tp | process temperature | °C. | 65 |
| Dadd | addition time | min | 120 |
| Cp | average specific heat | J/g/°C. | 2.3 |
| tfin | End of thermal power after the addition | min | 60 |
| Q | released energy (if exotherm, negative result) | kJ | −53.5 |
| $\Delta$Hr | reaction enthalpy by mol of Hyox (if exotherm, negative result) | kJ/mol | −382.1 |
| Qr | reaction heat by kg of the total reaction mixture (if exotherm, negative result) | kJ/kg | −187.5 |
| Qr | reaction heat by kg of added reactant (if exotherm, negative result) | kJ/kg | −1656.3 |
| Pmax | maximum observed power | W/kg | 52 |
| Pr | Average observed power | W/kg | 32 |
| Acc max | maximum accumulation of xx % of the addition | % | 6% after 20% added |

TABLE 24-continued

Calorimetric Data

| symbols | description | unit | step 1:addition of $H_2O_2$ |
|---|---|---|---|
| Acc fin | Accumulation at the end of the addition | % | 5% |
| | gas release | Y/N | N |
| Δtad | potential adiabatic temperature rise | ° C. | 81.5 |
| Tf batch | maximum final temperature with 100% accumulation | ° C. | 146.5 |
| MTSR max | maximum final temperature with max observed accumulation | ° C. | 70.2 |

Thermal stability data are shown in Table 25 below (DSC).

TABLE 25

Thermal stability

| TYPE | DESCRIPTION | REFERENCE | THERMAL PHENOMENON | | | | | KINETIC | ENERGY | |
|---|---|---|---|---|---|---|---|---|---|---|
| Raw material | Sodium tungstate | alfa | 1: endotherm | from | 87 | ° C. to | 130 | ° C. fast | 75 | J/g |
| | | | 2: exotherm | from | 236 | ° C. to | 305 | ° C. slow | −120 | J/g |
| Raw material | $H_2O_2$ 35% | acros | 1: exotherm | from | 47 | ° C. to | 149 | ° C. fast | −981 | J/g |
| | | | 2: endotherm | from | 275 | ° C. to | 378 | ° C. slow | 226 | J/g |
| raw material | Stade 3 | SHD 390 173 | 1: endotherm | from | 141 | ° C. to | 155 | ° C. fast | 114 | J/g |
| reaction mixture | ACN + $H_2O_2$ | SHD | 1: exotherm | from | 79 | ° C. to | 138 | ° C. slow | −33 | J/g |
| | | | 2: exotherm | from | 174 | ° C. to | 212 | ° C. fast | −42 | J/g |
| | | | 3: exotherm | from | 272 | ° C. to | 371 | ° C. fast | −492 | J/g |
| reaction mixture | before $H_2O_2$ addition | If 19 05 08 | 1: endotherm | from | 234 | ° C. to | 284 | ° C. slow | 28 | J/g |
| | | | 2: exotherm | from | 284 | ° C. to | 362 | ° C. slow | −32 | J/g |
| reaction mixture | after $H_2O_2$ addition +3 h at 65° C. | If 19 05 08 | 1: exotherm | from | 308 | ° C. to | 384 | ° C. slow | −28 | J/g |
| crude product | isolated, wet, not washed | If 19 05 08 | 1: endotherm | from | 189 | ° C. to | 214 | ° C. fast | 93 | J/g |
| | | | 2: exotherm | from | 339 | ° C. to | 400 | ° C. fast | −260 | J/g |

The addition of $H_2O_2$ is exothermal and the energy release is well controlled by the rate of $H_2O_2$ addition (the maximum heat accumulation is 6% after around 20% added). The reaction mixture is homogeneous and stays easily stirrable. In DSC, $H_2O_2$ exhibits an important exotherm from 47° C. (−981 J/g). The mixture acetonitrile/$H_2O_2$ is unstable from 272° C. (−492 J/g). The reaction mixture before and after addition are more stable with very small exotherms starting at 284° C. Under normal synthesis conditions, the semi batch process is safe. The MSTR is 70° C. and a TD24 of 144° C. can be calculated. The risk of triggering a decomposition is low but the rate of addition must be well controlled and the reaction has to be correctly triggered to avoid $H_2O_2$ accumulation.

TABLE 26

Additional Data

| symbols | description | unit | result |
|---|---|---|---|
| Tf batch | maximum final temperature with 100% accumulation | ° C. | 146 |
| Tdec | lowest decomposition temperature by DSC | ° C. | 47 |
| $TD_{24}$ | Temperature for TMR = 24 h | ° C. | non disponible |

TABLE 26-continued

Additional Data

| symbols | description | unit | result |
|---|---|---|---|
| $TD_8$ | Temperature for TMR = 8 | ° C. | non disponible |
| Eb | boiling point of the reaction mixture | ° C. | 82 |
| Tp | process temperature | ° C. | 65 |
| | main reaction heat potential | | average |
| | secondary reaction heat potential | | high |
| | step ranking | | 4 |

The energy of the main reaction can increase the mass temperature to 146° C. At this temperature, the decomposition which could be triggered is the $H_2O_2$ decomposition, giving an extra energy of 981 J/g of $H_2O_2$. If we consider that half $H_2O_2$ decomposes and the other half is used for the reaction, the adiabatic temperature rise would be 24° C. and the final temperature 170° C. The decomposition of the reaction mixture should not be initiated. If a closed vessel is used, the pressure could reach 9 bars. If an open vessel is used, without condenser, the boiling point would be reached. The whole energy could vaporize 72 g i.e. 38% of the initial amount of acetonitrile. The power of the reaction can be estimated at 1 SOW/kg a 82° C. The vapor rate is calculated at around 230 m³ of ACN/h. The risk of flooding is likely. The safety of the process depends on the respect of the temperature and time of $H_2O_2$ addition. Additional data are shown in Table 26.

Figure 17:
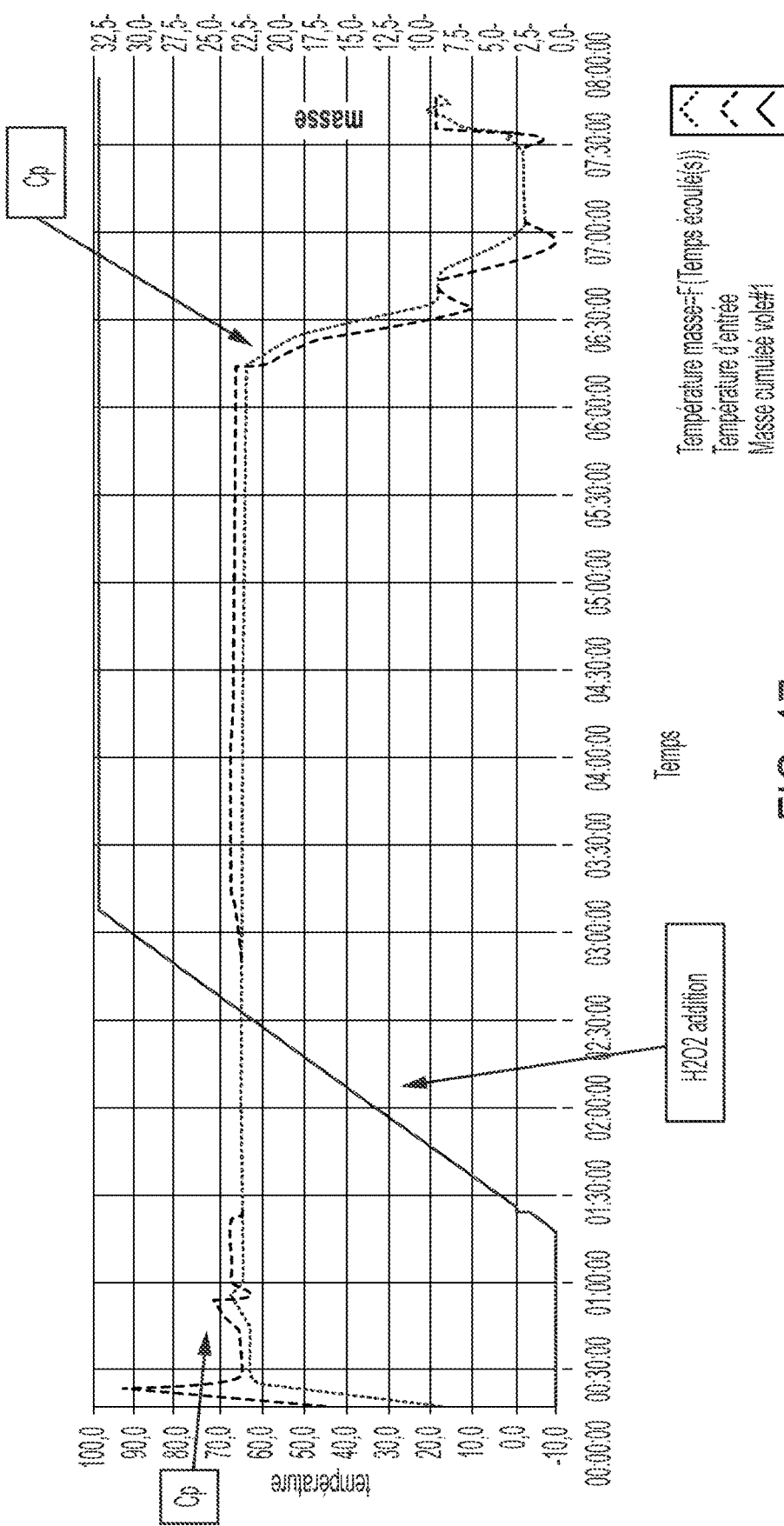
FIG. 17 shows a general scheme of the oxidation reaction.
Figure 18:
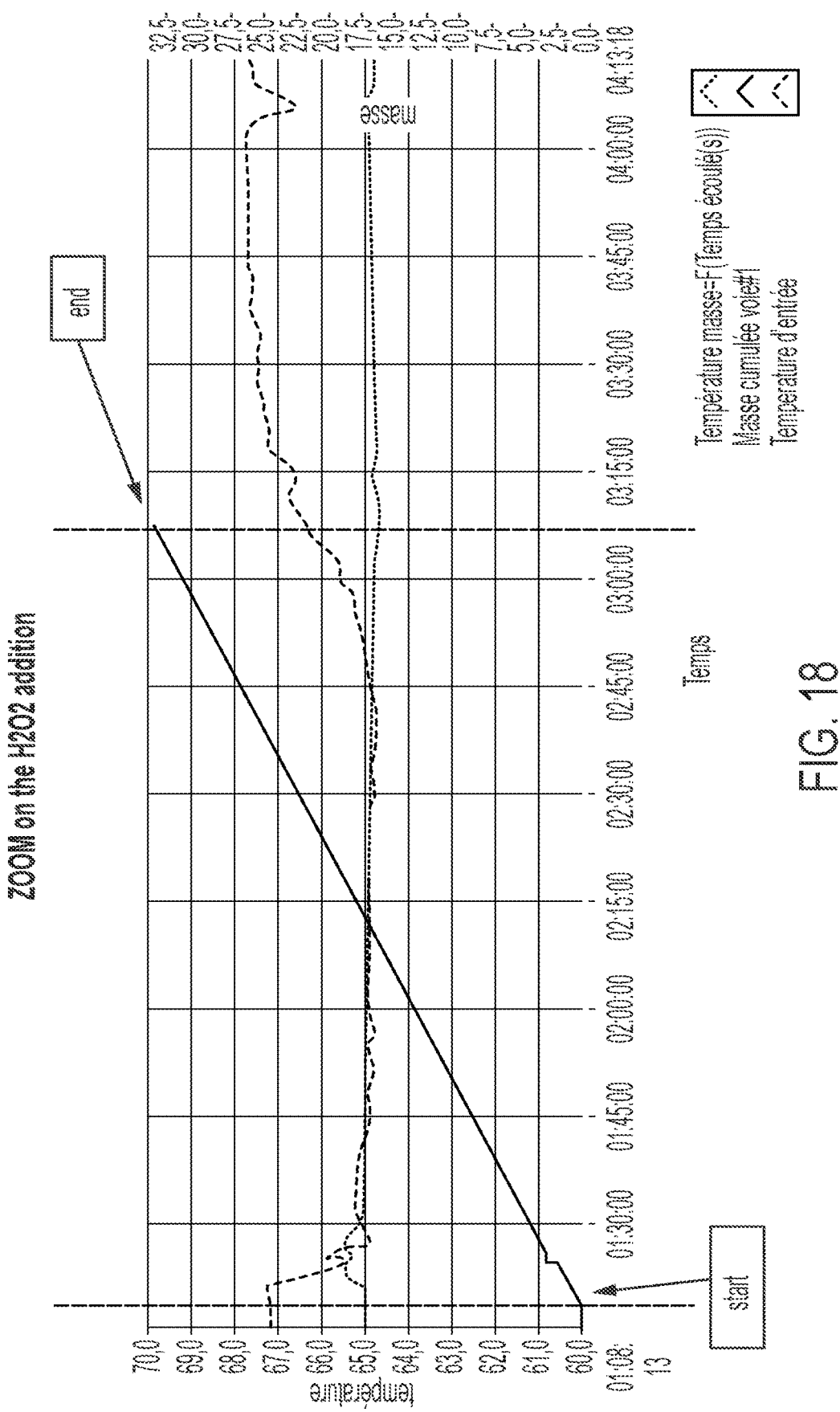
FIG. 18 shows a focus on $H_2O_2$ addition.
Figure 19:
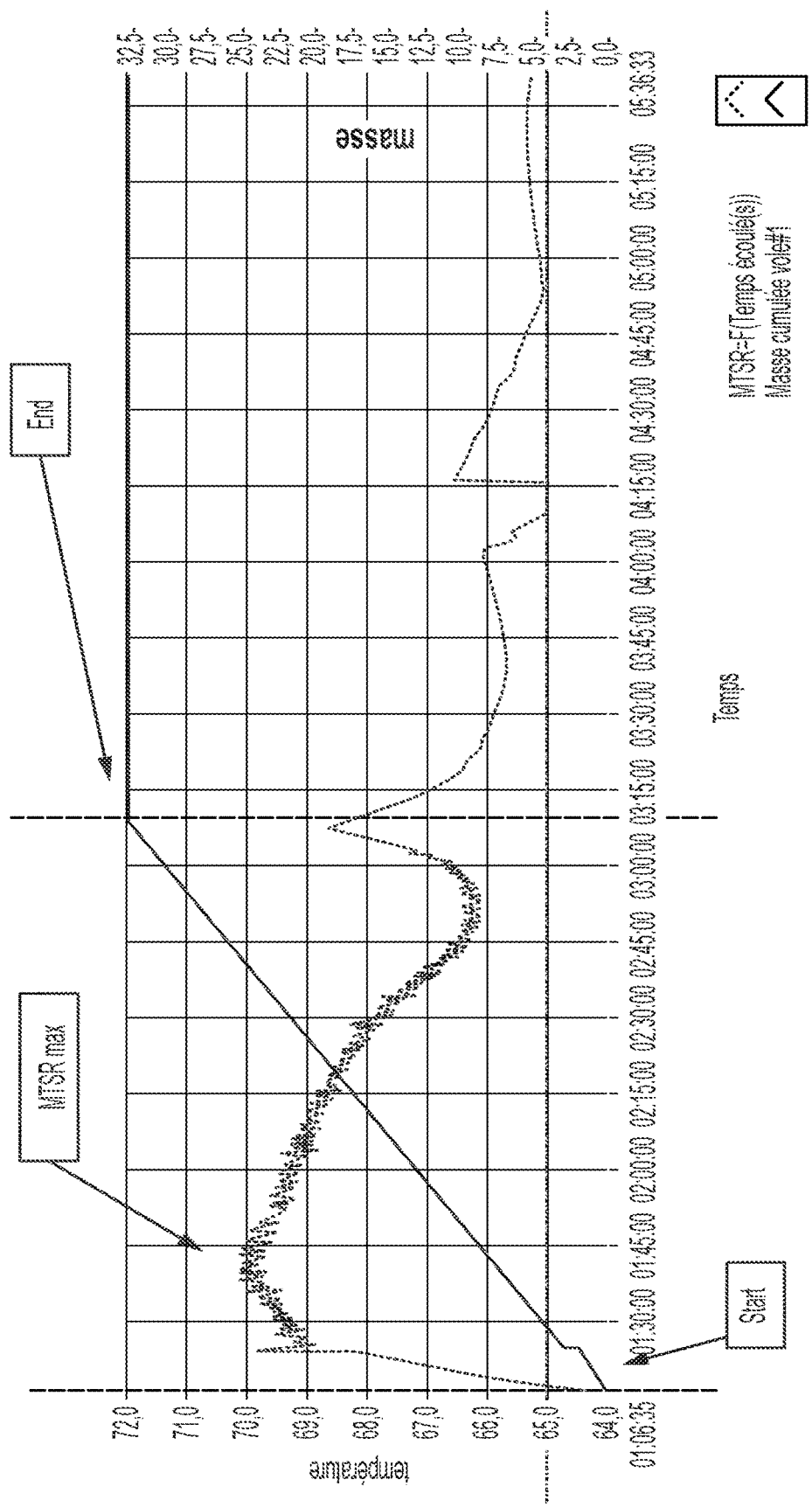
FIG. 19 shows maximum temperature attainable by the synthesis reaction.
Figure 20:
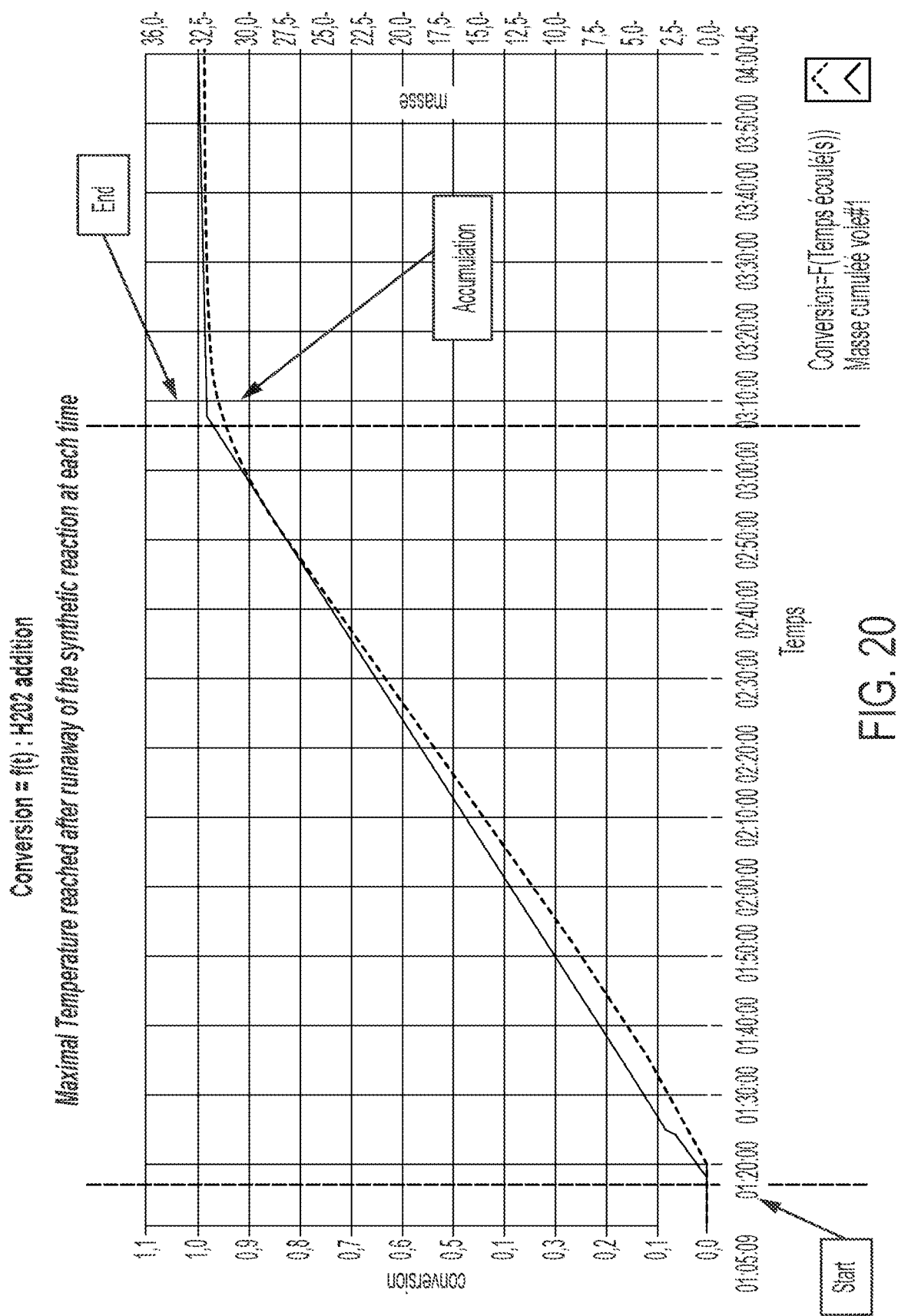
FIG. 20 shows conversion to product.
Figure 21:
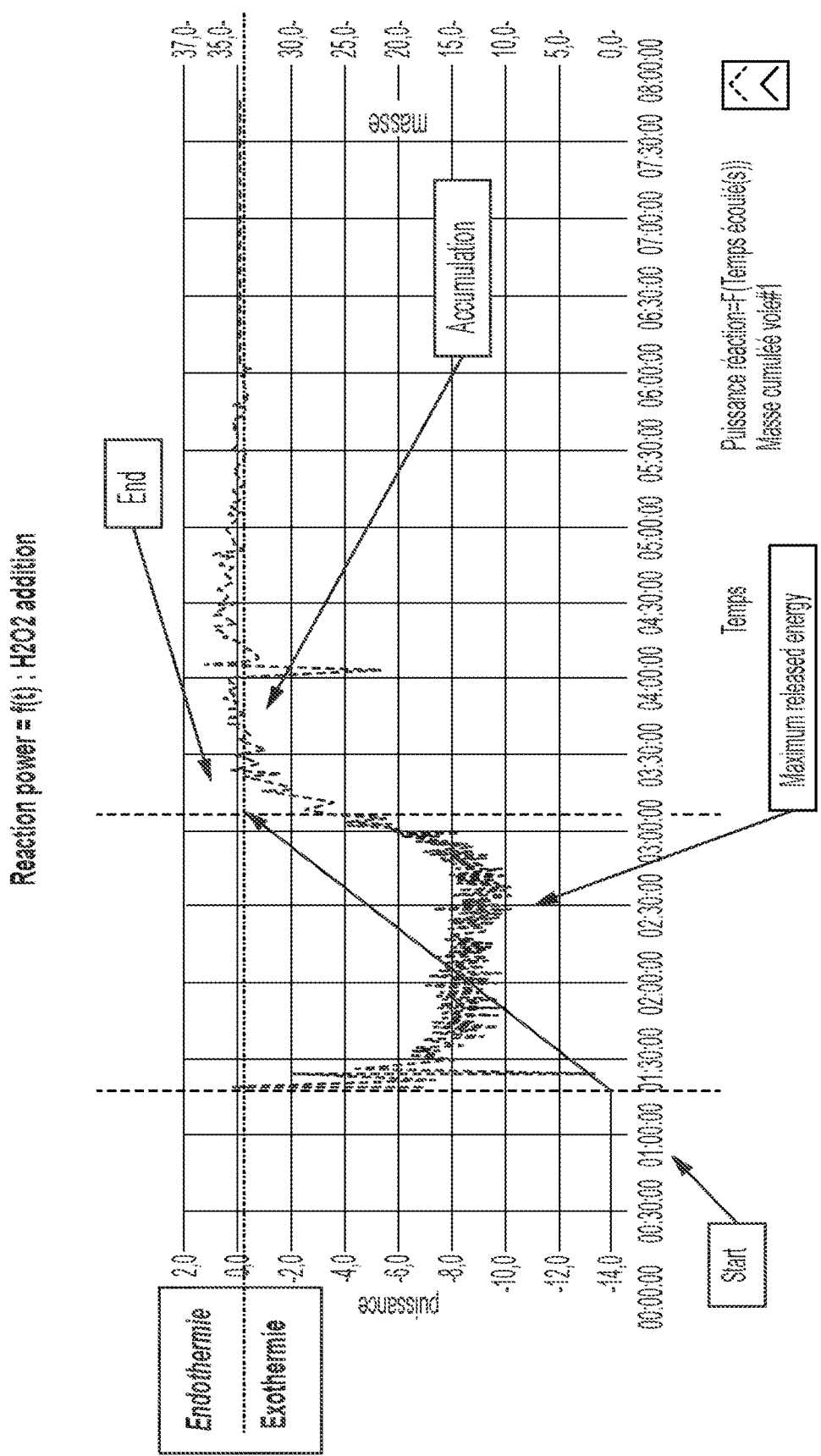
FIG. 21 shows oxidation reaction power.

FIG. 17 shows a general scheme of the oxidation reaction. FIG. 18 shows a focus on $H_2O_2$ addition. FIG. 19 shows maximum temperature attainable by the synthesis reaction (TSR). FIG. 20 shows the conversion to reaction product. FIG. 21 shows oxidation reaction power.

Figure 22:
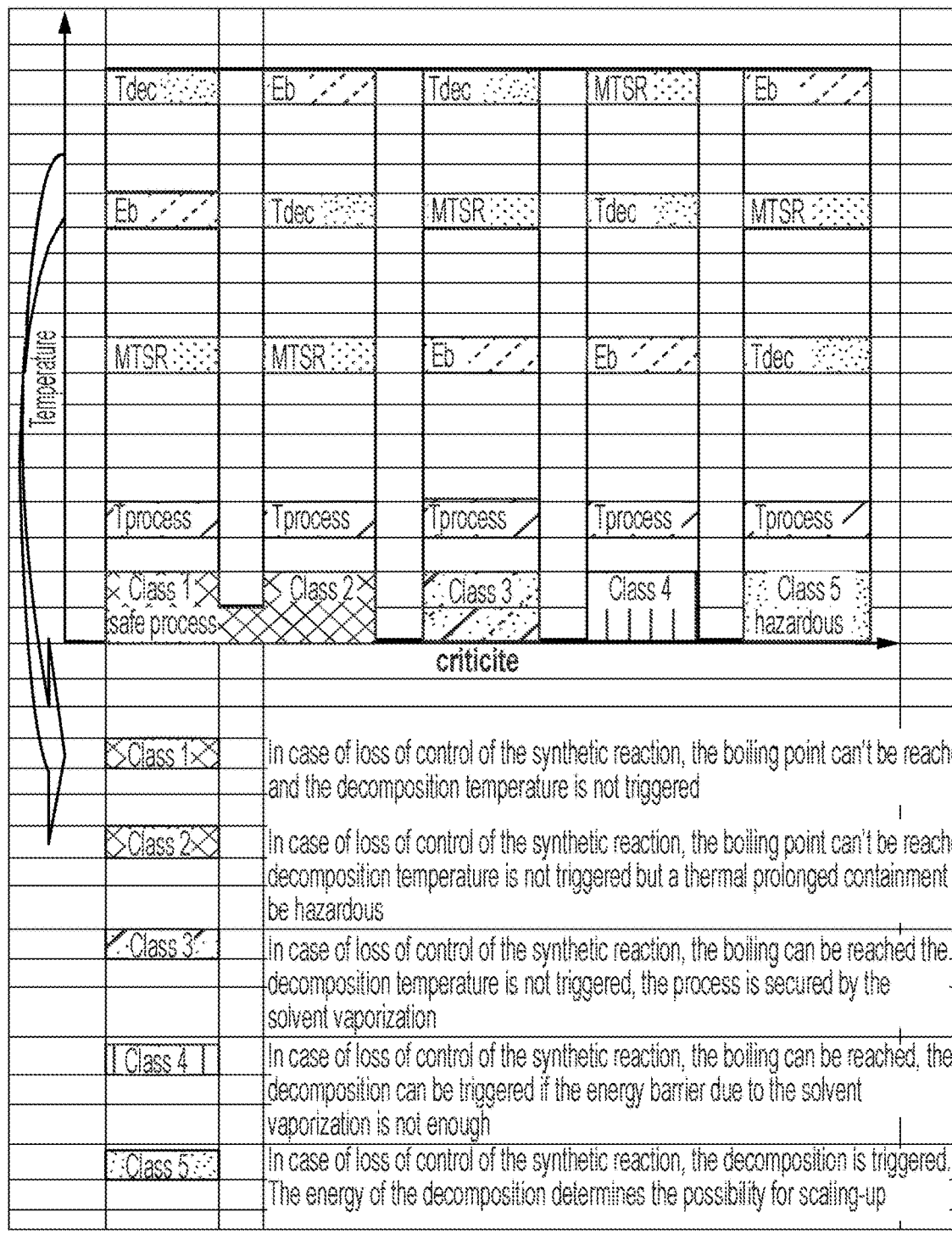
FIG. 22 shows reaction classification system.

Table 27 shows the values used for the classification of the reaction. The reaction classification is also shown in FIG. 22.

TABLE 27

Values used for the classification of the reaction

| Reaction type | −ΔH (J/g) | ΔT ad. (° C.) | TMRad (h) |
|---|---|---|---|
| Violent exothermic decomposition | >800 | 400 | |
| High reaction (high risk) | 400-800 | 200-400 | <8 |
| Average reaction (average risk) | 100-400 | 50-200 | 8-24 |
| Current reaction (low risk in absence of pressure increase) | <100 | <50 | >24 |

Example 9—Computational Mutagenicity Analysis of Rofecoxib (TRM-201)-Related Impurities Introduction The subject matter described herein also relates to an evaluation of the potential mutagenicity of impurities of rofecoxib (TRM-201). The evaluation is performed by testing the structures in several different in silico software programs, followed by expert review of the in silico data.

Over the last several years, use of in silico (computational) tools to predict toxicity has increased significantly and has now become well-established not only in the pharmaceutical industry, but also in the chemical and cosmetic space. This is specifically reflected in the area of potential genotoxic impurities and finalization in 2015 of the International Council for Harmonization of Technical Requirements for Pharmaceuticals for Human Use (ICH) M7 guideline, which is the first regulatory document that supports use of in silico tools as an initial surrogate for conducting in vitro or in vivo testing (ICH M7_Step 5, 2015). The purpose of the M7 guidance is to aid in the identification and characterization of impurities with mutagenic risk and to outline the control strategy for the various classes (Class 1-5) of compounds in order to limit potential carcinogenic risk to subjects. According to ICH M7, "the absence of structural alerts from two complimentary quantitative structure activity relationship [(Q)SAR] methodologies (expert rule-based and statistical) is sufficient to conclude that the impurity is of no mutagenic concern, and no further testing is recommended (Class 5 in FIG. 23)".

In silico software programs to predict toxicity have combined biology and chemistry with modeling and computational science in order to increase the predictive power in the field of toxicology. In silico techniques that employ knowledge-based expert systems like DEREK Nexus (Lhasa, Ltd.), Leadscope Expert Alerts (Leadscope, Inc.), and GT_Expert (Multicase, Inc.) are based upon the presence of structural rules. Expert knowledge based on toxicity data and mechanisms is used to create rules on the likelihood of toxicity in a structure, with information from all applicable rules used to make an overall prediction. Rules are usually encoded as one or more substructures that are matched against the test chemical. A prediction is made when a predictive alert matches. These rules often indicate a mechanistic basis for any positive prediction. Statistical-based systems like Model Applier (Leadscope, Inc.), Case Ultra (Multicase, Inc.) and EPA T.E.S.T. (US EPA) are often referred to as Quantitative Structure-Activity Relationship (QSAR) models and are used to predict various toxicity endpoints based on the chemical structure. These models are constructed from historical laboratory data (training set) where chemical substructures and molecular properties (descriptors) are generated from the list of chemicals. Statistically-based mathematical models are built using these descriptors to predict the target toxicological effect.

The primary endpoint of concern in the ICH M7 guidance is DNA reactive mutagenicity, with the Ames bacterial mutagenicity assay being the preferred assay for this endpoint. The structure based in silico evaluations have good ability to differentiate mutagens from non-mutagens with generally high concordance when compared with Ames assay results (Sutter et al, 2013). Genotoxicants that are non-mutagenic typically have threshold mechanisms and usually do not pose carcinogenic risk to subjects at levels generally present as impurities (EMEA Guideline on the Limits of Genotoxic Impurities, 2006).

Materials and Methods

The current ICH M7 guideline (ICH M7(R1), 2018) states that two complimentary in silico methodologies should be used to qualify certain drug impurities as not mutagenic. To satisfy the ICH M7 guidance, this report encompasses in silico analyses using a rule-based system (DEREK Nexus) and a statistical-based system (Leadscope Model Applier). The predictive data from each of the in silico software programs was reviewed in order to provide additional supportive evidence on the relevance of any positive or negative predictions and to elucidate any underlying reasons for conflicting results. Dobo et al. (2012) have demonstrated a 94% negative predictive value across industry to predict negative results using in silico methods, and this value was increased to 99% when an expert review was also conducted. Following a review of the data, an overall mutagenicity prediction was made (positive or negative).

For recommended control actions, the results were used to classify the structure from 1-5 according to the ICH M7 control strategy originally developed by Muller et al. (2006). For example, if an impurity is found to have no structural alerts or has an alert that is concluded to have sufficient data to demonstrate a lack of mutagenicity, then the impurity can be treated as Class 5 (non-mutagenic). If the impurity has an alert but the alert is the same as the non-mutagenic parent, or if the alert can be scientifically dismissed, it can also be considered non-mutagenic (Class 4). If the impurity has an alerting structure that cannot be ruled out for potential mutagenicity, the impurity will be considered Class 3 and should be controlled at or below the generic threshold of toxicological concern (TTC) value of 1.5 µg/day or the adjusted TTC, based on duration of dosing.

In Silico Software—DEREK Nexus

DEREK is a knowledge and rule based predictive toxicology software program that makes qualitative estimations of endpoint risk. A knowledge based system is a computer program that contains expert knowledge rules in toxicology and applies the rules to make predictions about the toxicity of chemicals, usually when no experimental data are available. The qualitative estimations of risk are categorized, in descending order of probability, as 'certain', 'probable', 'plausible', 'equivocal', 'doubted', 'improbable', 'impossible' or 'inactive'.

DEREK Nexus contains expert derived functionality to provide negative (inactive) predictions for bacterial in vitro mutagenicity. The Lhasa Ames reference set was composed of a variety of data sets (e.g., NTP, FDA CFSAN, ISSSTY, Kirkland, Bursi, Benchmark, Acid Halide Data, Member Data, etc.) and is comprised of 9,900 compounds with 132 mutagenicity alerts (Lhasa Knowledge Suite, Nexus 2.2 Release Notes).

Non-alerting compounds are evaluated to identify unclassified and misclassified features. Misclassified features in the molecule are derived from non-alerting mutagens in the Lhasa reference set. Features in the molecule that are not found in the Lhasa reference set are considered unclassified. For compounds where all features in the molecule are found in accurately classified compounds from the reference set, a negative prediction (inactive) is displayed. Predictions for compounds with misclassified or unclassified features remain negative, and these features are highlighted to enable expert assessment of the prediction. Negative predictivity has been reported to be high (86-94%), comparable to the Ames assay, for compounds with no misclassified or unclassified features.

The DEREK analysis was conducted specifically using the mutagenicity endpoint.

In Silico Software—CASE Ultra

CASE Ultra (CASE) software is a statistical (GT1_BMut model) and rule-based (GT_Expert) system designed to uncover the relationship between the structure of the chemicals and their activity in a specific biological assay. It has been designed to deal with "non-congeneric" databases, that is, databases consisting of structurally unrelated molecules that are not normally amenable to treatment with traditional Quantitative Structure-Activity Relationship (QSAR) type techniques. As such, its main goal is to find the structural entities that discriminate active molecules from the inactive ones and its success is dependent on the validity of the working hypothesis that a relationship does indeed exist between chemical structure and activity. As indicated above, the program selects its own descriptors from a number of possible substructural units and creates a dictionary of molecular descriptors without human intervention. The selected descriptors are characterized either as activating (biophore) or as inactivating (biophobe). The program also considers several other factors, such as molecular weight, octanol/water Log P, water solubility, Lipinski's Rule of 5, and intestinal absorption. All of the alert contributions are considered and a scaled alert weight and regression coefficient are used in the final overall probability calculation. Unknown fragments, positive (activating) and deactivating alerts are highlighted in the program, and an overall positive probability is also provided. The ability of CASE Ultra to select alerts that are readily recognized as being part of a molecule is a major advantage of the method. Indeed, the identification by CASE Ultra of structural components embedded in the molecule offers a foothold that human intelligence can exploit with respect to the possible structural site of metabolism or receptor binding. The modules were developed through a collaborative effort between the U.S. FDA and Multicase, Inc. The database (version 3.0) contains 13,514 unique structures (6982 positives, 6532 negatives).

Konsolidator is a knowledge driven algorithm that generates useful supporting evidence in order to assist those performing expert review. It generates supporting evidence required for expert review and regulatory submissions of in silico predictions. It takes test results from multiple statistical and expert rule models and re-evaluates the alerts by running queries with a large database of chemicals. Konsolidator was introduced with CASE Ultra version 1.6.0.0 and at present only supports bacterial mutagenicity models.

Model Applier

Leadscope® FDA Model Applier (LSMA) is a statistical-based system that uses (Q)SAR models to provide a quantitative predictive probability for the potential toxicity of chemicals. All of the Model Applier (Q)SARs were constructed at the FDA by the Informatics and Computational Safety Analysis Staff (ICSAS). Complete documentation of the weight of evidence methodology used for the preparation of the model training sets and the sources of the data have been published by the ICSAS group (Matthews et al., 2008).

The LSMA assessment was conducted with domain analysis using the ICH M7 settings. The settings for this application specify a Prediction Probability under 0.4 to be negative and a probability of greater than or equal to 0.6 to be positive. If the Prediction indicates "Indeterminate" then the probability fell between those cutoffs. For analysis purposes in this report, prediction probability scores of >0.61-0.79 are considered moderately positive and >0.80-1.0 are considered strongly positive.

The Bacterial Mut model is new in the 2018 software. It was constructed to incorporate data from the SAR Genetox database, Bacterial Mutation alerts reference set and the existing FDA RCA models (*Salmonella* Mut and *E Coli*-TA 102 A-T Mut) in order to improve performance across the board. The training set contains 9109 training compounds (4710 positive/3752 negative). The performance metrics for the model (version 1.0) when tested against itself and cross-validated are as follows:

| Actual | | Cross-validated (5% LMO) |
|---|---|---|
| 83.4 | Accuracy | 84.6 |
| 82.9 | Sensitivity | 84.1 |
| 84.3 | Specificity | 85.3 |
| 86.6 | Positive Predictivity | 87.8 |
| 79.9 | Negative Predictivity | 81.0 |

For all structures, the Model Applier analysis was conducted specifically using the mutagenicity endpoint.

EPA T.E.S.T.

The EPA Toxicity Estimation Software Tool (TEST) has been developed by the Environmental Protection Agency to allow users to easily estimate toxicity using a variety of QSAR methodologies. TEST provides multiple prediction methodologies (hierarchal, FDA, single model, group contribution, nearest neighbor, consensus and random forest) so that one can have greater confidence in the predicted toxicities. Several endpoints are available for evaluation; however, only the Ames mutagenicity endpoint was used in this evaluation. The predicted toxicity from the consensus method represents the average of the predicted toxicities from all the different QSAR methods incorporated into the TEST software. The consensus method achieved the best prediction accuracy (concordance) and prediction coverage for the Ames assay, and this was the method used for the current evaluation. In TEST, predicted values $\geq 0.50$ are considered positive. For analysis purposes, prediction probability scores of $\geq 0.61$-0.79 are considered moderately positive and $\geq 0.80$-1.0 are considered strongly positive.

Molecular descriptors (physical characteristics of the structure) were calculated using computer code written in Java. The basis of the molecular calculations was the Chemistry Development Kit (Steinbeck et al., 2003). The descriptor values were validated using MDL QSAR, Dragon, and Molconn-z. The descriptor values were generally in good agreement (aside from small differences in the descriptor definitions for descriptors such as the number of hydrogen bond acceptors). The final dataset consists of 5743 chemicals, which were based of the dataset compiled by Hansen et al. (2009).

Rofecoxib (TRM-201)

Per NDA 21,042 (1999) and the drug label for VIOXX® (rofecoxib tablets and oral suspension) (2016):

Rofecoxib (L-748,731) was tested in a battery of genotoxicity assays and was not found to be mutagenic or clastogenic. L-748,731 was negative for mutagenicity in *Salmonella typhimurium* (TA98, TA100, TA1535, TA97a) and *E. coli* (WP2, WP2uvrA, WP2 uvrA pKM101) in the presence and absence of an exogenous metabolic activation system (S9) when tested up to 6000 µg/plate. L-748,731 was negative in the in vitro assay for mutations in Chinese hamster lung cells at all concentrations tested with and without S-9. In the chromosomal aberration study conducted using CHO cells, there were no significant increases in the percent of aberrant cells at 25 to 125 µM with S-9 or 25 to 100 µM without S-9 activation.

Rofecoxib was also not carcinogenic in mice or rats at dose levels up to 60 mg/kg and 8 mg/kg, respectively.

Structures Evaluated

1. A-RSM1-00
Name: 1-(4-(ethylthio)phenyl)ethan-1-one
Molecular Weight: 180.27 g/mol

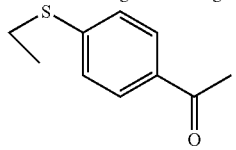

2. A-RSM1-01
Name: ethyl(phenyl)sulfane
Molecular Weight: 138.23 g/mol

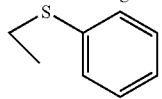

3. A-RSM1-02
Name: 1-(2-(methylthio)phenyl)ethan-1-one
Molecular Weight: 166.24 g/mol

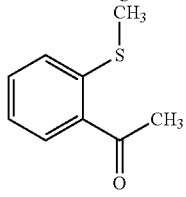

4. A-RSM2-00
Name: 2-phenylacetic acid
Molecular Weight: 136.15 g/mol

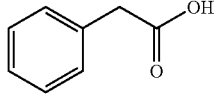

5. A-RSM2-01
Name: 2-phenylacetonitrile
Molecular Weight: 117.15 g/mol

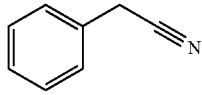

6. A-RSM2-02
Name: 2-phenylacetamide
Molecular Weight: 135.17 g/mol

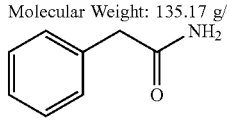

7. A-CRM1-00
Name: tetrabutylammonium
Molecular Weight: 239.17 g/mol

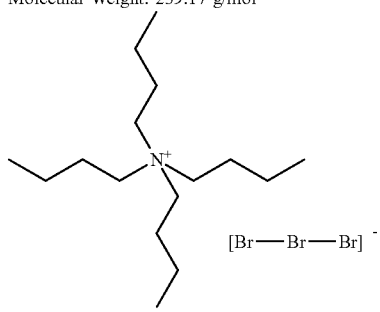

[Br—Br—Br]⁻

8. A-STG1-00
Name: 2-bromo-1-(4-(methylthio)phenyl)ethan-1-one
Molecular Weight: 245.13 g/mol

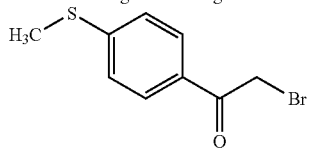

9. A-STG1-01
Name: 2,2-dibromo-1-(4-(methylthio)phenyl)ethan-1-one
Molecular Weight: 324.03 g/mol

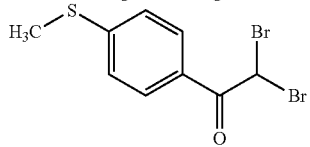

10. A-STG2-00
Name: 2-(4-(methylthio)phenyl)-2-oxoethyl 2-phenylacetate
Molecular Weight: 300.37 g/mol

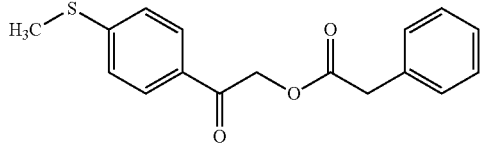 [SMILES: CSc1ccc(C(=O)COC(=O)Cc2ccccc2)cc1]

11. A-STG2-01
Name: 1-bromo-2-(4-(methylthio)phenyl)-2-oxoethyl 2-phenylacetate
Molecular Weight: 379.27 g/mol

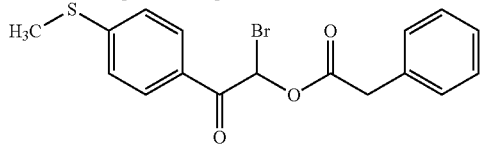 [SMILES: CSc1ccc(C(=O)C(Br)OC(=O)Cc2ccccc2)cc1]

12. A-STG3-00
Name: 4-(4-(methylthio)phenyl)-3-phenylfuran-2(5H)-one
Molecular Weight: 282.36 g/mol

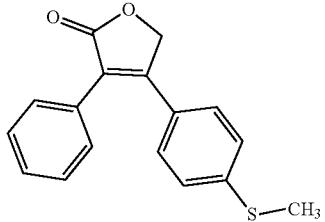 [SMILES: CSc1ccc(C2=C(c3ccccc3)C(=O)OC2)cc1]

13. A-STG3-01
Name: 5-hydroxy-4-(4-(methylthio)phenyl)-3-phenylfuran-2(5H)-one
Molecular Weight: 298.36 g/mol

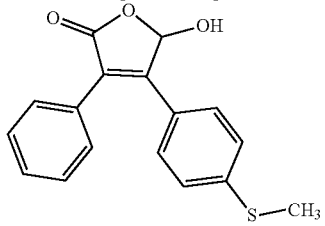

14. A-STG4-01
Name: 4-(4-(methylsulfinyl)phenyl)-3-phenylfuran-2(5H)-one
Molecular Weight: 298.36 g/mol

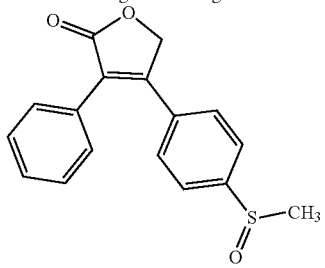

15. A-STG4-02
Name: 5-hydroxy-4-(4-(methylsulfonyl)phenyl)-3-phenylfuran-2(5H)-one
Molecular Weight: 330.35 g/mol

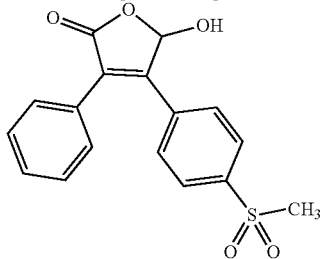 [SMILES: CS(=O)(=O)c1ccc(C2=C(c3ccccc3)C(=O)OC2O)cc1]

16. A-STG4-03
Name: 3-(4-(methylsulfonyl)phenyl)-4-phenylfuran-2,5-dione
Molecular Weight: 328.34 g/mol

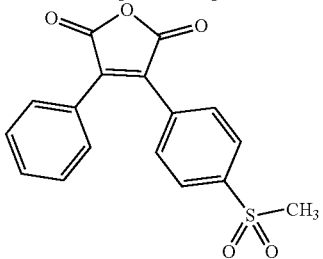

Results

1. A-RSM1-00

In rule-based DEREK, A-RSM1-00 was predicted inactive (negative) for 'mutagenicity in vitro bacterium (*Salmonella typhimurium* and *Escherichia coli*)', with no misclassified or unclassified features.

In statistical-based Leadscope Model Applier, A-RSM1-00 was predicted negative in the Bacterial Mut model with a probability score of 0.399. Most of the main features of the structure were covered in the model and several analogs were shown to support the prediction.

2. A-RSM1-01

In rule-based DEREK, A-RSM1-01 was predicted inactive (negative) for 'mutagenicity in vitro bacterium (*Salmonella typhimurium* and *Escherichia coli*)', with no misclassified or unclassified features.

In statistical-based Leadscope Model Applier, a prediction for A-RSM1-01 was not made because the predictive value was 0.472, which is in the gray zone where a confident prediction cannot be made by the software. However, non-mutagenic 1,2-bis(phenylthio)ethane (LS-1491) is shown as an analog in the training set, with 79% similarity. Due to the inconclusive prediction in Model Applier, A-RSM1-01 was also evaluated using Case Ultra. It was predicted negative in the GT1_BMut model with a calculated probability of 22.9%; no alerts were identified.

3. A-RSM1-02

In rule-based DEREK, A-RSM1-02 was predicted inactive (negative) for 'mutagenicity in vitro bacterium (*Salmonella typhimurium* and *Escherichia coli*)', with no misclassified or unclassified features.

In statistical-based Leadscope Model Applier, a prediction for A-RSM1-02 was not made because the predictive value was 0.4, which is in the gray zone where a confident prediction cannot be made by the software. Due to the inconclusive prediction in Model Applier, A-RSM1-02 was also evaluated using Case Ultra. It was predicted inconclusive in the GT1_BMut model with a calculated probability of 48.3%, which is within the gray zone of 40-60%. One positive alert was identified but it was dismissed by the software because the analogs were negative, and all the positive analogs contained reactive groups not present in A-RSM1-02. The Konsolidator overall outcome call was negative because all of the identified alerts/features were found to be irrelevant to mutagenic activity.

For further confidence in the statistical-based predictions, A-RSM1-02 was analyzed using TEST and it was predicted negative for mutagenicity with a predicted value of 0.09. The similarity coefficients from the analogs in the external and training sets were as high as 0.80 and relevant analogs were shown to support the prediction, including non-mutagenic CASRN 123-09-1 (p-Chlorophenyl methyl sulfide) (Leber et al., 1993).

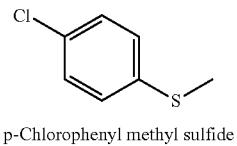

p-Chlorophenyl methyl sulfide

4. A-RSM2-00

In rule-based DEREK, A-RSM2-00 was predicted inactive (negative) for 'mutagenicity in vitro bacterium (*Salmonella typhimurium* and *Escherichia coli*)', with no misclassified or unclassified features.

In statistical-based Leadscope Model Applier, A-RSM2-00 was predicted negative in the Bacterial Mut model with a probability score of 0.072. The main features of the structure were covered in the model and relevant analogs were shown to support the prediction, including LS-7536 (alpha-Naphthylacetic acid) with 72% similarity.

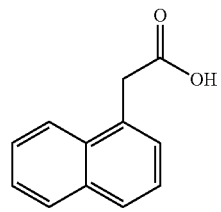

alpha-Naphthylacetic acid

5. A-RSM2-01

In rule-based DEREK, A-RSM2-01 was predicted inactive (negative) for 'mutagenicity in vitro bacterium (*Salmonella typhimurium* and *Escherichia coli*)', with no misclassified or unclassified features.

In statistical-based Leadscope Model Applier, A-RSM2-01 was predicted negative in the Bacterial Mut model with a probability score of 0.145. The main features of the structure were covered in the model and A-RSM2-01 was an exact match in the Leadscope data base with LS-817 (phenylacetonitrile), which was experimentally negative for mutagenicity.

6. A-RSM2-02

In rule-based DEREK, A-RSM2-02 was predicted inactive (negative) for 'mutagenicity in vitro bacterium (*Salmonella typhimurium* and *Escherichia coli*)', with no misclassified or unclassified features.

In statistical-based Leadscope Model Applier, A-RSM2-02 was predicted negative in the Bacterial Mut model with a probability score of 0.170. The main features of the structure were covered in the model and several analogs were shown to support the prediction.

7. A-CRM1-00

In rule-based DEREK, A-CRM1-00 was predicted inactive (negative) for 'mutagenicity in vitro bacterium (*Salmonella typhimurium* and *Escherichia coli*)', with no misclassified or unclassified features. The $Br^{[III]}$ salt feature was considered as an unclassified feature. Unclassified features (are those that were not found in the Lhasa Ames test reference set and do not match any structural alerts or examples for (bacterial in vitro) mutagenicity in Derek. It is predicted to be inactive in the bacterial in vitro (Ames) mutagenicity test.

In statistical-based Leadscope Model Applier, A-CRM1-00 was predicted negative in the Bacterial Mut model with a probability score of 0.055. The main features of the structure were covered in the model and relevant analogs were shown to support the prediction, including non-mutagenic LS-190530 (tetrapropylammonium bromide; CASRN 1941-30-6).

8. A-STG1-00

In rule-based DEREK, A-STG1-00 was predicted inactive (negative) for 'mutagenicity in vitro bacterium (*Salmonella typhimurium* and *Escherichia coli*)', with no misclassified or unclassified features. While contains an alkyl bromide, the 027 alert in DEREK contains several exclusion criteria, including one for primary alpha-halo ketones. Studies suggest that some phenacyl bromides may be oxidized by the DMSO solvent to afford mutagenic phenylglyoxals, which give rise to positive responses that are not observed when using acetone as the solvent (Azuma, et al., 1997).

In statistical-based Leadscope Model Applier, A-STG1-00 was predicted positive in the Bacterial Mut model with a probability score of 0.770. The positive prediction was mainly due to the alkyl bromide feature. While several analogs with an alkyl halide feature were shown to support the prediction, analog LS-188087 (2-bromoacetophenone) with 62% similarity was shown and was experimentally negative for mutagenicity, and analog LS-394467 (2-Bromo-1-[4-(methylsulfonyl)phenyl]-1-ethanone), with 54% similarity was experimentally positive for mutagenicity.

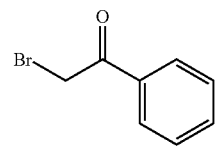

phenacyl bromide

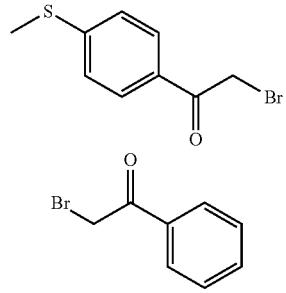

2-bromoacetophenone

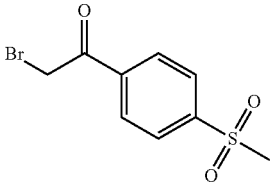

2-Bromo-1-[4-(methylsulfonyl)phenyl]-1-ethanone

For further confidence in the statistical-based predictions, A-STG1-00 was analyzed using TEST and it was predicted negative for mutagenicity with a predicted value of 0.40.

The similarity coefficients from the analogs in the external and training sets were as high as 0.66 and relevant alkyl halide analogs were shown to support the prediction.

9. A-STG1-01

In rule-based DEREK, A-STG1-01 was predicted plausible for 'mutagenicity in vitro bacterium (*Salmonella typhimurium* and *Escherichia coli*)' in DEREK due to matched alert 326 for gem-Dihalide (alerting pharmacophore highlighted below in gray). Compounds in this class have been shown to be mutagenic in the Ames test, both in the presence and absence of metabolic activation and activity has generally been demonstrated for terminal gem-dihalides, gem-dibromides and gem-mixed dihalides which are alpha to an unsaturated carbon atom, for example alpha,alpha-dichlorotoluene (Zeiger, et al., 1992).

In statistical-based Leadscope Model Applier, A-STG1-01 was predicted positive in the Bacterial Mut model with a probability score of 0.870. The positive prediction was mainly due to the alkyl dibromide feature, and several analogs with an alkyl bromide feature were shown to support the prediction. Although not a dihalide, 2-bromoacetophenone (LS-188087) was shown as an analog and was experimentally negative for mutagenicity.

The mechanism by which gem-dihalides exert their mutagenic effect is not clear but it is likely to involve the direct reaction of these compounds with DNA since they are inherently electrophilic species. The reactivity of a given gem-dihalide will depend on a number of factors including the steric and electronic environment surrounding the reactive center and the nature of the halogen atoms forming the functional group, with dichloro compounds being less reactive than dibromo compounds.

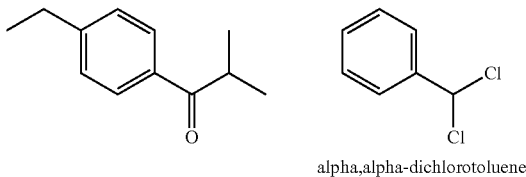

alpha,alpha-dichlorotoluene

10. A-STG2-00

In rule-based DEREK, A-STG2-00 was predicted inactive (negative) for 'mutagenicity in vitro bacterium (*Salmonella typhimurium* and *Escherichia coli*)', with no misclassified or unclassified features.

In statistical-based Leadscope Model Applier, A-STG2-00 was predicted negative in the Bacterial Mut model with a probability score of 0.235. The main features of the structure were covered in the model and relevant analogs were shown to support the prediction.

11. A-STG2-01

In rule-based DEREK, A-STG2-01 was predicted plausible for 'mutagenicity in vitro bacterium (*Salmonella typhimurium* and *Escherichia coli*)' in DEREK due to matched alert 027 for an alkylating agent (alerting pharmacophore highlighted below in gray). The 027 alert covers alkylating agents where the carbon bearing the functional group is a primary or secondary alkyl carbon atom, and it includes alkyl sulphinates, sulphonates and sulphates which lack a hydroxyl group directly bonded to the sulphur.

In statistical-based Leadscope Model Applier, A-STG2-01 was predicted positive in the Bacterial Mut model with a probability score of 0.739. The positive prediction was mainly due to the alkyl bromide feature, and several analogs with an alkyl bromide feature were shown to support the prediction.

Alkyl halides are electrophilic species that are capable of directly alkylating DNA. Shorter chain alkyl chlorides, such as methyl chloride, are known to be mutagenic (Andrews et al., 1976).

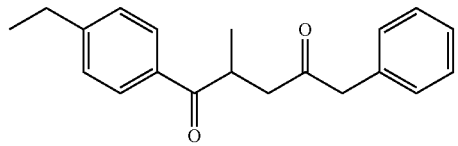 [SMILES: CCc1ccc(C(=O)C(C)CC(=O)Cc2ccccc2)cc1]

12. A-STG3-00

In rule-based DEREK, A-STG3-00 was predicted inactive (negative) for 'mutagenicity in vitro bacterium (*Salmonella typhimurium* and *Escherichia coli*)', with no misclassified or unclassified features.

In statistical-based Leadscope Model Applier, a prediction for A-STG3-00 was not made because the predictive value was 0.488, which is in the gray zone where a confident prediction cannot be made by the software. However, rofecoxib is shown as an analog in the training set, with 59% similarity.

Due to the inconclusive prediction in Model Applier, A-STG3-00 was also evaluated using Case Ultra. It was predicted negative in the GT1 BMut model with a calculated probability of 17.8%; 2 alerts and 1 deactivating feature were identified. All of the alerts were dismissed by the software because a majority of the analogs were negative, and the positive analogs contained reactive groups not present in A-STG3-00. Rofecoxib was also shown as an analog in the database, with 90.4% similarity.

13. A-STG3-01

In rule-based DEREK, A-STG3-01 was predicted inactive (negative) for 'mutagenicity in vitro bacterium (*Salmonella typhimurium* and *Escherichia coli*)', with no misclassified or unclassified features.

In statistical-based Leadscope Model Applier, a prediction for A-STG3-01 was not made because the predictive value was in the gray zone at 0.486. However, rofecoxib is shown as an analog in the training set, with 43% similarity.

Due to the inconclusive prediction in Model Applier, A-STG3-01 was also evaluated using Case Ultra. It was predicted inconclusive in the GT1_BMut model with a calculated probability of 42.4%; 2 alerts were identified. All of the alerts were dismissed by the software because a majority of the analogs were negative, and the majority of positive analogs contained reactive groups not present in A-STG3-00. Rofecoxib was also shown as an analog in the database, with 50% similarity. The Konsolidator suggested outcome is a negative call because the alerts/features were found to be irrelevant to mutagenic activity.

14. A-STG4-01

In rule-based DEREK, A-STG4-01 was predicted inactive (negative) for 'mutagenicity in vitro bacterium (*Salmonella typhimurium* and *Escherichia coli*)', with no misclassified or unclassified features.

In statistical-based Leadscope Model Applier, A-STG4-01 was predicted negative in the Bacterial Mut model with a probability score of 0.353. Most of the main features of the structure were covered in the model and relevant analogs, including non-mutagenic rofecoxib, were shown to support the prediction.

15. A-STG4-02

In rule-based DEREK, A-STG4-02 was predicted inactive (negative) for 'mutagenicity in vitro bacterium (*Salmonella typhimurium* and *Escherichia coli*)', with no misclassified or unclassified features.

In statistical-based Leadscope Model Applier, A-STG4-02 was predicted negative in the Bacterial Mut model with a probability score of 0.162. The main features of the structure were covered in the model and relevant analogs, including non-mutagenic rofecoxib, were shown to support the prediction.

16. A-STG4-03

In rule-based DEREK, A-STG4-03 was predicted inactive (negative) for 'mutagenicity in vitro bacterium (*Salmonella typhimurium* and *Escherichia coli*)', with no misclassified or unclassified features.

In statistical-based Leadscope Model Applier, A-STG4-01 was predicted negative in the Bacterial Mut model with a probability score of 0.182. The main features of the structure were covered in the model and relevant analogs, including non-mutagenic rofecoxib, were shown to support the prediction.

The emphasis of the overall computational assessment of toxicity was placed on the potential for DNA reactive mutagenicity. A summary of the in silico results and overall mutagenicity predictions are listed below in FIG. 23.

CONCLUSIONS

In accordance with ICH M7 criteria, the potential mutagenicity of impurities of TRM-201 was evaluated in silico in at least 2 complimentary software programs followed by expert review of the data. Individual model results and overall mutagenicity predictions are presented in FIG. 23.

A-RSM1-00, A-CRM1-00, A-RSM2-00, A-RSM2-02, and A-STG2-00 were predicted clearly negative in rule-based DEREK and statistical-based Model Applier. No alerts were identified, and relevant analogs were shown to support the predictions. Therefore, according to ICH M7, they can be considered non-mutagenic (Class 5).

A-RSM1-01 was predicted clearly negative in rule-based DEREK and statistical-based Case Ultra. No alerts were identified, and relevant analogs were shown to support the predictions. Therefore, according to ICH M7, it can be considered non-mutagenic (Class 5).

A-RSM1-02 was predicted negative for mutagenicity in rule-based DEREK and in statistical-based methods, it was considered inconclusive in both Model Applier and Case Ultra but was predicted negative in TEST. Relevant analogs were shown to support the prediction. The negative prediction and lack of structural alerts suggests A-RSM1-02 is non-mutagenic. Therefore, it is considered a Class 5 impurity.

A-RSM2-01 was predicted clearly negative in rule-based DEREK and statistical-based Model Applier. It was an exact match in the Leadscope database, with negative mutagenicity data. Therefore, it is considered a Class 5 impurity.

A-STG1-00 was predicted negative in rule-based DEREK and positive in statistical-based Model Applier due to an alert for the alkyl bromide feature. The alkyl halide feature did not alert in DEREK due to an exclusion for phenacyl bromides, which may be oxidized by DMSO used in the Ames assay resulting in false positive results. In the case for A-STG1-00, the sulfur will be electron withdrawing because of its ability to have some double bond character, thus supporting the decreased reactivity of this structure. A-STG1-00 was also predicted negative in statistical-based TEST. Thus, the evidence suggests A-STG1-00 is non-mutagenic (Class 4).

A-STG1-01 was predicted positive in rule-based DEREK and statistical-based Model Applier due to alerts for the alkyl dibromide feature. While the mechanism by which gem-dihalides exert their mutagenic effect is not clear, it likely involves a direct interaction with DNA due to the inherent electrophilicity of these species. The actual reactivity of any given gem-dihalide depends on a number of factors, and considering A-STG1-01 does not afford much in the way of steric hindrance and it contains a dibromide feature, which is typically more reactive than a dichloro feature, A-STG1-01 is considered potentially mutagenic until tested in an Ames assay (Class 3).

A-STG2-01 was predicted positive in rule-based DEREK and statistical-based Model Applier due to alerts for the alkyl bromide feature. Alkyl halides are electrophilic species that are capable of directly alkylating DNA, and with positive predictions in two complimentary in silico systems, A-STG2-01 is considered potentially mutagenic (Class 3).

A-STG3-00 was predicted negative for mutagenicity in rule-based DEREK and in statistical-based Case Ultra. Although a prediction was not made in Model Applier, non-mutagenic rofecoxib was shown as a close analog. A-STG3-00 was predicted negative in two complimentary in silico systems and is therefore considered non-mutagenic (Class 5).

A-STG3-01 only differs from A-STG3-00 (above) by the presence of a hydroxyl group on the furan ring, as such, the prediction was similar. A-STG3-01 was predicted negative for mutagenicity in rule-based DEREK and in statistical-based methods, it was considered inconclusive in both Model Applier and Case Ultra. Although a prediction was not made in the statistical models, non-mutagenic rofecoxib was shown as a close analog. The negative prediction and similarity to the non-mutagenic parent compound suggests A-STG3-01 is non-mutagenic. Therefore, it is considered a Class 5 impurity.

A-STG4-01, A-STG4-02, and A-STG4-03 were predicted clearly negative in rule-based DEREK and statistical-based Model Applier. No alerts were identified, and relevant analogs, including rofecoxib, were shown to support the predictions. These structures are very structurally similarity to the non-mutagenic parent compound, rofecoxib. Therefore, according to ICH M7, they can be considered non-mutagenic (Class 5).

REFERENCES FOR EXAMPLE 9

Andrews A W, Zawistowski E S, Valentine C (1976). A comparison of the mutagenic properties of vinyl chloride and methyl chloride. Mutation Research. 40: 273-275.

Case Ultra, version 1.7.0.5., Multicase, Inc. (Beachwood, Ohio).

DEREK Nexus, version 6.0.1 (2018), Nexus v.2.2.1, Lhasa Limited (Leeds, UK).

Dobo K, Greene N, Fred C, et al. (2012). In silico methods combined with expert knowledge rule out mutagenic potential of pharmaceutical impurities: An industry survey. Regul Toxicol Pharmcol., 62(3):449-55.

EMEA/CHMP/QWP/251344/2006 (2006). Guideline on the Limits of Genotoxic Impurities.

EPA T.E.S.T., version 4.2.1 (2016). A Program to Estimate Toxicity from Molecular Structure. U.S. EPA.

Hansen K, Mika S, Schroeter T, et al. (2009). Benchmark Data Set for in silico Prediction of Ames Mutagenicity. Journal of Chemical Information and Modeling, 49 (9): 2077-2081.

ICH M7 Guideline (2015). Assessment and Control of DNA Reactive (Mutagenic) Impurities in Pharmaceuticals to Limit Potential Carcinogenic Risk. May 2015.

ICH M7(R1) Guideline (2018). Assessment and Control of DNA Reactive (Mutagenic) Impurities in Pharmaceuticals to Limit Potential Carcinogenic Risk. March 2018.

Leadscope (2018). Model Applier v2.4.1-36, Enterprise v3.7.1-36; Personal v4.7.1-36. LeadScope®, Inc. (Columbus, Ohio).

Leber A, Dacre J, Thake D, et al. (1993). p-Chlorophenyl methyl sulfide, p-Chlorophenyl methyl sulfoxide, and p-Chlorophenyl methyl sulfone-acute toxicity and bacterial mutagenicity studies. J. Am. Coll. Toxicol., 12(4): 369-376.

Matthews E, Kruhlak N, Benz D, Contrera J. (2008). Combined Use of MC4PC, MDL-QSAR, BioEpisteme, Leadscope PDM, and Derek for Windows Software to Achieve High-Performance, High-Confidence, Mode of Action-Based Predictions of Chemical Carcinogenesis in Rodents. Toxicology Mechanisms and Methods, 18:189-206.

Müller L, Mauthe R, Riley C, et al. (2006). A rationale for determining, testing, and controlling 724 specific impurities in pharmaceuticals that possess potential for genotoxicity. Regul Toxicol Pharmacol. 44:198-211.

NDA 21,042 (1999). VIOXX (rofecoxib). Merck & Co.

Steinbeck C, Han Y, Kuhn S, et al. (2003). The Chemistry Development Kit (CDK): An Open-Source Java Library for Chemo- and Bioinformatics. Journal of Chemical Information and Computer Sciences, 43:493-500.

Sutter A, Amberg A, Boyer S, Brigo A, et al. (2013). Use of in silico systems and expert knowledge for structure-based assessment of potentially mutagenic impurities. Reg. Toxicol. Pharmacol., 67:39-52.

US Food and Drug Administration. VIOXX (Rofecoxib) U.S. Prescribing Information May 9, 2016.

Zeiger E, Anderson B, Haworth S, Lawlor T and Mortelmans K (1992). *Salmonella* mutagenicity tests: V. Results from the testing of 311 chemicals., Environmental and Molecular Mutagenesis, 19 (supplement 21), 2-141.

EQUIVALENTS

The subject matter described herein can be embodied in other specific forms without departing from the spirit or essential characteristics thereof. The foregoing embodiments are therefore to be considered in all respects illustrative rather than limiting on the subject matter described herein. Scope of the subject matter described herein is thus indicated by the appended claims rather than by the foregoing description, and all changes that come within the meaning and range of equivalency of the claims are intended to be embraced therein.

What is claimed is:

1. A pharmaceutical composition comprising rofecoxib or a pharmaceutically acceptable salt thereof and a pharmaceutically acceptable carrier, wherein the rofecoxib or a pharmaceutically acceptable salt thereof comprises less than 0.05% of 4-[4-(methylsulfonyl)phenyl]-3-phenyl-5-hydroxyfuran-2-one wherein the rofecoxib or a pharmaceutically acceptable salt thereof comprises less than 0.10% total impurities.

2. The pharmaceutical composition of claim 1, wherein the rofecoxib or a pharmaceutically acceptable salt thereof is free of 4-[4-(methylsulfonyl)phenyl]-3-phenyl-5-hydroxyfuran-2-one.

3. The pharmaceutical composition of claim 1, wherein the rofecoxib or a pharmaceutically acceptable salt thereof is free of 4-[4-(methylsulfonyl)phenyl]-3-phenyl-2,5-furandione.

4. The pharmaceutical composition of claim 1, wherein the rofecoxib or a pharmaceutically acceptable salt thereof comprises less than 0.10% of 4-[4-(methylthio)phenyl]-3-phenyl-2(5H)-furanone.

5. The pharmaceutical composition of claim 1, wherein the rofecoxib or a pharmaceutically acceptable salt thereof comprises less than 0.10% of 4-[4-(methylsulfinyl)phenyl]-3-phenyl-2(5H)-furanone.

6. The pharmaceutical composition of claim 1, wherein the pharmaceutical composition is suitable for one or more of oral, nasal, inhalation, topical, buccal, sublingual, rectal, vaginal, and parenteral administration to a human subject.

7. The pharmaceutical composition of claim 6, wherein the pharmaceutical composition is suitable for oral administration to a human subject.

8. The pharmaceutical composition of claim 1, wherein the rofecoxib or a pharmaceutically acceptable salt thereof has a d90 particle size of about 10 μm to about 12 μm, a d50 particle size of about 3 μm to about 4 μm, and a d10 particle size of about 0.5 μm to about 1.0 μm.

9. A pharmaceutical composition comprising about 12.5 mg rofecoxib or a pharmaceutically acceptable salt thereof and a pharmaceutically acceptable carrier, wherein the rofecoxib or a pharmaceutically acceptable salt thereof comprises less than 0.05% of 4-[4-(methylsulfonyl)phenyl]-3-phenyl-5-hydroxyfuran-2-one wherein the rofecoxib or a pharmaceutically acceptable salt thereof comprises less than 0.10% total impurities.

10. The pharmaceutical composition of claim 9, wherein the rofecoxib or a pharmaceutically acceptable salt thereof is free of 4-[4-(methylsulfonyl)phenyl]-3-phenyl-5-hydroxyfuran-2-one.

11. The pharmaceutical composition of claim 9, wherein the rofecoxib or a pharmaceutically acceptable salt thereof is free of 4-[4-(methylsulfonyl)phenyl]-3-phenyl-2,5-furandione.

12. The pharmaceutical composition of claim 9, wherein the rofecoxib or a pharmaceutically acceptable salt thereof comprises less than 0.10% of 4-[4-(methylthio)phenyl]-3-phenyl-2(5H)-furanone.

13. The pharmaceutical composition of claim 9, wherein the rofecoxib or a pharmaceutically acceptable salt thereof comprises less than 0.10% of 4-[4-(methylsulfinyl)phenyl]-3-phenyl-2(5H)-furanone.

14. The pharmaceutical composition of claim 9, wherein the pharmaceutical composition is suitable for one or more of oral, nasal, inhalation, topical, buccal, sublingual, rectal, vaginal, and parenteral administration to a human subject.

15. The pharmaceutical composition of claim 14, wherein the pharmaceutical composition is suitable for oral administration to a human subject.

16. The pharmaceutical composition of claim 9, wherein the rofecoxib or a pharmaceutically acceptable salt thereof has a d90 particle size of about 10 μm to about 12 μm, a d50 particle size of about 3 μm to about 4 μm, and a d10 particle size of about 0.5 μm to about 1.0 μm.

17. A pharmaceutical composition comprising about 17.5 mg rofecoxib or a pharmaceutically acceptable salt thereof and a pharmaceutically acceptable carrier, wherein the rofecoxib or a pharmaceutically acceptable salt thereof comprises less than 0.05% of 4-[4-(methylsulfonyl)phenyl]-3-phenyl-5-hydroxyfuran-2-one wherein the rofecoxib or a pharmaceutically acceptable salt thereof comprises less than 0.10% total impurities.

18. The pharmaceutical composition of claim 17, wherein the rofecoxib or a pharmaceutically acceptable salt thereof is free of 4-[4-(methylsulfonyl)phenyl]-3-phenyl-5-hydroxyfuran-2-one.

19. The pharmaceutical composition of claim 17, wherein the rofecoxib or a pharmaceutically acceptable salt thereof is free of 4-[4-(methylsulfonyl)phenyl] phenyl-2,5-furandione.

20. The pharmaceutical composition of claim 17, wherein the rofecoxib or a pharmaceutically acceptable salt thereof comprises less than 0.10% of 4-[4-(methylthio)phenyl]-3-phenyl-2(5H)-furanone.

21. The pharmaceutical composition of claim 17, wherein the rofecoxib or a pharmaceutically acceptable salt thereof comprises less than 0.10% of 4-[4-(methylsulfinyl)phenyl]-3-phenyl-2(5H)-furanone.

22. The pharmaceutical composition of claim 17, wherein the pharmaceutical composition is suitable for one or more of oral, nasal, inhalation, topical, buccal, sublingual, rectal, vaginal, and parenteral administration to a human subject.

23. The pharmaceutical composition of claim 22, wherein the pharmaceutical composition is suitable for oral administration to a human subject.

24. The pharmaceutical composition of claim 17, wherein the rofecoxib or a pharmaceutically acceptable salt thereof has a d90 particle size of about 10 μm to about 12 μm, a d50 particle size of about 3 μm to about 4 μm, and a d10 particle size of about 0.5 μm to about 1.0 μm.

25. A pharmaceutical composition comprising about 20 mg rofecoxib or a pharmaceutically acceptable salt thereof and a pharmaceutically acceptable carrier, wherein the rofecoxib or a pharmaceutically acceptable salt thereof comprises less than 0.05% of 4-[4-(methylsulfonyl)phenyl]-3-phenyl-5-hydroxyfuran-2-one wherein the rofecoxib or a pharmaceutically acceptable salt thereof comprises less than 0.10% total impurities.

26. The pharmaceutical composition of claim 25, wherein the rofecoxib or a pharmaceutically acceptable salt thereof is free of 4-[4-(methylsulfonyl)phenyl]-3-phenyl-5-hydroxyfuran-2-one.

27. The pharmaceutical composition of claim 25, wherein the rofecoxib or a pharmaceutically acceptable salt thereof is free of 4-[4-(methylsulfonyl)phenyl]-3-phenyl-2,5-furandione.

28. The pharmaceutical composition of claim 25, wherein the rofecoxib or a pharmaceutically acceptable salt thereof comprises less than 0.10% of 4-[4-(methylthio)phenyl]-3-phenyl-2(5H)-furanone.

29. The pharmaceutical composition of claim 25, wherein the rofecoxib or a pharmaceutically acceptable salt thereof comprises less than 0.10% of 4-[4-(methylsulfinyl)phenyl]-3-phenyl-2(5H)-furanone.

30. The pharmaceutical composition of claim 25, wherein the pharmaceutical composition is suitable for one or more of oral, nasal, inhalation, topical, buccal, sublingual, rectal, vaginal, and parenteral administration to a human subject.

31. The pharmaceutical composition of claim 30, wherein the pharmaceutical composition is suitable for oral administration to a human subject.

32. The pharmaceutical composition of claim 25, wherein the rofecoxib or a pharmaceutically acceptable salt thereof has a d90 particle size of about 10 μm to about 12 μm, a d50 particle size of about 3 μm to about 4 μm, and a d10 particle size of about 0.5 μm to about 1.0 μm.

\* \* \* \* \*